United States Patent
Lyden et al.

(10) Patent No.: US 12,259,389 B2
(45) Date of Patent: Mar. 25, 2025

(54) NANOPARTICLES AND DISTINCT EXOSOME SUBSETS FOR DETECTION AND TREATMENT OF CANCER

(71) Applicant: CORNELL UNIVERSITY, Ithaca, NY (US)

(72) Inventors: David C. Lyden, Old Chatham, NY (US); Haiying Zhang, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 18/082,368

(22) Filed: Dec. 15, 2022

(65) Prior Publication Data
US 2023/0266329 A1    Aug. 24, 2023

Related U.S. Application Data

(63) Continuation of application No. 16/873,700, filed as application No. PCT/US2018/063612 on Dec. 3, 2018, now abandoned.

(60) Provisional application No. 62/623,992, filed on Jan. 30, 2018, provisional application No. 62/593,504, filed on Dec. 1, 2017.

(51) Int. Cl.
G01N 33/574    (2006.01)
C12Q 1/6886    (2018.01)
G01N 33/68     (2006.01)

(52) U.S. Cl.
CPC ..... *G01N 33/57484* (2013.01); *C12Q 1/6886* (2013.01); *G01N 33/68* (2013.01); *C12Q 2600/106* (2013.01); *C12Q 2600/118* (2013.01); *G01N 33/6893* (2013.01)

(58) Field of Classification Search
CPC .............................................. G01N 33/57484
USPC ....................................................... 435/6.11
See application file for complete search history.

(56) References Cited

U.S. PATENT DOCUMENTS

| | | |
|---|---|---|
| 2002/0172987 A1 | 11/2002 | Terstappen et al. |
| 2003/0129676 A1 | 7/2003 | Terstappen et al. |
| 2011/0151460 A1 | 6/2011 | Klass et al. |
| 2012/0295286 A1 | 11/2012 | Berg |
| 2014/0038901 A1 | 2/2014 | Lyden et al. |
| 2014/0045915 A1 | 2/2014 | Skog et al. |
| 2014/0094383 A1 | 4/2014 | Lee et al. |
| 2014/0228233 A1* | 8/2014 | Pawlowski ...... G01N 33/57484 435/7.92 |
| 2016/0041153 A1 | 2/2016 | Brown et al. |
| 2017/0227550 A1 | 8/2017 | Nikrad et al. |

FOREIGN PATENT DOCUMENTS

| | | |
|---|---|---|
| CN | 1946841 A | 4/2007 |
| CN | 101336298 A | 12/2008 |
| CN | 102348979 A | 2/2012 |
| CN | 103221535 A | 7/2013 |
| CN | 104619388 A | 5/2015 |
| CN | 105143887 A | 12/2015 |
| CN | 105505772 A | 4/2016 |
| CN | 105899191 A | 8/2016 |
| CN | 106029906 A | 10/2016 |
| CN | 107076709 A | 8/2017 |
| CN | 107405377 A | 11/2017 |
| EP | 1614461 A2 | 1/2006 |
| EP | 1642887 A1 | 4/2006 |
| EP | 3181705 A1 | 6/2017 |
| WO | 2010147274 A1 | 12/2010 |
| WO | 2012/048372 A1 | 4/2012 |

(Continued)

OTHER PUBLICATIONS

Tockman et al (Cancer Res., 1992, 52:2711s-2718s).*
Second Office Action for corresponding Chinese Application CN201880088472.3 and English translation, mailed Oct. 20, 2023.
Chinese Office Action for corresponding CN201880088472.3, mailed Feb. 10, 2023.
Chinese Search Report for corresponding CN201880088472.3, mailed Feb. 9, 2023.
PCT International Preliminary Report on Patentability for corresponding PCT/US2018/063612, mailed Jun. 2, 2020.

(Continued)

*Primary Examiner* — Sean E Aeder
(74) *Attorney, Agent, or Firm* — Troutman Pepper Locke LLP (Rochester)

(57) ABSTRACT

The present invention is directed to methods of diagnosing, prognosing, and managing treatment of cancer in a subject. These methods involve selecting a subject having cancer and obtaining, from the selected subject, a population of either exomeres having a diameter less than 50 nm, small exosomes having a diameter of 60-80 nm, or large exosomes having a diameter of 90-120 nm. The exomeres, small exosomes, or large exosomes are recovered from the sample, and the exomeres, small exosomes, or large exosomes or portions thereof are contacted with one or more reagents suitable to detect: (1) higher or lower levels, relative to a standard for subjects not having cancer, or the presence or absence, of one or more proteins contained in said exomeres, small exosomes, or large exosomes, (2) higher or lower levels, relative to a standard for subjects not having cancer, or the presence or absence, of one or more N-glycans contained in said exomeres, small exosomes, or large exosomes, (3) higher or lower levels, relative to a standard for subjects not having cancer, or the presence or absence, of one or more lipids contained in said exomeres, small exosomes, or large exosomes, (4) the presence or absence of one or more genetic mutations in nucleic acid molecules associated with cancer and contained in said exomeres, small exosomes, or large exosomes, or (5) combinations thereof. Cancer is then diagnosed, prognosed, or treatment is modified based on this information.

3 Claims, 51 Drawing Sheets

(56) References Cited

FOREIGN PATENT DOCUMENTS

| WO | 2015/082372 A1 | 6/2015 |
|---|---|---|
| WO | 2015/085096 A1 | 6/2015 |
| WO | 2016/172710 A2 | 10/2016 |
| WO | 2017/149206 A1 | 9/2017 |
| WO | 2017194499 A1 | 11/2017 |

OTHER PUBLICATIONS

PCT International Search Report and Written Opinion for corresponding PCT/US2018/063612, mailed Apr. 30, 2019.
Zhang et al., "Identification of Distinct Nanoparticles and Subsets of Extracellular Vesicles by Asymmetric Flow Field-Flow Fractionation," Nat. Cell Biol. 20:332-343 (2018).
Kowal et al., "Proteomic Comparison Defines Novel Markers to Characterize Heterogenous Populations of Extracellular Vesicle Subtypes," PNAS 113(8):E968-977 (2016).
Hoog and Lotvall, "Diversity of Extracellular Vesicles in Human Ejaculates Revealed by Cryo-Electron Microscopy," Journal of Extracellular Vesicles 4:28680 (2015).
Arraud et al., "Extracellular Vesicles From Blood Plasma: Determination of Their Morphology, Size, Phenotype and Concentration," Journal of Thrombosis and Haemostasis 12:614-627 (2014).
Kahlert et al., "Identification of double-stranded genomic DNA spanning all chromosomes with mutated KRAS and p53 DNA in the serum exosomes of patients with pancreatic cancer," J Biol Chem 289(7):3869-75 (2014).
Ashby et al., "Distribution Profiling of Circulating MicroRNAs in Serum," Anal. Chem. 86:9343-9349 (2014).
Agarwal et al., :"Analysis of Exosome Release as a Cellular Response to MAPK Pathway Inhibition," Langmuir 31(19):5440-8 (2015).
Petersen et al., "A Review of Exosome Separation Techniques and Characterization of B16-F10 Mouse Melanoma Exosomes with AF4-UV-MALS-DLS-TEM," Anal Bioanal Chem 406(30):7855-66 (2014).
Zabeo et al., "Exosomes Purified from a Single Cell Type Have Diverse Morphology," J Extracell Vesicles 6(1):1329476 (2017).
Lasser et al., "Subpopulations of Extracellular Vesicles and Their Therapeutic Potential," Mol Aspects Med 60:1-14 (2018).
Raposo et al., "B Lymphocytes Secrete Antigen-presenting Vesicles," J Exp Med 183(3):1161-72 (1996).
Raposo and Stoorvogel, "Extracellular Vesicles: Exosomes, Microvesicles, and Friends," J Cell Biol 200(4):373-83 (2013).
Van Niel et al., "Intestinal Epithelial Cells Secrete Exosome-like Vesicles," Gastroenterology 121(2):337-49 (2001).
Escola et al., "Selective Enrichment of Tetraspan Proteins on the Internal Vesicles of Multivesicular Endosomes and on Exosomes Secreted by Human B-lymphocytes," J Biol Chem 273(32):20121-7 (1998).
Melo et al., "Glypican-1 Identifies Cancer Exosomes and Detects Early Pancreatic Cancer," Nature 523(7559):177-82 (2015).
Yang et al., Size Dependent Lipidomic Analysis of Urinary Exosomes from Patients with Prostate Cancer by Flow Field-Flow Fractionation and Nanoflow Liquid Chromatography-Tandem Mass Spectrometry, Anal Chem 89(4):2488-2496 (2017).
Nuzhat et al., "Tumour-derived Exosomes as a Signature of Pancreatic Cancer—Liquid Biopsies as Indicators of Tumour Progression," Oncotarget 8(10):17279-17291 (2017).
Gerlach and Griffin, "Getting to Know the Extracellular Vesicle Glycome," Molecular BioSystems 4:1071-1081 (2016).
Extended European Search Report for European Application Serial No. 18882781.0, dated Jan. 11, 2022.
Gorin et al., "Circulating Tumour Cells as Biomarkers of Prostate, Bladder, and Kidney Cancer," Nature Reviews Urology 14:90-97 (2017).
Li et al., "Role of Exosomal Proteins in Cancer Diagnosis," Mol Cancer. 16:145 (2017).
Thakur et al., "Double-stranded DNA in Exosomes: A Novel Biomarker in Cancer Detection," Cell Res. 24(6):766-769 (2014).
Elshimali et al., "The Clinical Utilization of Circulating Cell Free DNA (CCFDNA) in Blood of Cancer Patients," Int J Mol Sci. 14(9):18925-18958 (2013).
Gold et al., "Do Circulating Tumor Cells, Exosomes, and Circulating Tumor Nucleic Acids Have Clinical Utility?," J Mol Diagn. 17(3):209-224 (2015).
Partial Supplemental Search Report for EP 18882781.0, mailed Oct. 8, 2021.
Vella et al., "A Rigorous Method to Enrich for Exosomes From Brain Tissue," Journal of Extracellular Vesicles 6(1):1348885 (2017).
Wang et al., "Proteomic Analysis of Urine Exosomes by Multidimensional Protein Identification Technology (MudPIT)," Proteomics 12:329-338 (2012).
Bijnsdorp et al., "Exosomal ITGA3 Interferes With Non-cancerous Prostate Cell Functions and is Increased in Urine Exosomes of Metastatic Prostate Cancer Patients," Journal of Extracellular Vesicles 2(22097):1-10 (2013).
Beckham et al., "Bladder Cancer Exosomes Contain EDIL-3/Del1 and Facilitate Cancer Progression," The Journal of Urology 192:583-592 (2014).
Alegre et al., "Circulating Melanoma Exosomes as Diagnostic and Prognosis Biomarkers," Clinica Chinnica Acta 454:28-32 2016).
Dai et al., "Phase I Clinical Trial of Autologous Ascites-derived Exosomes Combined With GM-CSF for Colorectal Cancer," Molecular Therapy 16(4):782-790 (2008).
Yuan and Song, "Exosome and its Roles in Regulation of Tumor Cell," China Biotechnology 33(8):106-113 (2013) with English Abstract.
Wang and Xie, "Research Progress on the Biological Characteristics and Clinical Applications of Tumor Exosomes," Chinese Journal of Cancer Prevention and Treatment 24(9):653-658 (2017) with English Abstract.
Yang et al., "Size Dependent Lipidomic Analysis of Urinary Exosomes from Patients with Prostate Cancer by Flow Field-Flow Fractionation and Nanoflow Liquid Chromatography-Tandem Mass Spectrometry," Analytical Chem 89(4):2488-2496 (2017).
Théry et al., "Exosomes: Composition, Biogenesis and Function," Nat Rev Immunol 2(8):569-579 (2002).
Kalluri, "The Biology and Function of Exosomes in Cancer," J Clin Invest 126(4):1208-1215 (2016).
Syn et al., "Exosomes in Cancer Nanomedicine and Immunotherapy: Prospects and Challenges," Trends Biotechnol 35(7):665-676 (2017).
Supplemental Search Report for corresponding Chinese Application CN201880088472.3 and English Translation, mailed Mar. 22, 2024.

\* cited by examiner

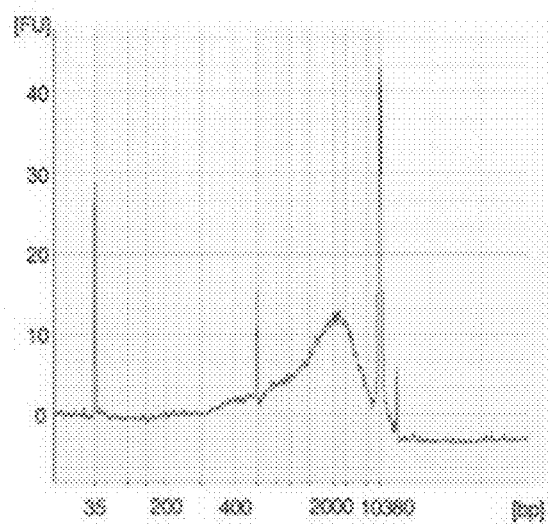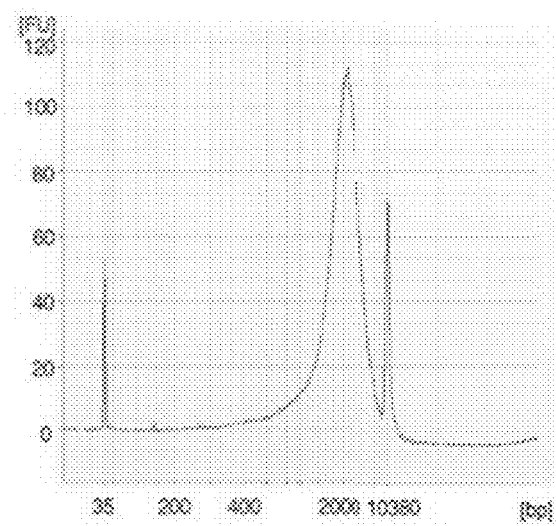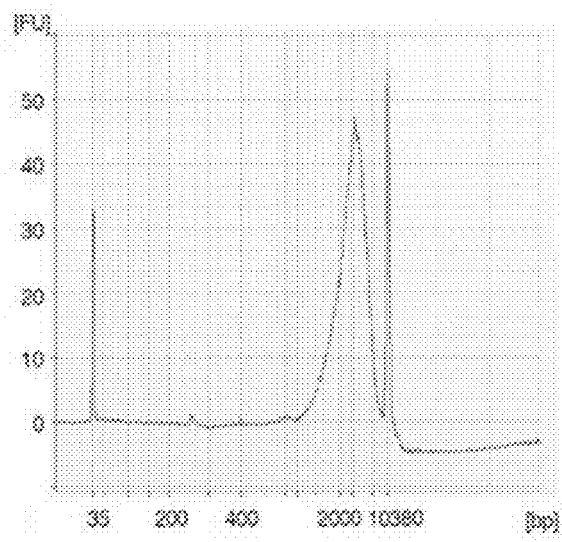
FIG. 12

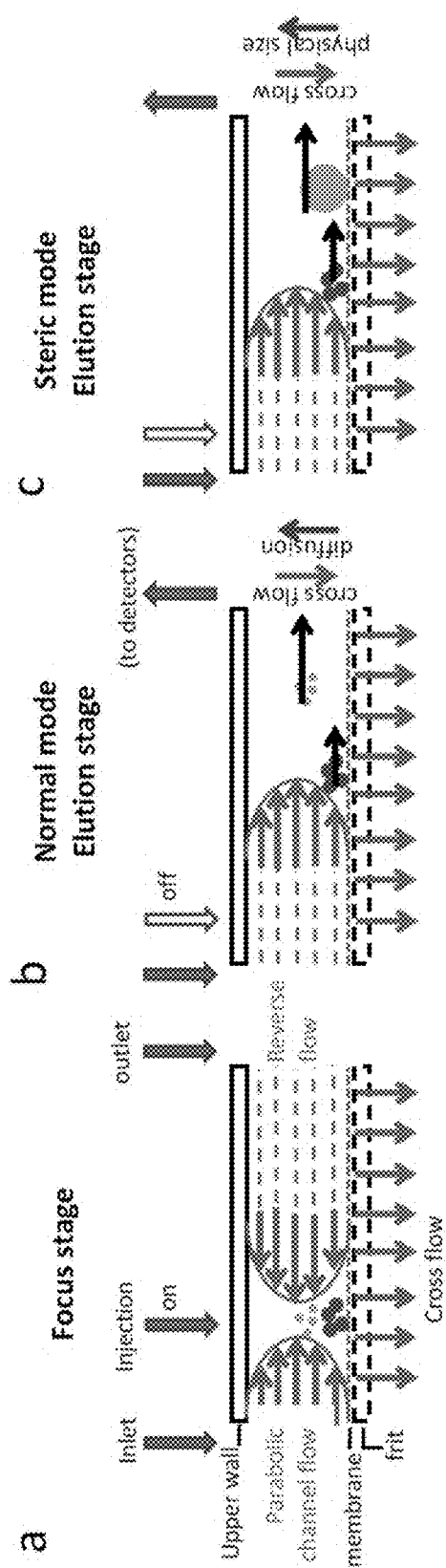
FIG. 15 A-C a Top Canonical Pathways – Exomere vs P85

Name
- EIF2 Signaling
- mTOR Signaling
- Regulation of eIF4 and p70S6K Signaling
- Molecular Mechanisms of Cancer
- Glucocorticoid Receptor Signaling b Top Canonical Pathways – Exo-S vs P85

Name
- EIF2 Signaling
- Regulation of eIF4 and p70S6K Signaling
- mTOR Signaling
- Mitochondrial Dysfunction
- Oxidative Phosphorylation c Top Canonical Pathways – Exo-L vs P85

Name
- EIF2 Signaling
- Regulation of eIF4 and p70S6K Signaling
- mTOR Signaling
- NGF Signaling
- Insulin Receptor Signaling d Top Canonical Pathways – Exomere vs Exo-S

Name
- Acute Phase Response Signaling
- FXR/RXR Activation
- Toll-like Receptor Signaling
- LPS/IL-1 Mediated Inhibition of RXR Function
- Aryl Hydrocarbon Receptor Signaling e Top Canonical Pathways – Exomere vs Exo-L

Name
- Superpathway of Cholesterol Biosynthesis
- Cholesterol Biosynthesis I
- Cholesterol Biosynthesis II (via 24,25-dihydrolanosterol)
- Cholesterol Biosynthesis III (via Desmosterol)
- IGF-1 Signaling

FIGs. 25A-25E

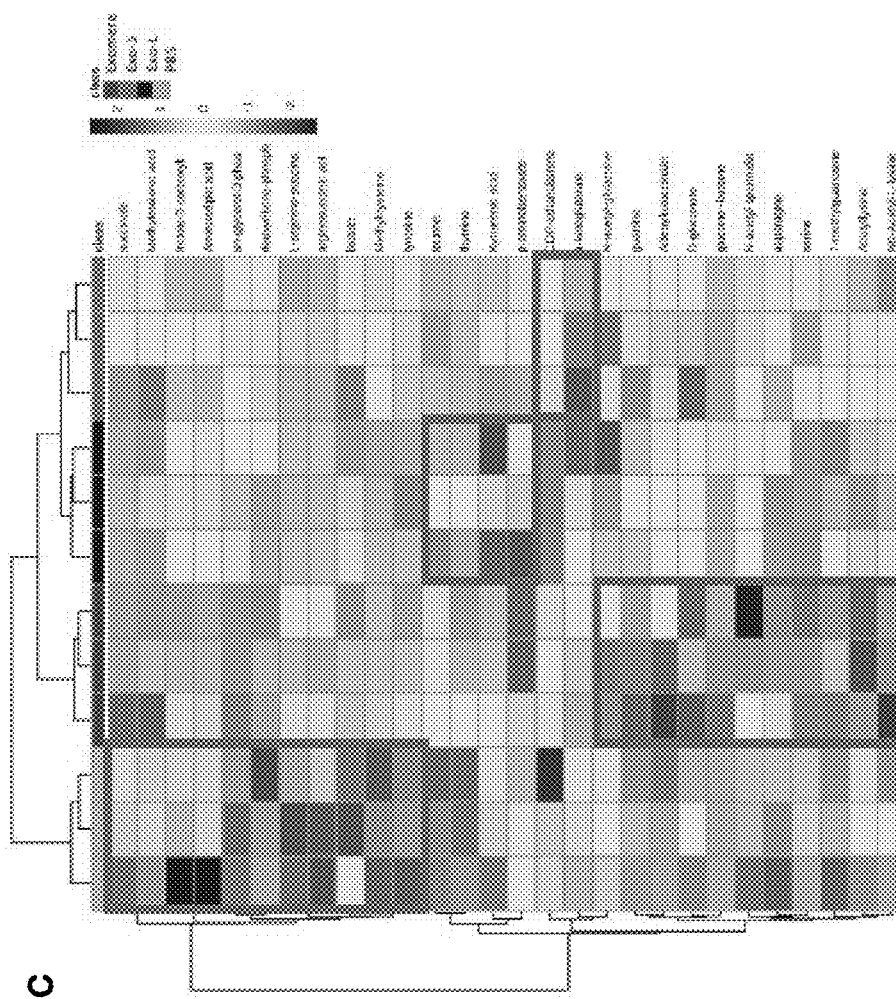
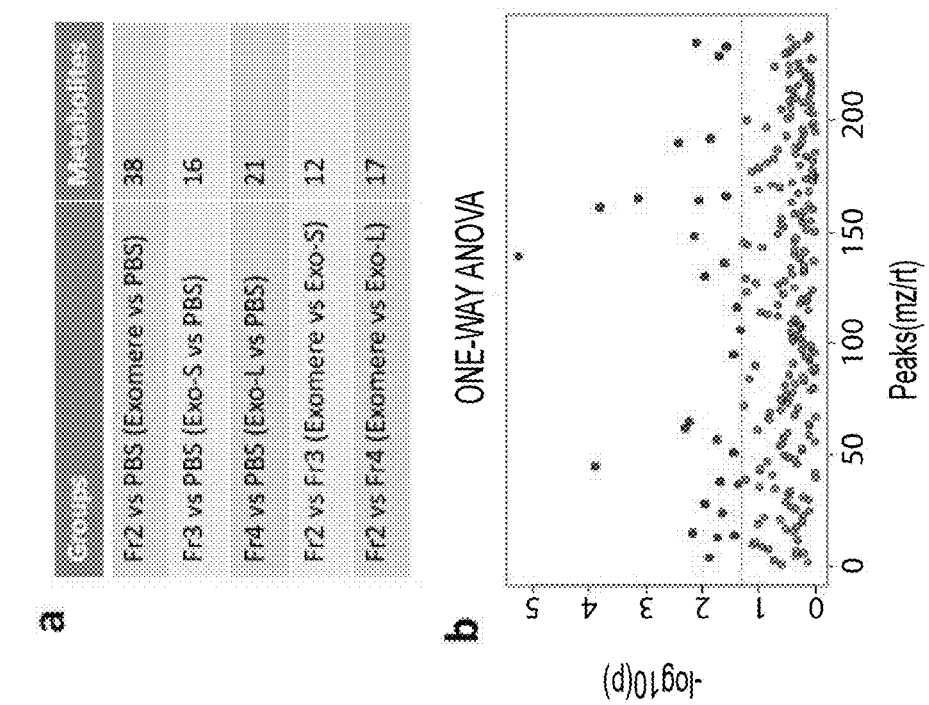
FIGs. 26A-26C

NANOPARTICLES AND DISTINCT EXOSOME SUBSETS FOR DETECTION AND TREATMENT OF CANCER This application is a continuation of U.S. patent application Ser. No. 16/873,700, filed Jun. 1, 2022, which is a national stage application under 35 U.S.C. § 371 of International Application No. PCT/US2018/063612, filed Dec. 3, 2018, which claims the priority benefit of U.S. Provisional Patent Application Ser. Nos. 62/623,992 and 62/593,504, filed Jan. 30, 2018 and Dec. 1, 2017, respectively, which are each hereby incorporated by reference in its entirety.

This invention was made with government support under grant nos. CA218513, CA169416, and CA169538 awarded by National Institutes of Health and grant nos. W81XWH-13-1-0249 and W81XWH-13-1-0427 awarded by Department of Defense. The government has certain rights in the invention.

FIELD OF THE INVENTION

The present invention relates to nanoparticles and distinct exosome subsets for detection and treatment of cancer.

BACKGROUND OF THE INVENTION

Cells secrete a wide variety of soluble factors and extracellular vesicles (EVs) to mediate intercellular communication (locally and systemically) under both physiological and pathological conditions, including cancers (Théry et al., "Exosomes: Composition, Biogenesis and Function," *Nat Rev Immunol* 2:569-579 (2002); Andaloussi et al., "Extracellular Vesicles: Biology and Emerging Therapeutic Opportunities," *Nat Rev Drug Discov* 12:347-357 (2013); Raposo & Stoorvogel, "Extracellular Vesicles: Exosomes, Microvesicles, and Friends," *J Cell Biol* 200:373-383 (2013)). EVs are heterogeneous and comprise various subclasses, including exosomes, which are small (50 nm to 150 nm) extracellular membrane vesicles of endosomal origin, and microvesicles, which are large (150 nm to 500 nm or even larger to >10 μm) vesicles shed directly by budding from the cellular plasma membrane. Cancer cells shed atypically large vesicles, known as large oncosomes (0.5 μm to 10 μm) which result from alterations in specific signaling pathways (e.g. Ras Homolog Family Member A/Rho-associated protein kinase (RhoA/Rock) signaling) (Di Vizio et al., "Oncosome Formation in Prostate Cancer: Association with a Region of Frequent Chromosomal Deletion in Metastatic Disease," *Cancer Res* 69:5601-5609 (2009); Morello et al., "Large Oncosomes Mediate Intercellular Transfer of Functional MicroRNA," *Cell Cycle* 12:3526-3536 (2013); Minciacchi et al., "MYC Mediates Large Oncosome-Induced Fibroblast Reprogramming in Prostate Cancer," *Cancer Res* 77:2306-2317 (2017)). Extensive research has shown that functional molecules, including proteins, genetic material, metabolites and lipids, are selectively recruited and packaged into EVs and horizontally transferred to recipient cells, thereby acting as vehicles of intercellular communication (Balaj et al., "Tumour Microvesicles Contain Retrotransposon Elements and Amplified Oncogene Sequences," *Nat Commun* 2:180 (2011); Choi et al., "Proteomics, Transcriptomics and Lipidomics of Exosomes and Ectosomes," *Proteomics* 13:1554-1571 (2013); Thakur et al, "Double-Stranded DNA in Exosomes: A Novel Biomarker in Cancer Detection," *Cell Res* 24:766-769 (2014); Tetta et al., "Extracellular Vesicles as an Emerging Mechanism of Cell-to-Cell Communication," *Endocrine* 44:11-19 (2013)). In addition, through the work described herein, a novel population of non-membranous nanoparticles termed 'exomeres' (~35 nm) have been identified, which are indeed the predominant extracellular nanoparticles (ENPs) secreted by most types of cells.

Exosomes are nanosized extracellular membrane vesicles of endosomal origin secreted by most cell types, including cancer cells (Thery et al., "Exosomes: Composition, Biogenesis and Function," *Nature Reviews. Immunology* 2:569-579 (2002); El Andaloussi et al, "Extracellular Vesicles: Biology and Emerging Therapeutic Opportunities," *Nature Reviews. Drug Discovery* 12:347-357 (2013); Raposo et al., "Extracellular Vesicles: Exosomes, Microvesicles, and Friends," *The Journal of Cell Biology* 200:373-383 (2013)). Proteins, genetic material (e.g., mRNAs, miRNAs, lnRNAs, DNA), metabolites and lipids, are selectively recruited and packaged into exosomes, which horizontally transfer their cargo to recipient cells, thereby acting as vehicles of intercellular communication in both physiological and pathological conditions (Balaj et al., "Tumour Microvesicles Contain Retrotransposon Elements and Amplified Oncogene Sequences," *Nature Communications* 2:180 (2011); Choi et al., "Proteomics, Transcriptomics and Lipidomics of Exosomes and Ectosomes," *Proteomics* 13:1554-1571 (2013); Thakur et al., "Double-Stranded DNA in Exosomes: a Novel Biomarker in Cancer Detection," *Cell Research* 24:766-769 (2014); Tetta et al., "Extracellular Vesicles as an Emerging Mechanism of Cell-to-Cell Communication," *Endocrine* 44:11-19 (2013)). Harnessing this knowledge, translational researchers have focused on developing exosome-based diagnostic/prognostic biomarkers and therapeutic strategies.

The present invention is directed to overcoming these and other deficiencies in the art.

SUMMARY OF THE INVENTION

A first aspect of the present invention is directed to a method of diagnosing cancer in a subject. This method involves selecting a subject having cancer and obtaining, from the selected subject, a population of either exomeres having a diameter of less than 50 nm, small exosomes having a diameter of 60-80 nm, or large exosomes having a diameter 90-120 nm. The exomeres, small exosomes, or large exosomes are recovered from the sample, and the exomeres, small exosomes, or large exosomes or portions thereof are contacted with one or more reagents suitable to detect: (1) higher or lower levels, relative to a standard for subjects not having cancer, or the presence or absence, of one or more proteins contained in said exomeres, small exosomes, or large exosomes, (2) higher or lower levels, relative to a standard for subjects not having cancer, or the presence or absence, of one or more N-glycans contained in said exomeres, small exosomes, or large exosomes, (3) higher or lower levels, relative to a standard for subjects not having cancer, or the presence or absence, of one or more lipids contained in said exomeres, small exosomes, or large exosomes, (4) the presence or absence of one or more genetic mutations in nucleic acid molecules associated with cancer and contained in said exomeres, small exosomes, or large exosomes, or (5) combinations thereof. Cancer is then diagnosed based on the contacting step.

Another aspect of the present invention is directed to a method of prognosing cancer in a subject. This method involves selecting a subject having cancer and obtaining, from the selected subject, a population of either exomeres having a diameter of less than 50 nm, small exosomes having a diameter of 60-80 nm, or large exosomes having a diameter of 90-120 nm. The exomeres, small exosomes, or large exosomes are recovered from the sample, and the exomeres, small exosomes, or large exosomes or portions thereof are contacted with one or more reagents suitable to detect: (1) higher or lower levels, relative to a standard or to the level in a prior sample obtained from the subject, or the presence or absence, of one or more proteins contained in said exomeres, small exosomes, or large exosomes, (2) higher or lower levels, relative to a standard or to the level in a prior sample obtained from the subject, or the presence or absence, of one or more N-glycans contained in said exomeres, small exosomes, or large exosomes, (3) higher or lower levels, relative to a standard or to the level in a prior sample obtained from the subject, or the presence or absence, of one or more lipids contained in said exomeres, small exosomes, or large exosomes, (4) the presence or absence of one or more genetic mutations in nucleic acid molecules associated with cancer and contained in said exomeres, small exosomes, or large exosomes, or (5) combinations thereof. Cancer is then prognosed based on the contacting step.

Another aspect of the present invention is directed to a method of managing treatment in a subject. This method involves selecting a subject undergoing treatment for cancer and obtaining, from the selected subject, a population of either exomeres having a diameter of less than 50 nm, small exosomes having a diameter of 60-80 nm, or large exosomes having a diameter of 90-120 nm. The exomeres, small exosomes, or large exosomes are recovered from the sample, and the exomeres, small exosomes, or large exosomes or portions thereof are contacted with one or more reagents suitable to detect: (1) higher or lower levels, relative to a standard or to the level in a prior sample obtained from the subject, or the presence or absence, of one or more proteins contained in said exomeres, small exosomes, or large exosomes, (2) higher or lower levels, relative to a standard or to the level in a prior sample obtained from the subject, or the presence or absence, of one or more N-glycans contained in said exomeres, small exosomes, or large exosomes, (3) higher or lower levels, relative to a standard or to the level in a prior sample obtained from the subject, or the presence or absence, of one or more lipids contained in said exomeres, small exosomes, or large exosomes, (4) the presence or absence of one or more genetic mutations in nucleic acid molecules associated with cancer and contained in said exomeres, small exosomes, or large exosomes, or (5) combinations thereof. Treatment is then modified based on the contacting step.

Another aspect of the present invention relates to a kit suitable for diagnosing cancer. The kit includes one or more reagents suitable to detect: (1) higher or lower levels, relative to a standard or to a sample from a subject, or the presence or absence, of one or more proteins contained in exomeres, small exosomes, or large exosomes, (2) higher or lower levels, relative to a standard or to a sample from a subject, or the presence or absence, of one or more N-glycans contained in exomeres, small exosomes, or large exosomes, (3) higher or lower levels, relative to a standard or to a sample from a subject, or the presence or absence, of one or more lipids contained in exomeres, small exosomes, or large exosomes, (4) the presence or absence of one or more genetic mutations in nucleic acid molecules associated with cancer and contained in exomeres, small exosomes, or large exosomes, or (5) combinations thereof, wherein said exomeres have a diameter of less than 50 nm, said small exosomes have a diameter of 60 to 80 nm and said large exosomes have a diameter of 90 to 120 nm.

Through studies described herein, the influence of several key parameters of AF4 that were shown to be critical for high-resolution separation of distinct exosome subsets were evaluated. These influencing factors included cross-flow, channel height, sample focusing, type of membrane, and the amount of loaded sample. It should be noted that these factors collectively determine fractionation quality, and changing one parameter usually affects the influence of other factors on resolution power. Testing different combinations of these factors, however, can be expensive, time-consuming, and labor-intensive, and thus can be impractical. Understanding the working principles of AF4 and determining the complexity of the analyzed samples will be useful to guide the method development process.

The present invention describes identification of a novel type of nanoparticle secreted by most cell types, including cancer cells, which are termed exomeres. Exomeres are a prominent and heterogeneous population of small (<50 nm hydrodynamic diameter, with a peak about 35 nm), weakly negatively charged (−2.7 mV to −9.7 mV), and highly stiff (~145-816 MPa) nanoparticles secreted by cells. Structural analysis revealed the kick of external lipid-bilayer membrane structure of exomeres, and molecular characterization showed its composition of a variety of biologically functional molecules, including proteins, lipids, nucleic acids (DNA and RNAs), metabolites, and glycans. Besides exomeres, two distinct subsets of exosomes, namely the small exosomes (Exo-S, 60-80 nm) and large exosomes (Exo-L, 90-120 nm) were separated, by employing the technique of asymmetric flow field-flow fractionation (AF4). In contrast to exomeres, both Exo-S and Exo-L have external lipid-bilayer membrane structures, carry more negative charges, and are softer than exomeres.

The studies described herein reveal that each nanoparticle type, i.e. exomeres, Exo-S and Exo-L, contain unique molecular signatures in comparison to each other. These nanoparticles are secreted into both the surrounding environment of cells and the peripheral circulation system and other types of body fluids. Therefore, these nanoparticles represent a reservoir of biomarkers for cancer diagnosis, prognosis and monitoring disease progression and recurrence post treatment.

Furthermore, both exomeres and exosome subsets can horizontally transfer their cargo to recipient cells, thereby acting as vehicles of intercellular communication in both physiological and pathological conditions, thus representing targets of therapeutics development. Specifically, exomere proteomic profiling revealed an enrichment in metabolic enzymes and hypoxia, microtubule and coagulation proteins and specific pathways, such as glycolysis and mTOR signaling. Exo-S and Exo-L contained proteins involved in endosomal function and secretion pathways, and mitotic spindle and IL-2/STAT5 signaling pathways, respectively. Biodistribution examination revealed that exomeres target organs such as liver, spleen, and bone marrow primarily, implicating their potential function in systemic regulation during tumor progression. In distinction to the observation of exomeres, Exo-S demonstrated higher uptake by the lung and Exo-L by lymph nodes, suggesting their potential roles in mediating organ-specific metastasis and immune response during disease progression, respectively.

Taken together, the newly identified exomeres, Exo-S and Exo-L present unique potential of serving as biomarkers and therapeutic targets for cancer patients.

BRIEF DESCRIPTION OF THE DRAWINGS

FIG. 1A shows a representative AF4 fractionation profile of B16-F10-derived exosomes. x-axis, time (min); y-axis (scale) and black dots, hydrodynamic radius (nm); red and blue lines illustrate the QELS (DLS) intensity and UV absorbance (shown on a relative wale), respectively. P1-P5 marks the peaks detected based on UV absorbance. Fractions were pooled for exomeres (hydrodynamic diameter<50 nm,); Exo-S (60-80 nm); and Exo-L (90-120 nm). FIG. 1B shows a representative correlation function at peak 3 (P3), t=25.1 min. For 1A and 1B the experiment was repeated independently 50 times with similar results. FIG. 1C shows TEM imaging analysis of exosome input mixture (pre-fractionation) and fractionated exomeres, Exo-S and Exo-L subpopulations. Arrows point to exomeres (red), Exo-S (blue) and Exo-L (green). Scale bar, 200 nm. This experiment was repeated 7 times independently with similar results. FIG. 1D shows Western blotting analysis of exosomal marker proteins in fractionated samples. 100 μg of whole cell extract (WCE) and 10 μg of exosome and exomere mixture input and each subset were analyzed. This experiment was done once. FIG. 1E shows measurement of hydrodynamic diameters of exomeres, Exo-S and Exo-L derived from representative cell lines (i.e. B16-F10 (F10), AsPC-1, Pan02, MDA-MB-4175 (4175) and 4T1) in the batch mode using Zetasizer after pooling fractions collected for each subset of nanoparticles from an individual AF4 fractionation. Data are presented as mean±SEM (standard error of the mean), in the order of exomere, Exo-S and Exo-L: B16-F10 (n=10, 9, and 8 independent measurements, respectively); Pan02 (n=11, 6, 11); AsPC-1 (n=5, 5, 5); 4175 (n=3, 5, 3); 4T1 (n=5, 5, 5)). FIG. 1F shows TEM imaging analysis of fractions collected from explant culture of fresh human melanoma tissue. Scale bar, 200 nm. This experiment was performed with two independent specimens with similar results. FIG. 1G shows a batch mode measurement of hydrodynamic diameters of fractions shown in FIG. 1F. Data are presented as mean±SEM (exomeres and Exo-L, n=6; Exo-S, n=7 independent measurements). Unprocessed blots are provided in FIG. 14.

FIG. 2A shows TEM analysis of particles in AF4 peaks P1 and P5 of B16-F10. The experiment was repeated independently 3 times with similar result. Scale bar, 500 nm. FIG. 2B shows a comparison of the hydrodynamic diameter of each fraction determined by AF4-QELS versus NTA. Individual fractions (time slice, 0.5 min/fraction) were taken every 2 minutes from 20 to 44 minutes during the AF4 time course, and subjected to NTA. Results shown are mean±SEM (n=3 independent samples). Mode size from NTA was utilized. X-axis, time course of AF4 (min); Y-axis, hydrodynamic diameter (nm). FIG. 2C shows the size distribution profiles of representative fractions by NIA (input, unfractionated samples; fractions at 20, 32, and 44 minutes). Multiple peaks were detected for fractions at 20 and 44 minutes by NTA. A mode size of 126 nm of input indicates that NTA cannot efficiently resolve polydisperse samples and is biased towards large particles. This experiment was repeated 3 times independently with similar results. FIG. 2D shows the particle concentration of each fraction measured by NTA. The hydrodynamic diameter of the peak fraction (28 minutes) was 77 nm. Results shown are mean±SEM (n=3 independent samples). FIGS. 2E-2I show AF4 profiles of B16-F10 sEVs collected from technical (blue tines, replicate #1; red lines, replicate #2) (FIG. 2E) and biological replicates (red lines, QELS; blue lines, UV; black (replicate #1) and green dots (replicate #2), hydrodynamic radius; Differences in UV and QELS signal intensity is due to the different amount of input samples for two replicates) (FIG. 2F), kept at either 4° C. or −80° C. for one week (red lines, QELS; blue lines, UV; black (fresh) and green dots (frozen), hydrodynamic radius) (FIG. 2G), cells of different passage numbers (blue and red lines, UV of cells at passage 10 and 18, respectively; black dots, hydrodynamic radius) (FIG. 2H), and under hypoxic versus normoxic conditions for 48 h (blue and red lines, UV for samples cultured with 20% and 1% $O_2$, respectively; black dots, hydrodynamic radius) (FIG. 2I). Experiments were repeated independently 3 times for FIGS. 2E-2G and twice for FIG. 2H with similar results. For FIG. 2I, the experiment was repeated with 3 different cell lines independently with similar results. FIGS. 2J and 2$k$ show AF4 (FIG. 2J) and TEM (FIG. 2K) analysis of nanoparticles isolated in parallel from the blank media control and CM of 3-day cultures of B16-F10 and MDA-MB-231-4175. This experiment was done once. (Red and Blue lines, UV; black dots, hydrodynamic radius; Scale bar, 200 nm.)

FIG. 4A is an AF4 profile of exosomes isolated from explant culture of fresh human melanoma tissues. Red and blue lines illustrate the QELS (DLS) intensity and UV absorbance, respectively. This experiment was repeated with 4 independent specimens with similar results. FIG. 4B shows TEM images of exosome samples isolated from the explain culture of normal mouse mammary fat pad and lung tissues. This experiment was repeated independently 2 times with similar results. Scale bar, 500 nm.

FIG. 5C shows a representative AFM image of exomeres derived from B16F10. This experiment was repeated with samples derived from 3 different cell lines with similar results. FIG. 5D shows AFM imaging analysis of the height (z-dimension) of exomeres derived from B16F10 (n=754 particles analyzed), AsPC1 (n=475) and MDA-MB-4175 (n=160). Mean±SEM is depicted.

FIG. 6A shows a Venn diagram of proteins identified in each subset of particles. FIG. 6B shows principal component analysis and FIG. 6C shows consensus clustering analysis of normalized proteomic mass spectrometry datasets from human (MDA-MB-4175 and AsPC1) and mouse (B16F10, 4T1, and Pan02) cell lines. FIG. 6D shows a heat map illustration of unique proteins specifically associated with exomeres, Exo-S and Exo-L. Scale shown is intensity (area) subtracted by mean and divided by row standard deviation (i.e. Δ (area-mean)/SD). FIG. 6E shows Western blot analysis of representative signature proteins in fractionated samples. An equal amount (10 μg) of exosome and exomere input mixture and each subset were analyzed. This experiment was done once. FIG. 6F shows a heat map illustration of the relative abundance of conventional exosome markers in exomeres, Exo-S and Exo-L. Scale shown is intensity (area) subtracted by mean and divided by row standard deviation (i.e. Δ (area-mean)/SD). FIG. 6G shows identification of top candidate gene sets enriched in exomere, Exo-S and Exo-L populations by gene set enrichment analysis (GSEA). Proteins in each subset of nanoparticles are ranked by GSEA based on their differential expression level. Whether a pre-specified pathway is significantly overrepresented toward the top or bottom of the ranked gene list in each subset of nanoparticle is evaluated using the normalized enrichment score (the green line). Black vertical lines mark the positions where the members of a particular pathway appear in the ranked list of genes. Proteins that contributed most to the enrichment score are listed below the plot. For all proteomic analysis (FIGS. 6B-6D, FIGS. 6F-6G), a total of 30 samples (3 nanoparticle subtypes derived from 5 different cell lines; and two independent biological replicates for each nanoparticle sample) were subjected to statistical analysis. Unprocessed blots are provided in FIG. 14.

FIG. 7A shows principal component analysis of normalized proteomic mass spectrometry data of exomeres, Exo-S and Exo-L derived from multiple cell lines, including MDA-MB-231-4175, AsPC-1, 4T1, B16F-10 and Pan02. Two independent biological replicates were analyzed for each nanoparticle sample. FIG. 7B is a heat map illustration of the relative abundance of the Rab family proteins in exomeres, Exo-S and Exo-L. Scale shown is intensity (area) subtracted by mean and divided by row standard deviation (i.e., Δ (area-mean)/SD). FIG. 7C shows evaluation of the presence of lipoprotein-particle associated proteins (listed in Table 2) among the total proteins detected in the exomere, Exo-S and Exo-L derived from different cell lines. Results shown are mean of 2 biologically independent experiments. FIG. 7D shows TEM imaging analysis of HDL, LDL and VLDL. Scale bar, 200 nm. This experiment was done once with multiple images showing similar results. FIG. 7E shows identification of specific association of signaling pathways including hypoxia (FDR, q value=0.004), microtubule (FDR, q value=0.002) and coagulation (FDR, q value=0.013) with exomeres by GSEA (left panel) and the heat map illustration of the expression level of related proteins in different subsets of nanoparticles (right panel). A total of n=30 samples (3 nanoparticle subtypes derived from 5 different cell lines; and two independent biological replicates for each nanoparticle samples) were subjected for Kolmogorov-Smirnov statistical analysis.

FIG. 8A shows lectin blotting analysis of N-glycan profile of proteins associated with exomeres versus exosome subpopulations Exo-S and Exo-L. *Phaseolus vulgaris* erythroagglutinin (E-PHA) and *Phaseolus vulgaris* leucoagglutinin (L-PHA) recognize bisected and branched N-glycans, respectively. *Aleuria aurantia* lectin (AAL) recognizes Fucα6GlcNAc and Fucα3GlcNAc. *Sambucus nigra* lectin (SNA) recognizes α-2,6-linked slake acid. All experiments were repeated independently twice with similar results except for AAL and E-PHA blotting for B16-F10 and 4175 which were done once. FIG. 8B shows mass spectrometric analysis of N-glycans of glycoproteins present in exomeres, Exo-S and Exo-L subsets of B16F10. One representative experiment of two biologically independent replicates is shown. FIG. 8C shows a comparison of the relative abundance of the top six most abundant N glycan structures among exomere, Exo-S and Exo-L of B16F10. The assignments (m/z) [charge; neutral exchange] for MALDI-MS and nanoLC-ESI-MS/MS are the following: (2015.8 [—H; 0]; $1007.4^a$ [-2H; 0]), (2209.8 [—H; 0]; $1104.4^a$ [-2H: 0]), $(2237.7^b$ [—H; Na—H]; $732.57^a$ [-3H; 0]), $(2365.5^b$ [—H; 4K -4H]); $783.9^a$ [-3H; 0] and $1182.4^{a,b}$ [-2H; 4K -4H]), and $(2404.8^b$ [—H; 2K -2H]; $1201.9^b$ [-2H; 2K -2H]). Data shown were quantified and normalized to the most abundant structure in the sample. Results are represented as average of three independent analytical measurements of one representative experiment. Unprocessed blots are provided in FIG. 14. Note: $^a$The product ion spectra for this species did not allow a complete structural assignment. $^b$Assignments admit neutral exchanges of protons with cations in sialoglycans, including the presence of potassium and sodium.

FIG. 9A shows the total protein profile content of the isolated exomere, Exo-S and Exo-L subpopulations derived from AsPC-1, MDA-MB-231-4175 and B16-F10 assessed by silver staining. This experiment was repeated independently twice for B16-F10 and 4175 with similar results and done once for AsPC-1. FIG. 9B shows the N-glycan mass spectra of particles derived from AsPC-1 (left panel) and MDA-MB-231-4175 (right panel), respectively. This experiment was done once with 3 analytic replicates with similar results. FIG. 9C and FIG. 9D shows quantification of the top six most abundant N-glycan structures identified in the study of AsPC-1 and MDA-MB-231-4175 derived particles. Data shown were quantified and normalized to the most abundant structure in the sample. Results are represented as mean of 2 and 3 independent analytical measurements for AsPC-1 for MDA-MB-231-4175, respectively. NanoHPLC-PGC-HRMS extracted ion chromatograms (EIC) and CID-MS/MS spectra for FIGS. 9E-9G the ion at m/z 1007.38(2-), corresponding to a core-fucosylated complex type N-glycan, characteristic of exomere, and FIGS. 9H-9J the ion at m/z 1111.39 (2-), corresponding to a disialylated complex-type N-glycan found in all fractions of B16F10. Fragmentation analysis for extracted ion chromatogram m/z 1007.38 (2-) confirming the structure of this N-glycan in exomeres (FIG. 9E and FIG. 9G) and demonstrating the absence of this N-glycan in Exo-S (FIG. 9F). According to the relative retention time on the PGC column, exomeres contain both α2,3-linked and α2,6-linked sialoglycoforms of the ions at m/z 1111.39(2-) (FIG. 9H). The N-glycan m/z 1111.39(2-) from Exo-S showed N-glycans displaying exclusively α2,3-linked sialic acids based on PGC-LC relative retention time (FIG. 9I). This experiment (FIGS. 9E-9J) was done once.

FIG. 10A shows a comparison of total lipid content of each subset of nanoparticles derived from different cell lines. Total signal intensity of each sample after normalization to sample weight and internal standards was compared to that of exomeres from the same set of samples (expressed as fold change). Data are presented as mean±SEM (n=3 biologically independent samples). FIG. 10B shows the relative abundance of each lipid class present in each subset of nanoparticles from different cell lines. Data are presented as mean±SEM (n=3 biologically independent samples). FIG. 10C shows a heat map illustration of lipid classes specifically associated with exomeres, Exo-S and Exo-L (ANOVA test, q<0.05). Statistical analysis was performed on a total of 9 samples for each cell line (3 different nanoparticle subtypes and 3 independent biological repeats for each nanoparticle sample). Abbreviation: Cer, ceramide; CerG1-3, glucosylceramides; CL, cardiolipin; DG, diglyceride; LPC, lysophosphatidylcholine; LPE, lysophosphatidylethanolamine; LPG, lysophosphatidylglycerol; LPI, lysophosphatidylinositol; MG, monoglyceride; PC, phosphatidylcholine; PE, phosphatidylethanolamine; PG, phosphatidylglycerol; PI, phosphatidylinositol; PS, phosphatidylserine; SM, sphingomyelin: TG, triglyceride.

FIG. 11A shows the relative abundance of DNA associated with each subpopulation of particles from representative fractionations of B16F10, AsPC1 and MDA-MB-4175. FIG. 11B shows Agilent Bioanalyzer analysis of the size distribution of DNA associated with different subsets of particles. Data shown are the electropherograms (left) and electrophoresis images (right) from a representative of two independent experiments on AsPC1-derived particles. Black arrows, internal standards (35 bp and 10380 bp). Red line, exomeres; blue line, Exo-S; green line, Exo-L. FIG. 11C shows the relative abundance of total RNA associated with each subpopulation of particles from representative fractionations of B16F10 and AsPC1. FIG. 11D shows the size distribution of RNA isolated from different fractions of B16F10. Shown are representative profiles from one of two independent experiments. For FIG. 11A and FIG. 11C, data shown are mean (n=2 biologically independent samples).

FIG. 13A shows whole organ imaging of NIR dye-labeled exomeres, Exo-S and Exo-L from a representative experiment using the Odyssey imaging system (LI-COR Biosciences; n=4 independent experiments). The dynamic range of signal intensity was adjusted for each organ so that the differences among these nanoparticle subsets can be easily recognized. Scale bar, 2.5 mm. FIG. 13B shows quantification of the nanoparticle uptake in different organs in one representative experiment. This experiment was repeated independently 4 times with similar results. Signal intensity in each organ was acquired using the Image Studio (LI-COR Biosciences), and normalized to the brain from the same animal due to undetectable uptake of nanoparticles in this organ. Fold changes (y axis) were then calculated for each organ between the experimental group (i.e. input, exomere, Exo-S and Exo-L) versus the mock control. n=3 animals per group, results shown are mean±SEM. Statistical significance determined using one way ANOVA (* $p<0.05$; ** $p<0.01$, unmarked, not significant). For lymph nodes, the p value for comparison between input versus Exo-L, exomere versus Exo-L and Exo-S versus Exo-L are 0.022, 0.001 and 0.01 respectively.

FIGS. 15A-15C show a schematic illustration of the AF4 working principle. FIGS. 15A-15C show the side views of the AF4 channel, whose height is usually several hundreds of μm. The part size shown in the figure is for illustration only and not drawn to scale. FIG. 15A shows that in the Focus stage, two flows in opposing directions are pumped into the channel from the inlet and outlet ports and balanced near the injection port. Samples are injected during the Focus stage and focused in a thin band. Particles reach level heights related to their diffusion coefficients. FIG. 15B shows that in the Elution stage of the normal mode, particles with small hydrodynamic size and high diffusion coefficient are eluted at an early time point, whereas particles with large hydrodynamic size and low diffusion coefficient elute late. FIG. 15C shows that when the physical size of a particle is too large to be considered as a point mass compared to the channel height, it elutes in the Steric mode. In contrast to the Normal model as shown in FIG. 15B, large particles elute earlier than the smaller ones.

FIG. 16A shows a representative AF4 fractionation profile of B16-F10 sEVs collected by applying a linear cross-flow gradient with an initial flow rate at 0.5 mL/min within 45 minutes (Peaks are marked as P0-P5; UV (red line), QELS (blue line), $R_h$ (black dots)), or (FIG. 16B) with an initial flow rate at 0.3 mL/min (blue line), 0.5 mL/min (red line) or 1.0 mL/min (black line) and dropping to 0 mL/min over 45 minutes, or (FIG. 16C) with an initial flow rate at 0.5 mL/min and dropping to 0 mL/min over 15 minutes (blue), 30 minutes (black) or 45 minutes (red). Top, QELS at 100°; bottom, UV absorbance at 280 nm. The other AF4 parameters are: channel flow rate, 1.0 mL/min; channel height, 490 μm; sample focus time, 2 minutes; membrane, regenerated cellulose (RC), input amount, 40 μg.

Top, QELS at 100°; bottom, UV absorbance at 280 nm. The other AF4 parameters are: channel flow rate, 1.0 mL/min; a linear gradient of cross-flow decreasing from 0.5 mL/min to 0 mL/min over 45 minutes; channel height, 490 µm; sample focus time, 2 minutes; membrane, regenerated cellulose (RC).

Figure 20:
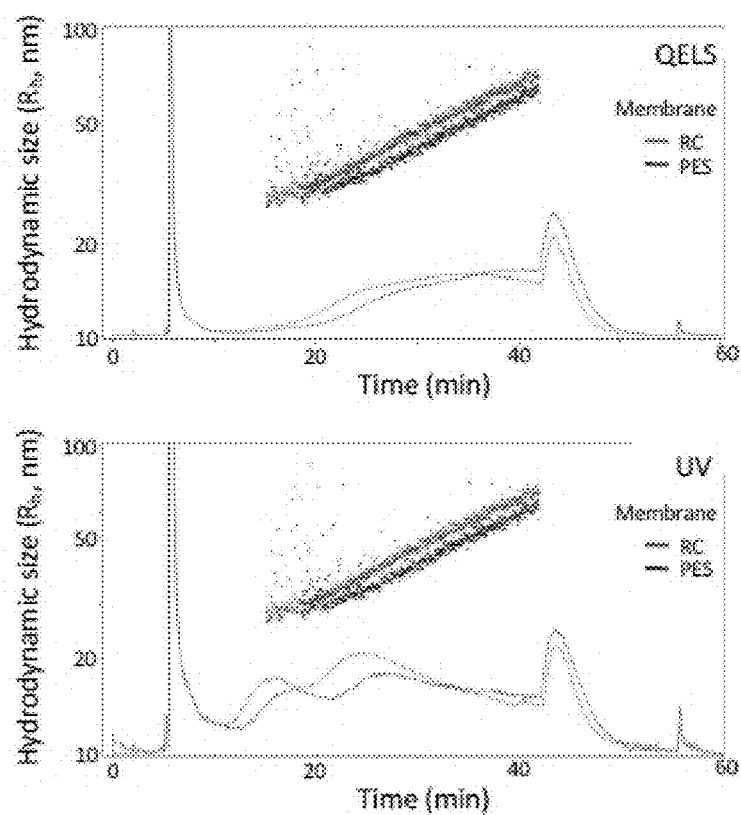

FIG. 20 shows a comparison of the AF4 performance for separating EVs using different membranes: regenerated cellulose (RC, red) versus poly(ether)sulfone (PES, blue). B16-F10 sEVs were analyzed using the following AF4 parameters: channel flow rate, 1.0 mL/min; a linear gradient of cross-flow decreasing from 0.5 mL/min to 0 mL/min over 45 minutes; channel height, 490 µm; sample focus time, 2 minutes; input amount, 40 µg. Top, QELS at 100°; bottom, UV absorbance at 280 nm.

Figures 21A, 21B:
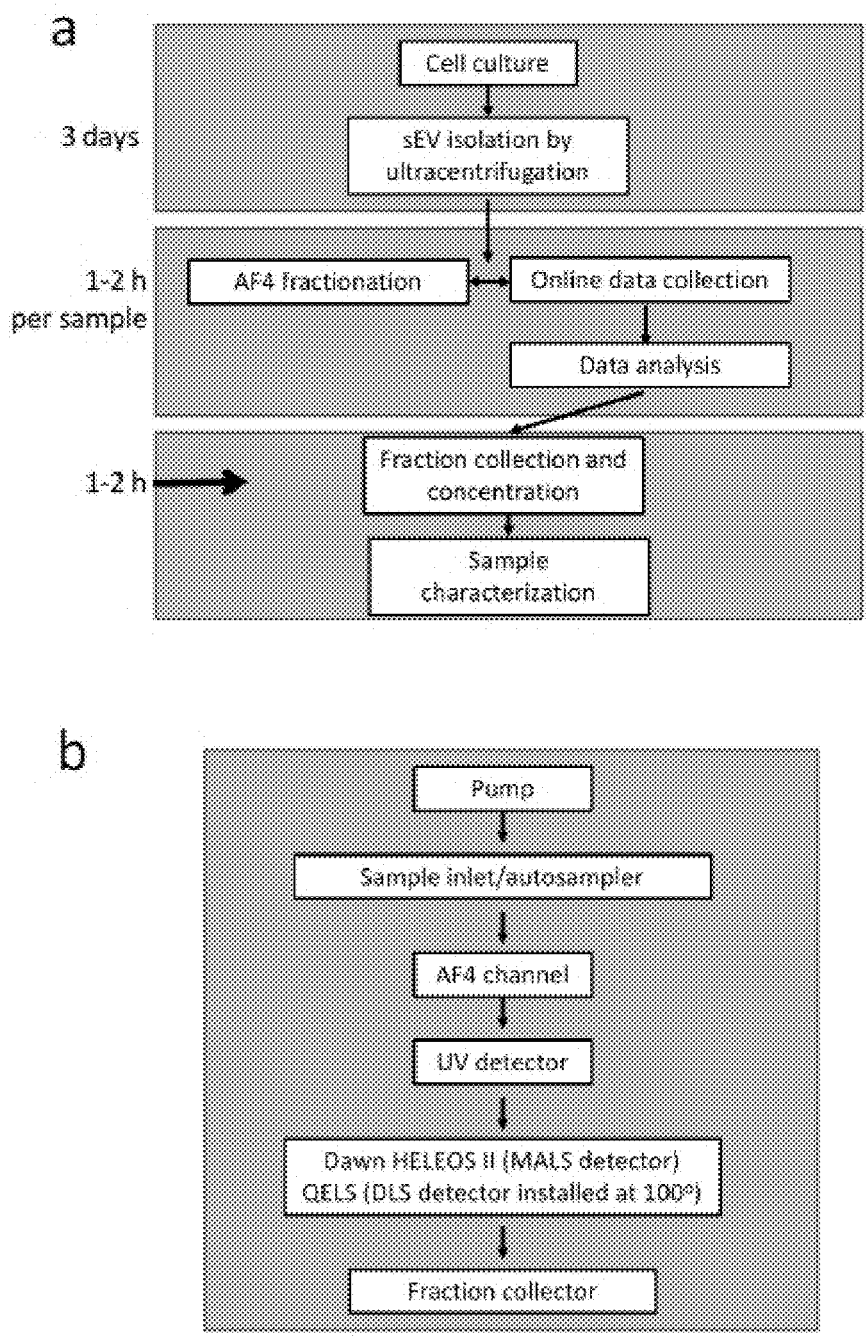

FIGS. 21A-21B show a schematic illustration of the overall procedure and the flow route of AF4. FIG. 21A shows the overview of experimental design for cell culture-derived sEV isolation and AF4 fractionation. FIG. 21B is an illustration of the AF4 flow route and arrangement of online detectors.

Figures 22A, 22B, 22C:
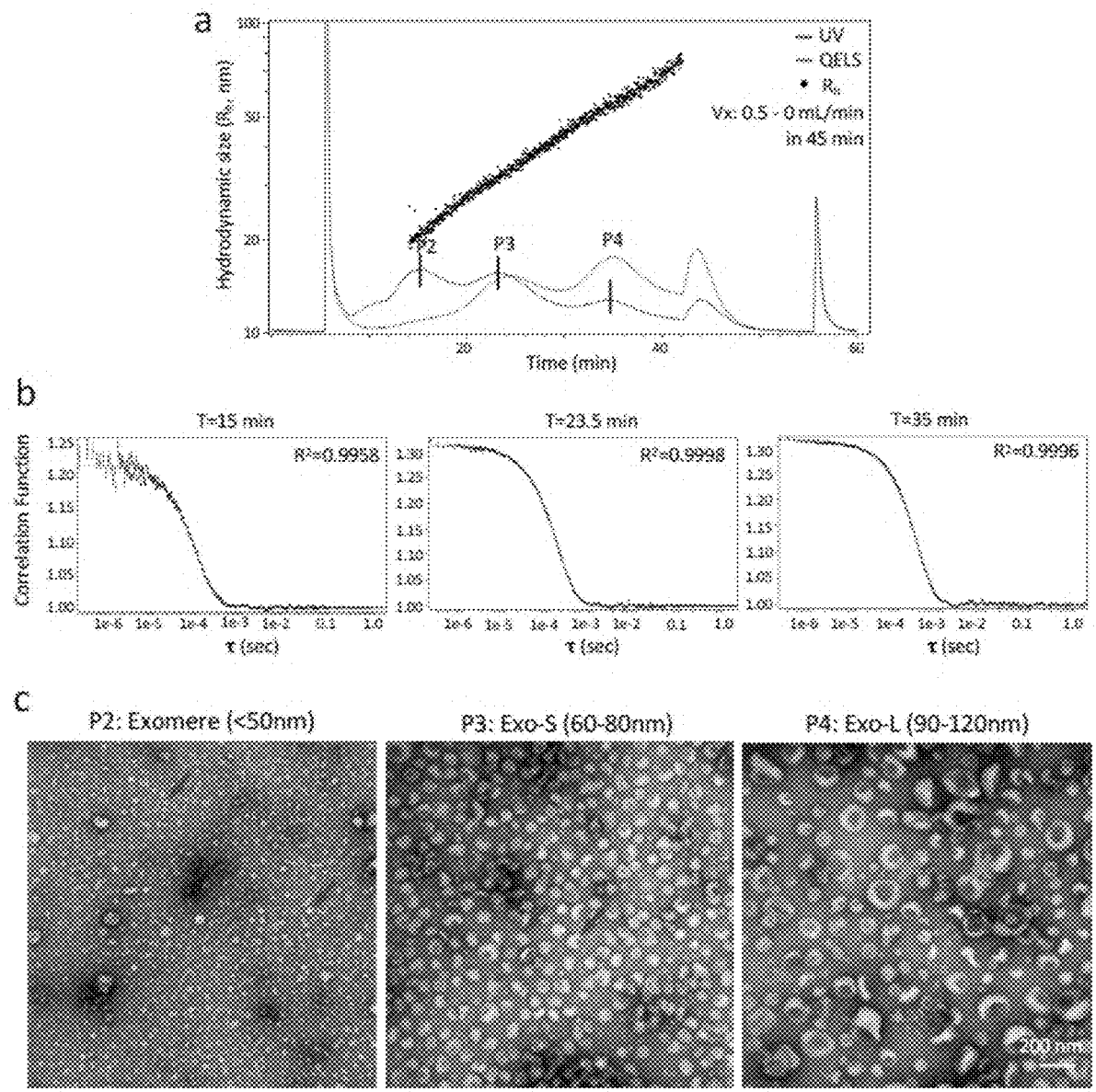

FIGS. 22A-22C shows representative AF4 fractionation analysis of B16-F10 sEVs. Shown are representative AF4 fractionation profile of B16-F10 sEVs (FIG. 22A) and autocorrelation functions at specific time points (FIG. 22B). FIG. 22C shows TEM imaging analysis of combined fractions for peaks P2 (exomere), P3 (Exo-S), and P4 (Exo-L). Scale bar, 200 nm. Colored arrows point to representative particles in each subpopulation.

Figures 23A, 23B:
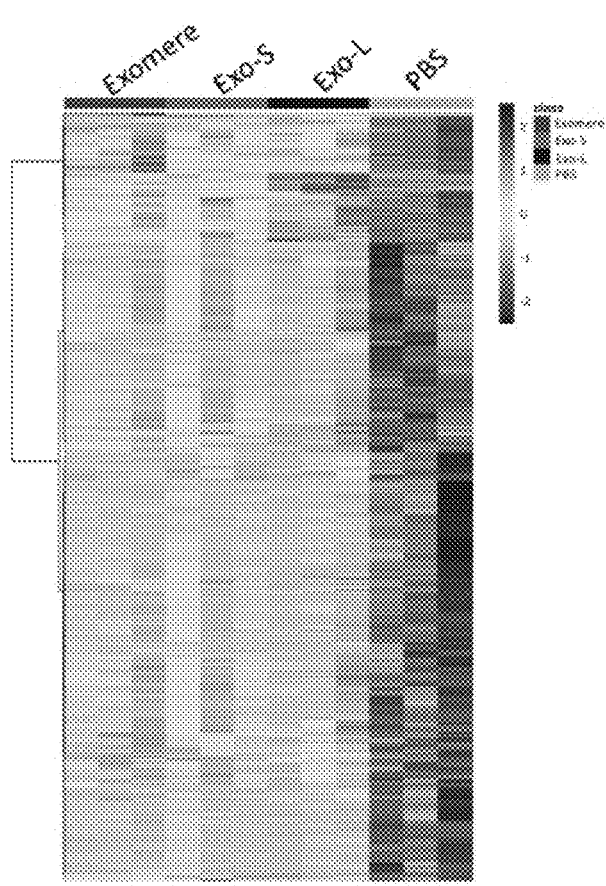

FIGS. 23A-23B show gene expression analysis of the livers from mice 24 hours post injection of B16-F10 derived exomeres, Exo-S and Exo-L, in comparison with PBS control. 10 µg of exomeres, Exo-S, and Exo-L, and equal volume of PBS were intravenously injected into C57B1/6 mice, respectively. The livers of the mice were collected for RNA extraction and sequencing analysis 24 hours post injection. The total numbers of genes that are differently expressed in each comparison group are listed in FIG. 23A, and Clustering analysis of top 2000 genes that are significantly changed in comparison with the PBS control are shown in FIG. 23B. n=3 per group.

Figures 24A, 24B:
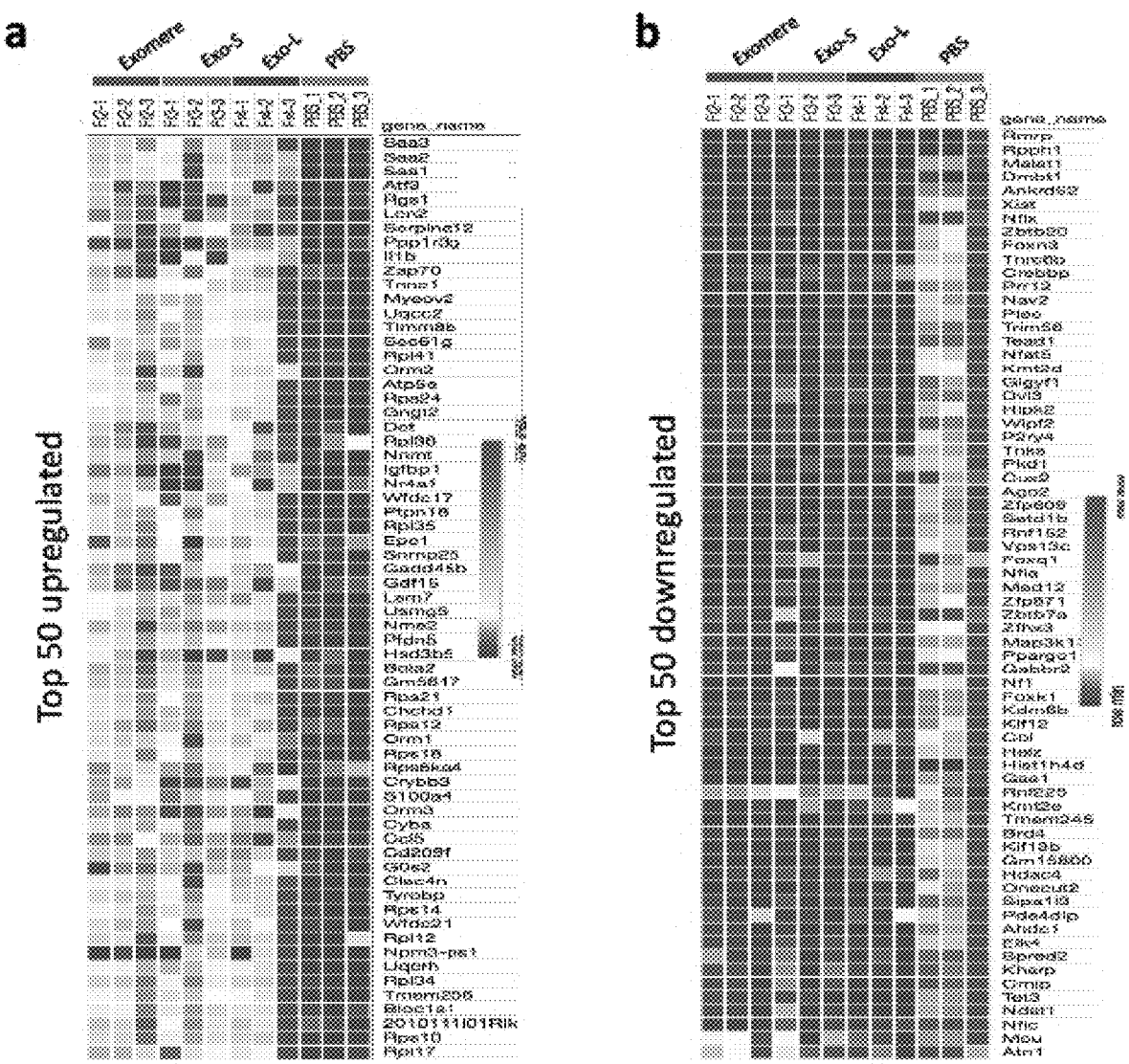

FIGS. 24A-24B show a heatmap illustration of the top 50 upregulated genes (FIG. 24A) and top 50 downregulated genes (FIG. 24B) in the livers of mice treated with exomere, Exo-S or Exo-L, compared with the PBS control group. n=3 per group.

FIGS. 25A-25E show Ingenuity Pathway Analysis (IPA) of differently expressed genes in the livers of mice 24 hours post injection of B16-F10 derived exomeres, Exo-S and Exo-L, in comparison with PBS control. Shown are representative top pathways that are significantly affected between Exomere and PBS (FIG. 25A), Exo-S and PBS (FIG. 25B), Exo-L and PBS (FIG. 25C), Exomere and Exo-S(FIG. 25D), and Exomere and Exo-L (FIG. 25E).

FIGS. 26A-26C show metabolic mass spectrometry analysis of the livers from mice treated with B16-F10-derived exomeres, Exo-S and Exo-L, compared with PBS control. Metabolites whose abundance were significantly changed are identified using unpaired t test (FIG. 26A) and one-way ANOVA analysis (FIGS. 26B-26C) (metabolites differently detected in each group via one-way ANOVA are shown as specific individual data points in (FIG. 26B), or as clusters highlighted in boxes in (FIG. 26C)). n=3 mice per group.

Figures 27A, 27B:
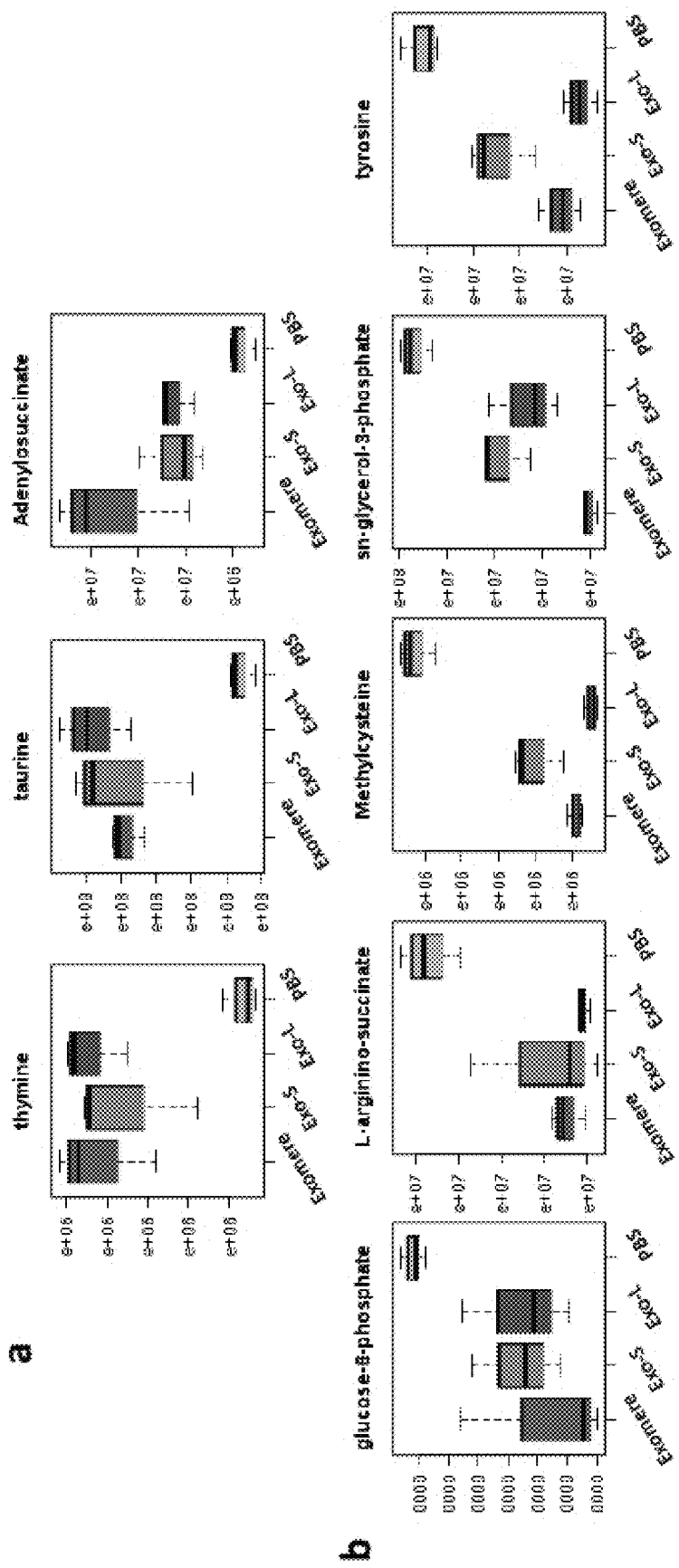

FIGS. 27A-27B shows that metabolites that are upregulated or downregulated in all three groups of exomeres, Exo-S and Exo-L-treated mouse livers in comparison with the PBS control were identified via one-way ANOVA analysis, and the changes in their abundance are displayed in FIG. 27A and FIG. 27B, respectively. n=3 mice per group.

Figure 28A:
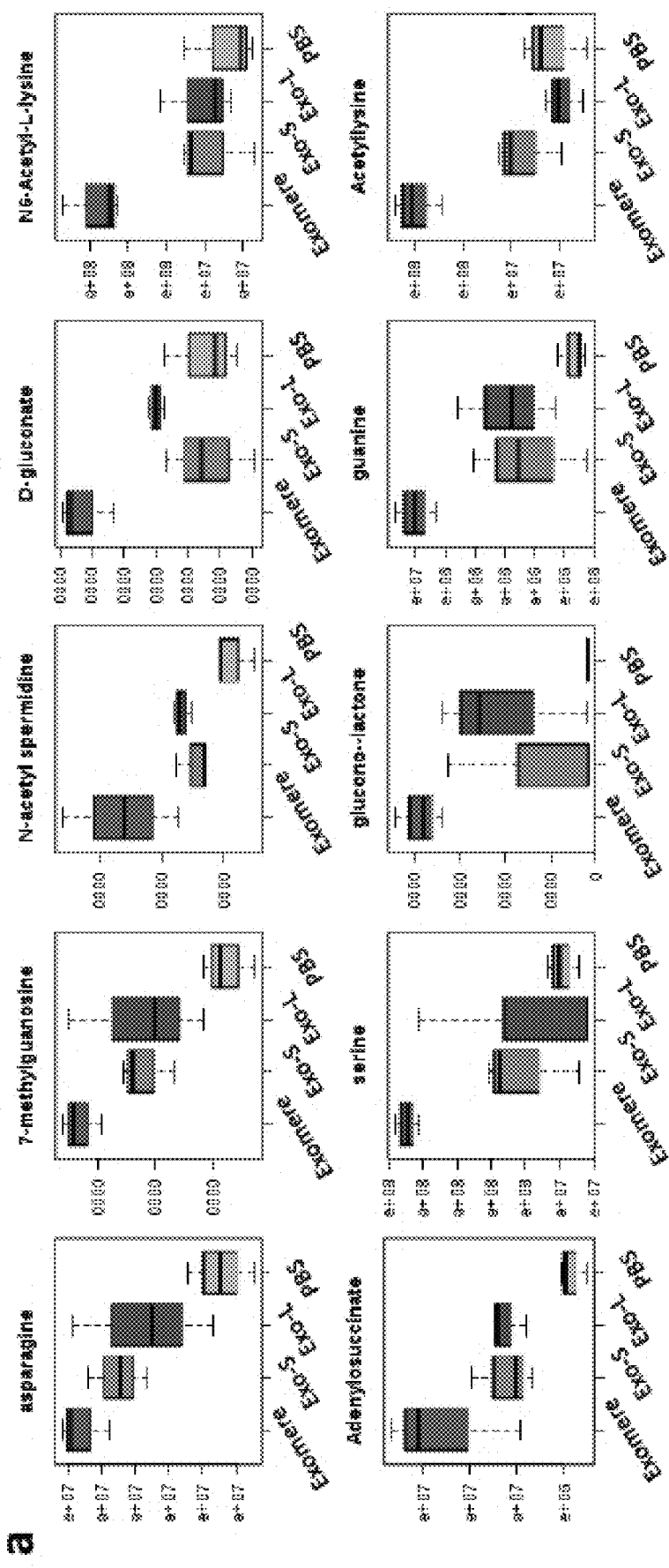
Figures 28B, 28C:
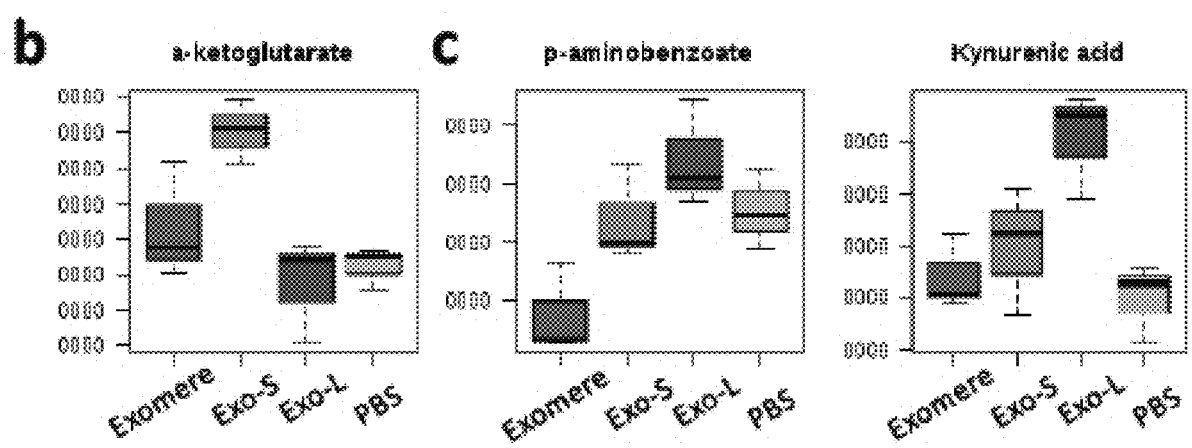

FIGS. 28A-28C show a demonstration of representative metabolites that are specifically upregulated in exomeres (FIG. 28A), Exo-S(FIG. 28B), and Exo-L (FIG. 28C), respectively, compared with the PBS control group. n=3 mice per group.

Figure 29:
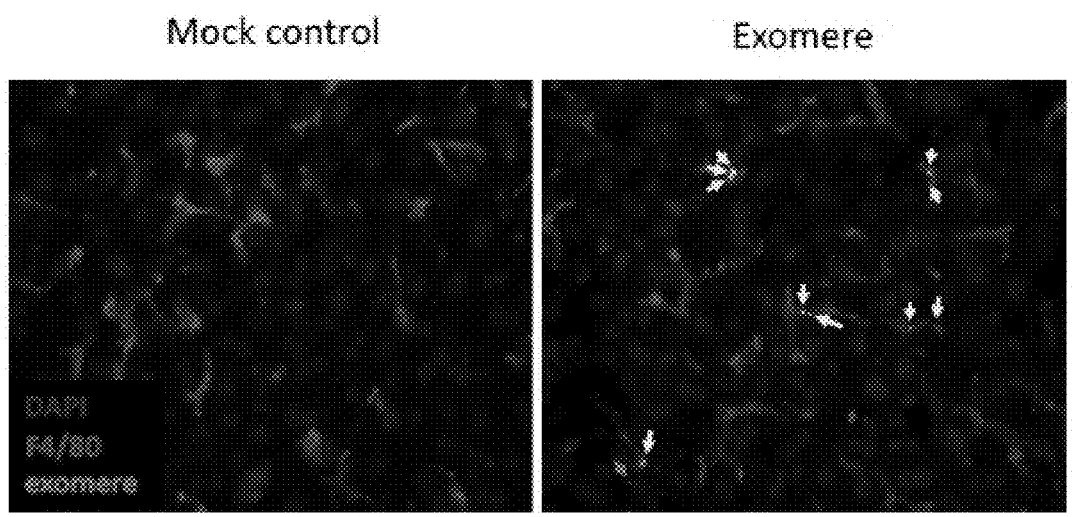

FIG. 29 shows an immunofluorescence colocalization study that revealed that kupffer cells, the liver resident macrophages, are the primary cell type that uptakes B16-F10 melanoma-derived exomeres. Exomeres that are labeled with green fluorescent lipophilic PKH67 dye or the mock labeling reaction mixture were injected intravenously into naïve, syngeneic C57BL/6 mice and 24 hours post injection, the livers were harvest and fixed for immunofluorescence colocalization analysis. n=3 mice per group. F4/80 was stained (in red) to identify the macrophages in the liver.

DETAILED DESCRIPTION OF THE INVENTION

A first aspect of the present invention is directed to a method of diagnosing cancer in a subject. This method involves selecting a subject having cancer and obtaining, from the selected subject, a population of either exomeres having a diameter of less than 50 nm, small exosomes having a diameter of 60-80 nm, or large exosomes having a diameter of 90-120 nm. The exomeres, small exosomes, or large exosomes are recovered from the sample, and the exomeres, small exosomes, or large exosomes or portions thereof are contacted with one or more reagents suitable to detect: (1) higher or lower levels, relative to a standard for subjects not having cancer, or the presence or absence, of one or more proteins contained in said exomeres, small exosomes, or large exosomes, (2) higher or lower levels, relative to a standard for subjects not having cancer, or the presence or absence, of one or more N-glycans contained in said exomeres, small exosomes, or large exosomes, (3) higher or lower levels, relative to a standard for subjects not having cancer, or the presence or absence, of one or more lipids contained in said exomeres, small exosomes, or large exosomes, (4) the presence or absence of one or more genetic mutations in nucleic acid molecules associated with cancer and contained in said exomeres, small exosomes, or large exosomes, or (5) combinations thereof. Cancer is then diagnosed based on the contacting step.

Another aspect of the present invention is directed to a method of prognosing cancer in a subject. This method involves selecting a subject having cancer and obtaining, from the selected subject, a population of either exomeres having a diameter of less than 50 nm, small exosomes having a diameter of 60-80 nm, or large exosomes having a diameter of 90-120 nm. The exomeres, small exosomes, or large exosomes are recovered from the sample, and the exomeres, small exosomes, or large exosomes or portions thereof are contacted with one or more reagents suitable to detect: (1) higher or lower levels, relative to a standard or to the level in a prior sample obtained from the subject, or the presence or absence, of one or more proteins contained in said exomeres, small exosomes, or large exosomes, (2) higher or lower levels, relative to a standard or to the level in a prior sample obtained from the subject, or the presence or absence, of one or more N-glycans contained in said exomeres, small exosomes, or large exosomes, (3) higher or lower levels, relative to a standard or to the level in a prior sample obtained from the subject, or the presence or absence, of one or more lipids contained in said exomeres, small exosomes, or large exosomes, (4) the presence or absence of one or more genetic mutations in nucleic acid molecules associated with cancer and contained in said exomeres, small exosomes, or large exosomes, or (5) combinations thereof. Cancer is then prognosed based on the contacting step.

Another aspect of the present invention is directed to a method of managing treatment in a subject. This method involves selecting a subject undergoing treatment for cancer and obtaining, from the selected subject, a population of either exomeres having a diameter of less than 50 nm, small exosomes having a diameter of 60-80 nm, or large exosomes having a diameter of 90-120 nm. The exomeres, small exosomes, or large exosomes are recovered from the sample, and the exomeres, small exosomes, or large exosomes or portions thereof are contacted with one or more reagents suitable to detect: (1) higher or lower levels, relative to a standard or to the level in a prior sample obtained from the subject, or the presence or absence, of one or more proteins contained in said exomeres, small exosomes, or large exosomes, (2) higher or lower levels, relative to a standard or to the level in a prior sample obtained from the subject, or the presence or absence, of one or more N-glycans contained in said exomeres, small exosomes, or large exosomes, (3) higher or lower levels, relative to a standard or to the level in a prior sample obtained from the subject, or the presence or absence, of one or more lipids contained in said exomeres, small exosomes, or large exosomes, (4) the presence or absence of one or more genetic mutations in nucleic acid molecules associated with cancer and contained in said exomeres, small exosomes, or large exosomes, or (5) combinations thereof. Treatment is then modified based on the contacting step.

Cancer prognosis as described herein includes determining the probable progression and course of the cancerous condition, and determining the chances of recovery and survival of a subject with the cancer, e.g., a favorable prognosis indicates an increased probability of recovery and/or survival for the cancer patient, while an unfavorable prognosis indicates a decreased probability of recovery and/or survival for the cancer patient. A subject's prognosis can be determined or modified by the availability of a suitable treatment (i.e., a treatment that will increase the probability of recovery and survival of the subject with cancer). Accordingly, another aspect of the present invention includes selecting a suitable cancer therapeutic based on the determined prognosis and administering the selected therapeutic to the subject.

Prognosis also encompasses the metastatic potential of a cancer. For example, a favorable prognosis based on the presence or absence of a protein, N-glycan, lipid, and/or genetic phenotype can indicate that the cancer is a type of cancer having low metastatic potential, and the patient has an increased probability of long term recovery and/or survival. Alternatively, an unfavorable prognosis, based on the presence or absence of a protein, N-glycan, lipid, and/or genetic phenotype can indicate that the cancer is a type of cancer having a high metastatic potential, and the patient has a decreased probability of long term recovery and/or survival.

Prognosis further encompasses prediction of sites of metastasis, determination of the stage of the cancer, or identifying the location of a primary tumor in a subject.

A change in the levels of certain proteins, N-glycans, lipids, and/or the mutational status of genes associated with cancer (e.g., BRAF and/or EGFR) indicates that a cancer is present or a change in the cancer phenotype has occurred with disease progression. For example, detecting the presence of a genetic mutation in an exomere, small exosomal, or large exosomal dsDNA sample from a subject whereas no genetic mutation was detected in an earlier exomere, small exosomal, or large exosomal dsDNA sample obtained from the same subject, can be indicative of a particular site of metastasis or progression to a more advanced stage of the cancer. Therefore, periodic monitoring of exomere, small exosomal, or large exosomal dsDNA mutational status provides a means for detecting primary tumor progression, metastasis, and facilitating optimal targeted or personalized treatment of the cancerous condition.

The detection of certain proteins, N-glycans, lipids, and/or exomere, small exosomal, or large exosomal dsDNA mutations in a metastatic cancer sample can also identify the location of a primary tumor. For example, the detection of one or more BRAF mutations in a metastatic tumor or cancer cell-derived exomere, small exosomal, or large exosomal sample can indicate that the primary tumor or cancer was melanoma or a form of brain cancer, e.g. glioblastoma. The detection of one or more EGFR mutations in a metastatic tumor or cancer cell derived exomere, small exosomal, or large exosomal dsDNA sample indicates that the primary tumor originated in the lung, or alternatively the primary cancer was head and neck cancer, ovarian cancer, cervical cancer, bladder cancer, or esophageal cancer.

As described above, another aspect of the present invention is directed to a method of managing treatment of a subject having cancer. In accordance with this aspect, cancer treatment is modified based on the contacting step.

In accordance with all aspects of the present invention, a "subject" or "patient" encompasses any animal, but preferably a mammal, e.g., human, non-human primate, a dog, a cat, a horse, a cow, or a rodent. More preferably, the subject or patient is a human. In some embodiments of the present invention, the subject has cancer, for example and without limitation, melanoma, breast cancer, or pancreatic cancer. In some embodiments, the cancer is a primary tumor, while in other embodiments, the cancer is a secondary or metastatic tumor.

"Exosomes" are microvesicles released from a variety of different cells, including cancer cells (i.e., "cancer-derived exosomes"). These small vesicles (50-100 nm in diameter) derive from large multivesicular endosomes and are secreted into the extracellular milieu. The precise mechanisms of exosome release/shedding remain unclear; however, this release is an energy-requiring phenomenon, modulated by extracellular signals. They appear to form by invagination and budding from the limiting membrane of late endosomes, resulting in vesicles that contain cytosol and that expose the extracellular domain of membrane-bound cellular proteins on their surface. Using electron microscopy, studies have shown fusion profiles of multivesicular endosomes with the plasma membrane, leading to the secretion of the internal vesicles into the extracellular environment. The rate of exosome release is significantly increased in most neoplastic cells and occurs continuously. Increased release of exosomes and their accumulation appear to be important in the malignant transformation process.

As described herein, two exosome subpopulations (i.e., Exo-S and Exo-L) have been identified. "Exo-S", as used herein, refers to a population of small exosomes having a diameter of 60 to 80 nm, an average surface charge of −9.0 mV to −12.3 mV, and a particle stiffness of 70 to 420 mPa. Exo-S are also enriched in genes involved in membrane vesicle biogenesis and transport, protein secretion and receptor signaling "Exo-L", as used herein, refers to a population of large exosomes having a diameter of 90 to 120 nm, an average surface charge of −12.3 to −16.0 mV, and a particle stiffness of 26 to 73 mPa. Exo-L are also enriched in genes involved in the mitotic spindle, IL-2/Stat5 signaling, multi-organism organelleorganization, and G-protein signaling.

In addition to Exo-S and Exo-L subpopulations, a novel extracellular nanoparticle has also been identified. As used herein, the term "exomere" refers to a non-membranous nanoparticle having a diameter of less than 50 nm, often approximately 35 nm, an average surface charge of −2.7 mV to −9.7 mV, and a particle stiffness of 145 to 816 mPa. Exomeres are enriched in metabolic enzymes and hypoxia, microtubule and coagulation proteins as well as proteins involved in glycolysis and mTOR signaling In accordance with the methods of the present invention, exomeres, small exosomes, and large exosomes can be isolated or obtained from most biological fluids including, without limitation, blood, serum, plasma, ascites, cyst fluid, pleural fluid, peritoneal fluid, cerebrospinal fluid, tears, urine, saliva, sputum, nipple aspirates, lymph fluid, fluid of the respiratory, intestinal, and genitourinary trances, breast milk, infra-organ system fluid, conditioned media from tissue explant culture, or combinations thereof.

A population of either exomeres, small exosomes or large exosomes can be obtained from a biological sample using methods described herein. For example, exomeres, small exosomes, or large exosomes may be concentrated or isolated from a biological sample asymmetric flow field-flow fractionation (AF4) (Fraunhofer et al., "The Use of Asymmetrical Flow Field-Flow Fractionation in Pharmaceutics and Biopharmaceutics," *European Journal of Pharmaceutics and Biopharmaceutics* 58:369-383 (2004); Yohannes et al., "Asymmetrical Flow Field-Flow Fractionation Technique for Separation and Characterization of Biopolymers and Bioparticles," *Journal of chromatography. A* 1218: 4104-4116 (2011)).

Exomeres, small exosomes, or large exosomes isolated from a bodily fluid (i.e., peripheral blood, cerebrospinal fluid, urine) can be enriched for those originating from a specific cell type, for example, lung, pancreas, stomach, intestine, bladder, kidney, ovary, testis, skin, colorectal, breast, prostate, brain, esophagus, liver, placenta, and fetal cells. Because the exomeres, small exosomes, or large exosomes often carry surface molecules such as antigens from their donor cells, surface molecules may be used to identify, isolate or enrich for exomeres, small exosomes, or large exosomes from a specific donor cell type. In this way, exomeres, small exosomes, or large exosomes originating from distinct cell populations can be analyzed for their nucleic acid content. For example, tumor (malignant and non-malignant) exosomes carry tumor-associated surface antigens and these exosomes can be isolated or enriched via these specific tumor-associated surface antigens. In one example, the tumor-associated surface antigen is epithelial-cell-adhesion-molecule (EpCAM), which is specific to exosomes from carcinomas of lung, colorectal, breast, prostate, head and neck, and hepatic origin, but not of hematological cell origin (Balzar et al., "The Biology of the 17-1A Antigen (Ep-CAM)," *J Mol Med* 77(10): 699-712 (1999); Went et al. "Frequent EpCam Protein Expression in Human Carcinomas," *Hum Pathol* 35(1): 122-8 (2004), which are hereby incorporated by reference in their entirety). In another example, the surface antigen is CD24, which is a glycoprotein specific to urine microvesicles (Keller et al. "CD24 is a Marker of Exosomes Secreted into Urine and Amniotic Fluid," *Kidney Int* 72(9): 1095-102 (2007), which is hereby incorporated by reference in its entirety). In yet another example, the surface antigen is CD70, carcinoembryonic antigen (CEA), EGFR, EGFRvIII and other variants, Fas ligand, TRAIL, tranferrin receptor, p38.5, p97 and HSP72. Alternatively, tumor specific exosomes may be characterized by the lack of surface markers, such as the lack of CD80 and CD86 expression.

The isolation of exomeres, small exosomes, or large exosomes from specific cell types can be accomplished, for example, by using antibodies, aptamers, aptamer analogs, or molecularly imprinted polymers specific for a desired surface antigen. In one embodiment, the surface antigen is specific for a cancer type. In another embodiment, the surface antigen is specific for a cell type which is not necessarily cancerous. One example of a method of exosome separation based on cell surface antigen is provided in U.S. Pat. No. 7,198,923, which is hereby incorporated by reference in its entirety. As described in, e.g., U.S. Pat. No. 5,840,867 to Toole and 5,582,981 to Toole, which are hereby incorporated by reference in their entirety, aptamers and their analogs specifically bind surface molecules and can be used as a separation tool for retrieving cell type-specific exosomes. Molecularly imprinted polymers also specifically recognize surface molecules as described in, e.g., U.S. Pat. Nos. 6,525,154, 7,332,553 and 7,384,589, which are hereby incorporated by reference in their entirety, and are a tool for retrieving and isolating cell type-specific exosomes. These methods can be adapted for use in isolating exomeres, small exosomes, or large exosomes.

In accordance with this aspect and other aspects of the invention, the recovered exomeres, small exosomes, or large exosomes are then contacted with one or more reagents suitable to detect higher or lower levels, relative to a standard for subjects not having cancer or to a prior sample from a subject having cancer, or the presence or absence of one or more proteins in the exomere, small exosome, or large exosome sample.

For purposes of prognosing or managing treatment of cancer, a subject is selected that has or is undergoing treatment for cancer.

In one embodiment, exomeres are recovered from the sample and the method is carried out by detecting, higher or lower levels, relative to a standard for subjects not having cancer, or the presence or absence, of one or more of the proteins selected from the group consisting of PP1D, GANAB, MAT1A, CPYD, FAT4, GMPPB, ERP44, CALR, GPD1, BZW1, PFKL, OLFML3, HGD, LGALS3BP, GCLC, PEPD, MTHFD1, PGD, ACTR3, XPNPEP1, UGP2, SNX2, ALDOC, SEPT11, HSPA13, AARS, SERP1NH1, CNDP2, PDE5A, AGL, EXT1, IDH1, SERP1NC1, RRM1, CKB, HMGCS1, HPD, PSMC4, NPEPPS, CAT, EXT2, CORO1C, B4GAT1, RACK1, MAPRE1, PGM1, PD1A3, ADK, SHMT1, ACO1, GSN, ESD, PPP2R1A, ALDH1L1, OLA1, ACLY, EEF1G, FLNB, PSMD11, ANGPTL3, FERMT3, PYGL, MDH1, and EIFA2.

In another embodiment, small exosomes are recovered from the sample and the method is carried out to by detecting, higher or lower levels, relative to a standard for subjects not having cancer, or the presence or absence, of one or more of the proteins selected from the group consisting of TTYH3, FLOT1, FLOT2, TSPAN14, LAMC1, CD63, MVB12A, ZDHHC20, VAMP3, VPS37B, ARRDC1, and TGFBR2.

In a further embodiment, large exosomes are recovered from the sample and the method is carried out by detecting, higher or lower levels, relative to a standard for subjects not having cancer, or the presence or absence, of one or more of the proteins selected from the group consisting of SQSTM1, ST1P1, H1NT1, WASF2, RASA3, EPB41L2, G1PC1, S100A10, MPP6, K1F23, RACGAP1, ANXA5, CASK, DLG1, TJP1, BAG5, TXN, AB11, ANXA1, CAPE, DB1, S100A6, CHMP2B, CMMP3, ANXA2, MYO1C, ANXA4, SNX12, LIN7C, STXBP3, CEP55, ALCAM, VCL, CHMP1A, FARP1, ACSL4, BA1AP2, SH3GL1, DSTN, LGALS1, CYF1P1, CTNNA1, RAB31, ARF6, SLC1A5, EPS8, FMNL2, PGAM1, CNP, CHMP4B, ANXA3, VPS4B, GNG12, PACSIN3, GLG1, VTA1, LYN, VPS37C, CHMP5, F3, DNAJA1, RHOC, GNA13, CHMP2A, ATP2B1, RDX, ATP1B1, CAPZB, EHD1, DNAJA2, and CTNND1.

The methods described herein may be performed to diagnose, prognose, or manage treatment of specific types of cancer. For example, in some embodiments, melanoma, breast cancer, or pancreatic cancer may be diagnosed or prognosed. In other embodiments, treatment of melanoma, breast cancer, or pancreatic cancer may be modified.

In one embodiment, the method is performed to diagnose, prognose, or manage treatment of melanoma. For purposes of prognosing or managing treatment of melanoma, a subject is selected that has or is undergoing treatment for melanoma.

According to this embodiment, exomeres are recovered from the sample and the method is carried out by detecting, higher or lower levels, relative to a standard for subjects not having melanoma or to a prior sample from the subject, or the presence or absence, of one or more of the proteins selected from the group consisting of 1T1H2, 1T1H3, H2AFX, PMEL, MAT1A, HPD, ALB, B4GAT1, ARF1, GCLC, HGD, PPP2CB, PAH, AGL, RNPEP, PP1D, BZW1, ME1, DPYD, CA6, OLFML3, NPEPPS, PREP, ERP44, RELN, GPD1, GFPT1, CNDP2, PFKL, ALDH8A1, ATP6V1A, ENO2, THBS3, CORO1C, EXT1, CAT, XPN-PEP1, PYGL, CALR, and LGALS3BP.

In another embodiment, small exosomes are recovered from the sample and the method is carried by detecting, higher or lower levels, relative to a standard for subjects not having melanoma or to a prior sample from the subject, or the presence or absence, of one or more of the proteins selected from the group consisting of TYRP1, SDCBP, SDCBP, CD63, IGSF8, HSPA8, MLANA, HBA1/HBA2, GPNMB, DCT, HSPA2, HSPA1L, HSPA5, Fv4, PDCD6IP, RAB7A, ENV1, CD81, GNB1, SYT4, GNB2, HIST1H2AH, GNA12, GAPDH, APOE, BC035947, Hist1h2a1, ACTG1, ACTB, GNB4, GNA13, SLC3A2, ACTC1, GNAS, SLC38A2, HIST2H2BF, ATP1A1, TFRC, TMEM176B, VAMP8, TSPAN10, ADGRG1, Hist1h4a, PMEL, UBL3, PP1A, ACTBL2, CD9, BACE2, and TSPAN4.

In a further embodiment, large exosomes are recovered from the sample and the method is carried out by detecting, higher or lower levels, relative to a standard for subjects not having melanoma, or the presence or absence, of one or more of the proteins selected from the group consisting of HSPA8, TYRP1, SDCBP, HSPA2, RPS27A, HSPA1L, MLANA, HSPA5, CD63, 1GSF8, GPNMB, Fv4, ENV1, PDCD6IP, HSPA1A/HSPA1B, DCT, ACTG1, ACTB, PP1A, SLC3A2, ACTC1, CD81, ITM2C, RAB7A, GNB1, TSPAN4, DNAJA1, GNB2, TFRC, HBA1/HBA2, GNA12, SYT4, GAPDH, APOE, PMEL, MFGE8, GNB4, GNA13, GNAO1, DNAJA2, ATP1A1, ITGB1, TMEM59, SLC38A2, GNA12, 1TM2B, GNAS, HIST1H2AH, LAMP1, and EEF1A1.

In another embodiment, the method is performed to diagnose, prognose, or manage treatment of breast cancer. For purposes of prognosing or managing treatment of breast cancer, a subject is selected that has or is undergoing treatment for breast cancer.

According to this embodiment, exomeres are recovered from the sample and the method is carried out to by detecting, higher or lower levels, relative to a standard for subjects not having breast cancer or to a prior sample from the subject, or the presence or absence, of one or more of the proteins selected from the group consisting of FGB, HIST2H2AB, COMP, HIST1H2BJ, C7, GSTA5, ENO3, ARF3, SULT1C4, EIF4A2, MAT1A, GNB2, UGDH, AKR1B10, MTHFD1, CTSC, DPP3, RPSA, OTUB1, ALDH8A1, F11, CTPS2, MGAT1, HYH1, LGALSL, GSTM3, GSTM5, PSMC1, F8, PRKAR2B, RPL10A, HNRNPK, SEMA6D, SNX5, IARS, LCP2, ARPC4, PPP6C, PSMD6, PTPRS, TIE1, PSMD8, PABPC4, RPS18, CHAD, IPO5, FABP3, GALNT2, QPCT, STAT5A, SEMA3A, NT5C2, IDE, STAT3, DPYSL3, PDXK, ARF5, PSMD5, GNE, NBEAL2, FHL1, TIMP3, POSTN, MAPRE2, ITIH3, C3, ENO2, PP1D, 01T3, CAND1, SEPT2, UBE2N, DPYSL2, CKB, PTGES3, DSTN, PKLR, THBS3, RAP1B, HIST2H2AB, ACTBL2, TUBB2A, F10, CNTN1, HPD, ACE, EML2, HSPA13, TNXB, HEXB, CALR, ADH5, GPX1, CFL2, KRT76, TCP1, COTL1, DYNLL1, HGD, ALDOC, EPRS, GLO1, MAN2A1, FLT4, NAPL4, RARS, HMGCS1, GANAB, SEPT7, FKBP4, COL12A1, ADSL, AKR1C20, VASN, DDX39B, ME1, COMT, ALDH1A1, EIF4A3, CDH11, PRPSI13, PNPEP, NPEPPS, SEPT11, CMBL, PSMD1, ACTR1B, PSMD3, GCLC, FAT4, LPL, GPD1L, GCLM, VARS, PHPT1, CACNA2D1, SEPT9, GLRX3, AARS, GMPPB, SNX2, GLOD4, PTPRF, CSAD, PXDN, AGL, DPYD, PRKACB, LARS, PP1D, LTA4H, PSMD7, CAPNS1, ETF1, IARS, VPS35, TKFC, HYOU1, PGM2, TKT, HMCN1, CYB5R3, GPS1, UMPS, SND1, RTCB, RPL26, CARM1, PLCG2, P4HA2, CORO6, GMPS, IGSF8, PPP1R7, TIMP3, UXS1, DNM2, MEMO, RPS3, ARHGD1A, PTGES3, NRP2, RAB1A, HBG2, and YWHAQ.

In another embodiment, small exosomes are recovered from the sample and the method is carried out to by detecting, higher or lower levels, relative to a standard for subjects not having breast cancer or to a prior sample from the subject, or the presence or absence, of one or more of the proteins selected from the group consisting of SDCBP, HIST1H2BN, HIST1H2AH, HBA1/HBA2, ITGB1, Hist1h4a, PDCD6IP, HIST3H2BB, H2AFX, CD9, CD63, ITGA3, ITIH2, MFGE8, H2AFZ, PTGFRN, Hist1h3b, HSPA8, ACTG1, ACTB, ARRDC1, ACTC1, ITIH3, IGSF8, GSN, TUBA4A, HIST1H1D, TUBA1A, HIST1H1C, THBS1, HSPA2, ENO1, MVB12A, HTRA1, GAPDH, Hist1h1e, VPS28, TSG101, TUBB, TUBB4A, RAP1B, PFN1, CD81, VPS37B, TUBB6, RAP1A, EPCAM, Hist1h1b, PP1A, ADAM10, HBA1, HIST1H2BK, A2M, ED1L3, SDCBP, MFGE8, GSN, HIST2H2AC, HIST1H2AC, H2AFX, ACTB, THBS1, 1T1H4, TUBB, TUBB2A, TUBB4B, F10, H2AFZ, TUBB4A, TUBB6, TUBB1, HSPA8, CD9, CD81, GAPDH, PFN1, HIST1H4A, HSP90AA1, HSP90AB1, HSPA2, HIST2H3A, PGK1, THBS2, EEF1A1, GPX3, ITGB1, PP1A, PDCD6IP, EEF1A2, FBLN1, AT1C, CPNE8, TLN1, HSPA5, PKM, HIST1H1C, WDR1, RAN, PYGL, and ITGA3.

In a further embodiment, large exosomes are recovered from the sample and the method is carried out to by detecting, higher or lower levels, relative to a standard for subjects not having breast cancer, or the presence or absence, of one or more of the proteins selected from the group consisting of PDCD6IP, SDCBP, EHD1, ITGB1, S100A6, ITGA3, CD9, VPS37C, Hist1h4a, RAP1B, CTNNA1, MSN, HIST1H2AH, ITGA2, PTGFRN, ACTG1, HIST1H2BN, Calm1, EPCAM, ITGA6, YWHAE, HSPA1A/HSPA1B, GNB1, SLC3A2, GNB2, EHD2, H2AFX, PP1A, NT5E, VPS4B, GNB4, Cdc42, SlC1A5, GNA12, CFL1, YWHAH, EEF1A1, YWHAB, Hist1h3b, TSG101, YWHAG, ANXA5, GNA13, F5, H3F3A/H3F3B, CHMP4B, HSPA5, EZR, GAPDH, CD81, ED1L3, HBA1/HBA2, UBC, SDCBP, HSPA8, ITGB1, CD9, HSPA2, ACTC1, ACTB, ACTG1, PDCD61P, AFP, HBG2, ANXA2, 1TGA3, HIST1H2BK, GAPDH, CD81, SLC3A2, GNA12, GNA13, GNA11, ATP1A1, HIST2H2AC, CPNE8, 1ST1, PFN1, TUBA4A, H2AFX, TUBA1C, HSPA5, YWHAZ, ENO1, ANXA5, GNAS, DNAJA1, CHMP5, EEF1A1, RHOA, KRT1, CEP55, GNB1, ACTBL2, ITGA2, EPHA2, GNA13, PP1A, RAP1A, and CD59.

In another embodiment, the method is performed to diagnose, prognose, or manage treatment of pancreatic cancer. For purposes of prognosing or managing treatment of pancreatic cancer, a subject is selected that has or is undergoing treatment for pancreatic cancer.

According to this embodiment, exomeres are recovered from the sample and the method is carried out to by detecting, higher or lower levels, relative to a standard for subjects not having pancreatic cancer, or the presence or absence, crone or more of the proteins selected from the group consisting of SULT1E1, PKLR, ENO2, AKR1B1, FH, MGAT2, GPX1, DPP3, SEMA4B, GPD1, CSAD, NCAM1, PCMT1, NARS, THOP1, UMPS, PDE5A, CACNA2D1, TIE1, CDH11, AOX1, F8, GLB1, RPL10A, ACAP2, UXS1, ADSL, BMP1, PSMD3, LANCL1, GLO1, PPP2CA, ESD, PSMD5, FARSB, PAFAH1B1, SNX5, XPO1, MAPRE1, APRT, NEO1, GSA, THBS1, PYGL, THBS2, FAT4, CNTN1, AKR1C20, EIF4A2, ESD, BPGM, VASN, MAT1A, MAT2A, PFKL, CLIC5, HOD, GLOD4, AGL, PLEKHB2, CLSTN1, STI3, CMBL, AKRIE2, PRKAR2A, GPD1, LGALSL, GLA, IL1RAP, GMPPB, PCSK6, SEPT9, PSMC6, FYN, PAFAH1B1, VPS37C, CTNND1, NRBP1, ERP44, SHMT1, DARS, ADSL, GCLM, ALDOC, EPHA4, PEPD, CKB, PCMT1, UGDH, PRKAR1A, and GNAS.

In another embodiment, small exosomes are recovered from the sample and the method is carried out to by detecting, higher or lower levels, relative to a standard for subjects not having pancreatic cancer, or the presence or absence, of one or more of the proteins selected from the group consisting of SDCBP, PDCD6IP, HSPA8, IGSF8, CD9, PTGFRN, ACTC1, LY6E, ACTB, MFGE8, HSPA2, CD81, ITGA3, ITGB1, ITIH2, VPS28, CD63, HTRA1, ENV1, Fv4, GSN, ENO1, EDIL3, MVB12A, IFITM3, SERPINC1, ACTBL2, TUBA4A, PP1A, HSPA1A/HSPA1B, HSPA5, GAPDH, TSG101, TUBB, PLEKHB2, TUBA1C, TUBB4B, PFN1, GPC1, GJA1, EHD1, GNB2, TSPAN4, GNA12, SLC3A2, VPS37B, GNA13, RAB7A, EEF1A1, GNAS, ALB, HBA1/HBA2, CD9, UBC, SDCBP, F2, ACTG1, ACTB, CD59, ACTC1, ACTA2, A2M, HIST1H2BK, HIST1H2BJ, HSPA8, TSPAN3, HIST2H2AC, CD55, H3F3A/H3F3B, HIST2H3PS2, PDCD6IP, ITGB1, POTEJ, SERINC5, H2AFZ, ARRDC1, CLDN3, NT5E, EPCAM, CDH17, ATP1A1, ALPPL2, HIST2H2AB, ALPP, HSPA2, TSPAN8, MVP, ADAM10, THBS1, VNN1, ITGAV, IGSF8, MYOF, ATP1A2, AHCY, GSN, TSPAN1, PP1A, SDCBP2, and HSPA5.

In a further embodiment, large exosomes are recovered from the sample and the method is carried out to by detecting, higher or lower levels, relative to a standard for subjects not having pancreatic cancer, or the presence or absence, of one or more of the proteins selected from the group consisting of ACTC1, ACTG1, ACTB, MFGE8, ITGB1, HSPA8, ITGA3, SDCBP, GAPDH, LGALS1, ENV1, Fv4, YWHAZ, PP1A, GNB1, GNA12, GNB2, ACTBL2, GNA13, CFL1, Marcks, GNAS, EEF1A1, ENO1, BSG, Calm1, S100A4, MSN, EZR, RDX, PTGFRN, PKM, SLC3A2, HBA1/HBA2, EDIL3, GNA13, RHOA, RHOC, S100A6, YWHAE, ALDOA, PDCD6IP, PFN1, HSP90AB1, YWHAQ, ANXA1, ANXA2, ATP1A1, ITGA6, UBC, HBA1/HBA2, CD9, ACTG1, ACTB, CD59, MVP, SDCBP, ACTC1, ACTA2, HIST1H2BK, HIST2H2AC, ALB, HSPA8, HIST1H2BJ, CD55, H3F3A, TSPAN3, HIST2H3PS2, POTEJ, DPP4, NT5E, EPCAM, VNN1, H2AFZ, ITGB1, ALPPL2, HIST2H2AB, ATP1A1, ALPP, IST1, PDCD6IP, MUC13, ANXA11, HSPA2, CDH17, GPA33, ANXA2, S100A6, ATP1A2, PP1A, EGFR, TSPAN8, MYOF, GNA11, GNA12, GNA13, S100A4, CLDN3, and A2M.

The one or more protein levels are compared to a "standard" level of the same one or more proteins to identify a subject as one that has cancer or is at risk for metastatic disease. In one embodiment, the standard level of a protein is the average expression level of the protein in exomere, small exosomal, or large exosomal samples taken from a cohort of healthy individuals (i.e., the average level in non-cancerous exomere, small exosomal, or large exosomal samples). In another embodiment, the standard level is the average level of the marker in exomere, small exosomal, or large exosomal samples taken from individuals having a primary tumor, e.g., a gastrointestinal tumor that never metastasized to the liver or other organ of the body. In another embodiment, the standard level of a protein is the level of the protein in an exomere, small exosomal, or large exosomal sample taken from the subject being tested, but at an earlier time point (e.g., a pre-cancerous time point).

In accordance with all aspects of the present invention, a "higher level" refers to an expression level (i.e., protein or gene expression level) that is higher than the standard level. For example, a higher expression level is at least 50% higher than the standard expression level. A "lower level" refers to an expression level (i.e., protein or gene expression level) that is lower than the standard level. For example, a lower expression level is at least 50% lower than the standard expression level.

In accordance with this aspect and other aspects of the invention relating to detecting higher or lower levels or the presence or absence of one or more proteins in the sample, suitable methods for detecting proteins include, but are not limited to, measuring RNA expression level and measuring protein expression levels. These methods are commonly used in the art. For measuring protein expression levels, this method generally involve contacting the sample with one or more detectable reagents that is suitable for measuring protein expression, e.g., a labeled antibody or a primary antibody used in conjunction with a secondary antibody, and measuring protein expression level based on the level of detectable reagent in the sample after normalizing to total protein in the sample. Suitable methods for detecting protein expression level in an exosome sample that are commonly employed in the art include, for example and without limitation, western blot, immunoprecipitation, enzyme-linked immunosorbent assay (ELISA), radioimmunoassay (RIA), or fluorescent activated cell sorting (FACS). The measured protein expression level in the sample is compared to the protein expression level measured in a reference exosomal sample and the type of metastatic disease is identified based on this comparison.

Measuring gene expression by quantifying mRNA expression can be achieved using any commonly used method known in the art including northern blotting and in situ hybridization (Parker et al., "mRNA: Detection by in Situ and Northern Hybridization," *Methods in Molecular Biology* 106:247-283 (1999), which is hereby incorporated by reference in its entirety); RNAse protection assay (Hod et al., "A Simplified Ribonuclease Protection Assay," *Biotechniques* 13:852-854 (1992), which is hereby incorporated by reference in its entirety); reverse transcription polymerase chain reaction (RT-PCR) (Weis et al, "Detection of Rare mRNAs via Quantitative RT-PCR," *Trends in Genetics* 8:263-264 (1992), which is hereby incorporated by reference in its entirety); and serial analysis of gene expression (SAGE) (Velculescu et al., "Serial Analysis of Gene Expression," *Science* 270:484-487 (1995); and Velculescu et al., "Characterization of the Yeast Transcriptome," *Cell* 88:243-51 (1997), which is hereby incorporated by reference in its entirety).

In other embodiments, the exomeres, small exosomes, or large exosomes are then contacted with one or more reagents suitable to detect higher or lower levels, relative to a standard for subjects not having cancer or to a prior sample from a subject having cancer, or the presence or absence of one or more N-glycans in the exomere, small exosome, or large exosome sample.

For purposes of prognosing or managing treatment of cancer, a subject is selected that has or is undergoing treatment for cancer.

In accordance with this embodiment, exomeres are recovered from the sample and the method is carried out by detecting N-glycans selected from the group consisting of N-glycan (Fucose)+GlcNAcβ1-6(GlcNAcβ1-2)Manα1-6(GlcNA β1-4(GlcNAcβ1-2)Manα1-3)Manβ1-4GlcNAcβ1-4(Fucα1-6)GlcNAcβ1-Asn and N-glycan (Fucose)+Neu5Acα2-8Neu8Acα2-3Galβ1-3/4GlcNAcβ1-2Manα1-3(Manα1-3(Manα1-6))Manα1-6)Manβ1-4GlcNAcβ1-4GlcNAcβ1-Asn.

In another embodiment, small exosomes are recovered from the sample and the method is carried out by detecting N-glycans.

In a further embodiment, large exosomes are recovered from the sample and the method is carried out by detecting N-glycans.

Methods of analyzing glycoproteins are well known in the art. For example, as a first step, the nanoparticles are lysed and total protein is collected, which contains glycoproteins of interest. The complex carbohydrate portion of the glycoproteins may be readily analyzed if desired, by conventional techniques of carbohydrate analysis. For example, techniques such as lectin blotting, which is well-known in the art, reveal proportions of terminal mannose or other sugars such as galactose. Termination of mono-, bi-, tri-, or tetra-antennary oligosaccharide by sialic acids can be confirmed by release of sugars from the protein using anhydrous hydrazine or enzymatic methods and fractionation of oligosaccharides by ion-exchange or size exclusion chromatography or other methods well-known in the art. The isoelectric point (pi) of the glycoprotein can also be measured, before and after treatment with neuraminidase to remove sialic acids. An increase in pi following neuraminidase treatment indicates the presence of sialic acids on the glycoprotein.

The carbohydrates can be analyzed by any method known in the art including those methods described herein. Several methods are known in the art for glycosylation analysis and are useful in the context of the present invention. Such methods provide information regarding the identity and the composition of the oligosaccharide. Methods for carbohydrate analysis useful in the present invention include but are not limited to lectin chromatography; HPAEC-PAD, which uses high pH anion exchange chromatography to separate oligosaccharides based on charge; NMR; Mass spectrometry; HPLC; GPC; monosaccharide compositional analysis; sequential enzymatic digestion.

In some embodiments, as described in the Examples herein, glycoproteins extracts are reduced, alkylated and digested with sequencing-grade, modified trypsin (Promega) using a standard proteomics protocol (Ferreira et al., "Synthesis and Optimization of Lectin Functionalized Nanoprobes for the Selective Recovery of Glycoproteins from Human Body Fluids," *Analytical Chemistry* 83:7035-7043 (2011), which is hereby incorporated by reference in its entirety). The N-glycans can then be analyzed based on a modification of Jensen et al (Kolarich et al., "Isomer-Specific Analysis of Released N-Glycans by LC-ESI MS/MS with Porous Graphitized Carbon," *Methods in Molecular Biology* 1321:427-435 (2015), which is hereby incorporated by reference in its entirety). Briefly, N-Linked glycans are released with PNGase F (*Elizabethkingia meningoseptica*; Sigma), deaminated and partially purified using porous graphitized carbon solid-phase extraction cartridges (PGC-SPE, HyperSep-96-Hypercarb, 25 mg, Thermo Scientific) as described previously (Jensen et al., "Structural Analysis of N- and O-Glycans Released from Glycoproteins," *Nature Protocols* 7:1299-1310 (2012), which is hereby incorporated by reference in its entirety). Glycan profiling and characterization may be performed by MALDI TOF/TOF mass spectrometry (4800 Plus, SCIEX) using alpha-cyano-4-hydroxycinnamic acid (CHCA; 10 mg/mL in 50% ACN), operated in reflector negative mode (mass range of m/z 1000 to 5000) with external calibration (TOF/TOF calibration mixture, SCIEX). NanoHPLC-High Resolution Mass Spectrometry (HRMS) may be used to validate the presence of most discriminative ions in MALDI-MS spectra using a nanoHPLC system (Dionex, 3000 Ultimate RSLCnano) coupled on-line to a LTQ-Orbitrap XL mass spectrometer (Thermo Scientific) equipped with a nano-electrospray ion source (Thermo Scientific, EASY-Spray source). N-Glycan chromatographic separation using Porous Graphitized Carbon (PGC) may be adapted from a procedure previously described (Jensen et al., "Structural Analysis of N- and O-Glycans Released from Glycoproteins," *Nature Protocols* 7:1299-1310 (2012), which is hereby incorporated by reference in its entirety). A nanoflow PGC column (Hypercarb, 150 mm×75 μm ID, 3 μm particle size, Thermo Scientific) followed by a reversed phase C18 column (EASY-Spray C18 PepMap, 100 Å, 150 mm×75 μm ID and 3 μm particle size, Thermo Scientific) can be combined in series. This allows a better separation of carbohydrates and remaining tryptic peptides, while minimizing salt precipitation events encountered when a nanospray emitter was utilized directly after the PGC column. The mass spectrometer is operated in negative ion mode.

The monosaccharide compositions for the glycan precursors on MALDI-MS spectra may then be predicted using the GlycoMod tool considering mass accuracies below 10 ppm. The possibility of neutral exchanges with $Na^+$ and $K^+$ was considered for sialoglycans. The glycan structures are assigned based on nanoHPLC-PGC-HRMS analysis considering: i) molecular monoisotopic mass; (ii) CID-MS/MS de novo sequencing; and (iii) PGC-LC relative retention times. In particular, α2,3-linked and α2,6-linked sialylated N-glycans were differentiated based on retention time α2,6<α2,3)

(Kolarich et al., "Isomer-Specific Analysis of Released N-Glycans by LC-ES1 MS/MS with Porous Graphitized Carbon," *Methods in Molecular Biology* 1321:427-435 (2015), which is hereby incorporated by reference in its entirety). For further validation, MS/MS fragmentation profiles are matched to glycosidic fragments calculated in silica on GlycoWorkBench (Ceroni et al., "GlycoWorkbench: a Tool for the Computer-Assisted Annotation of Mass Spectra of Glycans," *Journal of Proteome Research* 7:1650-1659 (2008), which is hereby incorporated by reference in its entirety). General understanding of mammalian N-glycosylation may be used to determine some structural aspects. A semiquantitive approach may be used to compare glycan compositions based on MALDI-MS assignments, taking into account the monoisotopic peak intensity.

In other embodiments, the exomeres, small exosomes, or large exosomes are then contacted with one or more reagents suitable to detect higher or lower levels, relative to a standard for subjects not having cancer or to a prior sample from a subject having cancer, or the presence or absence of one or more lipids in the exomere, small exosome, or large exosome sample.

The term "lipidomics" refers to the use of metabolomics as applied to the evaluation of lipid metabolites in biological samples. Lipid profiling generally involves an evaluation of lipid metabolites in one or more lipid classes (e.g., fatty acids, triglycerides, diglycerides, cholesterol esters, and the phospholipid classes including phosphatidylcholine, phosphatidylethanolamine, lysophosphatidylcholine, sphingomyelin, phosphatidylcholine, phosphatidylserine, phosphatidylethanolamine and cardiolipin). As used herein, the term "lipid" is intended broadly and encompasses a diverse range of molecules that are relatively water-insoluble or nonpolar compounds of biological origin, including waxes, triglycerides, free fatty acids, diacylglyercols, fatty-acid derived phospholipids, sphingolipids, glycolipids and terpenoids, such as retinoids, cholesterol, cholesterol esters, and steroids. Some lipids are linear aliphatic molecules, while others have ring structures. Some are aromatic, while others are not.

The lipid profile can be quantitative, semi-quantitative and/or qualitative. For example, the lipid profile can evaluate the presence or absence of a lipid, can evaluate the presence of a lipid(s) above or below a particular threshold, and/or can evaluate the relative or absolute amount of a lipid(s). In some embodiments, a ratio among two, three, four or more lipids is determined. Changes or perturbations in lipid ratios can be advantageous in indicating where there are metabolic blocks (or releases of such blocks) or other alterations in metabolic pathways associated with disease, response to treatment, development of side effects, and the like. Methods of evaluating ratios of lipid precursors and products to evaluate enzyme activities and flow through metabolic pathways are known in the art (see, e.g., Attie et al., (2002) *J. Lipid Res.* 43:1899-1907 and Pan et al., (1995) *J. Clin. Invest.* 96:2802-2808, which are hereby incorporated by reference in their entirety).

Ratios of lipid metabolites can be used to reflect or assess changes in lipid metabolism. Generally, if the ratio is calculated from metabolites not present in the same lipid class, quantitative data are used to calculate the ratio. If the lipid metabolites reflected in the numerator and the denominator belong to the same lipid class, then relational data can be used.

In some embodiments, the level of a lipid metabolite is normalized against another lipid metabolite. For example, the ratio between two or more lipid metabolites can be normalized against an index associated with a pathway, enzymatic activity, class of metabolites, and/or status of certain metabolic activities.

Alternatively the level of a lipid metabolite can be normalized against a housekeeping lipid metabolite, e.g., a lipid metabolite that is relatively stable in amount under a variety of conditions in the subject. Quantitative metabolomic data include molar quantitative data, mass quantitative data and relational data by either moles or mass (mole % or weight %, respectively) for individual lipid metabolites or subsets of metabolites. In some embodiments, quantitative aspects of lipidomic analysis can be provided and/or improved by including one or more quantitative internal standards during the analysis, for instance, one standard for each lipid class. Internal standards are described in more detail in U.S. Patent Publication No. 2004/01434612, which is hereby incorporated by reference in its entirety.

Truly quantitative data can be integrated from multiple sources (e.g., the data do not need to be generated with the same assay, in the same location and/or at the same time) into a single seamless database regardless of the number of metabolites measured in each, discrete, individual analysis.

As used herein the term "level" is intended broadly and can mean a quantitative amount (e.g., weight or moles), a semi-quantitative amount, a relative amount (e.g., weight % or mole % within class or a ratio), a concentration, and the like.

For purposes of prognosing or managing treatment of cancer, a subject is selected that has or is undergoing treatment for cancer.

In accordance with this embodiment, exomeres are recovered from the sample and the method is carried out by detecting one or more lipids selected from the group consisting of phospholipids, sphingolipids, and glycerolipids. Exemplary specific lipids include, without limitation, TG, Cer, LPG, LPE, PC, PI, PE, LPI, PS, SM, MG, LPC, PG, DG, CerG3, and CerG1.

In another embodiment, small exosomes are recovered from the sample and the method is carried out by detecting lipids selected from the group consisting of LPE, PC, PI, PE, LPI, PS, PC, SM, and CerG3.

In further embodiment, large exosomes are recovered from the sample and the method is carried out by detecting lipids selected from the group consisting of LPE, PC, PI, PE, LPI, PS, PC, SM, and CerG3.

The lipid profile of the exomere, small exosomal, or large exosomal sample can be determined using any suitable method. The different classes of lipids and methods of detecting and optionally quantifying the same are well known in the art (e.g., thin layer chromatography, gas chromatography, liquid chromatography, mass and NMR spectrometry, and any combination thereof (e.g., GC/MS), and the like). One suitable method of detecting, and optionally quantifying, lipids in a biological sample employs stable isotope tracers to label the lipids. Methods of obtaining lipid profiles from biological samples have been described, see, e.g., U.S. Patent Publication No. 2004/0143461 to Watkins and Watkins et al. (2002) *J. Lipid Res.* 43(11): 1809-17, which are hereby incorporated by reference in their entirety.

In other aspects of the invention, the exomeres, small exosomes, or large exosomes are then contacted with one or more reagents suitable to detect higher or lower levels, relative to a standard for subjects not having cancer or to a prior sample from a subject having cancer, or the presence or absence of one or more genetic mutations in nucleic acid molecules associated with cancer in the exomere, small exosome, or large exosome sample.

For purposes of prognosing or managing treatment of cancer, a subject is selected that has or is undergoing treatment for cancer.

In accordance with this aspect, the nucleic acid molecule may be DNA or RNA.

The exomere, small exosome, or large exosome fraction from a bodily fluid of a subject can be pre-treated with DNase to eliminate or substantially eliminate any DNA located on the surface or outside of the exosomes. Without DNAse pre-treatment, short DNA fragments on the outside of the exosomes may remain and co-isolate with nucleic acids extracted from inside the exosomes. Thus, elimination of all or substantially all DNA associated with the outside or surface of the exosomes by pre-treatment of with DNase, has the ability to enrich for internal exomere, small exosome, or large exosome dsDNA. To distinguish DNA strandedness within exomeres, small exosomes, or large exosomes, Shrimp DNase specifically digests double-stranded DNA and S1 nuclease specifically digests single-stranded DNA.

In accordance with this and all other aspects of the present invention, DNA may be isolated by extracting the DNA from the exomeres, small exosomes, or large exosomes prior to or for analysis.

The extracted DNA can be analyzed directly without an amplification step. Direct analysis may be performed with different methods including, but not limited to, nanostring technology. NanoString technology enables identification and quantification of individual target molecules in a biological sample by attaching a color coded fluorescent reporter to each target molecule. This approach is similar to the concept of measuring inventory by scanning barcodes. Reporters can be made with hundreds or even thousands of different codes allowing for highly multiplexed analysis. The technology is described in a publication by Geiss et al. "Direct Multiplexed Measurement of Gene Expression with Color-Coded Probe Pairs," *Nat Biotechnol* 26(3): 317-25 (2008), which is hereby incorporated by reference in its entirety.

In another embodiment, it may be beneficial or otherwise desirable to amplify the nucleic acid of the exomeres, small exosomes, or large exosomes prior to analyzing it. Methods of nucleic acid amplification are commonly used and generally known in the art. If desired, the amplification can be performed such that it is quantitative. Quantitative amplification will allow quantitative determination of relative amounts of the various exosomal nucleic acids.

Nucleic acid amplification methods include, without limitation, polymerase chain reaction (PCR) (U.S. Pat. No. 5,219,727, which is hereby incorporated by reference in its entirety) and its variants such as in situ polymerase chain reaction (U.S. Pat. No. 5,538,871, which is hereby incorporated by reference in its entirety), quantitative polymerase chain reaction (U.S. Pat. No. 5,219,727, which is hereby incorporated by reference in its entirety), nested polymerase chain reaction (U.S. Pat. No. 5,556,773, which is hereby incorporated by reference in its entirety), self sustained sequence replication and its variants (Guatelli et al. "Isothermal, In vitro Amplification of Nucleic Acids by a Multienzyme Reaction Modeled after Retroviral Replication," *Proc Natl Acad Sci USA* 87(5): 1874-8 (1990), which is hereby incorporated by reference in its entirety), transcriptional amplification system and its variants (Kwoh et al. "Transcription-based Amplification System and Detection of Amplified Human Immunodeficiency Virus type 1 with a Bead-Based Sandwich Hybridization Format," *Proc Natl Acad Sci USA* 86(4): 1173-7 (1989), which is hereby incorporated by reference in its entirety), Qb Replicase and its variants (Miele et al. "Autocatalytic Replication of a Recombinant RNA," *J Mol Biol* 171(3): 281-95 (1983), which is hereby incorporated by reference in its entirety), cold-PCR (Li et al. "Replacing PCR with COLD-PCR Enriches Variant DNA Sequences and Redefines the Sensitivity of Genetic Testing," *Nat Med* 14(5): 579-84 (2008), which is hereby incorporated by reference in its entirety) or any other nucleic acid amplification and detection methods known to those of skill in the art. Especially useful are those detection schemes designed for the detection of nucleic acid molecules if such molecules are present in very low numbers.

In one embodiment, the isolated DNA is contacted with one or more reagents suitable to detect the presence or absence of one or more genetic mutations that are associated with cancer. Exemplary genetic mutations associated with cancer include, but are not limited to, BRAF, EGFR, APC, NOTCH, HRAS, KRAS, NRAS, MET, p53, PTEN, HER2, FLT3, BRCA1, BRCA2, PIK3CA, KIT, RET, AKT, ABL, CDK4, MYC, RAF, PDGFR, BCR-ABL, NPM1, CEBPalpha, and SRC.

The one or more mutations in the one or more identified genes can be detected using a hybridization assay. In a hybridization assay, the presence or absence of a gene mutation is determined based on the hybridization of one or more allele-specific oligonucleotide probes to one or more nucleic acid molecules in the exomere, small exosomal, or large exosomal DNA sample from the subject. The oligonucleotide probe or probes comprise a nucleotide sequence that is complementary to at least the region of the gene that contains the mutation of interest. The oligonucleotide probes are designed to be complementary to the wildtype, non-mutant nucleotide sequence and/or the mutant nucleotide sequence of the one or more genes to effectuate the detection of the presence or the absence of the mutation in the sample from the subject upon contacting the sample with the oligonucleotide probes. A variety of hybridization assays that are known in the art are suitable for use in the methods of the present invention. These methods include, without limitation, direct hybridization assays, such as northern blot or Southern blot (see e.g., Ausabel et al., Current Protocols in Molecular Biology, John Wiley & Sons, NY (1991), which is hereby incorporated by reference in its entirety). Alternatively, direct hybridization can be carried out using an array based method where a series of oligonucleotide probes designed to be complementary to a particular non-mutant or mutant gene region are affixed to a solid support (glass, silicon, nylon membranes). A labeled exomere, small exosomal, or large exosoma DNA or cDNA sample from the subject is contacted with the array containing the oligonucleotide probes, and hybridization of nucleic acid molecules from the sample to their complementary oligonucleotide probes on the array surface is detected. Examples of direct hybridization array platforms include, without limitation, the Affymetrix GeneChip or SNP arrays and Illumina's Bead Army. Alternatively, the sample is bound to a solid support (often DNA or PCR amplified DNA) and labeled with oligonucleotides in solution (either allele specific or short so as to allow sequencing by hybridization).

Other common genotyping methods include, but are not limited to, restriction fragment length polymorphism assays; amplification based assays such as molecular beacon assays, nucleic acid arrays, high resolution melting curve analysis (Reed and Wittwer, "Sensitivity and Specificity of Single-Nucleotide Polymorphism Scanning by High Resolution Melting Analysis," *Clinical Chem* 50(10): 1748-54 (2004), which is hereby incorporated by reference in its entirety); allele-specific PCR (Gaudet et al., "Allele-Specific PCR in SNP Genotyping," *Methods Mol Biol* 578: 415-24 (2009), which is hereby incorporated by reference in its entirety); primer extension assays, such as allele-specific primer extension (e.g., Illumina® Infinium® assay), arrayed primer extension (see Krjutskov et al., "Development of a Single Tube 640-plex Genotyping Method for Detection of Nucleic Acid Variations on Microarrays," *Nucleic Acids Res.* 36(12) e75 (2008), which is hereby incorporated by reference in its entirety), homogeneous primer extension assays, primer extension with detection by mass spectrometry (e.g., Sequenom® iPLEX SNP genotyping assay) (see Zheng et al., "Cumulative Association of Five Genetic Variants with Prostate Cancer," *N. Eng. J. Med.* 358(9):910-919 (2008), which is hereby incorporated by reference in its entirety), multiplex primer extension sorted on genetic arrays; flap endonuclease assays (e.g., the Invader® assay) (see Olivier M., "The Invader Assay for SNP Genotyping," *Mutat. Res.* 573 (1-2) 103-10 (2005), which is hereby incorporated by reference in its entirety); 5' nuclease assays, such as the TaqMan™ assay (see U.S. Pat. No. 5,210,015 to Gelfand et al. and 5,538,848 to Livak et al, which are hereby incorporated by reference in their entirety); and oligonucleotide ligation assays, such as ligation with rolling circle amplification, homogeneous ligation, OLA (see U.S. Pat. No. 4,988,617 to Lundgren et al., which is hereby incorporated by reference in its entirety), multiplex ligation reactions followed by PCR, wherein zipcodes are incorporated into ligation reaction probes, and amplified PCR products are determined by electrophoretic or universal zipcode array readout (see U.S. Pat. Nos. 7,429,453 and 7,312,039 to Barany et al., which are hereby incorporated by reference in their entirety). Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection. In general, the methods for analyzing genetic aberrations are reported in numerous publications, not limited to those cited herein, and are available to those skilled in the art. The appropriate method of analysis will depend upon the specific goals of the analysis, the condition/history of the patient, and the specific cancer(s), diseases or other medical conditions to be detected, monitored or treated.

Alternatively, the presence or absence of one or more mutations identified supra can be detected by direct sequencing of the genes, or preferably particular gene regions comprising the one or more identified mutations, from the patient sample. Direct sequencing assays typically involve isolating DNA sample from the subject using any suitable method known in the art, and cloning the region of interest to be sequenced into a suitable vector for amplification by growth in a host cell (e.g. bacteria) or direct amplification by PCR or other amplification assay. Following amplification, the DNA can be sequenced using any suitable method. A preferable sequencing method involves high-throughput next generation sequencing (NGS) to identify genetic variation. Various NGS sequencing chemistries are available and suitable for use in carrying out the claimed invention, including pyrosequencing (Roche® 454), sequencing by reversible dye terminators (Illumina® HiSeq, Genome Analyzer and MiSeq systems), sequencing by sequential ligation of oligonucleotide probes (Life Technologies® SOLID), and hydrogen ion semiconductor sequencing (Life Technologies®, Ion Torrent™). Alternatively, classic sequencing methods, such as the Sanger chain termination method or Maxam-Gilbert sequencing, which are well known to those of skill in the art, can be used to carry out the methods of the present invention.

In certain embodiments of the present invention, the selected subject has melanoma, breast cancer, or pancreatic cancer.

The methods described herein may further include selection of a suitable cancer therapeutic and administering the selected cancer therapeutic to a subject. In practicing the methods of the present invention, the administering step is carried out to treat the cancer, achieve inhibition of metastasis or metastatic disease progression. Such administration can be carried out systemically or via direct or local administration to the tumor site. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterially, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent (e.g., an antibody or an inhibitory nucleic acid molecule) and the disease to be treated.

Effective doses for the treatment of a metastatic disease vary depending upon many different factors, including type and stage of cancer, means of administration, target site, physiological state of the patient, other medications or therapies administered, and physical state of the patient relative to other medical complications. Treatment dosages need to be titrated to optimize safety and efficacy.

Another aspect of the present invention is directed to a kit suitable for diagnosing cancer. The kit includes one or more reagents suitable to detect: (1) higher or lower levels, relative to a standard or to a sample from a subject, or the presence or absence, of one or more proteins contained in exomeres, small exosomes, or large exosomes, (2) higher or lower levels, relative to a standard or to a sample from a subject, or the presence or absence, of one or more N-glycans contained in exomeres, small exosomes, or large exosomes, (3) higher or lower levels, relative to a standard or to a sample from a subject, or the presence or absence, of one or more lipids contained in exomeres, small exosomes, or large exosomes, (4) the presence or absence of one or more genetic mutations in nucleic acid molecules associated with cancer and contained in exomeres, small exosomes, or large exosomes, or (5) combinations thereof, wherein said small exosomes have a diameter of 60 to 80 nm and said large exosomes have a diameter of 90 to 120 nm.

In one embodiment, the kit contains one or more reagents suitable for isolating exomeres, small exosomes, or large exosomes. By way of example, suitable markers for isolation of exomeres include, without limitation, HSP90AB1, MTHFD1, ACTR3, PEPD, IDH1, HMGCS1, LGALS3BP, CALR, HSPA13, UGP2, MAT1A, GPD1, PFKL, HGD, GCLC, GSN, CNDP2, FAT4, ERP44, BZW1, AGL, B4GAT1, EXT1, CAT, XPNPEP1, CORO1C, RACK1, HPD, EXT2, ACLY, ADK, PSMC4, ACO1, RRM1, SERPINH1, PYGL, ALDH1L1, PGM1, EEF1G, and PPP2R1A. Suitable markers for isolation of small exosomes include, without limitation, FLOT1, FLOT2, TTYH3, TSPAN14, and VPS37B. Suitable markers for isolation of large exosomes include, without limitation, STIP1, MPP6, DLG1, AB11, ATP2B1, ANXA4, MYO1C, STXBP3, RDX, ANXA1, ANXA5, GNA13, PACSIN3, VPS4B, CHMP1A, CHMP5, CHMP2A, SH3GL1, CHMP4B, GNG12, and DNAJA1.

In some embodiments, the kit comprises one or more reagents suitable to detect higher or lower levels, relative to a standard or to a sample from a subject, or the presence or absence, of one or more proteins contained in exomeres. Exemplary proteins contained in exomeres are described above.

In some embodiments, the kit comprises one or more reagents suitable to detect higher or lower levels, relative to a standard or to a sample from a subject, or the presence or absence, of one or more proteins contained in small exosomes. Exemplary proteins contained in small exosomes are described above.

In some embodiments, the kit comprises one or more reagents suitable to detect higher or lower levels, relative to a standard or to a sample from a subject, or the presence or absence, of one or more proteins contained in large exosomes. Exemplary proteins contained in large exosomes are described above.

The kit of the present invention may also contain reagents suitable to determine if a subject has a particular type of cancer. In certain embodiments, the kit contains reagents suitable to determine if a subject has melanoma, breast cancer, and/or pancreatic cancer. Exemplary proteins suitable for detection in exomeres, small exosomes, or large exosomes of melanoma, breast cancer, or pancreatic cancer subjects are described above.

A number of kits are contemplated to encompass a variety of methods. These kits optionally include reagents to process a tissue or cell sample for the technique employed by that particular kit. By example, a kit for PCR or PCR enhanced in situ hybridization can include reagents to process the sample and isolate the RNA (for PCR). It will also contain suitable primers to amplify the target sequence and additional probes, if necessary, to detect the desired nucleic acid fragments as well as buffers and reagents for the polymerase chain reaction and the buffers and emulsions required for in situ hybridization methods. Other kits can alternatively include reagents for immunofluorescence or ELISA using antibodies or probes, primers and reagents for modifications of in situ or PCR in situ hybridization methods.

For the purposes of the kits of the present invention, the isolation of nucleic acids from the exomere, small exosomal, or large exosomal sample may be desirable. Accordingly, kits may contain reagents necessary to carry out such methods. Methods of isolating RNA and DNA from biological samples for use in the methods of the present invention are readily known in the art. These methods are described in detail in LABORATORY TECHNIQUES IN BIOCHEMISTRY AND MOLECULAR BIOLOGY: HYBRIDIZATION WITH NUCLEIC ACID PROBES, PART I. THEORY AND NUCLEIC ACID PREPARATION (P. Tijssen ed., Elsevier 1993), which is hereby incorporated by reference in its entirety. Total RNA can be isolated from a given sample using, for example, an acid guanidinium-phenol-chloroform extraction, a guanidinium isothiocyanate-ultracentrifugation method, or lithium chloride-SDS-urea method. PolyA® mRNA can be isolated using oligo (dT) column chromatography or (dT)n magnetic beads (See e.g., SAMBROOK AND RUSSELL, MOLECULAR CLONING: A LABORATORY MANUAL (Cold Springs Laboratory Press, 1989) or CURRENT PROTOCOLS IN MOLECULAR BIOLOGY (Fred M. Ausubel et al. eds., 1992) which are hereby incorporated by reference in their entirety). See also WO/2000024939 to Dong et al., which is hereby incorporated by reference in its entirety, for complexity management and other nucleic acid sample preparation techniques.

It may be desirable to amplify the nucleic acid sample prior to detecting protein levels. One of skill in the art will appreciate that a method which maintains or controls for the relative frequencies of the amplified nucleic acids to achieve quantitative amplification should be used.

Typically, methods for amplifying nucleic acids employ a polymerase chain reaction (PCR) (See e.g., PCR TECHNOLOGY: PRINCIPLES AND APPLICATIONS FOR DNA AMPLIFICATION (Henry Erlich ed., Freeman Press 1992); PCR PROTOCOLS: A GUIDE TO METHODS AND APPLICATIONS (Michael Innis ed., Academic Press 1990); Mattila et al., "Fidelity of DNA Synthesis by the *Thermococcus litoralis* DNA Polymerise—An Extremely Heat Stable Enzyme with Proofreading Activity," *Nucleic Acids Res.* 19:4967-73 (1991); Eckert et al., "DNA Polymerise Fidelity and the Polymerase Chain Reaction," *PCR Methods and Applications* 1:17-24 (1991); and U.S. Pat. Nos. 4,683,202, 4,683,195, 4,800,159, 4,965,188, and 5,333,675 all to Mullis et al., which are hereby incorporated by reference in their entireties for all purposes). The sample can also be amplified on an array as described in U.S. Pat. No. 6,300,070 to Boles, which is hereby incorporated by reference in its entirety.

Other suitable amplification methods include the ligase chain reaction (LCR) (e.g. Wu et al., "The Ligation Amplification Reaction (LAR)—Amplification of Specific DNA Sequences Using Sequential Rounds of Template-Dependent Ligation," *Genomics* 4:560-9 (1989), Landegren et al., "A Ligase-Mediated Gene Detection Technique," *Science* 241:1077-80 (1988), and Barringer et al., "Blunt-End and Single-Strand Ligations by *Escherichia coli* Ligase: Influence on an In Vitro Amplification Scheme," *Gene* 89:117-22 (1990), which are hereby incorporated by reference in their entirety); transcription amplification (Kwoh et al., "Transcription-Based Amplification System and Detection of Amplified Human Immunodeficiency Virus Type I with a Bead-Based Sandwich Hybridization Format," *Proc. Natl. Acad. Sci. USA* 86:1173-7 (1989) and WO 88/10315 to Gingeras, which are hereby incorporated by reference in their entirety); self-sustained sequence replication (Guatelli et al., "Isothermal, In Vitro Amplification of Nucleic Acids by a Multienzyme Reaction Modeled After Retroviral Replication," *Proc. Natl. Acad. Sci. USA* 87:1874-8 (1990) and WO 90/06995 to Gingeras, which are hereby incorporated by reference in their entirety); selective amplification of target polynucleotide sequences (U.S. Pat. No. 6,410,276 to Burg at al., which is hereby incorporated by reference in its entirety); consensus sequence primed polymerase chain reaction (CP-PCR) (U.S. Pat. No. 5,437,975 to McClelland, which is hereby incorporated by reference in its entirety); arbitrarily primed polymerase chain reaction (AP-PCR) (U.S. Pat. No. 5,413,909 to Bassam, and U.S. Pat. No. 5,861,245 to McClelland which are hereby incorporated by reference in their entirety); and nucleic acid based sequence amplification (NABSA) (See U.S. Pat. Nos. 5,409,818, 5,554,517, and 6,063,603 all to Davey, which are hereby incorporated by reference in their entirety). Other amplification methods that may be used are described in U.S. Pat. No. 5,242,794 to Whiteley; U.S. Pat. No. 5,494,810 to Barony; and U.S. Pat. No. 4,988,617 to Landgren, which are hereby incorporated by reference in their entirety.

The kits may also contain probes or primers which hybridize to complementary nucleic acid molecules in the exomere, small exosomal, or large exosomal sample. The probes comprise nucleotide sequences that are complementary to at least a region of mRNA or corresponding cDNA of the desired proteins. As used herein, the term "hybridization" refers to the complementary base-pairing interaction of one nucleic acid with another nucleic acid that results in formation of a duplex, triplex, or other higher-ordered structure. Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes to complementary and substantially complementary target sequences are well known in the art (see e.g., NUCLEIC ACID HYBRIDIZATION, A PRACTICAL APPROACH, B. Flames and S. Higgins, eds., IRL Press, Washington, D.C. (1985), which is hereby incorporated by reference in its entirety). In general, hybridization is influenced by, among other things, the length of the polynucleotides and their complements, the pH, the temperature, the presence of mono- and divalent cations, the proportion of G and C nucleotides in the hybridizing region, the viscosity of the medium, and the presence of denaturants. Such variables influence the time required for hybridization. Thus, the preferred hybridization conditions will depend upon the particular application. Such conditions, however, can be routinely determined by the person of ordinary skill in the an without undue experimentation. It will be appreciated that complementarity need not be perfect; there can be a small number of base pair mismatches that will minimally interfere with hybridization between the target sequence and single stranded nucleic acid probe. Thus, what is meant by complementarity herein is that the probes are sufficiently complementary to the target sequence to hybridize under the selected reaction conditions to achieve selective detection and measurement.

Detection of hybridization between probes and corresponding target molecules from an exomere, small exosomal, or large exosomal sample can be performed by several assays known in the art that permit detection of the expression level of the one or more proteins. As described herein, the "expression level" of a protein can be achieved by measuring any suitable value that is representative of the gene expression level. The measurement of gene expression levels can be direct or indirect. A direct measurement involves measuring the level or quantity of RNA or protein. An indirect measurement may involve measuring the level or quantity of cDNA, amplified RNA, DNA, or protein; the activity level of RNA or protein; or the level or activity of other molecules (e.g. a metabolite) that are indicative of the foregoing. The measurement of expression can be a measurement of the absolute quantity of a gene product. The measurement can also be a value representative of the absolute quantity, a normalized value (e.g., a quantity of gene product normalized against the quantity of a reference gene product), an averaged value (e.g., average quantity obtained at different time points or from different sample from a subject, or average quantity obtained using different probes, etc.), or a combination thereof.

In a preferred embodiment, hybridization is detected by measuring RNA expression level. Measuring gent expression by quantifying RNA expression can be achieved using any commonly used method known in the art including northern blotting and in situ hybridization (Parker et al., "mRNA: Detection by in Situ and Northern Hybridization," Methods in Molecular Biology 106:247-283 (1999), which is hereby incorporated by reference in its entirety); RNAse protection assay (Hod et al., "A Simplified Ribonuclease Protection Assay," Biotechniques 13:852-854 (1992), which is hereby incorporated by reference in its entirety); reverse transcription polymerase chain reaction (RT-PCR) (Weis et al., "Detection of Rare mRNAs via Quantitative RT-PCR," Trends in Genetics 8:263-264 (1992), which is hereby incorporated by reference in its entirety); and serial analysis of gene expression (SAGE) (Vekulescu et al., "Serial Analysis of Gene Expression," Science 270:484-487 (1995); and Velculescu et al., "Characterization of the Yeast Transcriptome," Cell 88:243-51 (1997), which is hereby incorporated by reference in its entirety).

In a nucleic acid hybridization assay, the expression level of nucleic acids corresponding to proteins can be detected using an array-based technique. These arrays, also commonly referred to as "microarrays" or "chips" have been generally described in the art, see e.g., U.S. Pat. No. 5,143,854 to Pirrung et al.; U.S. Pat. No. 5,445,934 to Fodor et al.; 5,744,305 to Fodor et al.; 5,677,195 to Winkler et al.; U.S. Pat. No. 6,040,193 to Winkler et al.; U.S. Pat. No. 5,424,186 to Fodor et al., which are all hereby incorporated by reference in their entirety. A microarray comprises an assembly of distinct polynucleotide or oligonucleotide probes immobilized at defined positions on a substrate. Arrays are formed on substrates fabricated with materials such as paper, glass, plastic (e.g., polypropylene, nylon), polyacrylamide, nitrocellulose, silicon, optical fiber or any other suitable solid or semi-solid support, and configured in a planar (e.g., glass plates, silicon chips) or three-dimensional (e.g., pins, fibers, beads, particles, microliter wells, capillaries) configuration. Probes forming the arrays may be attached to the substrate by any number of ways including (i) in situ synthesis (e.g., high-density oligonucleotide arrays) using photolithographic techniques (see Fodor et al., "Light-Directed, Spatially Addressable Parallel Chemical Synthesis," Science 251:767-773 (1991); Pease et al., "Light-Generated Oligonucleotide Arrays for Rapid DNA Sequence Analysis," Proc. Natl. Acad. Sci. U.S.A. 91:5022-5026 (1994); Lockhart et al., "Expression Monitoring by Hybridization to High-Density Oligonucleotide Arrays," Nature Biotechnology 14:1675 (19%); and U.S. Pat. No. 5,578,832 to Trulson; U.S. Pat. No. 5,556,752 to Lockhart; and U.S. Pat. No. 5,510,270 to Fodor, which are hereby incorporated by reference in their entirety); (ii) spotting/printing at medium to low-density (e.g., cDNA probes) on glass, nylon or nitrocellulose (Schena et al., "Quantitative Monitoring of Gene Expression Patterns with a Complementary DNA Microarray," Science 270:467-470 (1995), DeRisi et al, "Use of a cDNA Microarray to Analyse Gene Expression Patterns in Human Cancer," Nature Genetics 14:457-460 (1996); Shalon et al., "A DNA Microarray System for Analyzing Complex DNA Samples Using Two-Color Fluorescent Probe Hybridization," Genome Res. 6:639-645 (1996); and Schena et al., "Proc. Natl. Acad. Sci. U.S.A. 93:10539-11286) (1995), which are hereby incorporated by reference in their entirety); (iii) masking (Maskos et al., "Oligonucleotide Hybridizations on Glass Supports: A Novel Linker for Oligonucleotide Synthesis and Hybridization Properties of Oligonucleotides Synthesised In Situ," Nuc. Acids. Res. 20:1679-1684 (1992), which is hereby incorporated by reference in its entirety); and (iv) dotblotting on a nylon or nitrocellulose hybridization membrane (see e.g., SAMBROOK AND RUSSELL, MOLECULAR CLONING: A LABORATORY MANUAL (Cold Springs Laboratory Press, 1989), which is hereby incorporated by reference in its entirety). Probes may also be noncovalently immobilized on the substrate by hybridization to anchors, by means of magnetic beads, or in a fluid phase such as in microtiter wells or capillaries. The probe molecules are generally nucleic acids such as DNA, RNA, PNA, and cDNA.

Fluorescently labeled cDNA for hybridization to the array may be generated through incorporation of fluorescent nucleotides by reverse transcription of RNA extracted from exomere, small exosomal, or large exosomal samples. Labeled cDNA applied to the array hybridizes with specificity to each nucleic acid probe spotted on the array. After stringent washing to remove non-specifically bound cDNA, the array is scanned by confocal laser microscopy or by another detection method, such as a CCD camera. Quantitation of hybridization of each arrayed element allows for assessment of corresponding mRNA abundance. With dual color fluorescence, separately labeled cDNA samples generated from two sources of RNA are hybridized pairwise to the array. The relative abundance of the transcripts from the two sources corresponding to each specified gene is thus determined simultaneously. The miniaturized scale of the hybridization affords a convenient and rapid evaluation of the expression pattern for large numbers of genes. Such methods have been shown to have the sensitivity required to detect rare transcripts, which are expressed at a few copies per cell, and to reproducibly detect at least approximately two-fold differences in the expression levels (Schena et al., "Parallel Human Genome Analysis: Microarray-Based Expression Monitoring of 1000 Genes," "*Proc. Natl. Acad. Sci. USA* 93(20):10614-9 (1996), which is hereby incorporated by reference in its entirety).

A nucleic acid amplification assay that is a semi-quantitative or quantitative real-time polymerise chain reaction (RT-PCR) assay can also be performed. Because RNA cannot serve as a template for PCR, the first step in gene expression profiling by RT-PCR is the reverse transcription of the RNA template into cDNA, followed by its exponential amplification in a PCR reaction. The two most commonly used reverse transcriptases are avian myeloblastosis virus reverse transcriptase (AMV-RT) and Moloney murine leukemia virus reverse transcriptase (MLV-RT), although others are also known and suitable for this purpose. The reverse transcription step is typically primed using specific primers, random hexamers, or oligo-dT primers, depending on the circumstances and the goal of expression profiling. For example, extracted RNA can be reverse-transcribed using a GeneAmp RNA PCR kit (Perkin Elmer, CA, USA), following the manufacturer's instructions. The derived cDNA can then be used as a template in the subsequent PCR reaction.

Although the PCR step can use a variety of thermostable DNA-dependent DNA polymerases, it typically employs the Taq DNA polymerase, which has a 5'-3' nuclease activity but lacks a 3'-5' proofreading endonuclease activity. An exemplary PCR amplification system using Taq polymerase is TaqMan® PCR (Applied Biosystems, Foster City, CA). Taqman® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect the nucleotide sequence located between the two PCR primers. The probe is non-extendible by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

TaqMan® RT-PCR can be performed using commercially available equipment, such as, for example, the ABI PRISM 7700® Sequence Detection System® (Perkin-Elmer-Applied Biosystems, Foster City, CA, USA), or the Lightcycler (Roche Molecular Biochemicals, Mannheim, Germany).

In addition to the TaqMan® primer/probe system, other quantitative methods and reagents for real-time PCR detection that are known in the art (e.g. SYBR green, Molecular Beacons, Scorpion Probes, etc.) are suitable for use in the methods of the present invention.

To minimize errors and the effect of sample-to-sample variation, RT-PCR is usually performed using an internal standard or spike in control. The ideal internal standard is expressed at a constant level among different tissues. RNAs most frequently used to normalize patterns of gene expression are mRNAs for the housekeeping genes glyceraldehyde-3-phosphate-dehydrogenase (GAPDH) and β-actin.

Real time PCR is compatible both with quantitative competitive PCR, where internal competitor for each target sequence is used for normalization and quantitative comparative PCR using a normalization gene contained within the sample, or a housekeeping gene for RT-PCR. For further details see, e.g., Heid et al., "Real Time Quantitative PCR," *Genome Research* 6:986-994 (1996), which is incorporated by reference in its entirety.

When it is desirable to measure the expression level of proteins by measuring the level of protein expression, the kit may contain reagents suitable for performing any protein hybridization or immunodetection based assay known in the art. In a protein hybridization based assay, an antibody or other agent that selectively binds to a protein is used to detect the amount of that protein expressed in a sample. For example, the level of expression of a protein can be measured using methods that include, but are not limited to, western blot, immunoprecipitation, enzyme-linked immunosorbent assay (ELISA), radioimmunoassay (RIA), fluorescent activated cell sorting (FACS), immunohistochemistry, immunocytochemistry, or any combination thereof. Also, antibodies, aptamers, or other ligands that specifically bind to a protein can be affixed to so-called "protein chips" (protein microarrays) and used to measure the level of expression of a protein in a sample. Alternatively, assessing the level of protein expression can involve analyzing one or more proteins by two-dimensional gel electrophoresis, mass spectroscopy (MS), matrix-assisted laser desorption/ionization-time of flight-MS (MALDI-TOF), surface-enhanced laser desorption ionization-time of flight (SELDI-TOF), high performance liquid chromatography (HPLC), fast protein liquid chromatography (FPLC), multidimensional liquid chromatography (LC) followed by tandem mass spectrometry (MSMS), protein chip expression analysis, gene chip expression analysis, and laser densitometry, or any combinations of these techniques.

In certain embodiments, kits may contain an antibody that specifically binds a protein of interest. Optionally, the antibody can be fixed to a solid support to facilitate washing and subsequent isolation of the complex, prior to contacting the antibody with a sample. Examples of solid supports include glass or plastic in the form of a microtiter plate, a stick, a bead, or a microbead. Examples of solid supports encompassed herein include those formed partially or entirely of glass (e.g., controlled pore glass), polysaccharides (e.g., agarose), polyacrylamides, silicones, and plastics such as polystyrene, polypropylene and polyvinyl alcohol. The sample can be diluted with a suitable diluent or eluant before contacting the sample to the antibody.

After incubating the sample with antibodies, the mixture can be washed and the antibody-antigen complex formed can be detected. This can be accomplished by incubating the washed mixture with a detection reagent. This detection reagent may be a second antibody which is labeled with a detectable label, for example. Exemplary detectable labels include magnetic beads (e.g., DYNABEADS™), fluorescent dyes, radiolabels, enzymes (for example, horse radish peroxidase, alkaline phosphatase and others commonly used in an ELISA), and calorimetric labels such as colloidal gold or colored glass or plastic beads. Alternatively, the antigens in the sample can be detected using an indirect assay, wherein, for example, a second, labeled antibody is used to detect bound specific, primary antibody, and/or in a competition or inhibition assay wherein, for example, a monoclonal antibody which binds to a distinct epitope of the antigen (i.e., proteins uniquely associated with exomeres, small exosomes, or large exosomes) is incubated simultaneously with the mixture.

Immunoassays can be used to determine presence or absence of proteins in an exomere, small exosomal, and/or large exosomal sample as well as the quantity of the proteins in the sample. If a protein is present in the sample, it will form an antibody-protein complex with an antibody that specifically binds the protein under suitable incubation conditions described above. The amount of an antibody-protein complex can be determined by comparing to a standard. A standard can be a known compound or another protein known to be present in a sample, for example. As noted above, the test amount of antigen (i.e., proteins uniquely associated with exomeres, small exosomes, or large exosomes) need not be measured in absolute units, as long as the unit of measurement can be compared to a control.

In one embodiment, the kit contains one or more reagents suitable to detect higher or lower levels, or the presence or absence of one or more lipids contained in exomeres, small exosomes, or large exosomes.

Exemplary lipids to be detected are described above.

For the purposes of detecting the presence or absence or lipids, the kit comprises reagents and reference compounds suitable for detecting lipids. The reference compounds may be one or more of the following, but are not limited to, lipid standard(s), one or more control marker(s) that is/are regularly measured in a clinical setting, and positive and/or negative controls, internal and/or external standards.

In one embodiment, the lipid concentration(s), lipid ratio(s) or (a) lipid combination(s) thereof in a sample from a subject is (are) determined by using mass spectrometry. The sample may be subjected to purification and/or other sample pre-preparation step(s) before mass spectrometry analysis. The purification step may be, but is not limited to chromatography, for example, high performance liquid chromatography (HPLC), ultra performance liquid chromatography (UPLC) and or ultra high performance liquid chromatography (UHPLC). The sample pre-preparation step may be, but is not limited to solid-phase extraction (SPE), derivatization, liquid-liquid extraction and/or lipoprotein fractionation. The said mass spectrometry determination may be done by tandem mass spectrometry.

In another embodiment, the kit contains one or more reagents suitable to detect higher or lower levels, or the presence or absence of one or more N-glycans contained in exomeres, small exosomes, or large exosomes.

Exemplary N-glycans to be detected are described above.

In some embodiments, the kit contains one or more lectins for a specific glycan structure, in addition to detection reagents and buffers. In some embodiments, the kit contains reagents for identifying glycosylated protein (e.g., the glycosylation detection reagents) in addition to reagents for identifying glycan structures. In some embodiments, the kit contains all of the components necessary and/or sufficient to perform at least one detection assay, including all controls, directions for performing assays, and any necessary or desired software for analysis and presentation of results. In some embodiments, reagents (e.g., lectins) are fluorescently labeled.

EXAMPLES

The examples below are intended to exemplify the practice of the present invention but are by no means intended to limit the scope thereof.

Materials and Methods for Examples 1-7

Cell lines and cell culture. B16-F10, B16-F1, 4T1, MDA-MB-231 series (parental, −1833, −4175, and −831, gifts from Dr. J. Massagué), LLC, SW620, HCT116 (Horizon Discovery), PANC-1, AsPC-1, Pan02 (purchased from the National Cancer Institute Tumor Repository), and NIH3T3 cells were cultured in DMEM. Human melanoma cells (SK-Mel103, A375M and A375P were obtained from MSKCC), human prostatic carcinoma cell lines PC3 and DU145, as well as BXPC-3, HPAF-II, PC-9, ET2B (gift from Dr. P. Gao and J. Bromberg), K-562 (DSMZ) and NB-4 (DSMZ) cells were cultured in RPMI, supplemented with penicillin (100 U/ml) and streptomycin (100 μg/ml) and 10% FBS. Cell lines were obtained from American Type Culture Collection, if not otherwise mentioned, and authenticated using STR profiling by commercial providers. All cells were maintained in a humidified incubator with 5% $CO_2$ at 37° C. and routinely tested and confirmed to be free of mycoplasma contamination. When collecting conditioned media for exosome isolation, FBS (Gibco, Thermo Fisher Scientific) was first depleted of exosomes by ultracentrifugation at 100,000×g for 90 minutes. Cells were cultured for 3 days before supernatant collection.

Human specimens and processing. Fresh human tumor tissues were obtained from subjects with stage 1-3 melanoma at Memorial Sloan-Kettering Cancer Center (MSKCC) and had histologically confirmed melanoma. All individuals provided informed consent for tissue donation according to a protocol approved by the institutional review board of MSKCC (IRB #11-033A, MSKCC; IRB #0604008488, WCM), and the study is compliant with all relevant ethical regulations regarding research involving human participants. Tissues were cut into small pieces and cultured for 24 h in serum-free RPMI supplemented with penicillin/streptomycin. Conditioned media was processed for exosome isolation and AF4 fractionation as described below.

Exomere and exosome isolation and nanosight tracking analysis (NTA). SEV were prepared using differential ultracentrifugation methods (Peinado et al., "Melanoma Exosomes Educate Bone Marrow Progenitor Cells Toward a Pro-Metastatic Phenotype through MET," *Nature Medicine* 18:883-891 (2012), which is hereby incorporated by reference in its entirety) and resuspended in phosphate buffered saline (PBS, pH7.4) for subsequent analysis and AF4 fractionation. Isolated samples were quantified using BCA assay (Pierce, Thermo Fisher Scientific). NTA analysis of exosome size and particle number was performed using the LM10 or DS500 NanoSight system (Malvern Instruments) equipped with a blue laser (405 nm) following manufacturer's instructions.

AF4 fractionation. The detailed step-by-step AF4 fractionation protocol including sample preparation, AF4 setting parameters and running method, data collection and analysis, and fraction collection and characterization) is provided on ProtocolExchange (Zhang et al., "A Protocol for Asymmetric-Flow Field-Flow Fractionation (AF4) of Small Extracellular Vesicles," Protocol Exchange (2018), which is hereby incorporated by reference in its entirety).

Transmission electron microscopy (TEM) and atomic force microscopy (AFM). For negative staining TEM analysis, 5 µl of sample solution was placed on a formvar/carbon coated grid and allowed to settle for 1 minute. The sample was blotted and negative stained with 4 successive drops of 1.5% (aqu) uranyl actate, blotting between each drop. Following the last drop of stain, the grid was blotted and air-dried. Grids were imaged with a JEOL JSM 1400 (JEOL, USA, Ltd, Peabody, MA) transmission electron microscope operating at 100 Kv. Images were captured on a Veleta 2K×2K CCD camera (Olympus-SIS, Munich, Germany).

For AFM, dilutions were made for each sample and then plated on freshly cleaved mica substrate (SPN) for ~2 minutes before washing with 10 mL of Molecular Biology Grade $H_2O$ (Fisher BP2819-1) and being blown dry with nitrogen gas. Imaging was performed using an MFP-3D-B10 AFM (Asylum Research), with an Olympus AC240TS-R3 AFM probe (Asylum Research) in tapping mode at room temperature. Images were captured at 1 µm×1 µm. Image analysis was performed using a custom-written Image)/FIJI (NIH) code.

Zeta potential measurement. Fractionated samples were diluted in PBS (Phosphate-buffered saline; 0.01 M phosphate buffer, 0.0027 M KCl, 0.137 M NaCl; pH 7.4 tablets, Sigma) for ζ potential analysis using Zetasizer Nano ZS90 (Malvern Instruments). Samples were freshly prepared prior to loading onto the instrument at a 90° angle (respective to the light source). All experiments were performed at a constant temperature of 25° C.

Stiffness measurement. Freshly cleaved mica coverslips were first coated with Poly-L-lysine (0.1%, w/v in $H_2O$) for 30 minutes and then incubated with samples on the mica surface for 45 minutes. The samples were then rinsed with 1 ml of MilliPure water, washed three times with PBS buffer, then emerged in a drop of PBS on the mica surface. A stand-alone MFP-3D atomic force microscope (Asylum Research, Santa Barbara, CA) was utilized to perform the analysis. The spring constant of cantilever was determined as 559.73 pN/nm by the thermal noise method (Langlois et al., "Spring Constant Calibration of Atomic Force Microscopy Cantilevers with a Piezosensor Transfer Standard," The Review of Scientific Instruments 78:093705 (2007), which is hereby incorporated by reference in its entirety). The curvature radius of cantilever was ~15 nm, and the resonant frequency of 325 kHz were used for the stiffness analysis (i.e., indentation of cantilever) and imaging. Force measurements were performed with an approximate force distance of 300 nm and velocity of 500 nm/s.

Western blot analysis. Whole cell extract (WCE) and exosome fractions were lysed directly with SDS sample buffer and lysates were cleared by centrifugation at 14,000×g for 10 minutes. 100 µg of WCE and 10 µg of input and each nanoparticle subset were separated on a Novex 4-12% Bis-Tris Plus Gel (Life Technologies), and transferred onto a PVDF membrane (Millipore). Membranes were blocked for 1 hour at room temperature followed by primary antibody incubation overnight at 4° C. The following antibodies were used for western blot analysis: anti-Tsg101 (Santa Cruz sc-7964); anti-Alix1 (Cell Signaling 2171); anti-Hsp90 (Stressgen ADI-SPA-830-F), anti-MAT1A1 (Abeam ab174687); anti-IDH1 (Proteintech 23309-1-AP); anti-FLOT1 (BD Biosciences 610820); anti-TOLLIP (Abeam ab187198); anti-VPS4B (Santa Cruz sc-32922); anti-DNAJA1 (Abeam ab126774); anti-HSPA8/HSC70 (LifeSpan Biosciences LS-C312344-100). All primary antibodies were used at 1:1,000× dilution. IRDye 800CW Goat-anti-mouse IgG (LI-COR Biosciences P/N 926-32210, 1:15,000× dilution), HRP-linked Sheep-anti-Mouse IgG (GE Healthcare Life Sciences NA931, 1:2,500× dilution), and HRP-linked Donkey-anti-Rabbit IgG (GE Healthcare Life Sciences NA934, 1:2,500× dilution) were used as secondary antibody. The blot was analyzed either using the Odyssey Imaging system (LI-COR Biosciences) or enhanced chemiluminescence substrates (Thermo Fisher Scientific).

Analysis of Proteomic Profiling Data. Protein mass spectrometry analyses of fractionated exosomes were performed at the Rockefeller University Proteomics Resource Center as described previously (Costa-Silva et al., "Pancreatic Cancer Exosomes Initiate Pre-Metastatic Niche Formation in the Liver," Nature Cell Biology 17:816-826 (2015); Hoshino et al., "Tumour Exosome Integrins Determine Organotropic Metastasis," Nature 527:329-335 (2015), which are hereby incorporated by reference in their entirety), and conducted on two independent biological replicates for each sample (exomere, Exo-S and Exo-L) derived from 5 different cell lines (B16-F10, 4T1, Pan02, AsPC-1 and MDA-MB-4175).

For proteomic data processing and Principal Component Analysis (PCA), the proteomic expression data was processed using the 'Limma' package of the R program. Proteomic expression data was imported and was normalized using 'normalizeBetweenArrays' function (method+quantile) (Bolstad et al., "A Comparison of Normalization Methods For High Density Oligonucleotide Array Data Based on Variance and Bias," Bioinformatics 19:185-193 (2003), which is hereby incorporated by reference in its entirety). PCA was performed for data reduction, simplifying datasets to three dimensions for plotting purposes using 'princomp( )' function with default options, and illustrated using the 'rgl' package and 'plot3d( )' function.

For clustering and marker selection, Consensus clustering analysis, marker selection for each fraction, and heatmap generation were conducted using GENE-E software. Consensus clustering was conducted to assess whether proteomic expression differs between fraction (Monti et al, "Consensus Clustering: A Resampling-Based Method for Class Discovery and Visualization of Gene Expression Microarray Data," Mach Learn 52:91-118 (2003), which is hereby incorporated by reference in its entirety). To identify fraction-specific markers, the probe (based on UniProt ID) values were collapsed to protein-level using maximum probe. Only proteins detected in both replicates of a sample were included for further analysis. Proteins were sorted by signal-to-noise statistic, $(\mu_A-\mu_B)/(\alpha_A-\alpha_B)$ where µ and α represent the mean and standard deviation of proteomic expression, respectively, for each class (Golub et al., "Molecular Classification of Cancer: Class Discovery and Class Prediction by Gene Expression Monitoring" Science 286:531-537 (1999), which is hereby incorporated by reference in its entirety). Next, the signal to noise marker selection tool from GENE-E was used to identify fraction-specific markers with 1.000 permutations. The cutoff to select fraction-specific markers was fold change ≥5, false discovery rate (FDR)<0.05, and mean protein expression ≥10$^8$ with the positivity in ≥80% (i.e. at least 4 out 5 samples from 5 cell lines for each nanoparticle subset) of the corresponding fraction. Heat maps for visualization of differential protein expression patterns were generated for 65 markers (39 exomere-specific markers; 5 Exo-S markers; 21 Exo-L markers) using GENE-E with relative color scheme (by subtracting each mean protein expression, divide by each standard deviation for each row).

For Gene Set Enrichment Analysis (GSEA) the entire proteomic expression data set (Subramanian et al., "Gene Set Enrichment Analysis: A Knowledge-Based Approach for Interpreting Genome-Wide Expression Profiles," *Proc Natl Acad Sci USA* 102:15545-15550 (2005), which is hereby incorporated by reference in its entirety) was used. Gene sets from Molecular signatures database v5.1 were used for GSEA (H: 50 hallmark gene sets; C2:KEGG: 186 canonical pathways from Kyoto Encyclopedia of Genes and Genomes [KEGG] pathway database; C5: 825 gene sets based on Gene Ontology [GO] term) (Liberzon et al., "Molecular Signatures Database (MSigDB) 3.0," *Bioinformatics* 27:1739-1740 (2011), which is hereby incorporated by reference in its entirety). The default parameters were used to identify significantly enriched gene-sets (FUR q<0.25).

Figures 9A, 9B:
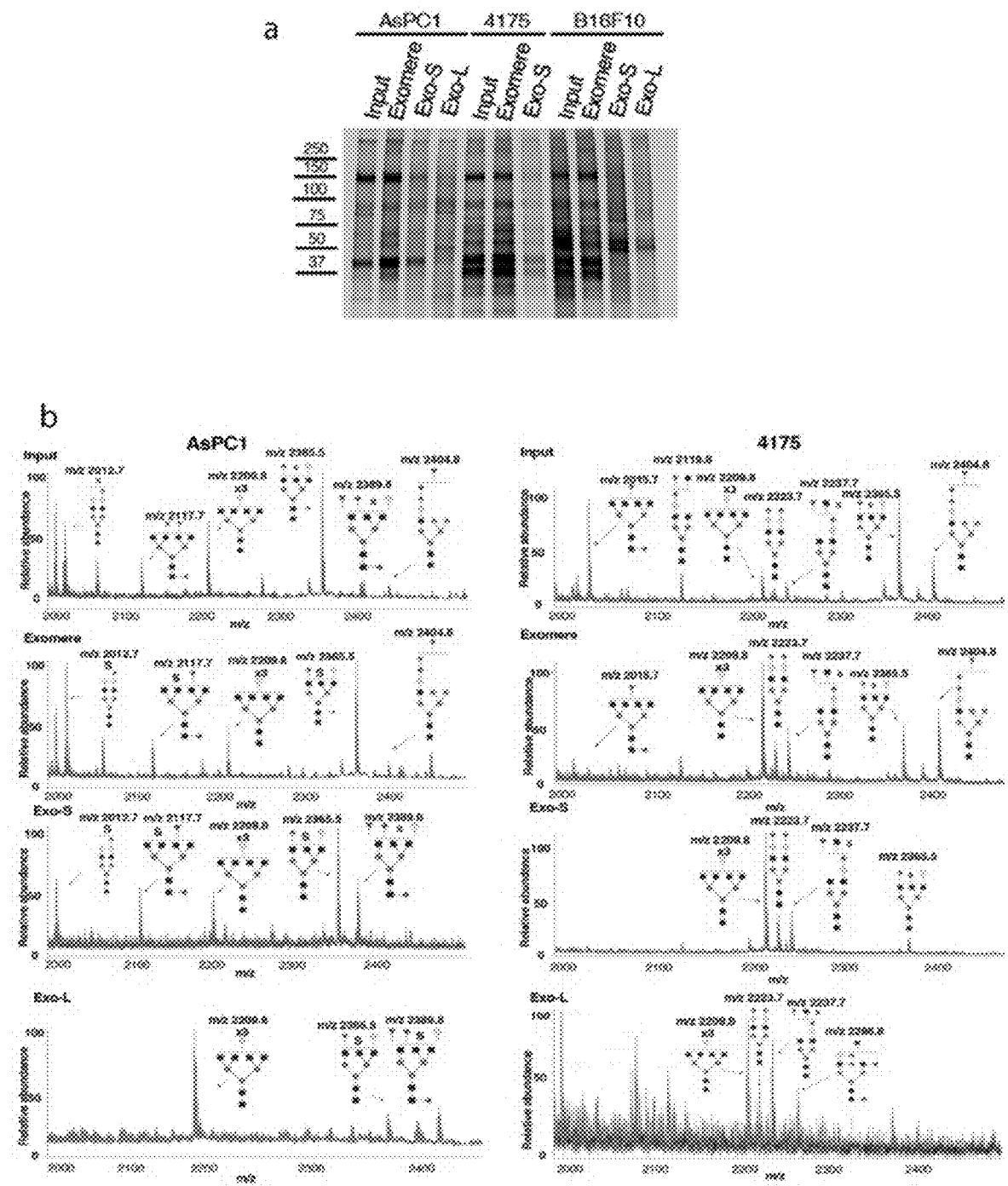
FIGS. 9A-9J show mass spectrometric analysis of N glycans enriched in exomeres, Exo-S and Exo-L derived from AsPC-1 and MDA-MB-231-4175.

Glycoprotein extraction and lectin blotting. Nanoparticles were lysed with RapiGest SF (Waters) containing 1 mM sodium orthovanadate and protease inhibitor cocktail (Roche), for 30 minutes on ice and centrifuged at 16,000×g for 20 minutes. For lectin blotting 0.5 µg of total protein extracts were separated using 4-15% gradient gels (Biorad) and transferred onto nitrocellulose membranes. Samples were incubated at room temperature (RT) for 1 hour with the following biotinylated lectins *Aleuria aurantia* Lectin (AAL; Fucα6GlcNAc and Fucα3GlcNAc), *Sambucus nigra* Lectin (SNA; Neu5Acα6(Gal or GalNAc)). *Phaseolus vulgaris* Leucoagglutinin (L-PHA; Galβ4GlcNAcβ6(GlcNAcβ2Manα3)Manα3), and *Phaseolus vulgaris* Erythroagglutinin (E-PHA; Galβ4GlcNAcβ2Manα6(GlcNAcβ4)(GlcNAcβ4Manα3)Manβ4) (Vector Laboratories, 1:2000 dilution except 1:1000 dilution for L-PHA). Vectastain Elite ABC HRP Kit (Vector Laboratories) was used for signal detection with ECL enhanced chemiluminescence technique (GE Healthcare Life Sciences). The total protein profile of the samples was assessed in parallel on a silver-stained gel (FIG. 9A). (Abbreviations: Fuc, fucose; GlcNAc, N-acetylglucosamine; Man, mannose; Neu5Ac, neuraminic acid; Gal, galactose; GalNAc, N-acetylgalactosamine.)

Glycomics analysis. The glycoproteins extracts from the different fractions were reduced, alkylated and digested with sequencing-grade, modified trypsin (Promega) using a standard proteomics protocol (Ferreira et al., "Synthesis and Optimization of Lectin Functionalized Nanoprobes for the Selective Recovery of Glycoproteins from Human Body Fluids," *Analytical Chemistry* 83:7035-7043 (2011), which is hereby incorporated by reference in its entirety). The N-glycans were analyzed based on a modification of Jensen et al (Kolarich et al., "Isomer-Specific Analysis of Released N-Glycans by LC-ESI MS/MS with Porous Graphitized Carbon," *Methods in Molecular Biology* 1321:427-435 (2015), which is hereby incorporated by reference in its entirety). Briefly, N-Linked glycans were released with PNGase F (*Elizabethkingia meningoseptica*; Sigma), deaminated and partially purified using porous graphitized carbon solid-phase extraction cartridges (PGC-SPE, HyperSep-96-Hypercarb, 25 mg, Thermo Scientific) as described previously (Jensen et al., "Structural Analysis of N- and O-Glycans Released from Glycoproteins," *Nature Protocols* 7:1299-1310 (2012), which is hereby incorporated by reference in its entirety). Glycan profiling and characterization was performed by MALDI TOF/TOF mass spectrometry (4800 Plus, SCIEX) using alpha-cyano-4-hydroxycinnamic acid (CHCA; 10 mg/mL in 50% ACN), operated in reflector negative mode (mass range of m/z 1000 to 5000) with external calibration (TOF/TOF calibration mixture, SCIEX). Three independent analytical measurements were performed. NanoHPLC-High Resolution Mass Spectrometry (HRMS) was used to validate the presence of most discriminative ions in MALDI-MS spectra using a nanoHPLC system (Dionex, 3000 Ultimate RSLCnano) coupled on-line to a LTQ-Orbitrap XL mass spectrometer (Thermo Scientific) equipped with a nano-electrospray ion source (Thermo Scientific, EASY-Spray source). N-Glycan chromatographic separation using Porous Graphitized Carbon (PGC) was adapted from a procedure previously described (Jensen et al., "Structural Analysis of N- and O-Glycans Released from Glycoproteins," *Nature Protocols* 7:1299-1310 (2012), which is hereby incorporated by reference in its entirety). A nanoflow PGC column (Hypercarb, 150 mm×75 µm ID, 3 µm particle size, Thermo Scientific) followed by a reversed phase C18 column (EASY-Spray C18 PepMap, 100 Å, 150 mm×75 µm ID and 3 µm particle size. Thermo Scientific) were combined in series. This allowed a better separation of carbohydrates and remaining tryptic peptides, while minimizing salt precipitation events encountered when a nanospray emitter was utilized directly after the PGC column. The mass spectrometer was operated in negative ion mode.

The monosaccharide compositions for the glycan precursors on MALDI-MS spectra were predicted using the GlycoMod tool considering mass accuracies bellow 10 ppm. The possibility of neutral exchanges with Na$^+$ and K$^+$ was considered for sialoglycans. The glycan structures were assigned based on nanoHPLC-PGC-HRMS analysis considering: i) molecular monoisotopic mass; (ii) CID-MS/MS de nova sequencing; and (iii) PGC-LC relative retention times. In particular, α2,3-linked and α2,6-linked sialylated N-glycans were differentiated based on retention time (α2,6<α2,3) (Kolarich et al., "Isomer-Specific Analysis of Released N-Glycans by LC-ESI MS/MS with Porous Graphitized Carbon," *Methods in Molecular Biology* 1321:427-435 (2015), which is hereby incorporated by reference in its entirety). For further validation, MS/MS fragmentation profiles were matched to glycosidic fragments calculated in silica on GlycoWorkBench (Ceroni et al., "GlycoWorkbench: a Tool for the Computer-Assisted Annotation of Mass Spectra of Glycans," *Journal of Proteome Research* 7:1650-1659 (2008), which is hereby incorporated by reference in its entirety). General understanding of mammalian N-glycosylation was used to determine some structural aspects, yet some structural ambiguity remained in a subset of the reported N-glycans as indicated with brackets. A semiquantitive approach was used to compare glycan compositions based on MALDI-MS assignments, taking into account the monoisotopic peak intensity. Glycan standards and negative controls were analyzed in parallel. These results were validated based on the intensity of each specie on nanoHPLC-HRMS ion chromatograms (EIC) (m/z=0.01).

Lipidomics: sample preparation, mass spectrometry and data analysis. Equal amount of each sample (based on BCA quantification) was subjected to lipidomic analysis. Samples were first sonicated with a Model Q700 QSonica sonicator equipped with an Oasis 180 Chiller (4° C.; Amplitude, 95; process, 5 minutes; pulse-on 30 sec; plus-off 55 sec), centrifuged at 14,800 rpm for 10 minutes at 4° C., and 50 µL of the extract supernatant was spiked with 2 µL 50 µg/mL internal standard mixture (Cer 18:1/12:0; PC 12:0/12:0; PE 14:0/14:0; PG 14:0/14:0; PS 14:0/14:0). Subsequently, the samples were analyzed by using the Thermo Q-Exactive MS system (Bremen, Germany) in the Metabolomics Laboratory of Roy J. Carver Biotechnology Center, University of Illinois at Urbana-Champaign. Software Xcalibur 3.0.63 was used for data acquisition and analysis. The Dionex Ultimate 3000 series HPLC system (Thermo, Germering, Germany) was used, and the LC separation was performed on a Thermo Accucore C18 column (2.1×150 mm, 2.6 µm) with mobile phase A (60% acetonitrile:40% $H_2O$ with 10 mM ammonium formate and 0.1% formic acid) and mobile phase B (90% isopropanol:10% acetonitrile with 10 mM ammonium formate and 0.1% formic acid) and a flow rate of 0.4 mL/min. The linear gradient was as follows: 0 minutes, 70% A; 4 minutes, 55% A; 12 minutes, 35% A; 18 minutes, 15% A; 20-25 minutes, 0% A; 26-33 minutes, 70% A. The autosampler was set to 15° C. and the column was kept at 45° C. The injection volume was 10 µL. Mass spectra were acquired under both positive (sheath gas flow rate, 50; aux gas flow rate: 13; sweep gas flow rate, 3; spray voltage, 3.5 kV; capillary temperature, 263° C.; Aux gas heater temperature, 425° C.) and negative electrospray ionization (sheath gas flow rate, 50; aux gas flow rate: 13; sweep gas flow rate, 3; spray voltage, −2.5 kV; capillary temperature, 263° C.; Aux gas heater temperature, 425° C.). The full scan mass spectrum resolution was set to 70,000 with the scan range of m/z 230~m/z 1,600, and the AGC target was 1E6 with a maximum injection time of 200 msec. For MS/MS scan, the mass spectrum resolution was set to 17,500, and the AGC target was 5E4 with a maximum injection time of 50 msec. Loop count was 10. Isolation window was 1.0 m/z with NCE of 25 and 30 eV. For data analysis, LipidSearch (v.4.1.30, Thermo) was used for lipid identification. The lipid signal responses were normalized to the corresponding internal standard signal response. For those lipid classes without corresponding internal standard, positive lipid ion signals were normalized with the signal of internal standard Cer 18:1/12:0 and negative ion signals were normalized with the signal of internal standard PG 14:0/14:0. The percentage of lipid classes within a sample was calculated by adding that of each of the individual molecular species quantified within a specific lipid class, and the relative abundance was represented by the mean percentage of 3 replicates for each group of samples. Differences among different subpopulations of particles derived from the same cell line were analyzed using ANOVA test (q<0.05).

Nucleic acid analysis. DNA was extracted from nanoparticles using the AMPure XP beads (Agencourt) following the manufacturer's protocol. An equal volume of nanoparticles in PBS and lysis buffer AL (QIAGEN) were mixed and incubated with Proteinase K (20 µg/ml, QIAGEN) at 56° C. for 10 minutes. The mixture was mixed with one volume of each, AMPure beads, isopropanol and PEG solution (Beckman), and incubated for 5 minutes at RT. DNA bound to the beads was then separated from the solution/supernatant on magnet for 5 minutes at RT. The supernatant was removed by pipetting and bead-bound DNA was washed twice with freshly prepared 80% ethanol, then air dried for 5 minutes. Lastly, DNA was eluted from beads with nuclease free water and quantified using QuBit assay (Life Technology). DNA extraction was performed for two independent biological replicates of each sample.

RNA was extracted using the Ambion mirVarna kit (Life technology), following the manufacturer's protocol with one modification: one volume of nanoparticles in PBS was first lysed with 7 volumes of lysis buffer. The samples were analyzed using Agilent Total RNA Pico kits. RNA extraction was performed for two independent biological replicates of each sample.

Biodistribution assessment. Fractionated nanoparticles were first labeled with the near infrared dye CellVue NIR815 (eBioscience) following manufacturer's protocol, followed by washing with 20 ml of PBS and pelleting by ultracentrifugation at 100,000×g for 70 minutes at 10° C. 10 µg of labeled nanovasicles resuspended in 100 µl of PBS, or an equivalent volume of mock reaction mixture was retro-orbitally injected into naïve mice (6-week-old female C57BL/6 mice purchased from Jackson Labs). 24 hours post injection, tissues were collected and analyzed using the Odyssey imaging system (LI-COR Biosciences). Two independent experiments with 3 animals per group were performed. No statistical method was used to predetermine sample size. The experiments were neither randomized, nor blinded. All animal experiments were performed in compliance with ethical regulations and in accordance with Weill Cornell Medicine institutional, IACUC and AAALAS guidelines, approved for animal protocol 0709-666A.

Statistics and Reproducibility. Error bars in graphical data represent means SEM. Statistical significance is determined using one way ANOVA. P<0.05 was considered statistically significant. Statistical analyses were performed using GraphPad Prism software. For lipid class analysis, ANOVA test (q<0.05) was performed using Qlucore Omics Explorer (Sweden). For proteomic analysis, proteins were sorted by signal-to-noise statistic, $(\mu A-\mu B)/(\alpha A+\alpha B)$ where $\mu$ and $\alpha$ represent the mean and standard deviation of proteomic expression, respectively. The cutoff to select fraction-specific markers was fold change ≥5, false discovery rate (FDR)<0.05, and mean protein expression $\geq 10^8$ with the positivity in ≥80% (i.e. at least 4 out 5 samples from 5 different cell lines for each subset of nanoparticles) of the corresponding fraction. For GSEA, Kolmogorov-Smirnov statistic was calculated to evaluate whether proteins from a pre-determined pathway are significantly overrepresented towards the top or bottom of the ranked gene list (FDR q<0.25).

Figures 1D, 1E, 1F, 1G:
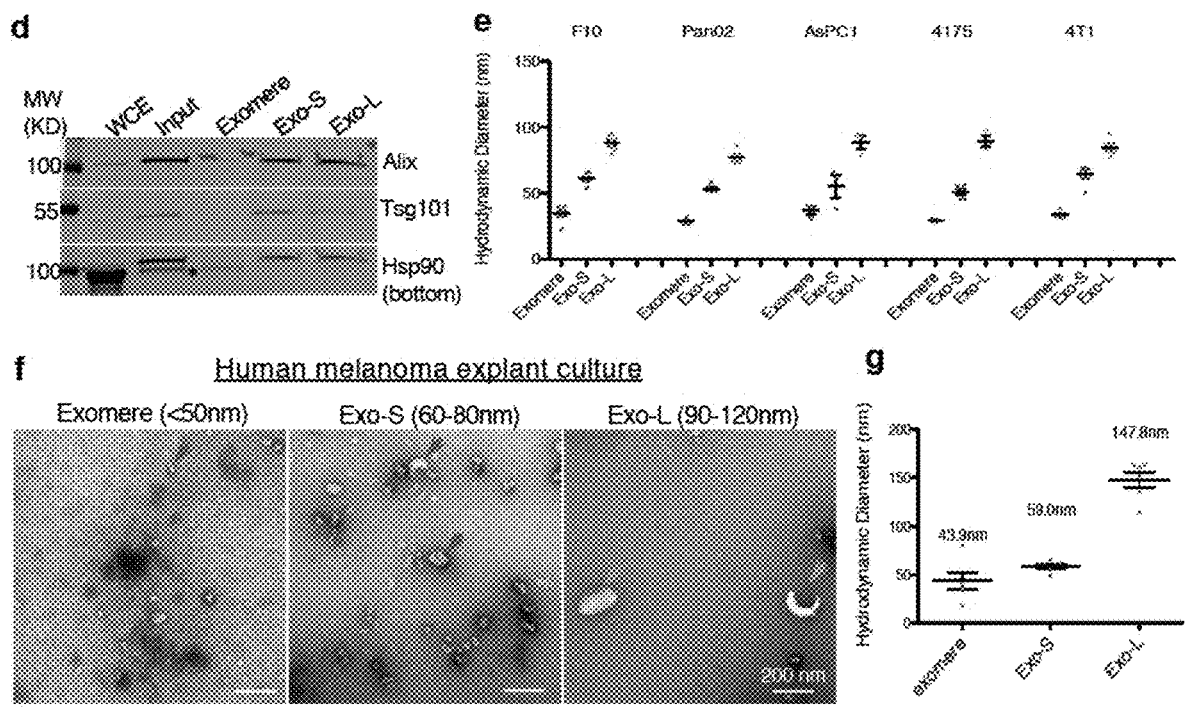
Figures 2A, 2B, 2C, 2D:
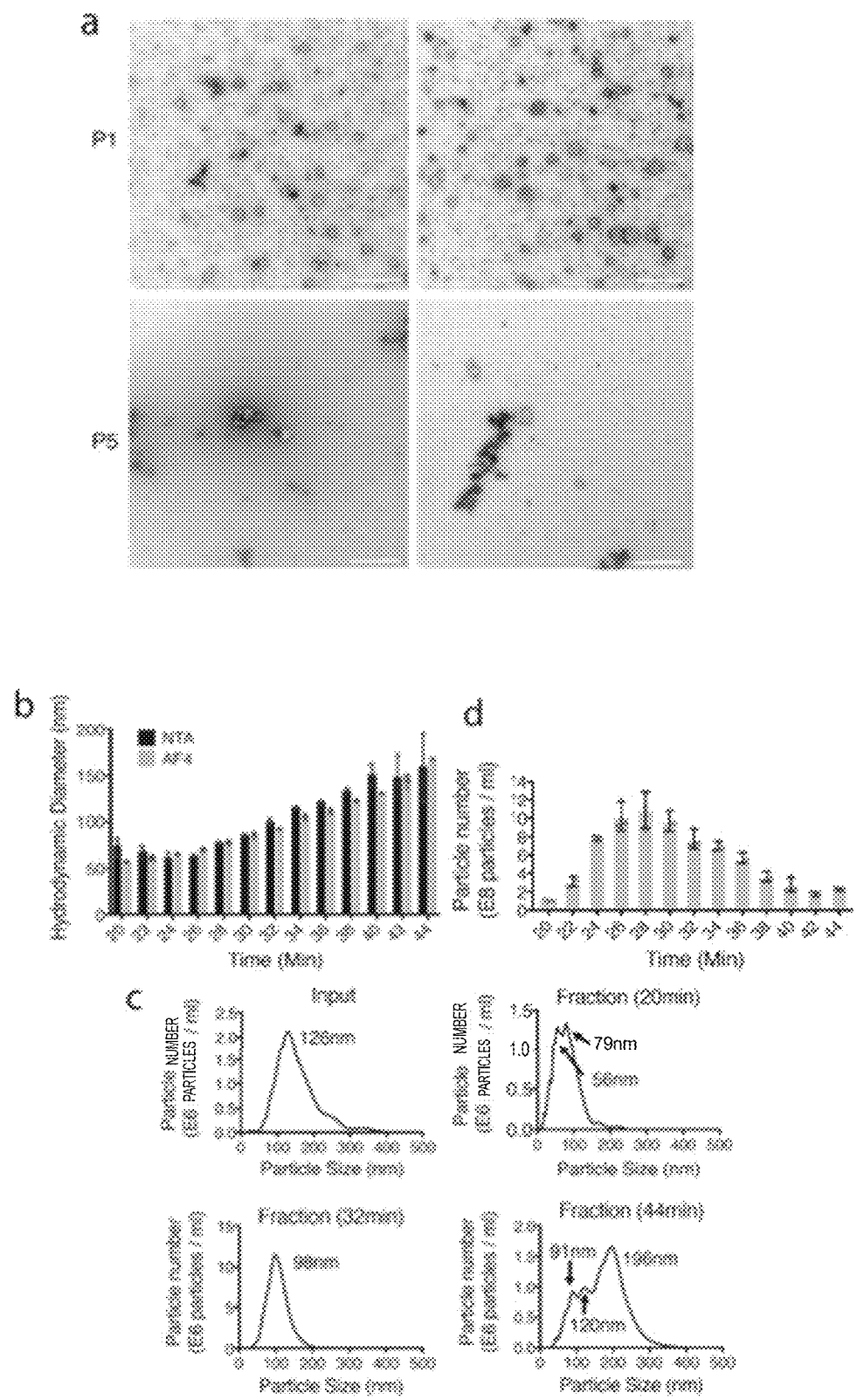
FIGS. 2A-2K shows characterization of AF4 fractions using TEM imaging and NTA analyses and examination of AF4 profiles of nanoparticles derived from cells under different culture and storage conditions.
Figures 2E, 2F, 2G, 2H, 2I, 2J, 2K:
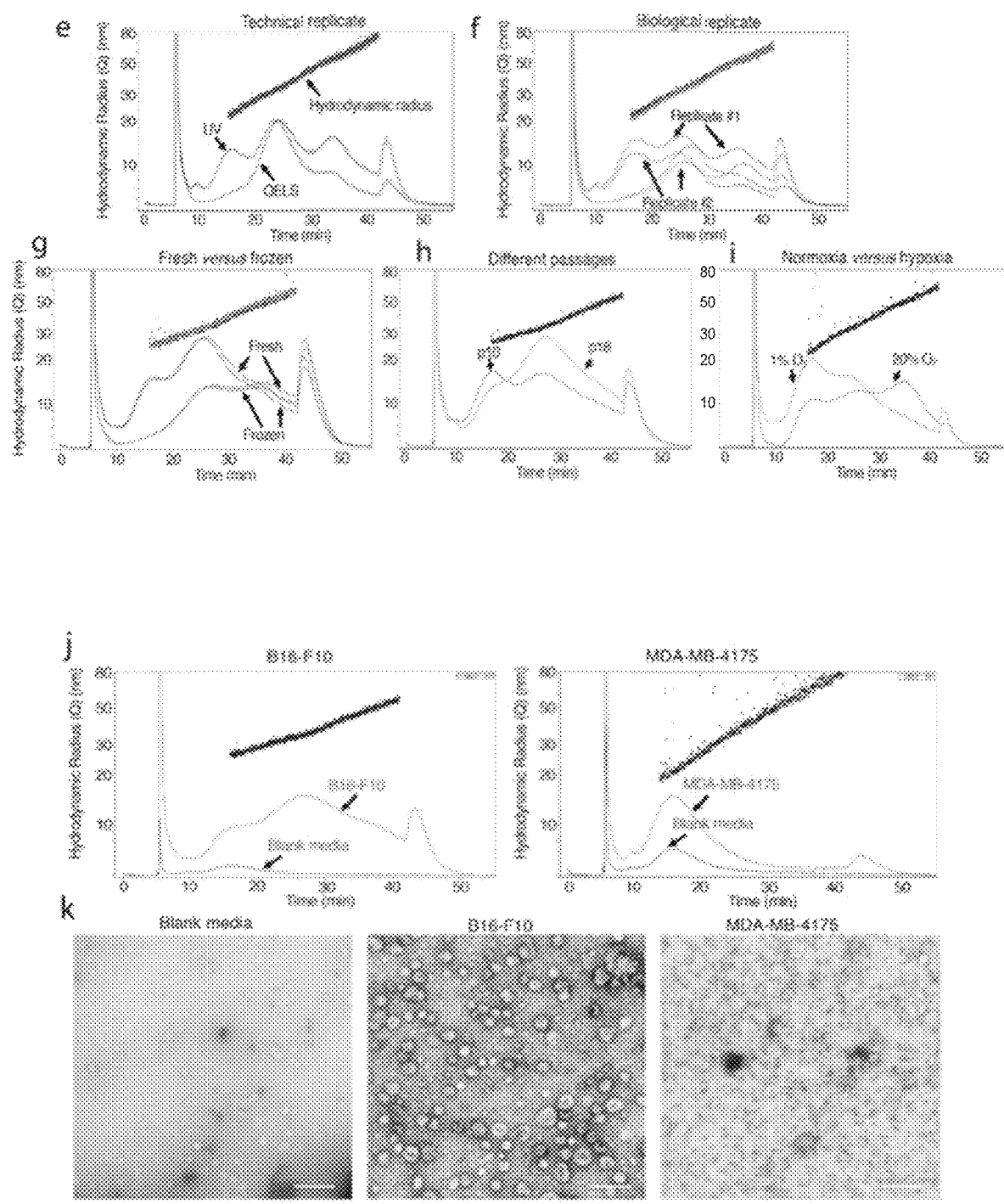
Figure 7D:
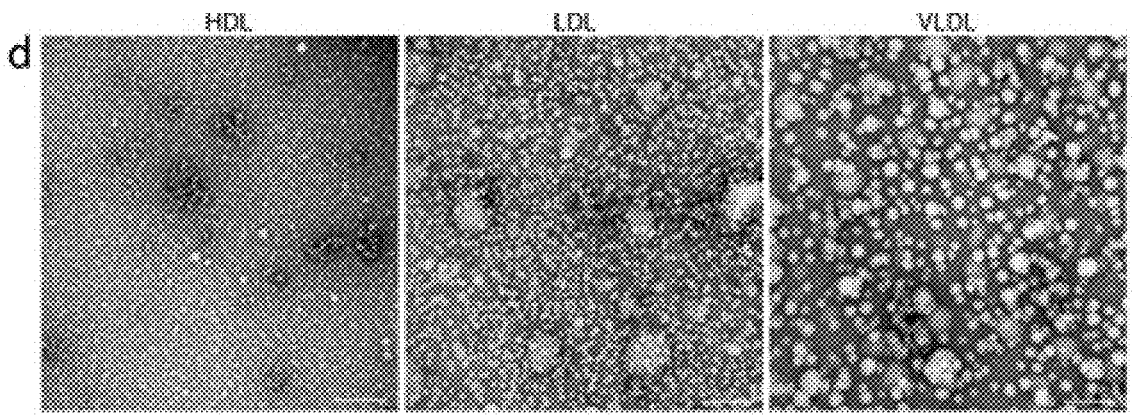
Figure 8A:
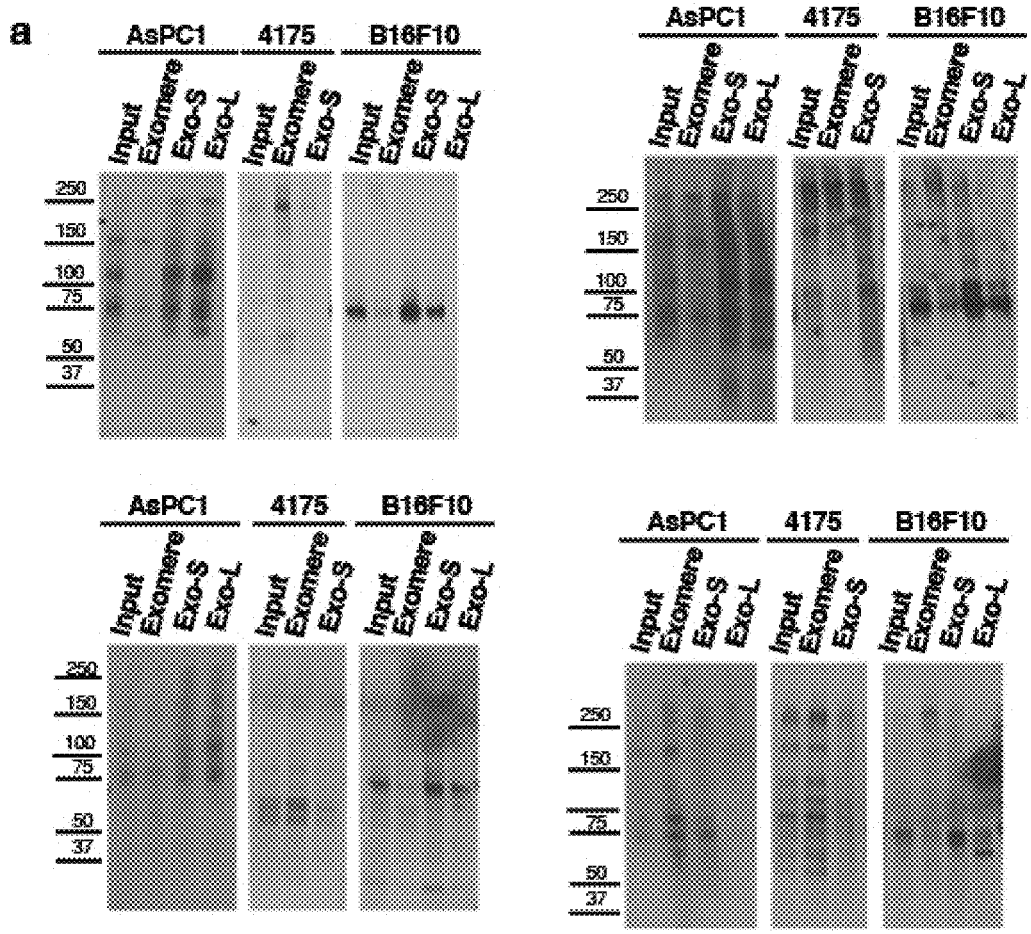
FIGS. 8A-8C show characterization of N-glycosylation of proteins associated with exomere, Exo-S and Exo-L.
Figure 8B:
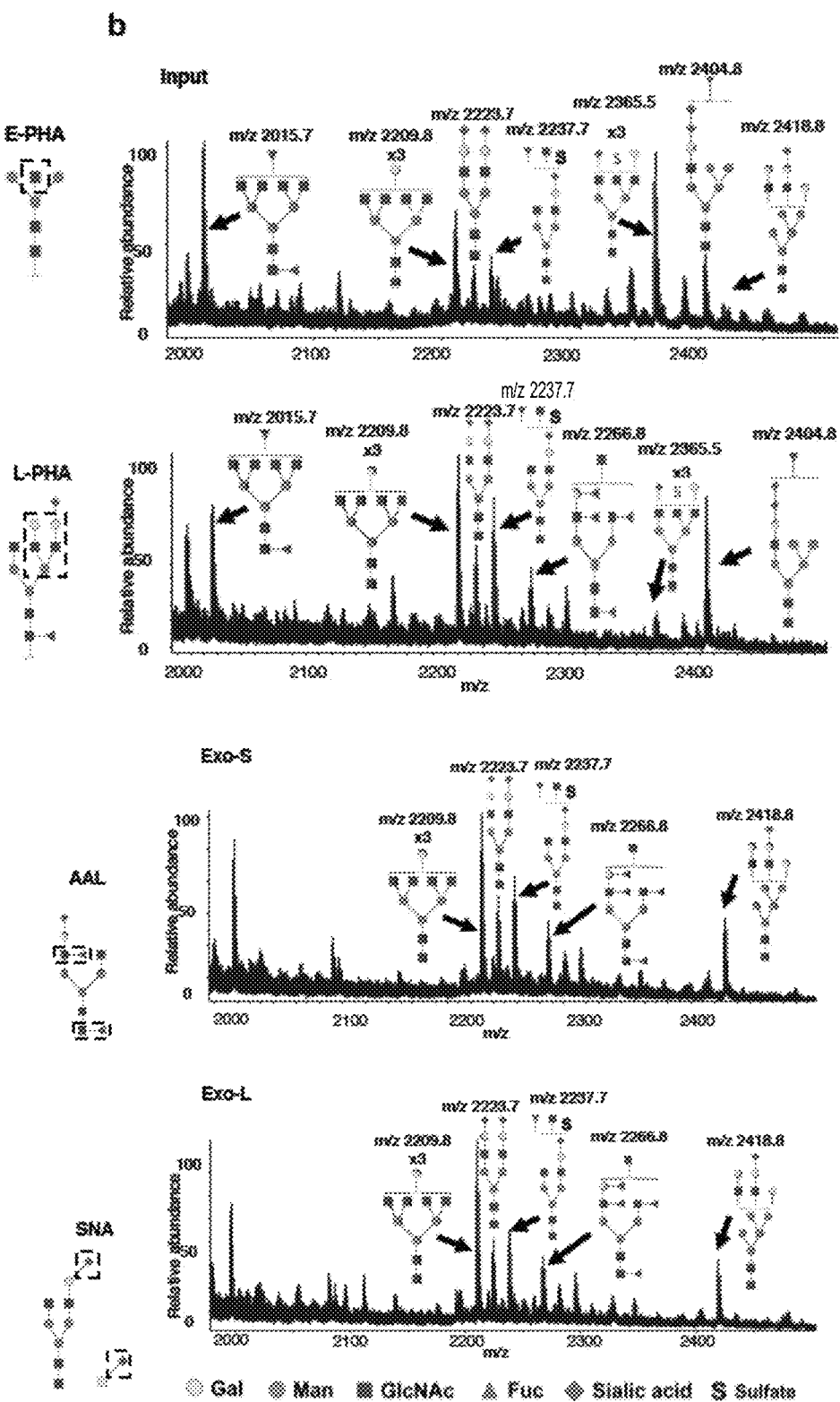
Figure 8C:
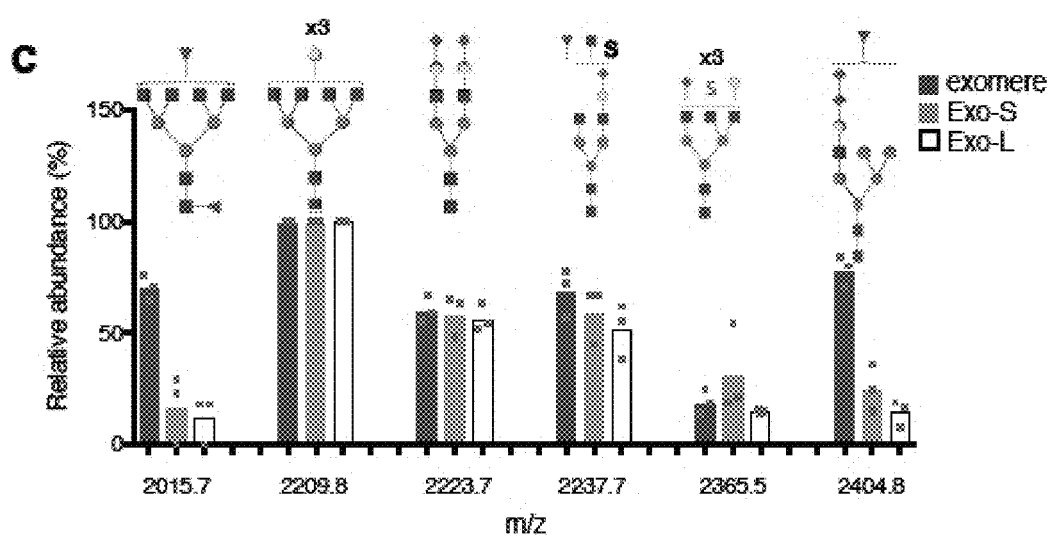
Figures 9C, 9D:
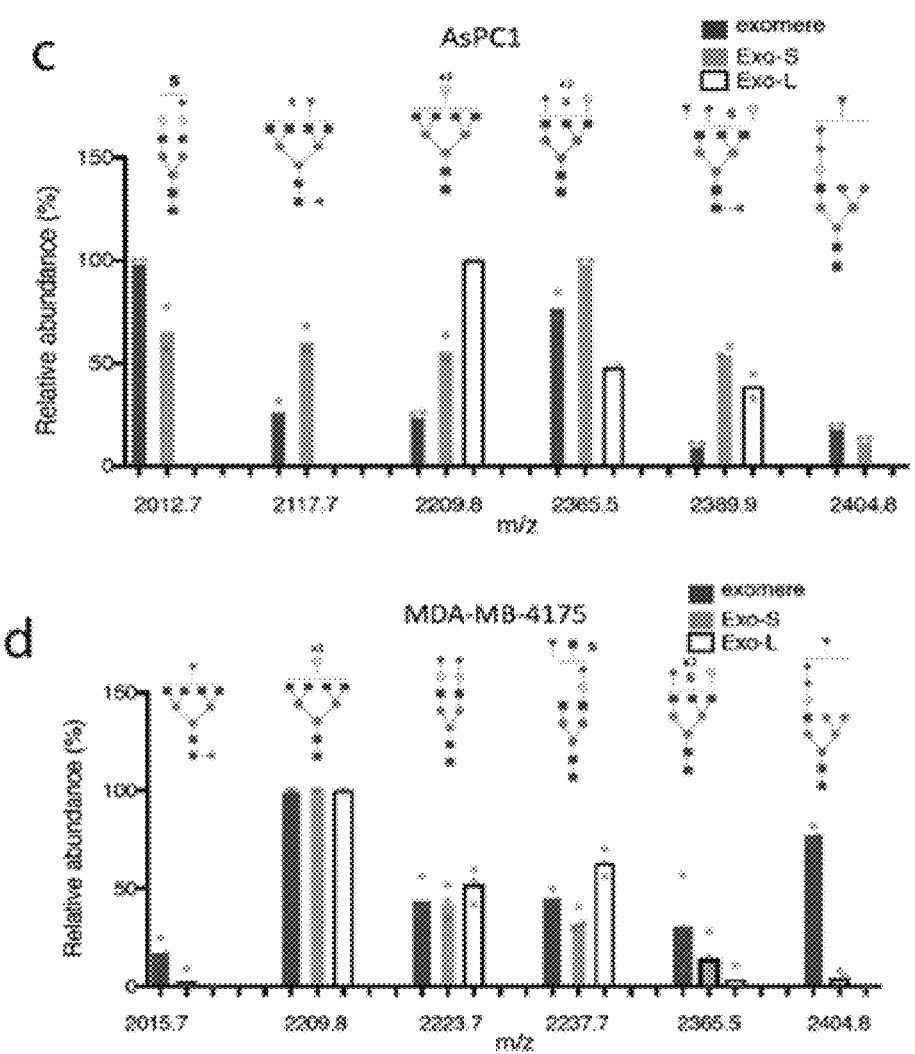
Figures 9E, 9F:
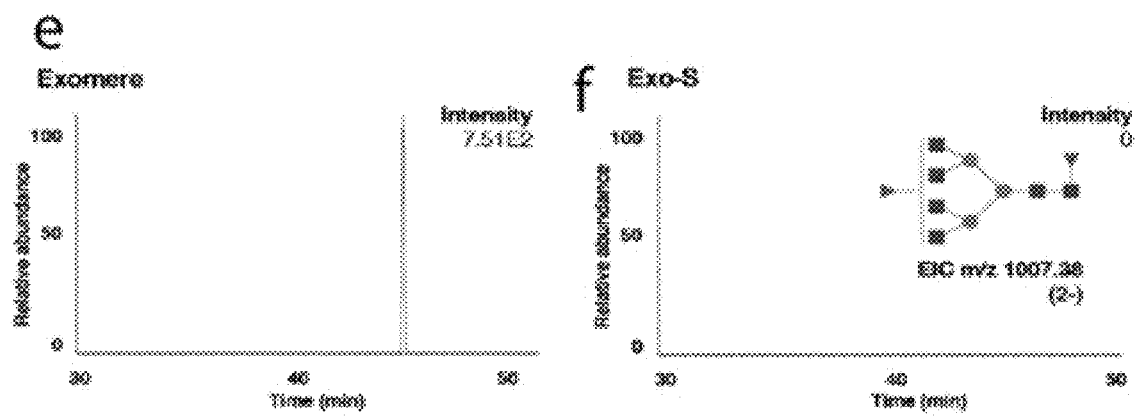
Figures 9G, 9H, 9I, 9J:
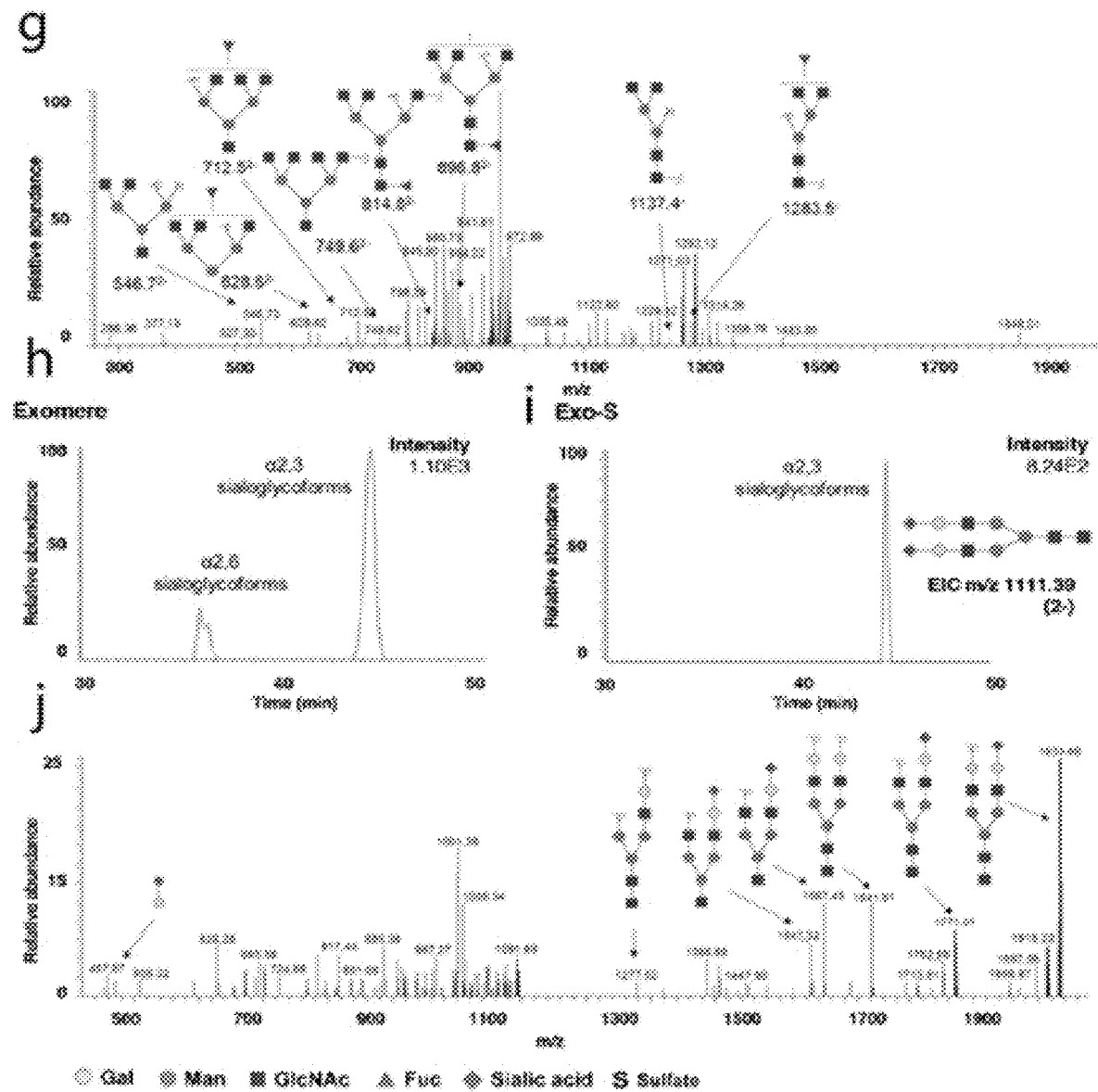

Multiple AF4 analyses were performed for each cell line studied in this work: B16-F10, >50× (repeated times); AsPC-1, 9×; Pan02, 16×; MDA-MB-4175 (4175), 17×; and 4T1, 10×. TEM imaging analysis of fractionated particles were conducted for B16-F10, 7×; AsPC-1, 3×; Pan02, 2×; 4175, 1×; and 4T1, 4×. Four independent human melanoma specimens were analyzed using AF4 and two of them were analyzed by TEM. Proteomic profiling of exomeres. Exo-S and Exo-L was performed on two biologically independent samples of each particle derived from five different cell lines (B16-F10; AsPC-1; Pan02; 4175; and 4T1). Western blotting validation of specific signature proteins of each particle subtype was done once (noted in the legend for FIG. 1D). For N-glycan study, lectin blotting was repeated independently twice except for AM- and E-PHA blotting for B16-F10 and 4175 which were done once (FIG. 8A). Glycomic MS was performed on two biologically independent B16-F10 samples and one sample of AsPC-1 and 4175 (FIGS. 9B-9D). Quantification of top 6 most abundant glycans was based on 3 independent analytical measurements of one experiment (FIG. 8C, FIGS. 9C and 9D). Silver stained-PAGE analysis was repeated independently twice for B16-F10 and 4175 and once for AsPC-1 (FIG. 9A). NanoHPLC-PGC-HRMS was done once (FIGS. 9E-9I). Lipidomic analysis was conducted on 3 biologically independent samples. DNA and RNA analyses of each particle subtype were repeated twice. Organ biodistribution analysis of each particle subtype was repeated 4× independently. NTA analysis was conducted using 3 biologically independent samples. TEM analysis was repeated 3 times for AF4 peaks P1 and P5 and once for HDL, LDL and VLDL (FIG. 7D). AF4 analysis of B16-F10 sEVs collected from technical and biological replicates, and samples kept at either 4° C. or −80° C. were repeated independently 3 times, cells of different passage numbers twice, and under hypoxic verxus normoxic conditions was repeated with 3 different cell lines independently. AF4 and TEM analysis of particles isolated from the blank media control and CM of B16-F10 and 4175 was done once (FIGS. 2J and 2K).

Independent measurements of hydrodynamic diameters of exomeres, Exo-S and Exo-L derived from different cell lines in batch mode were repeated (in the order of exomere, Exo-S and Exo-L): B16-F10 (n=10, 9, and 8 independent measurements, respectively); Pan02 (n=11, 6, 11); AsPC-1 (n=5, 5, 5); 4175 (n=3, 5, 3); 4T1 (n==5, 5, 5)). For zeta potential, independent measurements were repeated: B16-F10 (n=8, 10, 12); Pan02 (n=13, 11, 13); AsPC-1 (n=12, 12, 12); 4175 (n=17, 9, 6); 4T1 (n=13, 3, 9). For stiffness, B16-F10 (n=6, 6, 6); Pan02 (n=6, 6, 6); AsPC-1 (n=21, 19, 16); 4175 (n=11, 10, 5); 4T1 (n=9, 8, 9). For AFM imaging analysis of the height of exomeres: B16F10 (n=754 particles analyzed), AsPC1 (n=475) and 4175 (n=160). AFM imaging of exomeres was repeated with samples derived from 3 different cell lines.

For all experiments described above, all attempts at replication were successful with similar results.

Data Availability. The datasets for proteomic analysis of exomeres, Exo-S and Exo-L subpopulations derived from various cancer cell lines have been deposited.

Proteins that are uniquely associated with or among the top 50 most abundant proteins in exomere, Exo-S and Exo-L derived from different cancer cell lines are shown in Table 1 below.

TABLE 1

Tor 50 most abundant proteins identified in each subset of particles.

| exomere | Exo-S | Exo-L |
|---|---|---|
| B16F10 | | |
| HBA1/HBA2 | TYRP1 | MSPAB |
| ITIH2 | SDCBP | TYRP1 |
| GSN | SDCBP | SDCBP |
| ITIM3 | CD63 | HSPA2 |
| GAPDH | IGSF8 | RPS27A |
| ACTG1 | HSPA8 | HSPAIL |
| HISTIN2AH | MLANA | MLANA |
| H2AFX | HBA1/ | HSPA5 |
|  | HBA2 |  |
| ACTC1 | GPNMB | CD63 |
| TYRP1 | DCT | IGSF8 |
| SDCBP | HSPA2 | GPNMB |
| ENO1 | HSPAIL | Fv4 |
| PzP | H5PA5 | ENV1 |
| HSP90AB1 | Fv4 | PDCD61P |
| HSPA2 | FDCD6IP | HSPA1A/ |
|  |  | HSPA1B |
| TUBA4A | RAB7A | DCT |
| HSPAIL | ENV1 | ACTG1 |
| SERPINC1 | CD81 | ACTB |
| APOE | GNB1 | PPIA |
| TUBB | SYT4 | SLC3A2 |
| TUBB4B | GNB2 | ACTC1 |
| TUBB4A | HIST1N2AH | CD81 |
| HSPAS | GNAI2 | ITM2C |
| GALKI | GAPDH | RAB7A |
| PKM | APOE | GNB1 |
| IGSF8 | BC0359 | TSPAN4 |

TABLE 1-continued

Tor 50 most abundant proteins identified in each subset of particles.

| exomere | Exo-S | Exo-L |
|---|---|---|
| ALDH1L1 | Hist1h2a1 | DNAJA1 |
| RAN | ACTG1 | GNB2 |
| PPIA | ACTB | TFRC |
| ALB | GNB4 | HBA1/ |
|  |  | HBA2 |
| EEF1A1 | GNAI3 | GNAI2 |
| TLN1 | SLC3A2 | SYT4 |
| PDCD61P | ACTC1 | GAPDH |
| PGK1 | GNAS | APOE |
| THBS3 | SLC38A | PMEL |
| ALDH9A1 | HIST2H2BF | MFGE8 |
| RAB7A | ATP1A1 | GNB4 |
| ACO1 | TFRC | GNAI3 |
| Hist1h3b | TMEM176B | GNAO1 |
| CPNI | VAMP8 | DNAJA2 |
| GANMB | TSPAN10 | ATP1A1 |
| GDI2 | ADGRG1 | ITGB1I |
| DCT | Hist1h4a | TMEM59 |
| Gm5424 | PMEL | SLC38A2 |
| LGALS36P | PMEL | GNA12 |
| PGD | PPIA | ITM2B |
| EEF1A2 | ACTBL2 | GNAS |
| PYGL | CD9 | HIST1H2AH |
| PHGDH | BACE2 | LAMP1 |
| Hist1h4a | TSPAN4 | EEF1A1 |
| Pan02 | | |
| MBA1/ | SDCBP | ACTC1 |
| HBA2 |  |  |
| ITIN2 | PDCD6IP | ACTG1 |
| ACTB | HSPA8 | ACTB |
| ACTC1 | JGSF8 | MFGE8 |
| GSN | CD9 | ITG81 |
| SERPINC1 | PTGFRN | H5PA8 |
| NTRAI | ACTC1 | ITGA3 |
| ENO1 | LY6E | SDCBP |
| SDCBP | ACT8 | GAPDH |
| THBS1 | MFGE8 | LGALS1 |
| TUBB | HSPA2 | ENV1 |
| TUBB48 | CD81 | Fv4 |
| GAPDH | ITGA3 | YWHAZ |
| HSPA8 | ITGB1 | PPIA |
| TUBB6 | ITIH2 | GNB1 |
| TUBA4A | VPS28 | GNAI2 |
| HSP90AB1 | CD63 | GNB2 |
| PGK1 | HTRA1 | ACTBL2 |
| CD9 | ENV1 | GNA13 |
| EEF1A1 | Fv4 | CFL1 |
| TUBB4A | GSN | Marcks |
| LGAL538P | ENO1 | GNAS |
| ITGB1 | EDIL3 | EEF1A1 |
| PPIA | MVB12A | ENO1 |
| PKM | IFITM3 | BSG |
| TLN1 | SERPINC1 | Calm1 |
| HSPAS | ACTBL2 | S100A4 |
| FLNA | TUBA4A | MSN |
| PDCD61P | PP1A | EZR |
| CD81 | HSPA1A/ | RDX |
|  | HSPA1B |  |
| WDR1 | HSPAS | PTGFRN |
| CPN1 | GAPDH | PKM |
| IFITM3 | TSG1O1 | PKM |
| ENO3 | TUBB | SLC3A2 |
| PGK2 | PLEKHB2 | HBA1/ |
|  |  | HBA2 |
| HSP90B1 | TUBA1C | EDIL3 |
| ITGA3 | TUBB4B | GNA13 |
| FBLN1 | PFN1 | RHOA |
| IGSFB | GPC1 | RHOC |
| RAP1B | GJA1 | S100A6 |
| Gm5424 | EHD1 | YWHAE |
| MFGEB | GNB2 | ALDOA |
| ILK | TSPAN4 | PDCD6 |
| ADK | GNAI2 | PFN1 |
| PYGL | SLC3A2 | HSPP0AB1 |
| HPD | VPS37B | YWHAQ |

TABLE 1-continued

Tor 50 most abundant proteins identified in each subset of particles.

| exomere | Exo-S | Exo-L |
|---|---|---|
| GNB1 | GNAI3 | ANXA1 |
| ATIC | RAB7A | ANXA2 |
| AKR1B1 | EEF1A1 | ATP1A1 |
| THBS3 | GNAS | ITGA6 |

4T1

| exomere | Exo-S | Exo-L |
|---|---|---|
| Hbb-b1 | SDCBP | PDCD6IP |
| HBA1/HBA2 | HISTIN26N | SDCBP |
| HIST1H28N | HISTIN2AH | EHD1 |
| ITIH2 | HBA1/HBA2 | ITGB1 |
| HIST1H2AH | ITGB1 | 5100A6 |
| HBG2 | Hist1h4a | ITGA3 |
| H2AFX | PDCD61P | CD9 |
| Hist1H4A | HIST3N2BB | VPS37C |
| ACTG1 | H24FX | Hist1h4a |
| ACTB | CD9 | RAP1B |
| ACTC1 | CD63 | CTNNA1 |
| GSN | ITGA3 | MSN |
| HISTH2AB | ITIH2 | HISTIM2AH |
| H2AFZ | MFGEB | ITGA2 |
| Hist1h3b | H2AFZ | PTGFRN |
| Histh3A | FTGFRN | ACTG1 |
| ACTBL2 | Histh3b | HIST1H2BN |
| ENO1 | HSPA8 | Calm1 |
| GAPDH | ACTG1 | EPCAM |
| PFN1 | ACTB | ITGA6 |
| HTRA1 | ARRDC1 | YWHAE |
| TUBB | ACTC1 | HSPA1A/HSPA1B |
| TUBB2A | ITIH3 | GNB1 |
| TUBA4A | IGSFB | 5LC3A2 |
| EZR | GSN | GNB2 |
| TUBB4B | TUBA4A | EHD2 |
| TUBB4A | HISTIH1D | H2AFX |
| HSP90AB1 | TUBA1A | PP1A |
| HISTH1D | HISTIN1C | NT5E |
| HISTH1C | THBS1 | VPS4B |
| Histh1e | HSPA2 | GNB4 |
| TUBB6 | ENO1 | Cdc42 |
| PGK1 | MVB12A | SLC1A5 |
| TLN1 | HTRA1 | GNAI2 |
| PKM | GAPDH | CFL1 |
| SDCBP | Histh1e | YWHAH |
| PP1A | VPS28 | EEF1A1 |
| EEF1A1 | TSG101 | YWHAB |
| HSPA2 | TUBB | Hist1h3b |
| FLNA | TUBB4A | TSG1D1 |
| RAN | RAP1B | YWHAG |
| RAP1B | PFNI | ANXA5 |
| HSPA5 | CD81 | GNA13 |
| FBLN1 | VFS37B | F5 |
| PGK2 | TU886 | H3F3W/H3F3B |
| CPN1 | RAP1A | CHMP4B |
| WDR1 | EPCAM | MSPA5 |
| ENO3 | Hist1h1b | EZR |
| EEF2 | PPIA | GAPDH |
| PYGL | ADAM10 | CD81 |

MDA-MB-4175

| exomere | Exo-S | Exo-L |
|---|---|---|
| HBA1/HBA2 | HBA1 | EDIL3 |
| HBA1 | HIST1H2BK | HBA1/HBA2 |
| C3 | A2M | UBC |
| AFP | EDIL3 | 5DCBP |
| ITIH4 | SDC8P | HSPA8 |
| HBG2 | MFGE8 | ITGB1 |
| GSN | GSN | CD9 |
| ITIH3 | HIST2H2AC | HSPA2 |
| A2M | HIST1H2AC | ACTC1 |
| ACTG1 | H2AFX | ACTB |
| ACTC1 | ACTB | ACTG1 |
| ACTBL2 | THBS1 | PDCD6IP |
| FGB | ITIH4 | AFP |

| exomere | Exo-S | Exo-L |
|---|---|---|
| THBS1 | TUBB | HBG2 |
| ENO1 | TUBB2A | ANXA2 |
| HIST2H2AC | TUBB4B | ITGA3 |
| HISTIH2AB | FI0 | HISTIH2BK |
| HIST1H2BK | H2AFZ | GAPDH |
| COMP | TUBB4A | CD81 |
| LGALS3BP | TUBB6 | SLC3A2 |
| HIST1N2BJ | TUBB1 | GNA12 |
| GAPDH | HSPA8 | GNAI3 |
| C7 | CD9 | GNAI1 |
| TUBA4A | CD81 | ATP1A1 |
| PGK1 | GAPDH | HIST2H2AC |
| H5SP90AB1 | PFN1 | CPNE8 |
| TUBB | HIST1H4A | IST1 |
| TUBB2A | HSP90AA1 | PFN1 |
| TUBB4B | HSP90AB1 | TUBA4A |
| HIST2H2AB | HSPA2 | H2AFX |
| H2AFZ | HIST2H3A | TUBA1C |
| FBLN1 | RGK1 | HSPA5 |
| EEF1A1 | THBS2 | YWHAZ |
| TLN1 | EEF1A | ENO1 |
| HIST1H4A | GPX3 | ANXA5 |
| HSPAB | ITGB1 | GNAS |
| TUBB4A | PPIA | DNAPA1 |
| GPX3 | PDCD5IP | CHMP5 |
| PKM | EEF1A2 | EEF1A1 |
| F10 | FBLN1 | RHOA |
| THBS2 | ATTC | KRT1 |
| RAN | CPNE8 | CEPSS |
| TUBB6 | TLN1 | GNB1 |
| GSTP1 | HSPAS | ACTBL2 |
| PYGL | PKM | ITGA2 |
| EEF1A2 | HIST1H1C | EPHA2 |
| ASS1 | WDR1 | GNA13 |
| WDR1 | RAN | PPIA |
| FLNA | PYGL | RAPIA |
| HIST2H3A | ITGA3 | CD59 |

ASPC1

| exomere | Exo-S | Exo-L |
|---|---|---|
| ALB | ALB | UBC |
| HBA1/HBA2 | HBA1/HBA2 | HBA1/HBA2 |
| A2M | CD9 | CD9 |
| F2 | UBC | ACTG1 |
| ACTG1 | SDCBP | ACT8 |
| ACT8 | F2 | CD59 |
| ACTC1 | ACTG1 | MVP |
| ACTA2 | ACTB | SDCBP |
| POTEJ | CD59 | ACTC1 |
| GSN | ACTC1 | ACTA2 |
| AHCY | ACTA2 | HIST1H2BK |
| ENO1 | A2M | HIST2H2AC |
| THBS1 | HIST1N28K | ALB |
| LGALS3BP | HISTIH2BJ | HSPA8 |
| HSP90AA1 | HSPA8 | HISTIH2BJ |
| HSP90AB1 | T5PAN3 | CD55 |
| F5 | HIST2H2AC | H3F3A |
| PKM | CD55 | TSPAN3 |
| EEF1A1 | H3F3A/H3F3B | HIST2H3PS2 |
| TLN1 | HIST2H3PS2 | POTEJ |
| AHCYL2 | PDCD61P | DPP4 |
| AHCYL1 | ITGB1 | NT5E |
| EEF1A2 | POTEJ | EPCAM |
| TUBA4A | SERINC5 | VNN1 |
| PFN1 | H2AFZ | H2AFZ |
| TUBA1A | ARRDC1 | ITGB1 |
| HISTIH28K | CLDN3 | AUPPL2 |
| PRSS23 | NTSE | HIST2H2AB |
| HSP904B4P | EPCAM | ATP1A1 |
| HISTH2BJ | CDH17 | ALPP |
| TUBB4B | ATP1A1 | IST1 |
| TUBB | ALPPL2 | PDCD61P |
| A551 | HIST2H2AB | MUC13 |
| PGK1 | ALPP | ANXA11 |
| HSPA8 | HSPA2 | HSPA2 |

TABLE 1-continued

Tor 50 most abundant proteins identified in each subset of particles.

| exomere | Exo-S | Exo-L |
|---|---|---|
| ACO1 | TSPANB | CDHI7 |
| GAPDH | MVP | GPA33 |
| TUBB2A | ADAM10 | ANXA2 |
| TUBB4A | THBS1 | S100A6 |
| THBS2 | VNN1 | ATP1A2 |
| H3F3/ | ITGAV | PPIA |
| H3F3B | | |
| APOM | IGSF8 | EGFR |
| HIST2H3P52 | MYOF | TSPAN8 |
| ATR1A1 | ATP1A2 | MYOF |
| TUBB6 | AHCY | GNAI1 |
| TUBB3 | GSN | GNAI2 |
| RAN | TSPAN1 | GNAI3 |
| CAP1 | PPIA | S100A4 |
| F10 | SDCBP2 | CLDN3 |
| PPIA | HSPA5 | A2M |

Proteomics analysis of lipoprotein particles are shown in Table 2.

TABLE 2

| Accession | Gene Symbol | Gene Name | HDL | LDL | VLDL |
|---|---|---|---|---|---|
| P02768 | ALB | Serum albumin | 1.114E8 | 1.714E7 | 1.385E8 |
| P02760 | AMBP | Protein AMBP | 5.229E6 | | 4.802E7 |
| P02647 | APOA1 | Apolipoprotein A-I | 1.251E11 | 1.046E8 | 4.111E8 |
| P02652 | APOA2 | Apolipoprotein A-II | 6.485E10 | 8.811E7 | 3.404E8 |
| P06727 | APOA4 | Apolipoprotein A-IV | 7.529E8 | 1.501E7 | 3.977E7 |
| A0A087WTM7 | APOB | Apolipoprotein B-100 | 7.138E6 | 2.401E9 | 1.118E10 |
| P04114 | APOB | Apolipoprotein B-100 | 7.138E6 | 2.401E9 | 1.118E10 |
| K7ERI9 | APOC1 | Truncated apolipoprotein C-I (Fragment) | 1.144E10 | 2.412E8 | 9.354E9 |
| P02656 | APOC3 | Apolipoprotein C-III | 1.545E10 | 1.204E9 | 4.632E10 |
| K7ER74 | APOC4 | Apolipoprotein C-IV | 8.593E9 | 2.013E8 | 2.683E10 |
| P55056 | APOC4 | Apolipoprotein C-IV | 1.389E6 | 3.439E6 | 1.013E9 |
| P05090 | APDD | Apolipoprotein D | 6.067E9 | 2.328E8 | 1.093E9 |
| P02649 | APOE | Apolipoprotein E | 6.179E8 | 6.243E7 | 1.026E10 |
| Q13790 | APOF | Apolipoprotein F | 5.347E8 | 1.056E7 | |
| P02749 | APOH | Beta-2-glycoprotein 1 | | | 3.014E7 |
| O14791 | APOL1 | Apolipoprotein L1 | 7.094E8 | 8.268E6 | 2.637E7 |
| O95445 | APOM | Apolipoprotein M | 3.924E9 | 3.639E7 | 2.070E8 |
| P61769 | B2M | Beta-2-microglobulin | 6.130E6 | | 2.207E7 |
| P01024 | C3 | Complement C3 | 2.058E8 | 2.987E7 | 7.496E7 |
| B0UZ83 | C4A | Complement C4 beta chain | 1.006E8 | | 5.074E7 |
| F5GXS0 | C4B | C4b-B | 8.376E7 | | 5.074E7 |
| P49913 | CAMP | Cathelicidin antimicrobial peptide | 2.654E7 | | 1.211E8 |
| Q92496 | CFHR4 | Complement factor H-related protein 4 | | | 1.383E8 |
| P10909 | CLU | Clusterin | 4.354E7 | | 1.295E8 |
| P02671 | FGA | Fibrinogen alpha chain | | 5.793E6 | 2.376E7 |
| A0A087WU08 | HP | Haptoglobin | 2.265E6 | | 6.358E6 |
| A0A075B6H6 | IGKC | Ig kappa chain C region (Fragment) | 1.104E6 | | 2.19457 |
| P60985 | KRTDAP | Keratinocyte differentiation-associated protein | 8.309E6 | | 5.140E6 |
| P04180 | LCAT | Phosphatidylcholine-sterol acyltransferase | 2.616E7 | | |
| P08519 | LPA | Apolipoprotein(a) | | 9.171E6 | 8.704E7 |
| Q9UHG3 | PCYOX1 | Prenylcysteine oxidase 1 | 3.599E6 | 6.826E6 | 1.179E8 |
| Q13093 | PLA2G7 | Platelet-activating factor acetylhydrolase | 3.283E6 | | 3.818E7 |
| P55058 | PLTP | Phospholipid transfer protein | 2.825E7 | | |
| P27169 | PON1 | Serum paraoxonase/arylesterase 1 | 8.966E8 | 1.531E6 | 9.747E7 |
| Q15166 | PON3 | Serum paraoxonase/lactonase 3 | 3.961E8 | | 1.029E8 |
| P0DJI8 | SAA1 | Serum amyloid A-1 protein | 2.726E9 | 1.030E7 | 1.102E7 |
| P0DJI9 | SAA2 | Serum amyloid A-2 protein | 9.455E8 | 2.518E6 | 6.850E6 |
| A0A096LPE2 | SAA2-SAA4 | Protein SAA2-SAA4 | 1.620E10 | 4.256E7 | 3.075E9 |
| P01009 | SERPINA1 | Alpha-1-antitrypsin | 1.175E9 | 2.892E6 | 1.536E7 |
| P02766 | TTR | Transthyretin | 4.141E6 | | 9.975E6 |
| P04004 | VTN | Vitronectin | 1.668E7 | | 1.276E7 |

Gene set enrichment analysis (GSEA) of proteins associated with exomeres, Exo-S and Exo-L derived from various cancer cell lines are shown in Tables 3-5.

TABLE 3

GSEA for Exomeres.

| Name | Size | Es | Nes | P Value | Fdr Q Value (Cutoff < 0.05) |
|---|---|---|---|---|---|
| Hallmark_Mtorc1_Signaling | 105 | 0.45 | 2.60 | <0.001 | <0.001 |
| Hallmark_Glycolysis | 90 | 0.44 | 2.46 | <0.001 | <0.001 |

TABLE 3-continued

GSEA for Exomeres.

| Name | Size | Es | Nes | P Value | Fdr Q Value (Cutoff < 0.05) |
|---|---|---|---|---|---|
| Hallmark_Fatty_Acid_Metabolism | 53 | 0.43 | 2.11 | <0.001 | 0.002 |
| Hallmark_Myc_Targets_VI | 114 | 0.36 | 2.18 | <0.001 | 0.002 |
| Hallmark_Xenobiotic_Metabolism | 75 | 0.39 | 2.12 | <0.001 | 0.002 |
| Hallmark_Hypoxia | 75 | 0.37 | 1.99 | <0.001 | 0.004 |
| Hallmark_Unfolded_Protein_Response | 32 | 0.42 | 1.86 | 0.011 | 0.010 |
| Hallmark_Adipogenesis | 48 | 0.36 | 1.81 | 0.003 | 0.012 |
| Hallmark_Coagulation | 62 | 0.34 | 1.78 | 0.003 | 0.013 |
| Hallmark_Bile_Acid_Metabolism | 23 | 6.42 | 1.67 | 0.023 | 0.025 |
| Hallmark_Reactive_Oxigen_Species_Pathway | 24 | 0.39 | 1.60 | 0.032 | 0.037 |
| Kegg_Glycolysis_Gluconeogenesis | 32 | 0.72 | 3.22 | <0.001 | <0.001 |
| Kegg_Amino_Sugar_And_Nucleotide_Sugar_Metabolism | 23 | 0.77 | 3.12 | <0.001 | <0.001 |
| Kegg_Aminoacyl_Trna_Biosynthesis | 20 | 0.73 | 2.80 | <0.001 | <0.001 |
| Kegg_Fructose_And_Mannose_Metabolism | 16 | 0.78 | 2.78 | <0.001 | <0.001 |
| Kegg_Pentose_Phosphate_Pathway | 18 | 0.74 | 2.67 | <0.001 | <0.001 |
| Kegg_Starch_And_Sucrose_Metabolism | 18 | 0.69 | 2.58 | <0.001 | <0.001 |
| Kegg_Proteasome | 28 | 0.59 | 2.48 | <0.001 | <0.001 |
| Kegg_Drug_Metabolism_Cytochrome_P450 | 17 | 0.66 | 2.36 | 0.003 | 0.000 |
| Kegg_Glutathione_Metabolism | 29 | 0.56 | 2.36 | <0.001 | 0.000 |
| Kegg_Metabolism_Of_Xenobiotics_By_Cytochrome_P450 | 20 | 0.57 | 2.13 | 0.003 | 0.002 |
| Kegg_Cysteine_And_Methionine_Metabolism | 15 | 0.58 | 2.07 | <0.001 | 0.002 |
| Kegg_Purine_Metabolism | 40 | 0.40 | 1.93 | 0.003 | 0.007 |
| Kegg_Tyrosine_Metabolism | 15 | 0.52 | 1.83 | 0.003 | 0.013 |
| Kegg_Complement_And_Coagulation_Cascades | 31 | 0.39 | 1.69 | 0.018 | 0.030 |
| Go_Organic_Acid_Metabolic_Process | 252 | 0.52 | 3.52 | <0.001 | <0.001 |
| Go_Cellular_Amino_Acid_Metabolic_Process | 100 | 0.58 | 3.36 | <0.001 | <0.001 |
| Go_Adp_Metabolic_Process | 22 | 0.83 | 3.34 | <0.001 | <0.001 |
| Go_Oxidation_Reduction_Process | 171 | 0.51 | 3.33 | <0.001 | <0.001 |
| Go_Coenzyme_Metabolic_Process | 82 | 0.60 | 3.33 | <0.001 | <0.001 |
| Go_Nucleotide_Phosphorylation | 26 | 0.77 | 3.31 | <0.001 | <0.001 |
| Go_Oxidoreduction_Coenzyme_Metabolic_Process | 44 | 0.69 | 3.30 | <0.001 | <0.001 |
| Go_Cofactor_Metabolic_Process | 98 | 0.58 | 3.28 | <0.001 | <0.001 |
| Go_Cofactor_Binding | 54 | 0.63 | 3.27 | <0.001 | <0.001 |
| Go_Carbohydrate_Catabolic_Process | 44 | 0.67 | 3.23 | <0.001 | <0.001 |
| Go_Atp_Generation_From_Adp | 21 | 0.83 | 3.19 | <0.001 | <0.001 |
| Go_Generation_Of_Precursor_Metabolites_And_Energy | 60 | 0.61 | 3.18 | <0.001 | <0.001 |
| Go_Monosaccharide_Biosynthetic_Process | 25 | 0.76 | 3.11 | <0.001 | <0.001 |
| Go_Hexose_Catabolic_Process | 24 | 0.74 | 3.08 | <0.001 | <0.001 |
| Go_Carbohydrate_Biosynthetic_Process | 50 | 0.63 | 3.08 | <0.001 | <0.001 |
| Go_Alpha_Amino_Acid_Metabolic_Process | 67 | 0.58 | 3.08 | <0.001 | <0.001 |
| Go_Cellular_Modified_Ammo_Acid_Metabolic_Process | 76 | 0.56 | 3.07 | <0.001 | <0.001 |
| Go_Monosaccharide_Metabolic_Process | 59 | 0.58 | 3.03 | <0.001 | <0.001 |
| Go_Proteasome_Accessory_Complex | 21 | 0.75 | 3.01 | <0.001 | <0.001 |
| Go_Pyruvate_Metabolic_Process | 27 | 0.71 | 2.98 | <0.001 | <0.001 |
| Go_Hexose_Metabolic_Process | 48 | 0.62 | 2.97 | <0.001 | <0.001 |
| Go_Nadh_Metabolic_Process | 22 | 0.74 | 2.95 | <0.001 | <0.001 |
| Go_Oxidoreductase_Activity | 124 | 0.49 | 2.95 | <0.001 | <0.001 |
| Go_Small_Molecule_Metabolic_Process | 418 | 0.41 | 2.95 | <0.001 | <0.001 |
| Go_Carbohydrate_Metabolic_Process | 167 | 0.45 | 2.95 | <0.001 | <0.001 |
| Go_Small_Molecule_Biosynthetic_Process | 118 | 0.49 | 2.92 | <0.001 | <0.001 |
| Go_Monosaccharide_Catabolic_Process | 28 | 0.70 | 2.88 | <0.001 | <0.001 |
| Go_Sulfur_Compound_Metabolic_Process | 105 | 0.49 | 2.85 | <0.001 | <0.001 |
| Go_Nucleobase_Containing_Small_Molecule_Metabolic_Process | 152 | 0.45 | 2.85 | <0.001 | <0.001 |
| Go_Ribonucleoside_Diphosphate_Metabolic_Process | 31 | 0.63 | 2.85 | <0.001 | <0.001 |
| Go_Dicarboxylic_Acid_Metabolic_Process | 27 | 0.68 | 2.84 | <0.001 | <0.001 |
| Go_Monocarboxylic_Acid_Metabolic_Process | 114 | 0.48 | 2.82 | <0.001 | <0.001 |
| Go_Amino_Acid_Activation | 23 | 0.71 | 2.82 | <0.001 | <0.001 |
| Go_Glucose_Metabolic_Process | 37 | 0.60 | 2.79 | <0.001 | <0.001 |
| Go_Ligase_Activity_Forming_Carbon_Oxygen_Bonds | 20 | 0.73 | 2.79 | <0.001 | <0.001 |
| Go_Glutathione_Metabolic_Process | 29 | 0.65 | 2.79 | <0.001 | <0.001 |
| Go_Coenzyme_Binding | 35 | 0.61 | 2.78 | <0.001 | <0.001 |
| Go_Small_Molecule_Catabolic_Process | 71 | 0.53 | 2.77 | <0.001 | <0.001 |
| Go_Serine_Family_Amino_Acid_Metabolic_Process | 17 | 0.75 | 2.75 | <0.001 | <0.001 |
| Go_Tansferase_Activity_Trans-ferring_Alkyl_Or_Aryl_Other_Than_Methyl_Groups | 25 | 0.66 | 2.75 | <0.001 | <0.001 |
| Go_Nucleoside_Monophosphate_Metabolic_Process | 69 | 0.52 | 2.74 | <0.001 | <0.001 |
| Go_Nad_Binding | 20 | 0.71 | 2.73 | <0.001 | <0.001 |
| Go_Nad_Metabolic_Process | 28 | 0.65 | 2.73 | <0.001 | <0.001 |
| Go_Cellular_Carbohydrate_Metabolic_Process | 49 | 0.55 | 2.73 | <0.001 | <0.001 |
| Go_Purine_Containing_Compound_Metabolic_Process | 102 | 0.47 | 2.68 | <0.001 | <0.001 |
| Go_Glucose_Catabolic_Process | 17 | 0.76 | 2.68 | <0.001 | <0.001 |
| Go_Organic_Acid_Biosynthetic_Process | 68 | 0.52 | 2.68 | <0.001 | <0.001 |

TABLE 3-continued

GSEA for Exomeres.

| Name | Size | Es | Nes | P Value | Fdr Q Value (Cutoff < 0.05) |
|---|---|---|---|---|---|
| Go_Oxidoreductase_Activity_Acting_On_The_Ch_Oh_Group_Of_Donors_Nad_Or_Nadp_As_Acceptor | 38 | 0.58 | 2.67 | <0.001 | <0.001 |
| Go_Oxidoreductase_Activity_Acting_On_Ch_Oh_Group_Of_Donors | 40 | 0.58 | 2.67 | <0.001 | <0.001 |
| Go_Glutathione_Transferase_Activity | 15 | 0.77 | 2.66 | <0.001 | <0.001 |
| Go_Carbohydrate_Derivative_Metabolic_Process | 267 | 0.39 | 2.65 | <0.001 | <0.001 |
| Go_Trna_Metabolic_Process | 25 | 0.65 | 2.65 | <0.001 | <0.001 |
| Go_Sulfur_Compound_Biosynthetic_Process | 61 | 0.51 | 2.62 | <0.001 | <0.001 |
| Go_Carbohydrate_Binding | 68 | 0.50 | 2.61 | <0.001 | <0.001 |
| Go_Lyase_Activity | 39 | 0.56 | 2.61 | <0.001 | <0.001 |
| Go_Organic_Acid_Catabolic_Process | 27 | 0.61 | 2.60 | <0.001 | <0.001 |
| Go_Alpha_Amino_Acid_Biosynthetic_Process | 25 | 0.63 | 2.60 | <0.001 | <0.001 |
| Go_Nucleoside_Diphosphate_Metabolic_Process | 37 | 0.57 | 2.59 | <0.001 | <0.001 |
| Go_Monosaccharide_Binding | 29 | 0.58 | 2.55 | <0.001 | 0.000 |
| Go_Single_Organism_Catabolic_Process | 225 | 0.38 | 2.57 | <0.001 | 0.000 |
| Go_Nucleotide_Sugar_Metabolic_Process | 16 | 0.73 | 2.58 | <0.001 | 0.000 |
| Go_Glycosyl_Compound_Metabolic_Process | 104 | 0.43 | 2.51 | <0.001 | 0.000 |
| Go_Polysaccharide_Metabolic_Process | 31 | 0.58 | 2.52 | <0.001 | 0.000 |
| Go_Energy_Derivation_By_Oxidation_Of_Organic_Compounds | 38 | 0.54 | 2.52 | <0.001 | 0.000 |
| Go_Cellular_Amino_Acid_Biosynthetic_Process | 27 | 0.61 | 2.53 | <0.001 | 0.000 |
| Go_Cellular_Amide_Metabolic_Process | 248 | 0.38 | 2.54 | <0.001 | 0.000 |
| Go_Nucleobase_Metabolic_Process | 21 | 0.64 | 2.54 | <0.001 | 0.000 |
| Go_Cytosolic_Part | 105 | 0.43 | 2.49 | <0.001 | 0.000 |
| Go_Endoplasmic_Reticulum_Lumen | 47 | 0.51 | 2.49 | <0.001 | 0.000 |
| Go_Protein_Homotetramerization | 17 | 0.68 | 2.49 | <0.001 | 0.000 |
| Go_Cellular_Aldehyde_Metabolic_Process | 33 | 0.55 | 2.48 | <0.001 | 0.000 |
| Go_Alpha_Amino_Acid_Catabolic_Process | 77 | 0.62 | 2.46 | <0.001 | 0.000 |
| Go_Iron_Ion_Binding | 18 | 0.65 | 2.47 | <0.001 | 0.000 |
| Go_Cellular_Amino_Acid_Catabolic_Process | 22 | 0.62 | 2.47 | <0.001 | 0.000 |
| Go_Single_Organism_Biosynthetic_Process | 288 | 0.36 | 2.44 | <0.001 | 0.000 |
| Go_Oxidoreductase_Activity_Acting_On_The_Aldehyde_Or_Oxo_Group_Of_Donors | 18 | 0.65 | 2.45 | <0.001 | 0.000 |
| Go_Glutamine_Family_Amino_Acid_Metabolic_Process | 20 | 0.63 | 2.46 | <0.001 | 0.000 |
| Go_Peptide_Metabolic_Process | 203 | 0.36 | 2.38 | <0.001 | 0.000 |
| Go_Positive_Regulation_Of_Dna_Biosynthetic_Process | 20 | 0.62 | 2.38 | <0.001 | 0.000 |
| Go_Transferase_Activity_Transferring_Hexosyl_Groups | 39 | 0.52 | 2.36 | <0.001 | 0.000 |
| Go_Regulation_Of_Cellular_Amino_Acid_Metabolic_Process | 35 | 0.52 | 2.35 | <0.001 | 0.000 |
| Go_Hydrolase_Activity_Hydrolyzing_O_Glycosyl_Compounds | 26 | 0.56 | 2.34 | <0.001 | 0.000 |
| Go_Hydrolase_Activity_Acting_On_Glycosyl_Bonds | 31 | 0.54 | 2.34 | <0.001 | 0.001 |
| Go_Protein_Activation_Cascade | 27 | 0.55 | 2.34 | <0.001 | 0.001 |
| Go_Protein_Tetramerization | 34 | 0.52 | 2.32 | <0.001 | 0.001 |
| Go_Organonitrogen_Compound_Biosynthetic_Process | 309 | 0.34 | 2.32 | <0.001 | 0.001 |
| Go_Polysaccharide_Biosynthetic_Process | 18 | 0.63 | 2.30 | <0.001 | 0.001 |
| Go_Organonitrogen_Compound_Catabolic_Process | 90 | 0.40 | 2.29 | <0.001 | 0.001 |
| Go_Cellular_Carbohydrate_Biosynthetic_Process | 24 | 0.55 | 2.28 | <0.001 | 0.001 |
| Go_Proteasome_Complex | 43 | 0.48 | 2.28 | <0.001 | 0.001 |
| Go_Udp_Glycosyltransferase_Activity | 29 | 0.53 | 2.28 | <0.001 | 0.001 |
| Go_Secretory_Granule_Lumen | 25 | 0.57 | 2.28 | <0.001 | 0.001 |
| Go_Vesicle_Lumen | 37 | 0.49 | 2.27 | <0.001 | 0.001 |
| Go_Sulfur_Amino_Acid_Metabolic_Process | 17 | 0.63 | 2.26 | <0.001 | 0.001 |
| Go_Nucleoside_Triphosphate_Metabolic_Process | 52 | 0.46 | 2.26 | <0.001 | 0.001 |
| Go_Maintenance_Of_Location | 38 | 0.48 | 2.23 | <0.001 | 0.001 |
| Go_Purine_Containing_Compound_Biosynthetic_Process | 40 | 0.47 | 2.23 | <0.001 | 0.001 |
| Go_Oxidoreductase_Activity_Acting_On_The_Aldehyde_Or_Oxo_Group_Of_Donors_Nad_Or_Nadp_As_Acceptor | 15 | 0.64 | 2.22 | <0.001 | 0.001 |
| Go_Cellular_Modified_Amino_Acid_Biosynthetic_Process | 22 | 0.57 | 2.22 | <0.001 | 0.001 |
| Go_Electron_Carrier_Activity | 21 | 0.57 | 2.21 | <0.001 | 0.001 |
| Go_Regulation_Of_Telomere_Maintenance_Via_Telomere_Lengthening | 17 | 0.61 | 2.20 | <0.001 | 0.001 |
| Go_Erad_Pathway | 15 | 0.63 | 2.19 | <0.001 | 0.002 |
| Go_Regulation_Of_Cellular_Amine_Metabolic_Process | 42 | 0.46 | 2.17 | <0.001 | 0.002 |
| Go_Carbohydrate_Derivative_Biosynthetic_Process | 154 | 0.34 | 2.17 | <0.001 | 0.002 |
| Go_Microtubule | 88 | 0.38 | 2.16 | <0.001 | 0.002 |
| Go_Organophosphate_Metabolic_Process | 221 | 0.32 | 2.14 | <0.001 | 0.002 |
| Go_Carboxylic_Ester_Hydrolase_Activity | 25 | 0.52 | 2.12 | <0.001 | 0.003 |
| Go_Hydro_Lyase_Activity | 15 | 0.60 | 2.11 | <0.001 | 0.003 |
| Go_Regulation_Of_Telomere_Maintenance | 19 | 0.57 | 2.11 | <0.001 | 0.003 |
| Go_Carbon_Oxygen_Lyase_Activity | 19 | 0.55 | 2.11 | <0.001 | 0.003 |
| Go_Glucan_Metabolic_Process | 24 | 0.51 | 2.11 | <0.001 | 0.003 |
| Go_Posttranscriptional_Regulation_Of_Gene_Expression | 143 | 0.34 | 2.09 | <0.001 | 0.004 |
| Go_Tansferase_Activity_Transferring_One_Carbon_Groups | 19 | 0.55 | 2.09 | <0.001 | 0.004 |
| Go_Structural_Constituent_Of_Cytoskeleton | 44 | 0.44 | 2.07 | 0.003 | 0.005 |

TABLE 3-continued

GSEA for Exomeres.

| Name | Size | Es | Nes | P Value | Fdr Q Value (Cutoff < 0.05) |
|---|---|---|---|---|---|
| Go_Response_To_Endoplasmic_Reticulum_Stress | 54 | 0.41 | 2.06 | <0.001 | 0.005 |
| Go_Nucleoside_Monophosphate_Biosynthetic_Process | 30 | 0.48 | 2.06 | 0.003 | 0.005 |
| Go_Regulation_Of_Cellular_Ketone_Metabolic_Process | 46 | 0.42 | 2.05 | 0.003 | 0.006 |
| Go_Antigen_Processing_And_Presentation_Of_Peptide_Antigen_Via_Mhc_Class_I | 52 | 0.41 | 2.04 | <0.001 | 0.006 |
| Go_Unfolded_Protein_Binding | 47 | 0.41 | 2.03 | <0.001 | 0.006 |
| Go_Hydrolase_Activity_Acting_On_Carbon_Nitrogen_But_Not_Peptide_Bonds | 23 | 0.51 | 2.02 | 0.006 | 0.007 |
| Go_Nucleoside_Phosphate_Biosynthetic_Process | 55 | 0.40 | 2.02 | <0.001 | 0.007 |
| Go_Serine_Hydrolase_Activity | 50 | 0.40 | 2.01 | 0.003 | 0.007 |
| Go_Cellular_Catabolic_Process | 392 | 0.28 | 2.00 | <0.001 | 0.008 |
| Go_Purine_Nucleoside_Monophosphate_Biosynthetic_Process | 21 | 0.50 | 1.99 | 0.003 | 0.008 |
| Go_Monocarboxylic_Acid_Biosynthetic_Process | 36 | 0.43 | 1.99 | 0.003 | 0.008 |
| Go_Protein_Localization_To_Nucleus | 35 | 0.44 | 1.99 | 0.003 | 0.008 |
| Go_Aspartate_Family_Amino_Acid_Metabolic_Process | 17 | 0.55 | 1.99 | 0.003 | 0.008 |
| Go_T_Cell_Receptor_Signaling_Pathway | 57 | 0.39 | 1.99 | <0.001 | 0.008 |
| Go_Amide_Biosynthetic_Process | 174 | 0.31 | 1.98 | <0.001 | 0.009 |
| Go_Metalloexopeptidase_Activity | 16 | 0.55 | 1.98 | 0.003 | 0.009 |
| Go_Nucleotidyltransferase_Activity | 15 | 0.55 | 1.98 | 0.005 | 0.009 |
| Go_Exopeptidase_Activity | 37 | 0.43 | 1.97 | 0.003 | 0.009 |
| Go_Ligase_Activity_Forming_Carbon_Nitrogen_Bonds | 17 | 0.52 | 1.94 | 0.014 | 0.011 |
| Go_Nuclear_Export | 27 | 0.47 | 1.94 | <0.001 | 0.011 |
| Go_Anaphase_Promoting_Complex_Dependent_Catabolic_Process | 42 | 0.40 | 1.94 | <0.001 | 0.011 |
| Go_Positive_Regulation_Of_Canonical_Wnt_Signaling_Pathway | 53 | 0.38 | 1.93 | <0.001 | 0.012 |
| Go_Regulation_Of_Dna_Biosynthetic_Process | 26 | 0.45 | 1.92 | 0.006 | 0.013 |
| Go_Coenzyme_Biosynthetic_Process | 29 | 0.45 | 1.92 | 0.006 | 0.013 |
| Go_Meiotic_Cell_Cycle | 17 | 0.52 | 1.91 | 0.003 | 0.014 |
| Go_Organic_Cyclic_Compound_Catabolic_Process | 143 | 0.31 | 1.90 | <0.001 | 0.015 |
| Go_Blood_Microparticle | 50 | 0.37 | 1.89 | <0.001 | 0.016 |
| Go_Aminopeptidase_Activity | 18 | 0.51 | 1.89 | 0.003 | 0.016 |
| Go_Antigen_Processing_And_Presentation_Of_Exogenous_Peptide_Antigen_Via_Mhc_Class_I | 39 | 0.42 | 1.89 | <0.001 | 0.016 |
| Go_Platelet_Alpha_Granule_Lumen | 19 | 0.49 | 1.88 | 0.003 | 0.017 |
| Go_Innate_Immune_Response_Activating_Cell_Surface_Receptor_Signaling_Pathway | 53 | 0.37 | 1.88 | <0.001 | 0.017 |
| Go_Energy_Reserve_Metabolic_Process | 28 | 0.43 | 1.87 | 0.008 | 0.018 |
| Go_Antigen_Receptor_Mediated_Signaling_Pathway | 63 | 0.36 | 1.87 | <0.001 | 0.018 |
| Go_Cellular_Ketone_Metabolic_Process | 18 | 0.49 | 1.87 | 0.011 | 0.018 |
| Go_Transferase_Activity_Transferring_Glycosyl_Groups | 55 | 0.38 | 1.87 | <0.001 | 0.018 |
| Go_Myelin_Sheath | 99 | 0.32 | 1.86 | <0.001 | 0.019 |
| Go_Sarcoplasm | 19 | 0.49 | 1.86 | 0.008 | 0.019 |
| Go_Heparin_Binding | 45 | 0.38 | 1.85 | 0.009 | 0.020 |
| Go_Pyrimidme_Containing_Compound_Metabolic_Process | 22 | 0.47 | 1.85 | 0.003 | 0.020 |
| Go_Cofactor_Biosynthetic_Process | 35 | 0.40 | 1.84 | 0.006 | 0.021 |
| Go_Organic_Acid_Binding | 56 | 0.36 | 1.84 | <0.001 | 0.021 |
| Go_Regulation_Of_Reproductive_Process | 24 | 0.45 | 1.83 | 0.012 | 0.022 |
| Go_Sulfur_Compound_Binding | 63 | 0.35 | 1.83 | <0.001 | 0.022 |
| Go_Ribonucleoprotein_Complex_Localization | 18 | 0.50 | 1.82 | 0.016 | 0.023 |
| Go_Positive_Regulation_Of_Chromosome_Organization | 30 | 0.42 | 1.82 | 0.003 | 0.023 |
| Go_Extracellular_Matrix | 126 | 0.30 | 1.83 | <0.001 | 0.023 |
| Go_Inclusion_Body | 20 | 0.47 | 1.82 | 0.010 | 0.023 |
| Go_Regulation_Of_Cellular_Amide_Metabolic_Process | 97 | 0.32 | 1.82 | <0.001 | 0.023 |
| Go_Positive_Regulation_Of_Wnt_Signaling_Pathway | 60 | 0.35 | 1.81 | <0.001 | 0.024 |
| Go_Positive_Regulation_Of_Dna_Replication | 27 | 0.42 | 1.81 | 0.008 | 0.025 |
| Go_Fc_Epsilon_Receptor_Signaling_Pathway | 57 | 0.36 | 1.80 | <0.001 | 0.027 |
| Go_Hormone_Metabolic_Process | 35 | 0.40 | 1.80 | <0.001 | 0.027 |
| Go_Actin_Filament_Binding | 57 | 0.35 | 1.79 | <0.001 | 0.027 |
| Go_Cell_Redox_Homeostasis | 18 | 0.47 | 1.79 | 0.020 | 0.028 |
| Go_Nik_Nf_Kappab_Signaling | 45 | 0.37 | 1.78 | 0.015 | 0.029 |
| Go_Cellular_Lipid_Catabolic_Process | 25 | 0.43 | 1.78 | 0.008 | 0.030 |
| Go_Ncrna_Metabolic_Process | 102 | 0.31 | 1.78 | 0.003 | 0.030 |
| Go_Regulation_Of_Dna_Replication | 36 | 0.39 | 1.77 | 0.012 | 0.031 |
| Go_Isomerase_Activity | 43 | 0.38 | 1.76 | <0.001 | 0.032 |
| Go_Sister_Chromatid_Cohesion | 18 | 0.49 | 1.75 | 0.017 | 0.035 |
| Go_Purine_Containing_Compound_Catabolic_Process | 15 | 0.51 | 1.75 | 0.010 | 0.036 |
| Go_Rna_Localization | 33 | 0.39 | 1.74 | 0.014 | 0.037 |
| Go_Extracellular_Matrix_Structural_Constituent | 19 | 0.45 | 1.74 | 0.026 | 0.037 |
| Go_Response_To_Topologically_Incorrect_Protein | 43 | 0.37 | 1.74 | 0.015 | 0.037 |
| Go_Negative_Regulation_Of_Cellular_Amide_Metabolic_Process | 29 | 0.40 | 1.74 | 0.006 | 0.038 |
| Go_Organic_Hydroxy_Compound_Metabolic_Process | 102 | 0.29 | 1.73 | <0.001 | 0.038 |
| Go_Adenyl_Nucleotide_Binding | 425 | 0.24 | 1.73 | <0.001 | 0.040 |
| Go_Protein_Serine_Threonine_Phosphatase_Activity | 16 | 0.48 | 1.72 | 0.015 | 0.041 |
| Go_Antigen_Processing_And_Presentation_Of_Peptide_Antigen | 80 | 0.31 | 1.72 | 0.003 | 0.041 |

TABLE 3-continued

GSEA for Exomeres.

| Name | Size | Es | Nes | P Value | Fdr Q Value (Cutoff < 0.05) |
|---|---|---|---|---|---|
| Go_Glycosyl_Compound_Biosynthetic_Process | 35 | 0.38 | 1.72 | 0.020 | 0.042 |
| Go_Mitochondrion | 256 | 0.25 | 1.71 | <0.001 | 0.044 |
| Go_Proteoglycan_Metabolic_Process | 18 | 0.46 | 1.71 | 0.011 | 0.044 |
| Go_Supramolecular_Fiber | 153 | 0.27 | 1.69 | <0.001 | 0.048 |
| Go_Translation_Factor_Activity_Rna_Binding | 40 | 0.37 | 1.69 | 0.012 | 0.049 |

Es, Enrichment Score;
Nes, Normalized Enrichment Score;
Fdr, False Discovery Rate

TABLE 4

GSEA for Exo-S

| Name | Size | Es | Nes | P Value | Fdr Q Value (Cutoff < 0.05) |
|---|---|---|---|---|---|
| Hallmark_Apical_Surface | 16 | 0.58 | 2.16 | <0.001 | 0.005 |
| Hallmark_Protein_Secretion | 69 | 0.33 | 1.90 | <0.001 | 0.023 |
| Kegg_Ecm_Receptor_Interaction | 47 | 0.52 | 2.73 | <0.001 | <0.001 |
| Keg_Snare_Interactions_In_Vesicular_Transport | 23 | 0.53 | 2.26 | <0.001 | 0.004 |
| Kegg_Small_Cell_Lung_Cancer | 25 | 0.45 | 1.96 | <0.001 | 0.024 |
| Go_Intrinsic_Component_Of_Plasma_Membrane | 383 | 0.36 | 2.75 | <0.001 | 0.001 |
| Go_Late_Endosome_Membrane | 59 | 0.51 | 2.77 | <0.001 | 0.001 |
| Go_Endosomal_Part | 214 | 0.36 | 2.58 | <0.001 | 0.001 |
| Go_Vacuolar_Membrane | 293 | 0.33 | 2.49 | <0.001 | 0.001 |
| Go_Phagocytic_Vesicle_Membrane | 32 | 0.54 | 2.46 | <0.001 | 0.001 |
| Go_Late_Endosome | 106 | 0.40 | 2.50 | <0.001 | 0.001 |
| Go_Phagocytic_Vesicle | 46 | 0.50 | 2.50 | <0.001 | 0.001 |
| Go_Organelle_Membrane_Fusion | 39 | 0.50 | 2.46 | <0.001 | 0.001 |
| Go_Lytic_Vacuole_Membrane | 139 | 0.38 | 2.51 | <0.001 | 0.002 |
| Go_Endosome | 341 | 0.33 | 2.53 | <0.001 | 0.002 |
| Go_Extracellular_Structure_Organization | 119 | 0.38 | 2.45 | <0.001 | 0.002 |
| Go_Secretory_Granule_Membrane | 34 | 0.52 | 2.41 | <0.001 | 0.002 |
| Go_Single_Organism_Membrane_Fusion | 44 | 0.46 | 2.39 | <0.001 | 0.002 |
| Go_Vacuolar_Part | 332 | 0.31 | 2.39 | <0.001 | 0.002 |
| Go_Organelle_Fusion | 46 | 0.45 | 2.37 | <0.001 | 0.002 |
| Go_Monovalent_Inorganic_Cation_Transport | 64 | 0.41 | 2.36 | <0.001 | 0.003 |
| Go_Receptor_Activity | 216 | 0.32 | 2.33 | <0.001 | 0.004 |
| Go_Phagosome_Maturation | 23 | 0.57 | 2.31 | <0.001 | 0.004 |
| Go_Lipid_Transporter_Activity | 25 | 0.54 | 2.31 | <0.001 | 0.004 |
| Go_Vacuolar_Transport | 119 | 0.34 | 2.24 | <0.001 | 0.007 |
| Go_Atpase_Activity_Coupled_To_Movement_Of_Substances | 49 | 0.43 | 2.25 | <0.001 | 0.007 |
| Go_Sterol_Homeostasis | 24 | 0.52 | 2.23 | <0.001 | 0.007 |
| Go_Snap_Receptor_Activty | 23 | 0.53 | 2.23 | <0.001 | 0.008 |
| Go_Regulation_Of_Membrane_Lipid_Distribution | 16 | 0.62 | 2.21 | <0.001 | 0.008 |
| Go_Growth_Factor_Receptor_Binding | 32 | 0.47 | 2.20 | <0.001 | 0.009 |
| Go_Phagosome_Acidification | 15 | 0.59 | 2.17 | <0.001 | 0.010 |
| Go_Monovalent_Inorganc_Cation_Transmembrane_Transporter_Activity | 53 | 0.40 | 2.17 | <0.001 | 0.010 |
| Go_Signaling_Receptor_Activity | 160 | 0.32 | 2.18 | <0.001 | 0.010 |
| Go_Vacuole_Organization | 71 | 0.39 | 2.18 | <0.001 | 0.010 |
| Go_active_Transmembrane_Transporter_Activity | 93 | 0.35 | 2.14 | <0.001 | 0.012 |
| Go_Establishment_Of_Protein_Localization_To_Plasma_Membrane | 51 | 0.40 | 2.12 | 0.003 | 0.014 |
| Go_Sodium_Ion_Transport | 30 | 0.45 | 2.10 | <0.001 | 0.016 |
| Go_Vacuole | 491 | 0.25 | 2.08 | <0.001 | 0.017 |
| Go_Extracellular_Matrix_Disassembly | 33 | 0.45 | 2.09 | <0.001 | 0.017 |
| Go_Establishment_Of_Protein_Localization_To_Vacuole | 17 | 0.55 | 2.08 | 0.003 | 0.017 |
| Go_Regulation_Of_Receptor_Mediated_Endocytosis | 25 | 0.48 | 2.07 | <0.001 | 0.018 |
| Go_Movement_In_Environment_Of_Other_Organism_Involved_In_Symbiotic_Interaction | 45 | 0.41 | 2.07 | <0.001 | 0.018 |
| Go_Cellular_Monovalent_Inorganic_Cation_Homeostasis | 35 | 0.43 | 2.06 | <0.001 | 0.018 |
| Go_Protein_Localization_To_Vacuole | 29 | 0.45 | 2.06 | 0.006 | 0.019 |
| Go_Multivesicular_Body | 19 | 0.52 | 2.04 | 0.003 | 0.022 |
| Go_Monovalent_Inorganic_Cation_Homeostasis | 36 | 0.42 | 2.04 | <0.001 | 0.022 |
| Go_Positive_Regulation_Of_Exocytosis | 37 | 0.41 | 2.03 | <0.001 | 0.023 |
| Go_Endodermal_Cell_Differentiation | 15 | 0.55 | 2.01 | 0.003 | 0.027 |
| Go_Endocytic_Vesicle | 110 | 0.31 | 2.00 | <0.001 | 0.027 |
| Go_Membrane_Fusion | 52 | 0.36 | 1.98 | 0.003 | 0.029 |
| Go_Gdp_Binding | 37 | 0.40 | 1.99 | <0.001 | 0.029 |
| Go_Multivescular_Body_Organization | 28 | 0.44 | 1.98 | <0.001 | 0.030 |
| Go_Positive_Regulation_Of_Cell_Cell_Adhesion | 58 | 0.36 | 1.98 | <0.001 | 0.030 |

TABLE 4-continued

GSEA for Exo-S

| Name | Size | Es | Nes | P Value | Fdr Q Value (Cutoff < 0.05) |
|---|---|---|---|---|---|
| Go_Regulation_Of_Muscle_Cell_Differentiation | 33 | 0.43 | 1.97 | 0.006 | 0.031 |
| Go_Protein_Localization_To_Cell_Periphery | 66 | 0.35 | 1.97 | <0.001 | 0.031 |
| Go_Transmembrane_Receptor_Protein_Kinase_Activity | 46 | 0.37 | 1.94 | 0.003 | 0.032 |
| Go_Cation_Transmembrane_Transporter_Activity | 104 | 0.31 | 1.95 | <0.001 | 0.032 |
| Go_Gastrulation | 47 | 0.37 | 1.96 | 0.003 | 0.032 |
| Go_Ph_Reduction | 19 | 0.48 | 1.94 | 0.009 | 0.032 |
| Go_Positive_Regulation_Of_Endocytosis | 41 | 0.39 | 1.95 | 0.003 | 0.032 |
| Go_Regulation_Of_Cellular_Response_To_Growth_Factor_Stimulus | 72 | 0.33 | 1.94 | <0.001 | 0.032 |
| Go_Regulation_Of_Cellular_Ph | 27 | 0.44 | 1.94 | <0.001 | 0.032 |
| Go_Lytic_Vacuole | 231 | 0.27 | 1.95 | <0.001 | 0.032 |
| Go_Positive_Regulation_Of_Synaptic_Transmission | 18 | 0.50 | 1.96 | 0.009 | 0.032 |
| Go_Plasma_Membrane_Raft | 43 | 0.38 | 1.96 | 0.007 | 0.032 |
| Go_Snare_Complex | 28 | 0.43 | 1.95 | 0.006 | 0.032 |
| Go_Extracellular_Matrix_Component | 49 | 0.37 | 1.93 | <0.001 | 0.033 |
| Go_Lytic_Vacuole_Organization | 19 | 0.48 | 1.93 | 0.003 | 0.033 |
| Go_Early_Endosome | 129 | 0.29 | 1.92 | <0.001 | 0.034 |
| Go_Regulation_Of_Ph | 28 | 0.43 | 1.91 | <0.001 | 0.035 |
| Go_Recycling_Endosome | 57 | 0.35 | 1.91 | <0.001 | 0.036 |
| Go_Membrane_Protein_Complex | 279 | 0.25 | 1.91 | <0.001 | 0.036 |
| Go_Cytokine_Receptor_Binding | 45 | 0.36 | 1.89 | <0.001 | 0.040 |
| Go_Regulation_Of_Cellular_Response_To_Transforming_Growth_Factor_Beta_Stimulus | 37 | 0.39 | 1.88 | 0.003 | 0.040 |
| Go_Sh3_Domain_Binding | 38 | 0.38 | 1.88 | 0.003 | 0.041 |
| Go_Trivalent_Inorganic_Cation_Transport | 24 | 0.44 | 1.87 | 0.015 | 0.043 |
| Go_Regulation_Of_Toll_Like_Receptor_Signaling_Pathway | 15 | 0.51 | 1.87 | 0.006 | 0.044 |
| Go_Endosome_Organization | 37 | 0.38 | 1.86 | 0.003 | 0.044 |
| Go_Appendage_Development | 30 | 0.41 | 1.86 | 0.009 | 0.044 |
| Go_Escrt_Complex | 22 | 0.46 | 1.86 | 0.003 | 0.044 |
| Go_Virus_Receptor_Activity | 34 | 0.40 | 1.85 | 0.006 | 0.046 |
| Go_Lysosomal_Transport | 25 | 0.42 | 1.85 | 0.006 | 0.048 |
| Go_Lipid_Homeostasis | 28 | 0.42 | 1.84 | <0.001 | 0.048 |

Es, Enrichment Score;
Nes, Normalized Enrichment Score;
Fdr, False Discovery Rate

TABLE 5

GSEA for Exo-L.

| Name | Size | Es | Nes | P Value | Fdr Q Value (Cutoff < 0.25) |
|---|---|---|---|---|---|
| Hallmark_Mitotic_Spindle | 72 | 0.40 | 1.87 | <0.001 | 0.011 |
| Hallmark_Uv_Response_Dn | 55 | 0.41 | 1.83 | 0.002 | 0.014 |
| Hallmark_Il2_Stat5_Signaling | 64 | 0.41 | 1.89 | <0.001 | 0.019 |
| Hallmark_P53_Pathway | 53 | 0.40 | 1.75 | <0.001 | 0.026 |
| Kegg_Long_Term_Depression | 29 | 0.49 | 1.87 | 0.008 | 0.020 |
| Kegg_Cell_Cycle | 22 | 0.55 | 1.88 | <0.001 | 0.022 |
| Kegg_Regulation_Of_Actin_Cytoskeleton | 110 | 0.37 | 1.94 | 0.001 | 0.023 |
| Kegg_Endocytosis | 105 | 0.39 | 2.05 | <0.001 | 0.024 |
| Kegg_Tight_Junction | 61 | 0.44 | 1.98 | <0.001 | 0.025 |
| Kegg_Phosphatidylinositol_Signaling_System | 18 | 0.57 | 1.88 | 0.002 | 0.025 |
| Kegg_Melanogenesis | 38 | 0.46 | 1.91 | 0.002 | 0.026 |
| Kegg_Chemokine_Signaling_Pathway | 65 | 0.39 | 1.78 | 0.003 | 0.037 |
| Kegg_Snare_Interactions_In_Vesicular_Transport | 23 | 0.50 | 1.74 | 0.006 | 0.048 |
| Go_Multivesicular_Body_Organization | 28 | 0.69 | 2.63 | <0.001 | <0.001 |
| Go_Endosome_Organization | 37 | 0.63 | 2.55 | <0.001 | <0.001 |
| Go_Cell_Separation_After_Cytokinesis | 16 | 0.77 | 2.51 | <0.001 | 0.000 |
| Go_Small_Gtpase_Mediated_Signal_Transduction | 145 | 0.44 | 2.41 | <0.001 | 0.000 |
| Go_Multi_Organism_Organelle_Organization | 21 | 0.70 | 2.41 | <0.001 | 0.000 |
| Go_Endomembrane_System_Organization | 178 | 0.42 | 2.31 | <0.001 | 0.000 |
| Go_Ras_Protein_Signal_Transduction | 64 | 0.50 | 2.29 | <0.001 | 0.000 |
| Go_Multi_Organism_Membrane_Organization | 23 | 0.66 | 2.31 | <0.001 | 0.001 |
| Go_Metaphase_Plate_Congression | 19 | 0.70 | 2.30 | <0.001 | 0.001 |
| Go_Escrt_Complex | 22 | 0.69 | 2.45 | <0.001 | 0.001 |
| Go_Cytokinesis | 36 | 0.58 | 2.33 | <0.001 | 0.001 |
| Go_Cytoplasmic_Side_Of_Membrane | 70 | 0.48 | 2.26 | <0.001 | 0.001 |
| Go_Virion_Assembly | 31 | 0.59 | 2.24 | <0.001 | 0.001 |
| Go_Intercalated_Disc | 26 | 0.60 | 2.22 | <0.001 | 0.001 |
| Go_Mitotic_Sister_Chromatid_Segregation | 28 | 0.59 | 2.23 | <0.001 | 0.001 |
| Go_Mitotic_Cytokinesis | 20 | 0.65 | 2.21 | <0.001 | 0.002 |

TABLE 5-continued

GSEA for Exo-L.

| Name | Size | Es | Nes | P Value | Fdr Q Value (Cutoff < 0.25) |
|---|---|---|---|---|---|
| Go_Regulation_Of_Exosomal_Secretion | 15 | 0.70 | 2.20 | <0.001 | 0.002 |
| Go_Signal_Release | 39 | 0.54 | 2.20 | <0.001 | 0.002 |
| Go_Chromosome_Localization | 21 | 0.62 | 2.17 | <0.001 | 0.003 |
| Go_Nucleus_Organization | 37 | 0.53 | 2.17 | <0.001 | 0.003 |
| Go_Midbody | 64 | 0.47 | 2.17 | <0.001 | 0.003 |
| Go_Neurotransmitter_Transport | 37 | 0.53 | 2.15 | <0.001 | 0.003 |
| Go_Autophagy | 115 | 0.41 | 2.15 | <0.001 | 0.003 |
| Go_Presynaptic_Process_Involved_In_Synaptic_Transmission | 31 | 0.56 | 2.14 | <0.001 | 0.003 |
| Go_Macromolecular_Complex_Disassembly | 36 | 0.54 | 2.14 | <0.001 | 0.003 |
| Go_Synaptic_Signaling | 78 | 0.44 | 2.13 | <0.001 | 0.003 |
| Go_Protein_Domain_Specific_Binding | 189 | 0.37 | 2.13 | <0.001 | 0.003 |
| Go_Cell_Cell_Contact_Zone | 35 | 0.52 | 2.12 | <0.001 | 0.004 |
| Go_Extrinsic_Component_Of_Cytoplasmic_Side_Of_Plasma_Membrane | 40 | 0.51 | 2.12 | 0.002 | 0.004 |
| Go_Regulation_Of_I_Kappab_Kinase_Nf_Kappab_Signaling | 62 | 0.46 | 2.11 | <0.001 | 0.004 |
| Go_Regulation_Of_Exocytosis | 69 | 0.45 | 2.11 | <0.001 | 0.004 |
| Go_Cell_Division | 123 | 0.40 | 2.10 | <0.001 | 0.004 |
| Go_Regulation_Of_Cytokinesis | 19 | 0.62 | 2.09 | <0.001 | 0.005 |
| Go_Regulation_Of_Centrosome_Cycle | 17 | 0.64 | 2.08 | <0.001 | 0.005 |
| Go_Basolateral_Plasma_Membrane | 84 | 0.42 | 2.07 | <0.001 | 0.006 |
| Go_Apical_Junction_Complex | 42 | 0.50 | 2.07 | <0.001 | 0.006 |
| Go_Cytoskeleton_Dependent_Cytokinesis | 23 | 0.58 | 2.06 | <0.001 | 0.006 |
| Go_Regulation_Of_Cell_Division | 62 | 0.44 | 2.04 | <0.001 | 0.007 |
| Go_Heterotrimeric_G_Protein_Complex | 17 | 0.63 | 2.04 | 0.002 | 0.007 |
| Go_Cell_Cell_Signaling | 126 | 0.39 | 2.03 | <0.001 | 0.008 |
| Go_Calcium_Dependent_Phospholipid_Binding | 19 | 0.60 | 2.02 | 0.002 | 0.009 |
| Go_Regulation_Of_Centrosome_Duplication | 15 | 0.65 | 2.00 | <0.001 | 0.010 |
| Go_Plasma_Membrane_Organization | 95 | 0.40 | 2.00 | <0.001 | 0.010 |
| Go_Extrinsic_Component_Of_Plasma_Membrane | 61 | 0.44 | 2.00 | <0.001 | 0.011 |
| Go_Positive_Regulation_Of_Viral_Process | 29 | 0.52 | 1.98 | 0.002 | 0.013 |
| Go_G_Protein_Coupled_Receptor_Signaling_Pathway_Coupled_To_Cyclic_Nucleotide_Second_Messenger | 21 | 0.58 | 1.98 | <0.001 | 0.013 |
| Go_Positive_Regulation_Of_Cell_Division | 29 | 0.52 | 1.98 | <0.001 | 0.013 |
| Go_Regulation_Of_Ras_Protein_Signal_Transduction | 52 | 0.45 | 1.97 | <0.001 | 0.014 |
| Go_Nucleoside_Triphosphatase_Regulator_Activity | 82 | 0.40 | 1.97 | 0.002 | 0.014 |
| Go_Positive_Regulation_Of_I_Kappab_Kinase_Nf_Kappab_Signaling | 50 | 0.45 | 1.96 | <0.001 | 0.015 |
| Go_Amino_Acid_Transport | 31 | 0.52 | 1.94 | 0.002 | 0.017 |
| Go_Cell_Division_Site | 24 | 0.55 | 1.95 | <0.001 | 0.017 |
| Go_Pdz_Domain_Binding | 32 | 0.50 | 1.95 | <0.001 | 0.018 |
| Go_Cytoskeletal_Protein_Binding | 272 | 0.33 | 1.94 | <0.001 | 0.018 |
| Go_Membrane_Budding | 65 | 0.42 | 1.94 | <0.001 | 0.018 |
| Go_Filopodium | 52 | 0.44 | 1.92 | 0.002 | 0.019 |
| Go_Extrinsic_Component_Of_Membrane | 95 | 0.39 | 1.92 | <0.001 | 0.020 |
| Go_Regulation_Of_Small_Gtpase_Mediated_Signal_Transduction | 80 | 0.40 | 1.93 | <0.001 | 0.020 |
| Go_Organelle_Assembly | 123 | 0.36 | 1.92 | <0.001 | 0.020 |
| Go_Late_Endosome_Membrane | 59 | 0.42 | 1.93 | 0.002 | 0.020 |
| Go_Positive_Regulation_Of_Cell_Cycle_Process | 56 | 0.43 | 1.92 | <0.001 | 0.021 |
| Go_Sister_Chromatid_Segregation | 40 | 0.46 | 1.91 | 0.002 | 0.021 |
| Go_Rho_Guanyl_Nucleotide_Exchange_Factor_Activity | 15 | 0.61 | 1.91 | <0.001 | 0.021 |
| Go_Intracellular_Signal_Transduction | 426 | 0.31 | 1.90 | <0.001 | 0.023 |
| Go_G_Protein_Coupled_Receptor_Signaling_Pathway | 100 | 0.37 | 1.90 | <0.001 | 0.023 |
| Go_Cell_Projection_Assembly | 67 | 0.41 | 1.90 | <0.001 | 0.023 |
| Go_Side_Of_Membrane | 148 | 0.35 | 1.89 | <0.001 | 0.025 |
| Go_Organelle_Localization | 139 | 0.35 | 1.88 | <0.001 | 0.025 |
| Go_Leukocyte_Migration | 79 | 0.40 | 1.89 | <0.001 | 0.025 |
| Go_Positive_Regulation_Of_Hydrolase_Activity | 207 | 0.33 | 1.88 | <0.001 | 0.025 |
| Go_Postsynapse | 89 | 0.38 | 1.88 | 0.002 | 0.025 |
| Go_Synapse_Part | 149 | 0.35 | 1.88 | <0.001 | 0.025 |
| Go_Plasma_Membrane_Protein_Complex | 140 | 0.35 | 1.89 | <0.001 | 0.025 |
| Go_Adenylate_Cyclase_Modulating_G_Protein_Coupled_Receptor_Signaling_Pathway | 20 | 0.57 | 1.88 | <0.001 | 0.025 |
| Go_Synapse | 194 | 0.33 | 1.87 | <0.001 | 0.027 |
| Go_Regulation_Of_Nuclear_Division | 37 | 0.46 | 1.87 | <0.001 | 0.027 |
| Go_Positive_Regulation_Of_Peptidyl_Serine_Phosphorylation | 18 | 0.56 | 1.87 | 0.003 | 0.027 |
| Go_Atpase_Activity_Coupled_To_Transmembrane_Movement_Of_Ions_Phosphorylative_Mechanism | 18 | 0.57 | 1.86 | 0.002 | 0.028 |
| Go_Regulation_Of_Gtpase_Activity | 153 | 0.34 | 1.86 | <0.001 | 0.028 |
| Go_Metal_Ion_Transmembrane_Transporter_Activity | 67 | 0.40 | 1.86 | 0.002 | 0.029 |
| Go_Establishment_Of_Cell_Polarity | 31 | 0.48 | 1.85 | 0.002 | 0.030 |
| Go_Heat_Shock_Protein_Binding | 30 | 0.49 | 1.85 | 0.002 | 0.031 |
| Go_Protein_Localization_To_Cell_Periphery | 66 | 0.40 | 1.84 | 0.002 | 0.031 |
| Go_Ruffle | 85 | 0.37 | 1.84 | <0.001 | 0.031 |
| Go_Snare_Complex | 28 | 0.49 | 1.84 | 0.002 | 0.031 |
| Go_Negative_Regulation_Of_Cellular_Protein_Localization | 39 | 0.45 | 1.84 | 0.006 | 0.033 |
| Go_Neuron_Spine | 37 | 0.45 | 1.83 | 0.002 | 0.033 |
| Go_Regulation_Of_Protein_Complex_Disassembly | 70 | 0.38 | 1.83 | <0.001 | 0.033 |

TABLE 5-continued

GSEA for Exo-L.

| Name | Size | Es | Nes | P Value | Fdr Q Value (Cutoff < 0.25) |
|---|---|---|---|---|---|
| Go_Cytoskeleton_Organization | 262 | 0.31 | 1.83 | <0.001 | 0.033 |
| Go_Snare_Binding | 47 | 0.42 | 1.83 | <0.001 | 0.033 |
| Go_Anchoring_Junction | 328 | 0.30 | 1.83 | <0.001 | 0.033 |
| Go_Sodium_Ion_Transmembrane_Transporter_Activity | 29 | 0.48 | 1.82 | 0.003 | 0.035 |
| Go_Synaptic_Vesicle_Cycle | 24 | 0.51 | 1.82 | <0.001 | 0.035 |
| Go_Cell_Junction | 470 | 0.29 | 1.82 | <0.001 | 0.035 |
| Go_Vesicle_Organization | 130 | 0.34 | 1.82 | <0.001 | 0.035 |
| Go_Vacuole_Organization | 71 | 0.39 | 1.82 | 0.002 | 0.036 |
| Go_Enzyme_Activator_Activity | 112 | 0.35 | 1.81 | 0.001 | 0.037 |
| Go_Regulation_Of_Organelle_Assembly | 44 | 0.43 | 1.81 | <0.001 | 0.038 |
| Go_Membrane_Region | 384 | 0.29 | 1.80 | <0.001 | 0.040 |
| Go_Negative_Regulation_Of_Dephosphorylation | 15 | 0.57 | 1.80 | 0.005 | 0.040 |
| Go_Trans_Golgi_Network_Transport_Vesicle | 17 | 0.56 | 1.80 | 0.005 | 0.041 |
| Go_Calcium_Dependent_Protein_Binding | 30 | 0.46 | 1.79 | 0.002 | 0.042 |
| Go_Regulation_Of_Rho_Protein_Signal_Transduction | 31 | 0.46 | 1.79 | 0.002 | 0.042 |
| Go_Cell_Leading_Edge | 180 | 0.32 | 1.79 | <0.001 | 0.042 |
| Go_Myeloid_Cell_Homeostasis | 23 | 0.50 | 1.78 | 0.005 | 0.048 |
| Go_Regulation_Of_Tumor_Necrosis_Factor_Mediated_Signaling_Pathway | 16 | 0.55 | 1.78 | 0.008 | 0.048 |

Es, Enrichment Score;
Nes, Normalized Enrichment Score;
Fdr, False Discovery Rate Lipid classes identified in exomeres and exosome subsets derived from different cell lines (raw data and normalized data) are shown in Tables 6-8.

The values in the table are relative signal response (signal's peak area count is normalized to sample weight and peak area count of the internal standard signal)

TABLE 6

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| AcCa(14:0) + H | AcCa(14:0) + H | AcCa | (14:0) | 126403 | 74344 | 58450 | 450142 | 480444 | 253736 | 817233 | 627321 | 575713 |
| AcCa(16:0) + H | AcCa(16:0) + H | AcCa | (16:0) | 371349 | 132864 | 127435 | 848312 | 949956 | 635288 | 1613560 | 1298747 | 1254263 |
| AcCa(18:0) + H | AcCa(18:0) + H | AcCa | (18:0) | 271015 | 122806 | 111390 | 815152 | 1342063 | 663069 | 1274337 | 1373484 | 1164727 |
| AcCa(18:1) + H | AcCa(18:1) + H | AcCa | (18:1) | 177867 | 148820 | 162353 | 488628 | 684148 | 419700 | 727711 | 1055935 | 632886 |
| Cer(d18:1/10:0) + H | Cer(d28:1) + H | Cer | (d18:1/10:0) | 3285931 | 2456489 | 3071965 | 2826972 | 2522661 | 2574269 | 3282319 | 2529012 | 2859390 |
| Cer(d17:1/12:0) + H | Cer(d29:1) + H | Cer | (8!7:1/12:0) | 2136705 | 1658319 | 9710 | 2183085 | 2150140 | 16991 | 2086917 | 1905596 | 8847 |
| Cer(d18:0/12:0) + H | Cer(d30:0) + H | Cer | (d18:0/12:0) | 4662128 | 4717794 | 258831 | 5173465 | 4949391 | 308432 | 5318447 | 4537723 | 487676 |
| Cer(d18:1/13:0) + H | Cer(d31:1) + H | Cer | (d18:1/13:0) | 2061473 | 2314284 | 1781159 | 2389813 | 2394060 | 18082 | 2511543 | 1995862 | 12407 |
| Cer(d18:1/14:0) + H | Cer(d32:1) + H | Cer | (d18:1/14:0) | 16487509 | 17733378 | 11996128 | 27269296 | 20032631 | 24321417 | 24060587 | 19624829 | 17533611 |
| Cer(d17:1/16:0) + H | Cer(d33:1) + H | Cer | (d17:1/16:0) | 244972 | 145280 | 0 | 738922 | 511889 | 9284 | 404845 | 219652 | 11209 |
| Cer(d18:1/16:0) + H | Cer(d34:1) + H | Cer | (d18:1/16:0) | 1931662 | 2910272 | 592159 | 9687638 | 4994022 | 3596046 | 4689271 | 3395960 | 54370 |
| Cer(d18:2/16:0) + H | Cer(d34:2) + H | Cer | (d18:2/16:0) | 977946 | 515813 | 17723 | 5339763 | 3254669 | 219675 | 4266995 | 2334043 | 100282 |
| Cer(d18:1/18:0) + H | Cer(d36:1) + H | Cer | (d18:1/18:0) | 10496 | 8067 | 75944 | 181246 | 13750 | 344641 | 0 | 0 | 88007 |
| Cer(d18:2/18:0) + H | Cer(d36:2) + H | Cer | (d18:2/18:0) | 482498 | 373915 | 0 | 1612597 | 973300 | 43568 | 969446 | 468632 | 0 |
| Cer(d18:2/22:0) + H | Cer(d40:2) + H | Cer | (d18:2/22:0) | 103724 | 240980 | 0 | 236699 | 101293 | 11125 | 133378 | 55772 | 0 |
| Cer(d18:1/24:1) + H | Cer(d42:2) + H | Cer | (d18:1/24:11 | 89835 | 285185 | 75499 | 512209 | 187476 | 443205 | 262724 | 210714 | 112551 |
| Cer(d18:2/24:0) + H | Cer(d42:2) + H | Cer | (d18:2/24:01 | 21377 | 93184 | 7980 | 74370 | 140785 | 323620 | 50536 | 140395 | 215214 |
| Cer(d18:2/24:1) + H | Cer(d42:3) + H | Cer | (d18:2/24:1) | 586547 | 1726557 | 69366 | 1299561 | 635994 | 928491 | 700013 | 847586 | 439139 |
| CerG1(d18:1/16:0) + H | CerG1(d34:1) + H | CarG1 | (d18:1/16:0) | 2132797 | 3004216 | 265833 | 6754715 | 5248635 | 651347 | 6085606 | 7925052 | 471225 |
| CerG1(d18:2/16:0) + H | CerG1(d34:2) + H | CerG1 | (d18:2/16:0) | 68290 | 60670 | 0 | 322732 | 399905 | 7897 | 486115 | 632481 | 13728 |
| CerG1(d42:2) + H | CerG1(d42:2) + H | CerG1 | (d42:2) | 10524 | 102212 | 32440 | 59143 | 11325 | 16572 | 14912 | 48875 | 0 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| CerG1(d42:3) + H | CerG1(d42:3) + H | CerG1 | (d42:3) | 131300 | 207192 | 0 | 207152 | 84636 | 8467 | 183967 | 151961 | 0 |
| CerG2(d42:2) + H | CerG2(d42:2) + H | CerG2 | (d42:2) | 57300 | 162235 | 116293 | 35705 | 61052 | 46664 | 63418 | 54882 | 10286 |
| CerG3(d34:1) + H | CerG3(d34:1) + H | CerG3 | (d34:1) | 0 | 0 | 0 | 0 | 0 | 0 | 0 | 0 | 0 |
| CL(14:0/14:0/14:0/14:0) – H | CL(56:0) – H | CL | (14:0/14:0/14:0/14:0) | 190991 | 219438 | 306512 | 167571 | 239006 | 404403 | 118811 | 273244 | 327125 |
| CL(18:2/14:0/14:0/14:0) – H | CL(60:2) – H | CL | (18:2/14:0/14:0/14:0) | 2672710 | 2676445 | 2708643 | 1805136 | 2788450 | 2750814 | 2682683 | 1866518 | 3229918 |
| CL(63:3) – H | CL(63:3) – H | CL | (63:3) | 17718077 | 24443433 | 32685664 | 19052791 | 38979323 | 32187596 | 19983783 | 21116809 | 25096959 |
| cPA(18:0) – H | cPA(18:0) – H | cPA | (18:0) | 0 | 0 | 0 | 55012 | 68477 | 69059 | 61342 | 117027 | 47556 |
| DG(9:0/9:0) + NH4 | DG(9:0/9:0) + NH4 | DG | (9:0/9:0) | 947852 | 155466 | 0 | 387486 | 280845 | 9824 | 322159 | 429779 | 13833 |
| DG(10:0/10:0) + NH4 | DG(20:0) + NH4 | DG | (10:0/10:0) | 306078 | 40445 | 0 | 145346 | 58658 | 0 | 186129 | 106451 | 0 |
| DG(16:0/14:0) + NH4 | DG(30:0) + NH4 | DG | (16:0/14:0) | 23130 | 492892 | 0 | 204445 | 204748 | 3103 | 130175 | 449852 | 0 |
| DG(16:0/16:0) + NH4 | DG(32:0) + NH4 | DG | (35:0/16:0) | 312394 | 3034249 | 65213 | 1134564 | 992674 | 2401 | 639777 | 1625717 | 273211 |
| DG(18:0/16:0) + NH4 | DG(34:0) + NH4 | DG | (18:0/16:0) | 414414 | 1717524 | 81035 | 898847 | 870506 | 16324 | 625271 | 1282433 | 33465 |
| DG(16:0/18:1) + NH4 | DG(34:1) + NH4 | DG | (16:0/18:1) | 249570 | 5066477 | 56636 | 952503 | 1496482 | 194460 | 703700 | 3431420 | 216575 |
| DG(16:0/18:2) + NH4 | DG(34:2) + NH4 | DG | (16:0/18:2) | 155579 | 3053493 | 52764 | 455631 | 705511 | 205165 | 573647 | 1999847 | 99975 |
| DG(16:1/18:1) + NH4 | DG(34:2) + NH4 | DG | (36:1/18:1) | 52935 | 821634 | 607008 | 606602 | 1224260 | 966471 | 510087 | 2108477 | 747255 |
| DG(18:0/18:0) + NH4 | DG(36:0) + NH4 | DG | (18:0/18:0) | 420808 | 483464 | 44835 | 493869 | 434736 | 26845 | 456878 | 602752 | 38767 |
| DG(18:0/18:1) + NH4 | DG(36:1) + NH4 | DG | (18:0/18:1) | 128946 | 994984 | 36401 | 358221 | 522720 | 169726 | 311026 | 1296730 | 97520 |
| DG(18:1/18:1) + NH4 | DG(36:2) + NH4 | DG | (18:1/18:1) | 371258 | 7033571 | 211640 | 2544291 | 4636620 | 954483 | 3523810 | 10142038 | 1024211 |
| DG(18:0/20:4) + NH4 | DG(38:4) + NH4 | DG | (18:0/20:4) | 51341 | 592569 | 0 | 3687436 | 8075822 | 379742 | 2484564 | 19634348 | 336286 |
| LPA(16:0) – H | LPA(16:0) – H | LPA | (16:0) | 22497 | 11628 | 5227 | 339398 | 380104 | 125253 | 473472 | 590477 | 218149 |
| LPA(18:0) – H | LPA(18:0) – H | LPA | (18:0) | 6067 | 15389 | 0 | 565585 | 664690 | 308216 | 751856 | 867404 | 354941 |
| LPC(12:0) + H | LPC(12:0) + H | LPC | (12:0) | 24826009 | 20995058 | 22215516 | 21792204 | 25883459 | 17184909 | 22080168 | 22679379 | 19563762 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| LPC(14:0) + H | LPC(14:0) + H | LPC | (14:0) | 569880 | 382042 | 516804 | 2624194 | 2882195 | 2196724 | 4225292 | 3498731 | 2526682 |
| LPC(15:0) + H | LPC(15:0) + H | LPC | (15:0) | 197761 | 98604 | 105982 | 1311940 | 1442497 | 728764 | 1721614 | 1366126 | 979909 |
| LPC(16:0) + H | LPC(16:0) + H | LPC | (16:0) | 15828556 | 960967 | 8112646 | 87241945 | 118375088 | 64524003 | 131528490 | 14660735 | 86067477 |
| LPC(16:0e) + H | LPC(16:0e) + H | LPC | (16:0e) | 744785 | 349930 | 426467 | 5245638 | 7599868 | 4354204 | 7220750 | 7627865 | 5423455 |
| LPC(16:0p) + H | LPC(16:0p) + H | LPC | (16:0p) | 353470 | 95568 | 171801 | 2491768 | 2689720 | 1637153 | 2900592 | 2414546 | 2045586 |
| LPC(16:1) + H | LPC(16:1) + H | LPC | (16:1) | 280901 | 236419 | 341572 | 3367994 | 4859169 | 2381778 | 4343171 | 1967391 | 213444 |
| LPC(17:0) + H | LPC(17:0) + H | LPC | (17:0) | 647030 | 283200 | 306780 | 3784759 | 4389526 | 3249965 | 4225274 | 3911969 | 3897263 |
| LPC(17:1) + G | LPC(17:1) + H | LPC | (17:1) | 183977 | 168289 | 235204 | 641128 | 575440 | 249858 | 480601 | 379388 | 279067 |
| LPC(18:0) + H | LPC(18:0) + H | LPC | (18:0) | 1467413 | 856904 | 7242653 | 14028247 | 15991647 | 76847887 | 15435268 | 14024927 | 91960591 |
| LPC(18:0e) + H | LPC(18:0e) + H | LPC | (18:0e) | 357153 | 198069 | 193513 | 3017626 | 4339017 | 2074027 | 3502395 | 3365334 | 2386033 |
| LPC(18:0p) + H | LPC(18:0p) + H | LPC | (18:0p) | 240653 | 111201 | 168571 | 2529943 | 3891950 | 2081436 | 3033057 | 3016781 | 2337886 |
| LPC(18:1) + H | LPC(18:1) + H | LPC | (18:1) | 860980 | 408803 | 2199425 | 3995280 | 4396377 | 15853525 | 5050416 | 4586403 | 19619579 |
| LPC(18:1p) + H | LPC(18:1p) + H | LPC | (18:1p) | 30139 | 11829 | 0 | 379412 | 428169 | 38755 | 442946 | 310262 | 56709 |
| LPC(18:3) + H | LPC(18:3) + H | LPC | (18:3) | 612289 | 319665 | 593584 | 4110256 | 5583184 | 4216789 | 6334338 | 6122347 | 6072820 |
| LPC(19:0) + H | LPC(19:0) + H | LPC | (19:0) | 200029 | 108013 | 9599 | 2275904 | 2890343 | 1519032 | 2665408 | 2793374 | 1626281 |
| LPC(19:1) + H | LPC(19:1) + H | LPC | (19:1) | 88384 | 39189 | 13736 | 416823 | 715551 | 431350 | 1208577 | 584080 | 344782 |
| LPC(20:0) + H | LPC(20:0) + H | LPC | (20:0) | 607197 | 396865 | 403428 | 5726753 | 7985971 | 4099321 | 6209335 | 7234817 | 5152981 |
| LPC(20:0e) + H | LPC(20:0e) + H | LPC | (20:0e) | 634835 | 261588 | 9643 | 4931406 | 4772196 | 4124047 | 5174992 | 4586907 | 4079437 |
| LAC(20:1) + H | LPC(20:1) + H | LPC | (20:1) | 387845 | 189452 | 238530 | 3051230 | 3817347 | 2514088 | 3507684 | 3502342 | 3087582 |
| LPC(20:2) + H | LPC(20:2) + H | LPC | (20:2) | 36252 | 19249 | 15234 | 898457 | 912537 | 484067 | 1091403 | 789470 | 505463 |
| LPC(20:3) + H | LPC(20:3) + H | LPC | (20:3) | 491004 | 374138 | 408366 | 4823463 | 7201017 | 5170072 | 5206771 | 7586043 | 6895817 |
| LPC(20:4) + H | LPC(20:4) + H | LPC | (20:4) | 336922 | 135435 | 115338 | 1472907 | 1239627 | 607968 | 1194764 | 774417 | 499731 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| LPC(22:0) + H | LPC(22:0) + H | LPC | (22:0) | 297854 | 293971 | 119072 | 2195548 | 3766079 | 97011 | 1560850 | 2891930 | 954677 |
| LPC(22:3) + H | LPC(22:3) + H | LPC | (22:3) | 0 | 0 | 0 | 108584 | 158539 | 0 | 259681 | 302983 | 225370 |
| LPC(22:4) + H | LPC(22:4) + H | LPC | (22:4) | 130051 | 71536 | 70972 | 757447 | 902950 | 355253 | 670269 | 564642 | 346774 |
| LPC(22:5) + H | LPC(22:5) + H | LPC | (22:5) | 289181 | 147999 | 101529 | 1393529 | 1193595 | 542897 | 1095475 | 852414 | 590041 |
| LPC(22:6) + H | LPC(22:6) + H | LPC | (22:6) | 282143 | 118195 | 109571 | 1509678 | 1099101 | 490193 | 1051577 | 654953 | 475235 |
| LPC(24:0) + H | LPC(24:0) + H | LPC | (24:0) | 269284 | 469608 | 98479 | 2031193 | 3748373 | 810926 | 1846605 | 2876090 | 683853 |
| LPC(24:1) + H | LPC(24:1) + H | LPC | (24:1) | 172249 | 195506 | 32267 | 1375894 | 3447011 | 49999 | 1521861 | 3181981 | 506378 |
| LPC(26:1) + H | LPC(26:1) + H | LPC | (26:1) | 180284 | 203029 | 267546 | 934476 | 1965024 | 869741 | 1107557 | 1536510 | 879935 |
| LPC(28:0) + H | LPC(28:0) + H | LPC | (28:0) | 281142 | 271278 | 152632 | 616409 | 519593 | 165653 | 1217321 | 725813 | 196125 |
| LPE(16:0p) – H | LPE(16:0p) – H | LPE | (16:0p) | 112766 | 50167 | 73845 | 1005794 | 858598 | 946677 | 1406618 | 1160918 | 1004722 |
| LPE(18:0) – H | LPE(18:0) – H | LPE | (18:0) | 3921 | 1952 | 1640 | 118233 | 107913 | 99044 | 161225 | 165661 | 97721 |
| LPE(20:1) – H | LPE(20:1) – H | LPE | (20:1) | 14764 | 2049 | 3055 | 167698 | 122170 | 114049 | 231657 | 194669 | 150107 |
| LPE(20:4) – H | LPE(20:4) – H | LPE | (20:4) | 65288 | 12725 | 20948 | 468527 | 289518 | 235996 | 373155 | 288721 | 250355 |
| LPG(14:0) – H | LPG(14:0) – H | LPG | (14:0) | 548800 | 382595 | 407893 | 795783 | 463367 | 358026 | 604048 | 492052 | 342052 |
| LPG(16:0) – H | LPG(16:0) – H | LPG | (16:0) | 22384 | 1817 | 3695 | 95584 | 97453 | 88169 | 150234 | 144409 | 94669 |
| LPG(18:0) – H | LPG(18:0) – H | LPG | (18:0) | 7108 | 5883 | 2154 | 145050 | 199730 | 118565 | 180290 | 279239 | 125173 |
| LPI(16:0) – H | LPI(16:0) – H | LPI | (16:0) | 13139 | 8286 | 12324 | 160039 | 189966 | 142107 | 243454 | 316147 | 195268 |
| LPI(18:0) – H | LPI(18:0) – H | LPI | (18:0) | 129537 | 106151 | 124225 | 867843 | 1230904 | 952013 | 1366778 | 1930014 | 1195908 |
| LPI(18:1) – H | LPI(18:1) – H | LPI | (18:1) | 72701 | 47431 | 61357 | 460751 | 514012 | 440566 | 566097 | 674850 | 626513 |
| MG(14:0) + H | MG(14:0) + H | MG | (14:0) | 375837 | 88177 | 35665 | 448878 | 402458 | 5718 | 372448 | 550789 | 6515 |
| MG(16:0) + H | MG(16:0) + H | MG | (16:0) | 50604436 | 13533642 | 239524 | 33457708 | 25341368 | 552953 | 44808270 | 44882937 | 1700412 |
| MG(18:0) + H | MG(18:0) + H | MG | (18:0) | 73255584 | 24991877 | 36894 | 49725813 | 29224771 | 121072 | 61152875 | 53425253 | 1679694 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| MG(18:1) + H | MG(18:1) + H | MG | (18:1) | 544195 | 290230 | 28730 | 394439 | 311141 | 83987 | 583537 | 594474 | 89301 |
| MG(18:2)+H | MG(18:2) + H | MG | (18:2) | 4536076 | 1085419 | 10175 | 3024785 | 1303318 | 27108 | 3187788 | 2514511 | 117708 |
| MG(20:0) + H | MG(20:0) + H | MG | (20:0) | 603839 | 158129 | 0 | 278723 | 212540 | 0 | 352665 | 369659 | 0 |
| PA(16:0/18:1) − H | PA(16:0/18:1) − H | PA | (16:0/18:1) | 353279 | 1205140 | 767645 | 1083038 | 3038689 | 3051987 | 180867 | 3819385 | 3323318 |
| PA(36:1) − H | PA(18:0/18:1) − H | PA | (18:0/18:1) | 240583 | 545416 | 440200 | 917938 | 1190688 | 1413768 | 826834 | 1819319 | 1686643 |
| PA(36:2) − H | PA(18:1/18:1) − H | PA | (18:1/18:1) | 1146268 | 1346006 | 847163 | 870462 | 3412350 | 878946 | 3287797 | 1861009 | 1386024 |
| PA(38:3) − H | PA(18:0/20:3) − H | PA | (18:0/20:3) | 45040 | 305269 | 144750 | 32540 | 730895 | 353903 | 438562 | 1004844 | 522715 |
| PA(38:4) − H | PA(18:0/20:4) − H | PA | (18:0/20:4) | 1991604 | 1909483 | 752042 | 5211107 | 6353043 | 5173947 | 5216243 | 8408667 | 5567100 |
| PC(16:1) + H | PC(16:1) + H | PC | (16:1) | 711019 | 434839 | 562537 | 1292297 | 861033 | 891424 | 1090124 | 926343 | 1162390 |
| PC(19:1) + H | PC(19:1) + H | PC | (19:1) | 1103262 | 630501 | 684980 | 2531329 | 1712233 | 1404432 | 1883603 | 1278262 | 1261451 |
| PC(19:3) + H | PC(19:3) + H | PC | (19:3) | 140482 | 77031 | 94153 | 852857 | 1017233 | 660854 | 1057654 | 995593 | 611132 |
| PC(22:0) + H | PC(22:0) + H | PC | (22:0) | 1548077 | 1231441 | 1142048 | 1521914 | 1408181 | 1495404 | 1505859 | 1549520 | 1333985 |
| PC(23:0) +H | PC(23:0) + H | PC | (23:0) | 4548177 | 5231098 | 5636416 | 5055545 | 5205865 | 6244353 | 8873030 | 4752521 | 4671780 |
| PC(14:0e/10:1) + H | PC(14:0e/10:1) + H | PC | (14:0e/10:1) | 72125 | 212115 | 34016 | 1441291 | 2716842 | 105506 | 1380547 | 2972553 | 92509 |
| PC(25:0) + H | PC(25:0) + H | PC | (25:0) | 4682423 | 4220728 | 5093812 | 5029168 | 4921421 | 5523997 | 5163837 | 4899195 | 5012193 |
| PC(26:0) + H | PC(26:0) + H | PC | (26:0) | 9653915 | 10088128 | 9496506 | 12563166 | 12315442 | 11517050 | 12538366 | 12117458 | 10426993 |
| PC(28:0) + H | PC(28:0) + H | PC | (28:0) | 16142640 | 11250710 | 16890226 | 94512141 | 106893440 | 22203878 | 132708155 | 121460509 | 125699546 |
| PC(28:1) + H | PC(28:1) + H | PC | (28:1) | 949819 | 273215 | 600528 | 3359965 | 7404361 | 4706427 | 5146089 | 3037283 | 3884449 |
| PC(29:0) + H | PC(29:0) + H | PC | (29:0) | 3037216 | 2192472 | 3374639 | 16274102 | 12464795 | 21180937 | 23520211 | 17179205 | 23219766 |
| PC(29:0e)+H | PC(29:0e) + H | PC | (29:0e) | 500495 | 620882 | 20456 | 6004551 | 2453423 | 8616426 | 6489613 | 5092334 | 5676874 |
| PC(11:0/18:1) + H | PC(11:0/18:1) + H | PC | (11:0/18:1) | 709162 | 825698 | 1232231 | 2810267 | 3051219 | 8703188 | 3405470 | 2395242 | 8338689 |
| PC(29:1) + H | PC(29:1) + H | PC | (29:1) | 324087 | 372942 | 141198 | 1381426 | 1260238 | 952507 | 2420045 | 2388402 | 709915 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(29:2) + H | PC(29:2) + H | PC | (29:2) | 213308 | 195757 | 145685 | 1034052 | 1185309 | 619448 | 2054678 | 1895639 | 885229 |
| PC(30:0) + H | PC(30:0) + H | PC | (16:0/14:0) | 56691753 | 74998071 | 26091350 | 683027646 | 682017930 | 1255178435 | 881535926 | 616691128 | 193155930 |
| PC(30:0e)+H | PC(30:0e) + H | PC | (30:0e) | 4056228 | 7928194 | 6465647 | 28560737 | 27282829 | 63835789 | 25395469 | 27671702 | 32831475 |
| PC(14:0p/16:0) + H | PC(30:0p) + H | PC | (14:0p/16:0) | 629949 | 1061563 | 313243 | 5377894 | 5372113 | 2369887 | 4458921 | 4577410 | 1452818 |
| PC(30:1) + H | PC(30:1) + H | PC | (16:1/14:0) | 17130717 | 14079326 | 2801921 | 102492171 | 327551929 | 24616112 | 137777254 | 135604383 | 2061098 |
| PC(30:1e) + H | PC(30:1e) + H | PC | (30:1e) | 127004 | 106123 | 28357 | 532623 | 2368063 | 2282784 | 2994764 | 997185 | 2495350 |
| PC(30:2) + H | PC(30:2) + H | PC | (30:2) | 117858 | 51494 | 196119 | 1201953 | 2059520 | 1026838 | 1179636 | 1741418 | 884183 |
| PC(30:3) + H | PC(30:3) + H | PC | (30:3) | 478052 | 475953 | 130266 | 4145335 | 5388556 | 3875521 | 4350801 | 5055605 | 1524862 |
| PC(31:0) + H | PC(31:0) + H | PC | (31:0) | 5049251 | 6718203 | 7639633 | 42945618 | 31875039 | 65082122 | 47136067 | 37808345 | 49514068 |
| PC(31:0e) + H | PC(31:0e) + H | PC | (31:0e) | 304982 | 294402 | 1022945 | 446518 | 1492814 | 8992308 | 1738976 | 1983714 | 2628902 |
| PC(31:0p) + H | PC(31:0p) + H | PC | (31:0p) | 513233 | 308136 | 284850 | 5057611 | 4515500 | 6587243 | 5809117 | 4369020 | 5014587 |
| PC(31:1) + H | PC(31:1) + H | PC | (31:1) | 5485783 | 2847101 | 5842640 | 42743922 | 23288029 | 67963014 | 70199810 | 60046556 | 64138703 |
| PC(31:2) + H | PC(31:2) + H | PC | (31:2) | 5945625 | 3622633 | 1209331 | 24297871 | 19202789 | 9524323 | 40465789 | 29104789 | 10177023 |
| PC(31:3) + H | PC(31:3) + H | PC | (31:3) | 437194 | 451232 | 199097 | 1920300 | 2302406 | 1975122 | 1628067 | 1532974 | 1632507 |
| PC(32:0) + H | PC(32:0) + H | PC | (16:0/16:0) | 20914846 | 51875855 | 56025652 | 272222966 | 231440946 | 606142584 | 296810344 | 283458124 | 365355799 |
| PC(32:0e) + H | PC(32:0e) + H | PC | (32:0e) | 1678417 | 5491350 | 6736720 | 18836697 | 16249536 | 50019063 | 11061880 | 16511316 | 17616549 |
| PC(32:1) + H | PC(32:1) + H | PC | (16:0/16:1) | 381297293 | 292555198 | 257928169 | 2854649412 | 2778422049 | 3838279002 | 3906107098 | 3663791470 | 3307385068 |
| PC(32:1e) + H | PC(32:1e) + H | PC | (16:0e/16:1) | 29860775 | 32204686 | 25604326 | 179356767 | 190641317 | 283723830 | 173372115 | 179521306 | 182897168 |
| PC(14:0p/18:1) + H | PC(32:1p) + H | PC | (14:0p/18:1) | 4384602 | 4502370 | 3698127 | 32728425 | 32189364 | 43232252 | 22998160 | 15556946 | 23904388 |
| PC(16:1/16:1) + H | PC(32:2) + H | PC | (16:1/16:1) | 4364874 | 2633675 | 5055540 | 24904167 | 31306125 | 45184481 | 33133633 | 39017602 | 41647218 |
| PC(18:1/14:1) + H | PC(32:2) + H | PC | (18:1/14:1) | 4433024 | 1566012 | 1162020 | 14242256 | 12004576 | 5683688 | 19537697 | 10150760 | 4489765 |
| PC(21:1/31:1) + H | PC(32:2) + H | PC | (21:1/11:1) | 3317305 | 2457734 | 1751989 | 21068787 | 24306239 | 13490753 | 25989753 | 28806059 | 11913899 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(32:2) + H | PC(32:2) + H | PC | (32:2) | 853461 | 541674 | 133672 | 3198542 | 2183848 | 842944 | 4588838 | 2710601 | 1006746 |
| PC(32:3) + H | PC(32:3) + H | PC | (32:3) | 3880729 | 4838259 | 2174541 | 45142873 | 51367960 | 24333865 | 54761013 | 61607918 | 77516103 |
| PC(33:0) + H | PC(33:0) + H | PC | (33:0) | 2491221 | 4292191 | 2094083 | 9890003 | 8931707 | 21094550 | 17597727 | 11350499 | 11113297 |
| PC(33:0e) + H | PC(33:0e) + H | PC | (33:0e) | 179591 | 323333 | 127786 | 939808 | 767556 | 1925575 | 692899 | 578714 | 910127 |
| PC(33:0p) + H | PC(33:0p) + H | PC | (33:0p) | 5514046 | 5886622 | 3348197 | 29905909 | 26959989 | 46907116 | 25793887 | 20775585 | 24327880 |
| PC(17:1/16:0) + H | PC(17:1/16:0) + H | PC | (17:1/16:0) | 42531094 | 31192660 | 27351928 | 183770305 | 138000588 | 266593855 | 205479288 | 170692737 | 57118640 |
| PC(33:1) + H | PC(33:1) + H | PC | (33:1) | 2555311 | 1544070 | 330171 | 7479162 | 4246649 | 2664600 | 10271628 | 6775857 | 2096224 |
| PC(33:2) + H | PC(33:2) + H | PC | (33:2) | 24133640 | 13315080 | 8893252 | 58426262 | 32978893 | 3957620 | 94144054 | 51180448 | 63916967 |
| PC(33:3) + H | PC(33:3) + H | PC | (33:3) | 2890157 | 1836002 | 2189731 | 14117303 | 10932598 | 21356198 | 18716142 | 14843963 | 19206746 |
| PC(33:5) + H | PC(33:5) + H | PC | (33:5) | 166778 | 103006 | 0 | 885005 | 888997 | 130504 | 1375772 | 1181957 | 88887 |
| PC(34:0) + H | PC(34:0) + H | PC | (18:0/16:0) | 236340 | 1799346 | 2419061 | 6617209 | 5443136 | 19151215 | 2961868 | 6195521 | 7251254 |
| PC(34:0e) + H | PC(34:0e) + H | PC | (34:0e) | 32434 | 340654 | 688738 | 1323097 | 1158873 | 3721258 | 735292 | 1313962 | 1078602 |
| PC(34:1) + H | PC(34:1) + H | PC | (16:0/18:1) | 702164261 | 683856165 | 459756300 | 4090124888 | 3266409301 | 5915612417 | 5156552228 | 4423780802 | 4814401416 |
| PC(34:2) + H | PC(34:2) + H | PC | (16:1/18:1) | 95398188 | 59096879 | 102332012 | 1259473250 | 1426517920 | 1530374649 | 1586240129 | 1288377681 | 1251331204 |
| PC(34:2e) + H | PC(34:2e) + H | PC | (34:2e) | 13437906 | 12654633 | 10113848 | 86846844 | 92800877 | 131845330 | 78230081 | 78466379 | 78768625 |
| PC(16:1p/18:1) + H | PC(16:1p/18:1) + H | PC | (16:1p/18:1) | 2886633 | 2301135 | 2578631 | 18247260 | 15908218 | 21615372 | 12458478 | 10544133 | 12531595 |
| PC(12:0/22:3) + H | PC(34:2p) + H | PC | (12:0/22:3) | 2468111 | 1650994 | 1285428 | 17210347 | 16231266 | 18500053 | 20808370 | 18756574 | 16911357 |
| PC(16:1/18:2) + H | PC(34:3) + H | PC | (16:1/18:2) | 3827115 | 2184772 | 2443733 | 24237687 | 21051078 | 23434834 | 26957441 | 23196963 | 19148407 |
| PC(34:3) + H | PC(34:3) + H | PC | (34:3) | 1229610 | 2883678 | 4153532 | 13447228 | 14653650 | 44646699 | 12392809 | 16525324 | 3647163 |
| PC(34:3p) + H | PC(34:3p) + H | PC | (34:3p) | 309194 | 1462040 | 999891 | 8502590 | 9797227 | 18800853 | 7779018 | 10339160 | 11746995 |
| PC(34:4) + H | PC(34:4) + H | PC | (34:4) | 20475903 | 16110930 | 17293334 | 178336632 | 207525148 | 346713684 | 66644722 | 129599970 | 355127450 |
| PC(34:4p) + H | PC(34:4p) + H | PC | (34:4p) | 113809 | 73055 | 14857 | 1300014 | 976116 | 165784 | 1322693 | 710962 | 25528 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(35:0) + H | PC(35:0) + H | PC | (35:0) | 16436 | 82270 | 0 | 504377 | 182394 | 594817 | 575443 | 395473 | 307532 |
| PC(35:0p) + H | PC(35:0p) + H | PC | (35:0p) | 1632829 | 1320223 | 587682 | 3109538 | 4330640 | 5998432 | 4098800 | 3798103 | 3825167 |
| PC(19:1/16:0) + H | PC(35:1) + H | PC | (19:1/16:0) | 10484048 | 9928273 | 10530183 | 41897018 | 27918903 | 104647960 | 46798441 | 33327744 | 72186646 |
| PC(17:0/18:1) + H | PC(35:1) + H | PC | (17:0/18:1) | 5988186 | 3990995 | 6267876 | 28487945 | 16672598 | 65506113 | 34058556 | 19802587 | 25971953 |
| PC(35:1p) + H | PC(35:1p) + H | PC | (35:1p) | 1406045 | 1075172 | 780889 | 6214976 | 5934505 | 8837847 | 5501205 | 5518786 | 4576235 |
| PC(19:1/16:1) + H | PC(35:2) + H | PC | (19:1/16:1) | 6284334 | 3958153 | 1938327 | 38909168 | 31351637 | 14302206 | 40889367 | 32418462 | 23110869 |
| PC(24:1/11:1) + H | PC(35:2) + H | PC | (24:1/11:1) | 11336192 | 5493494 | 3466525 | 60657254 | 43008093 | 5664196 | 56058697 | 39110045 | 37049797 |
| PC(35:2) + H | PC(35:2) + H | PC | (35:2) | 270421 | 275264 | 399753 | 434132 | 342684 | 1731724 | 513537 | 324179 | 1291443 |
| PC(35:2p) + H | PC(35:2p) + H | PC | (35:2p) | 576576 | 405357 | 85747 | 2841268 | 4165956 | 6393422 | 2198415 | 3444787 | 394399 |
| PC(35:3) + H | PC(35:3) + H | PC | (35:3) | 890824 | 501653 | 134820 | 7341169 | 5110940 | 3697459 | 6873364 | 3882500 | 2474502 |
| PC(35:4) + H | PC(35:4) + H | PC | (35:4) | 4495931 | 3539087 | 1677683 | 14508832 | 9745045 | 13337298 | 19081414 | 13281655 | 11465781 |
| PC(35:5) + H | PC(35:5) + H | PC | (35:5) | 6177999 | 3293915 | 714103 | 32574085 | 24526286 | 2758482 | 44623939 | 32556959 | 3676579 |
| PC(35:6) + H | PC(35:6) + H | PC | (35:6) | 1730356 | 1078550 | 986403 | 12240209 | 8969559 | 8085536 | 25142649 | 13256355 | 6341940 |
| PC(18:0/18:1) + H | PC(36:1) + H | PC | (18:0/18:1) | 57594289 | 89875958 | 35364313 | 223467745 | 155762078 | 372979351 | 214701069 | 199982778 | 234112087 |
| PC(36:1e) + H | PC(36:1e) + H | PC | (36:1e) | 1847007 | 6001714 | 1695860 | 8139694 | 7983334 | 18083551 | 6069833 | 7533265 | 6988582 |
| PC(20:1p/16:0) + H | PC(36:1p) + H | PC | (20:1p/16:0) | 13855149 | 15166017 | 9015476 | 71011723 | 59946900 | 96568675 | 58680699 | 49404053 | 53153592 |
| PC(18:1/18:1) + H | PC(36:2) + H | PC | (18:1/18:1) | 219418964 | 149657065 | 113577755 | 1071681085 | 698669045 | 1306180416 | 1589090062 | 1186492716 | 1321526178 |
| PC(36:2e) + H | PC(36:2e) + H | PC | (36:2e) | 825058 | 2288822 | 294483 | 8515582 | 3268628 | 7341682 | 3029268 | 4351222 | 3631295 |
| PC(18:2p/18:0) + H | PC(36:2p) + H | PC | (18:2p/18:0) | 2449211 | 2105691 | 1581612 | 16482738 | 20454763 | 22202405 | 12080750 | 11324342 | 11224758 |
| PC(36:2p) + H | PC(36:2p) + H | PC | (36:2p) | 6876459 | 6830048 | 3760873 | 33276198 | 32117954 | 48103421 | 24897739 | 23696285 | 29387299 |
| PC(16:0/20:3) + H | PC(36:3) + H | PC | (16:0/20:3) | 19311332 | 10605539 | 18324108 | 149395954 | 99927597 | 203371700 | 148867851 | 105689176 | 144632970 |
| PC(18:2p/18:1) + H | PC(36:3p) + H | PC | (18:2p/18:1) | 9411864 | 7043705 | 8995220 | 65432592 | 64555739 | 34393429 | 46639296 | 42312142 | 59873318 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(36:4) + H | PC(36:4) + H | PC | (16:0/20:4) | 113125173 | 61796800 | 65443777 | 970392843 | 693468583 | 1084594991 | 833128331 | 554307442 | 579110379 |
| PC(36:4e) + H | PC(36:4e) + H | PC | (36:4e) | 2874252 | 5227401 | 2853530 | 13162899 | 13730432 | 35503097 | 8762435 | 10529267 | 15277003 |
| PC(36:4p) + H | PC(36:4p) + H | PC | (36:4p) | 429555 | 226608 | 186510 | 3247187 | 2450936 | 1938168 | 2500553 | 1822372 | 778536 |
| PC(18:4/18:1) + H | PC(18:4/18:1) + H | PC | (18:4/18:1) | 3674145 | 2141956 | 5301653 | 32576186 | 30079311 | 142867872 | 40885853 | 36775111 | 110522230 |
| PC(36:5) + H | PC(36:5) + H | PC | (36:5) | 3528133 | 4889012 | 6301483 | 43142563 | 43544554 | 154900750 | 54354927 | 51833930 | 11233573 |
| PC(16:0e/20:5) + H | PC(36:5e) + H | PC | (16:0e/20:5) | 9308764 | 6840060 | 6189331 | 75709670 | 68192259 | 88245724 | 48894220 | 37579300 | 41683517 |
| PC(36:5p) + H | PC(36:5p) + H | PC | (36:5p) | 300012 | 145095 | 200932 | 2676755 | 2129870 | 2012616 | 2121500 | 1438064 | 1139635 |
| PC(36:6) + H | PC(36:6) + H | PC | (36:6) | 278220 | 120514 | 175270 | 1752752 | 1469996 | 26512 | 2222469 | 1627227 | 207469 |
| PC(36:6p) + H | PC(36:6p) + H | PC | (36:6p) | 713070 | 281961 | 16664 | 4485149 | 4233808 | 256022 | 3465606 | 4096681 | 4331 |
| PC(37:1) + H | PC(37:1) + H | PC | (37:1) | 635507 | 1068698 | 248544 | 2118291 | 1839614 | 4592553 | 3160798 | 2464688 | 2145896 |
| PC(37:2) + H | PC(37:2) + H | PC | (37:2) | 5342789 | 4118992 | 2523957 | 18907786 | 12841693 | 24974380 | 22039493 | 15068689 | 17763612 |
| PC(37:3) + H | PC(37:3) + H | PC | (37:3) | 2127614 | 1681616 | 213678 | 13875476 | 7635188 | 4086475 | 10217137 | 6773494 | 2316787 |
| PC(37:4) + H | PC(37:4) + H | PC | (37:4) | 3885530 | 2134865 | 267675 | 22000044 | 14351369 | 3687400 | 17928177 | 10324880 | 2300350 |
| PC(15:0/22:5) + H | PC(37:5) + H | PC | (15:0/22:5) | 1610591 | 786405 | 319731 | 10709917 | 7968334 | 4210574 | 8464698 | 5426397 | 2278810 |
| PC(37:5) + H | PC(37:5) + H | PC | (37:5) | 989292 | 736530 | 12639 | 2600731 | 1874460 | 76215 | 3896763 | 3172358 | 49238 |
| PC(37:6) + H | PC(37:6) + H | PC | (37:6) | 1445085 | 1130607 | 687467 | 6992369 | 4823141 | 3961830 | 9639965 | 10234779 | 1459770 |
| PC(38:1) + H | PC(38:1) + H | PC | (38:1) | 1232660 | 2539576 | 946684 | 3607588 | 2224295 | 6355098 | 3320273 | 3067032 | 2726034 |
| PC(16:0/22:2) + H | PC(38:2) + H | PC | (16:0/22:2) | 19294815 | 12528607 | 5409361 | 41586519 | 28925428 | 62622778 | 52094191 | 40718260 | 45362110 |
| PC(38:2e) + H | PC(38:2e) + H | PC | (38:2e) | 229490 | 1436307 | 225156 | 887315 | 840060 | 3813085 | 2284921 | 1804058 | 1155137 |
| PC(28:1/10:2) + H | PC(38:3) + H | PC | (28:1/10:2) | 4842513 | 4871395 | 2382254 | 17875436 | 12136912 | 24497522 | 16650719 | 13501242 | 15299840 |
| PC(18:0/20:3) + H | PC(38:3) + H | PC | (18:0/20:3) | 22234637 | 18139485 | 10100957 | 79821396 | 47675284 | 98004247 | 63535991 | 43335502 | 53327351 |
| PC(38:3e) + H | PC(38:3e) + H | PC | (38:3e) | 430882 | 1130273 | 1348078 | 3737602 | 2261771 | 6064759 | 2587927 | 1235354 | 2914242 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(24:0/14:4) + H | PC(38:4) + H | PC | (24:0/14:4) | 13612374 | 9039205 | 2249372 | 91098010 | 74001720 | 28057296 | 76972831 | 51227131 | 15860636 |
| PC(18:0/20:4) + H | PC(38:4)+ H | PC | (18:0/20:4) | 95037046 | 63141328 | 41694806 | 563602124 | 335891571 | 651523426 | 469371087 | 261553147 | 339631844 |
| PC(38:4e) + H | PC(38:4e) + H | PC | (38:4e) | 7490326 | 7804870 | 1804445 | 42622033 | 42789404 | 30023761 | 27705185 | 26192846 | 9812738 |
| PC(38:4p) + H | PC(38:4p) + H | PC | (38:4p) | 8854264 | 6385455 | 5170890 | 61602988 | 60679872 | 88333270 | 47928163 | 34973778 | 40139805 |
| PC(18:1/20:4) + H | PC(38:5) + H | PC | (18:1/20:4) | 123488251 | 67188448 | 49637662 | 1026829551 | 699701692 | 603445846 | 785955557 | 494762868 | 328329122 |
| PC(16:0/22:6) + H | PC(38:6) + H | PC | (16:0/22:6) | 316250 | 205733 | 36226 | 3975732 | 3952772 | 1218213 | 4854762 | 4271139 | 1408910 |
| PC(18:1/20:5) + H | PC(38:6) + H | PC | (18:1/20:5) | 45908597 | 23103640 | 27490795 | 377976992 | 216516974 | 306444819 | 243072102 | 151122766 | 363755763 |
| PC(38:6) + H | PC(38:6) + H | PC | (38:6) | 1136205 | 717162 | 244153 | 12683883 | 10655358 | 3742676 | 11676613 | 10470000 | 2703754 |
| PC(38:6e) + H | PC(38:6e) + H | PC | (38:6e) | 13361334 | 10387237 | 7623356 | 111905865 | 106674264 | 102556065 | 71620916 | 57715219 | 44168763 |
| PC(38:6p) + H | PC(38:6p) + H | PC | (38:6p) | 15483207 | 11921944 | 2986285 | 186474003 | 148946710 | 42082868 | 109651586 | 83889829 | 19230427 |
| PC(38:7) + H | PC(38:7) + H | PC | (38:7) | 6194027 | 2910949 | 3775199 | 57266682 | 41523027 | 76273809 | 50017867 | 32127604 | 47411750 |
| PC(39:3) + H | PC(39:3) + H | PC | (39:3) | 623402 | 546156 | 149834 | 2065681 | 1141695 | 2377725 | 1849315 | 1089868 | 1295349 |
| PC(39:4) + H | PC(39:4) + H | PC | (39:4) | 758049 | 583494 | 17751 | 2942978 | 1588346 | 615509 | 3026951 | 1468087 | 496479 |
| PC(39:5) + H | PC(39:5) + H | PC | (39:5) | 2461024 | 1436182 | 351073 | 14695835 | 9264798 | 3285667 | 10916171 | 6029141 | 1899999 |
| PC(39:6) + H | PC(39:6) + H | PC | (39:6) | 2084165 | 1100748 | 136833 | 15968364 | 9660793 | 1536896 | 12472067 | 7024924 | 1066954 |
| PC(39:7) + H | PC(39:7) + H | PC | (39:7) | 114469 | 81599 | 28040 | 1373730 | 1290344 | 566521 | 1018109 | 751688 | 296566 |
| PC(40:1) + H | PC(40:1) + H | PC | (40:1) | 19628 | 548649 | 10711 | 320505 | 144391 | 649078 | 336368 | 480931 | 306415 |
| PC(40:2) + H | PC(40:2) + H | PC | (40:2) | 1316565 | 3898315 | 483061 | 3032979 | 2104152 | 5781091 | 3826304 | 3613235 | 3786897 |
| PC(40:3) + H | PC(40:3) + H | PC | (40:3) | 977860 | 857262 | 521195 | 3088227 | 2227626 | 4794615 | 3579280 | 2711439 | 3029600 |
| PC(40:3p) + H | PC(40:3p) + H | PC | (40:3p) | 1011619 | 1294865 | 432318 | 3408918 | 3007870 | 4986580 | 1860751 | 1354303 | 1985437 |
| PC(40:4) + H | PC(40:4) + H | PC | (40:4) | 8046549 | 8004170 | 5328022 | 23143083 | 19299996 | 32926987 | 19313266 | 11617315 | 24852471 |
| PC(40:5) + H | PC(40:5) + H | PC | (18:1/22:4) | 35476101 | 23868537 | 17154310 | 202180672 | 121659424 | 235623419 | 170254214 | 97410757 | 123354126 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(40:5e) + H | PC(40:5e) + H | PC | (40:5e) | 2307410 | 2136195 | 1247130 | 12360839 | 10362062 | 13311635 | 6702988 | 5753036 | 5438160 |
| PC(18:0/22:6) + H | PC(40:6) + H | PC | (18:0/22:6) | 16693392 | 8173425 | 7854470 | 145791613 | 98490232 | 124072849 | 113194090 | 67292012 | 62729425 |
| PC(20:3/20:3) + H | PC(40:6) + H | PC | (20:3/20:3) | 38490349 | 22084869 | 18171055 | 248754570 | 155666768 | 299018660 | 196182329 | 102666052 | 138892105 |
| PC(40:6e) + H | PC(40:6e) + H | PC | (40:6e) | 6604220 | 3954315 | 2997578 | 32893458 | 36758887 | 34131553 | 22076761 | 20657338 | 13658008 |
| PC(40:6p) + H | PC(40:6p) + H | PC | (40:6O) | 6254447 | 5934471 | 3846468 | 45809985 | 41286808 | 51568294 | 26209415 | 20174539 | 18324035 |
| PC(20:3/20:4) + H | PC(40:7) + H | PC | (20:3/20:4) | 11268944 | 5665070 | 6826212 | 89085576 | 63804657 | 91042333 | 67185541 | 42362806 | 45131328 |
| PC(40:7) + H | PC(40:7) + H | PC | (40:7) | 625562 | 301078 | 474227 | 5913374 | 4597529 | 15169575 | 4476428 | 3589157 | 9559417 |
| PC(40:7p) + H | PC(40:7p) + H | PC | (40:7p) | 6945861 | 4196537 | 958797 | 68908268 | 59375419 | 17057378 | 40961551 | 30962137 | 224930 |
| PC(40:8) + H | PC(40:8) + H | PC | (40:8) | 635421 | 229585 | 154945 | 13027015 | 10686928 | 17832081 | 11433796 | 5046720 | 9792159 |
| PC(40:9) + H | PC(40:9) + H | PC | (40:9) | 243955 | 14010 | 18188 | 21171238 | 19778222 | 12056950 | 1206641 | 163603 | 147944 |
| PC(41:5) + H | PC(41:5) + H | PC | (41:5) | 274828 | 215707 | 8525 | 1210076 | 549552 | 214202 | 882757 | 448922 | 123176 |
| PC(41:6) + H | PC(41:6) + H | PC | (41:6) | 416032 | 195420 | 126235 | 2087186 | 1286584 | 2068692 | 1688521 | 788683 | 1128524 |
| PC(41:7) + H | PC(41:7) + H | PC | (41:7) | 462302 | 198785 | 106902 | 3976977 | 2204088 | 159245 | 2805904 | 1497294 | 16894 |
| PC(42:1) + H | PC(42:1) + H | PC | (42:1) | 21921 | 194041 | 63453 | 35201 | 9395 | 271505 | 62485 | 114660 | 79275 |
| PC(42:10) + H | PC(42:10) + H | PC | (42:10) | 370351 | 246264 | 19589 | 2660492 | 2327177 | 208777 | 1759486 | 1406162 | 78571 |
| PC(42:2) + H | PC(42:2) + H | PC | (42:2) | 253232 | 738559 | 8974 | 510969 | 361646 | 1299045 | 698072 | 820622 | 739271 |
| PC(42:3p) + H | PC(42:3p) + H | PC | (42:3p) | 363646 | 741983 | 78597 | 1257336 | 1010573 | 2117577 | 610797 | 536191 | 452085 |
| PC(42:4p) + H | PC(42:4p) + H | PC | (42:4p) | 2326778 | 2136343 | 859992 | 6337502 | 5303164 | 10823482 | 3644317 | 2929616 | 3074872 |
| PC(42:6) + H | PC(42:6) + H | PC | (42:6) | 697545 | 351692 | 13399 | 6651920 | 3672793 | 1500680 | 5047201 | 2678595 | 686402 |
| PC(42:6e) + H | PC(42:6e) + H | PC | (42:6e) | 3281320 | 3528394 | 1633277 | 10986222 | 9522831 | 15595214 | 6976105 | 5637816 | 5377179 |
| PC(42:7) + H | PC(42:7) + H | PC | (42:7) | 1170406 | 624085 | 59451 | 7819357 | 4605787 | 6286859 | 6271700 | 3287507 | 3667056 |
| PC(42:7p) + H | PC(42:7p) + H | PC | (42:7p) | 304595 | 143764 | 17459 | 2186988 | 2477986 | 2982157 | 937663 | 1154367 | 532011 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(42:8) + H | PC(42:8) + H | PC | (42:8) | 559523 | 158973 | 469871 | 2441322 | 2105502 | 596625 | 1789640 | 1016874 | 2671616 |
| PC(42:9) + H | PC(42:9) + H | PC | (42:9) | 285002 | 96473 | 91760 | 6320647 | 5106113 | 47424 | 4786814 | 2985749 | 620202 |
| PC(44:1) + H | PC(44:1) + H | PC | (44:1) | 0 | 0 | 0 | 0 | 0 | 0 | 0 | 0 | 0 |
| PC(44:2) + H | PC(44:2) + H | PC | (44:2) | 0 | 0 | 0 | 31147 | 0 | 34726 | 28312 | 14838 | 15622 |
| PE(12:0/14:0) − H | PE(12:0/14:0) − H | PE | (12:0/14:0) | 877320 | 765934 | 1107693 | 479419 | 961567 | 392491 | 284392 | 391284 | 776168 |
| PE(26:0) − H | PE(26:0) − H | PE | (26:0) | 10461181 | 10193378 | 10101341 | 11474936 | 10941789 | 11531491 | 12749953 | 11031927 | 11394620 |
| PE(32:0p) − H | PE(32:0p) − H | PE | (32:0p) | 20315 | 31273 | 113871 | 516675 | 436257 | 840690 | 345402 | 542576 | 787825 |
| PE(32:1) − H | PE(32:1) − H | PE | (16:0/16:1) | 1079702 | 641093 | 530955 | 4259541 | 3407279 | 4157685 | 6354298 | 6636938 | 7424439 |
| PE(32:1p) − H | PE(32:1p) − H | PE | (16:0p/16:1) | 1407803 | 664223 | 691263 | 6902003 | 4179502 | 4350051 | 6229817 | 6216071 | 5535087 |
| PE(32:2) − H | PE(32:2) − H | PE | (16:1/16:1) | 63984 | 33617 | 52703 | 248508 | 608883 | 532581 | 1362998 | 1044307 | 864687 |
| PE(33:1) − H | PE(33:1) − H | PE | (17:1/16:0) | 29662 | 10943 | 44465 | 261173 | 245512 | 53221 | 727329 | 348259 | 564830 |
| PE(33:1p) − H | PE(33:1p) − H | PE | (33:1p) | 284615 | 207250 | 119774 | 974402 | 649777 | 781100 | 1246718 | 730405 | 697463 |
| PE(34:1) − H | PE(34:1) − H | PE | (16:0/18:1) | 4670374 | 3364575 | 2608414 | 18480259 | 12661967 | 15319787 | 21791565 | 26672687 | 29989326 |
| PE(34:1p) − H | PE(34:1p) − H | PE | (16:0p/18:1) | 7939089 | 6776006 | 4301086 | 29675616 | 22313983 | 30783198 | 20610189 | 39048166 | 31675888 |
| PE(34:2) − H | PE(34:2) − H | PE | (16:1/18:1) | 833382 | 496698 | 474042 | 4411219 | 3883160 | 4468359 | 7423287 | 6579351 | 6241736 |
| PE(34:2p) − H | PE(34:2p) − H | PE | (18:1p/16:1) | 1128790 | 747798 | 536745 | 5468672 | 5833160 | 6912104 | 6954297 | 6583106 | 4628105 |
| PE(34:2p) − H | PE(34:2p) − H | PE | (16:0p/18:2) | 261859 | 945372 | 111451 | 1475289 | 1079665 | 988558 | 7723369 | 1038837 | 995103 |
| PE(34:3) − H | PE(34:3) − H | PE | (16:1/18:2) | 0 | 0 | 0 | 290695 | 348797 | 313300 | 595403 | 520002 | 403197 |
| PE(34:3p) − H | PE(34:3p) − H | PE | (16:0p/18:3) | 180812 | 119867 | 116422 | 940853 | 870734 | 1073288 | 1207176 | 1189320 | 1194719 |
| PE(35:1) − H | PE(35:1) − H | PE | (17:0/18:1) | 160428 | 104560 | 69353 | 558367 | 463948 | 554162 | 750101 | 631768 | 725432 |
| PE(35:2) − H | PE(35:2) − H | PE | (17:1/18:1) | 443278 | 136018 | 138961 | 1424928 | 1047325 | 1323660 | 2812265 | 2239564 | 1668603 |
| PE(36:1) − H | PE(36:1) − H | PE | (18:0/18:1) | 1421789 | 1446827 | 1034206 | 5399013 | 4417839 | 6643745 | 5815534 | 8997591 | 9114083 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PE(36:1) - H | PE(36:1) - H | PE | (36:1) | 415360 | 215231 | 86790 | 2628405 | 2225986 | 1850515 | 3330956 | 5264515 | 491949 |
| PE(18:0/18:1) - H | PE(36:1p) - H | PE | (18:0p/18:1) | 1125679 | 1376566 | 837927 | 3805201 | 3763497 | 5404133 | 2848291 | 5172753 | 4825824 |
| PE(18:1/18:1) - H | PE(36:2p) - H | PE | (18:1/18:1) | 7505580 | 720840 | 507799 | 4538759 | 3216573 | 19669952 | 47228634 | 36522494 | 37490323 |
| PE(18:1p/18:1) - H | PE(36:2p) - H | PE | (18:1p/18:1) | 4858022 | 3206616 | 2390188 | 19194067 | 15306858 | 18719127 | 17525117 | 19272819 | 17619921 |
| PE(16:0/20:3) - H | PE(36:3) - H | PE | (16:0/20:3) | 184100 | 72617 | 72449 | 1339098 | 891690 | 1260412 | 1695811 | 948950 | 1924390 |
| PE(18:1/18:2) - H | PE(36:3) - H | PE | (18:1/18:2) | 997218 | 467752 | 489897 | 5924653 | 3813311 | 4451956 | 7377826 | 6046072 | 5674505 |
| PE(16:0p/20:3) - H | PE(36:3p) - H | PE | (16:0p/20:3) | 2060112 | 1513199 | 1234494 | 8966460 | 8777144 | 10026565 | 9017780 | 10548334 | 10147034 |
| PE(36:3p) - H | PE(36:3p) - H | PE | (36:3p) | 601284 | 267484 | 154108 | 2772190 | 2822090 | 2837733 | 2615126 | 3819494 | 1702071 |
| PE(16:0/20:4) - H | PE(36:4) - H | PE | (16:0/20:4) | 1533862 | 784905 | 839695 | 8299759 | 6949456 | 8296843 | 13349623 | 12490424 | 9798806 |
| PE(16:1/20:3) - H | PE(36:4) - H | PE | (16:1/20:3) | 0 | 0 | 0 | 63814 | 37695 | 135632 | 441949 | 371736 | 246019 |
| PE(16:0p/20:4) - H | PE(36:4p) - H | PE | (16:0p/20:4) | 14847809 | 9949236 | 7821593 | 87386040 | 82142785 | 64340444 | 70538600 | 82997643 | 61233670 |
| PE(16:0/20:5) - H | PE(36:5) - H | PE | (16:0/20:5) | 43235 | 18442 | 8097 | 276286 | 296682 | 265733 | 471119 | 542475 | 352664 |
| PE(16:1/20:4) - H | PE(36:5) - H | PE | (16:1/20:4) | 62913 | 18671 | 28242 | 620906 | 664982 | 244723 | 1181079 | 1281076 | 776997 |
| PE(18:0/20:2) - H | PE(38:2) - H | PE | (18:0/20:2) | 67636 | 158025 | 123852 | 487539 | 428430 | 617126 | 588560 | 807636 | 866364 |
| PE(16:0p/22:3) - H | PE(38:2p) - H | PE | (16:0p/22:3) | 281159 | 326553 | 235086 | 799865 | 754510 | 1097689 | 672784 | 1068174 | 954474 |
| PE(18:0/20:3) - H | PE(38:3) - H | PE | (18:0/20:3) | 503807 | 349186 | 293419 | 2141607 | 1641504 | 2550106 | 2498788 | 3067671 | 3259440 |
| PE(18:1/20:2) - H | PE(38:3) - H | PE | (18:1/20:2) | 604967 | 342597 | 279993 | 2858098 | 1777982 | 2810003 | 3207149 | 2737000 | 3129624 |
| PE(16:0p/22:3) - H | PE(38:3p) - H | PE | (16:0p/22:3) | 831740 | 700793 | 459821 | 2776342 | 2469757 | 3028879 | 2344400 | 5848869 | 5584451 |
| PE(38:3p) - H | PE(38:3p) - H | PE | (38:3p) | 390224 | 375759 | 223331 | 1299945 | 1222774 | 1608561 | 1180206 | 1670534 | 1558562 |
| PE(18:0/20:4) - H | PE(38:4) - H | PE | (18:0/20:4) | 2456039 | 1537488 | 1269299 | 12193195 | 8539222 | 9832922 | 13361844 | 15608337 | 12626893 |
| PE(18:1/20:3) - H | PE(38:4) - H | PE | (18:1/20:3) | 1007186 | 585209 | 382659 | 4607240 | 2626747 | 3983617 | 6232722 | 4777064 | 3920822 |
| PE(38:4e) - H | PE(38:4e) - H | PE | (38:4e) | 302434 | 225823 | 151889 | 1057487 | 979312 | 1186350 | 1045707 | 1293734 | 1225036 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PE(16:0p/22:4) - H | PE(38:4p) - H | PE | (16:00/22:4) | 2824362 | 2134283 | 1640321 | 14855295 | 12909492 | 14744387 | 13726783 | 13926467 | 13907923 |
| PE(18:0p/20:4) - H | PE(38:4p) - H | PE | (18:00/20:4) | 4212506 | 3217026 | 1968005 | 17286317 | 15334250 | 16677488 | 14756618 | 17797914 | 15074675 |
| PE(38:4p) - H | PE38:4p) - H | PE | (38:4p) | 1275250 | 803755 | 418564 | 7674815 | 4959208 | 4517960 | 5477709 | 5621069 | 5548156 |
| PE(18:0/20:5) - H | PE(38:5) - H | PE | (18:0/20:5) | 139250 | 46613 | 61625 | 490866 | 513134 | 465201 | 947568 | 1239005 | 703804 |
| PE(18:1/20:4) - H | PE(38:5) - H | PE | (18:1/20:4) | 2645119 | 1299988 | 1390329 | 19152712 | 12845909 | 15561483 | 24011724 | 19394560 | 16184988 |
| PE(16:0p/22:5) - H | PE(38:5p) - H | PE | (16:0p/22:5) | 1020332 | 750007 | 685545 | 5253798 | 4344806 | 5508538 | 5815080 | 6578847 | 4144991 |
| PE(18:1p/20:4) - H | PE(38:5p) - H | PE | (18:1p/20:4) | 18167898 | 9892029 | 9133217 | 109131302 | 94797038 | 93740973 | 99657388 | 97189853 | 78540805 |
| PE(16:0/22:6) - H | PE(38:6) - H | PE | (16:0/22:6) | 453256 | 298791 | 336584 | 4356562 | 2654738 | 9355479 | 6670098 | 5408285 | 4264692 |
| PE(16:1/22:5) - H | PE(38:6) - H | PE | (16:1/22:5) | 0 | 0 | 0 | 63696 | 40670 | 39605 | 185213 | 85136 | 49828 |
| PE(18:0/22:3) - H | PE(40:3) - H | PE | (18:0/22:3) | 10960 | 32758 | 5181 | 90268 | 86436 | 103635 | 98373 | 164864 | 157645 |
| PE(18:0p/22:3) - H | PE(40:3p) - H | PE | (18:0p/22:3) | 105813 | 100584 | 54648 | 222433 | 228302 | 279612 | 128884 | 274839 | 311913 |
| PE(18:0/22:4) - H | PE(40:4) - H | PE | (18:0/22:4) | 197285 | 133407 | 90504 | 722815 | 608975 | 751146 | 964835 | 1176101 | 1129595 |
| PE(18:0p/22:4) - H | PE(40:4p) - H | PE | (18:0p/22:4) | 341756 | 315309 | 166741 | 999742 | 1024226 | 1041341 | 772217 | 1158364 | 933855 |
| PE(40:4p) - H | PE(40:4p) - H | PE | (40:4p) | 313649 | 199013 | 137746 | 992144 | 892047 | 1081932 | 841184 | 1130327 | 856241 |
| PE(18:0/22:5) - H | PE(40:5) - H | PE | (18:0/22:5) | 527006 | 243609 | 209621 | 1989469 | 1550990 | 1452927 | 2519422 | 2904516 | 2123746 |
| PE(18:1/22:4) - H | PE(40:5) - H | PE | (18:1/22:4) | 163699 | 144849 | 203727 | 367469 | 1494992 | 2661305 | 3285923 | 1513453 | 259669 |
| PE(18:0p/22:5) - H | PE(40:5p) - H | PE | (18:0p/22:5) | 2041532 | 1489484 | 937204 | 9420474 | 8270899 | 8781302 | 8000425 | 8017983 | 7306739 |
| PE(40:5p) - H | PE(40:5p) - H | PE | (40:5p) | 898601 | 567161 | 378189 | 4555131 | 4354962 | 4492408 | 3859235 | 4318932 | 3492115 |
| PE(18:0/22:6) - H | PE(40:6) - H | PE | (18:0/22:6) | 456020 | 320955 | 351867 | 3453274 | 2887356 | 2770119 | 4424900 | 5133451 | 4233378 |
| PE(18:1/22:5) - H | PE(40:6) - H | PE | (18:1/22:5) | 244484 | 51197 | 79945 | 2122305 | 1002298 | 1681511 | 3048169 | 1158483 | 1137633 |
| PE(18:0p/22:6) - H | PE(40:6p) - H | PE | (18:0p/22:6) | 1800305 | 1170822 | 832720 | 9062998 | 7123449 | 7785257 | 7858181 | 8270007 | 6518608 |
| PE(18:1p/22:5) - H | PE(40:6p) - H | PE | (18:1p/22:5) | 3161341 | 1499520 | 1390375 | 18729479 | 16246040 | 35946927 | 17515537 | 14942159 | 12335392 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PE(18:1/22:6) - H | PE(40:7) - H | PE | (18:1/22:6) | 941525 | 355493 | 371498 | 3831991 | 4065602 | 3598662 | 8154213 | 6652706 | 4374268 |
| PE(18:1p/22:6) - H | PE(40:7p) - H | PE | (18:1p/22:6) | 3150208 | 1584213 | 1628730 | 23606459 | 18768736 | 19054191 | 21417700 | 18405634 | 15062359 |
| PEt(16:0/16:1) - H | PEt(32:1) - H | PEt | (16:0/16:1) | 64720 | 1344878 | 93787 | 1405990 | 546333 | 3045089 | 2114122 | 3800890 | 3855758 |
| PEt(32:4) - H | PEt(32:4) - H | PEt | (32:4) | 265879817 | 260099010 | 208850921 | 301831955 | 277220807 | 266517451 | 286189223 | 295454582 | 230243440 |
| PEt(18:0/16:1) - H | PEt(34:1) - H | PEt | (18:0/16:1) | 247830 | 545581 | 452038 | 913504 | 1187126 | 1405160 | 824157 | 1810344 | 1678593 |
| PEt(18:2/18:2) - H | PEt(36:4) - H | PEt | (18:2/18:2) | 1976185 | 1909483 | 752042 | 5211307 | 6353043 | 5173947 | 5470924 | 8408667 | 5567100 |
| PG(12:0/14:0) - H | PG(26:0) - H | PG | (12:0/14:0) | 3291637 | 2997687 | 3007356 | 3085481 | 2843118 | 3106016 | 3129105 | 3256623 | 3154080 |
| PG(16:0/14:0) - H | PG(30:0) - H | PG | (16:0/14:0) | 352443 | 336195 | 292120 | 328874 | 397200 | 394890 | 419035 | 471553 | 504201 |
| PG(16:0/16:1) - H | PG(32:1) - H | PG | (16:0/16:1) | 631058 | 418905 | 401284 | 4095250 | 5590127 | 4226058 | 3085287 | 3792768 | 2368527 |
| PG(17:1/16:0) - H | PG(33:1) - H | PG | (17:1/18:0) | 89999 | 63767 | 62562 | 719959 | 833553 | 483528 | 501273 | 357480 | 280114 |
| PG(16:0/18:1) - H | PG(34:1) - H | PG | (16:0/18:1) | 12340035 | 3640873 | 2211621 | 19828140 | 34567636 | 24318862 | 11385031 | 21286743 | 14349189 |
| PG(16:1/18:1) - H | PG(34:2) - H | PG | (16:1/18:1) | 10231708 | 1799465 | 2152385 | 74557729 | 67479992 | 50699450 | 45455230 | 43657072 | 31137299 |
| PG(17:0/18:1) - H | PG(35:1) - H | PG | (17:0/18:1) | 615295 | 394993 | 352068 | 1930499 | 1593585 | 1927138 | 2297579 | 2264977 | 2563620 |
| PG(17:1/18:2) - H | PG(35:2) - H | PG | (17:1/18:2) | 633193 | 3433325 | 1055848 | 11187622 | 5669506 | 4382943 | 2326950 | 2856001 | 4736977 |
| PG(18:0/18:1) - H | PG(36:1) - H | PG | (18:0/18:1) | 2700682 | 2248244 | 1988609 | 15456940 | 18792438 | 18941548 | 11082399 | 13481106 | 10600139 |
| PG(18:1/18:1) - H | PG(36:2) - H | PG | (18:1/18:1) | 6228328 | 5062662 | 3249408 | 80685389 | 79915316 | 70401269 | 37346626 | 48603600 | 32344300 |
| PG(18:1/18:2) - H | PG(36:3) - H | PG | (18:1/18:2) | 10905443 | 7427137 | 6063942 | 79899862 | 95911164 | 65157688 | 45814873 | 54018692 | 33232855 |
| PG(20:1/18:1) - H | PG(38:2) - H | PG | (20:1/18:1) | 1282635 | 1543031 | 2363373 | 23928820 | 14996281 | 10694865 | 13223606 | 17577282 | 5116248 |
| PG(18:1/20:2) - H | PG(38:3) - H | PG | (18:1/20:2) | 7731014 | 5596874 | 4185118 | 69259272 | 79775353 | 59832706 | 36801707 | 48658730 | 29691872 |
| PG(18:0/20:4) - H | PG(38:4) - H | PG | (18:0/20:4) | 107276 | 57097 | 47148 | 916269 | 601225 | 881476 | 1139632 | 867436 | 489997 |
| PG(18:1/20:3) - H | PG(38:4) - H | PG | (18:1/20:3) | 1677516 | 1689625 | 1307103 | 17350069 | 21925654 | 14982464 | 10423762 | 11158839 | 6163298 |
| PG(18:1/20:4) - H | PG(38:5) - H | PG | (18:1/20:4) | 247645 | 23761 | 44001 | 1569165 | 3109829 | 1470528 | 615768 | 1148114 | 428740 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PG(38:6) - H | PG(38:6) - H | PG | (16:0/22:6) | 343275 | 184533 | 177784 | 3384787 | 3202373 | 2231793 | 1852009 | 1870197 | 1111921 |
| PG(40:5) - H | PR(40:5) - H | PG | (18:1/22:4) | 851725 | 510407 | 341038 | 6050912 | 11603163 | 4860092 | 2647328 | 2217423 | 1912825 |
| PG(40:6) - H | PG(40:6) - H | PG | (18:0/22:6) | 294653 | 161602 | 101326 | 2756435 | 2810825 | 1916883 | 1142241 | 1241307 | 645921 |
| PG(40:6) - H | PG(40:6) - H | PG | (18:1/22:5) | 1056786 | 773603 | 596156 | 9313613 | 8612813 | 6405516 | 4518879 | 1540214 | 2326406 |
| PG(40:7) - H | PG(40:7) - H | PG | (18:1/22:6) | 5487140 | 3216550 | 2820380 | 55285913 | 56888693 | 39963708 | 29060838 | 29322371 | 17762536 |
| PG(42:7) - H | PG(42:7) - H | PG | (20:1/22:6) | 218470 | 169244 | 102094 | 1569794 | 2347954 | 1865542 | 956297 | 768939 | 756347 |
| PG(42:8) - H | PG(42:8) - H | PG | (20:2/22:6) | 46021 | 24702 | 7242 | 1425256 | 1696390 | 988736 | 549617 | 335515 | 176670 |
| PI(34:1) - H | PI(34:1) - H | PI | (16:0/18:1) | 5572244 | 3228984 | 3578165 | 28139255 | 15983205 | 16247138 | 29732089 | 21248249 | 24374785 |
| PI(34:2) - H | PI(34:2) - H | PI | (16:1/18:1) | 80636 | 29805 | 382839 | 6076637 | 6375888 | 5651124 | 6700759 | 6249597 | 5678897 |
| PI(36:1) - H | PI(36:1) - H | PI | (18:0/18:1) | 1353621 | 3328199 | 1118896 | 4262146 | 3103471 | 6042663 | 3657919 | 3354109 | 4531768 |
| PI(36:3) - H | PI(36:3) - H | PI | (16:0/20:3) | 54556 | 24544 | 37397 | 2047115 | 131263 | 487763 | 1224725 | 1109445 | 1350953 |
| PI(36:3) - H | PI(36:3) - H | PI | (18:1/18:2) | 444587 | 182945 | 282025 | 3105247 | 2107990 | 3027684 | 2622737 | 2039418 | 2258793 |
| PI(36:4) - H | PI(36:4) - H | PI | (16:0/20:4) | 598914 | 0 | 279422 | 7055833 | 4886231 | 5856008 | 6599973 | 6020985 | 5100684 |
| PI(37:4) - H | PI(37:4) - H | PI | (17:0/20:4) | 126712 | 42475 | 62953 | 833203 | 374643 | 743228 | 559695 | 389566 | 471825 |
| PI(38:2) - H | PI(38:2) - H | PI | (20:1/18:1) | 175259 | 86079 | 50923 | 439277 | 480013 | 581942 | 435423 | 360639 | 412422 |
| PI(38:3) - H | PI(38:3) - H | PI | (18:0/20:3) | 1217639 | 840910 | 794515 | 6808681 | 4892684 | 7298507 | 4936747 | 4987182 | 5263259 |
| PI(38:4) - H | PI(38:4) - H | PI | (18:1/20:3) | 1528781 | 834554 | 1015566 | 9297027 | 7322788 | 9009607 | 7010900 | 6398816 | 6206770 |
| PI(38:5) - H | PI(38:5) - H | PI | (18:0/20:5) | 105336 | 37219 | 42397 | 846382 | 386060 | 791803 | 770636 | 618613 | 509848 |
| PI(38:5) - H | PI(38:5) - H | PI | (18:1/20:4) | 3401763 | 567106 | 1327226 | 21639659 | 13688994 | 16648897 | 18552681 | 13090246 | 11532472 |
| PI(40:4) - H | PI(40:4) - H | PI | (18:0/22:4) | 70300 | 10342 | 44277 | 311169 | 606438 | 601805 | 311001 | 92442 | 302088 |
| PMe(28:0) - H | PMe(28:0) - H | PMe | (14:0/14:0) | 171922 | 180428 | 199438 | 130882 | 139796 | 213640 | 129113 | 162779 | 138701 |
| PMe(34:5) - H | PMe(34:5) - H | PMe | (34:5) | 168686234 | 186690542 | 176316357 | 200012780 | 179283160 | 213223306 | 159526553 | 188673115 | 187834497 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PMe(42:6) - H | PMe(42:6) - H | PMe | (42:6) | 5405393 | 4557433 | 4292756 | 23101077 | 15239469 | 28664591 | 20099893 | 26906824 | 25140106 |
| PS(12:0/14:0) - H | PS(26:0) - H | PS | (12:0/14:0) | 1747977 | 1622250 | 1682897 | 1716105 | 1618233 | 1662372 | 1717501 | 1719096 | 1615557 |
| PS(16:0/16:1) - H | PS(32:1) - H | PS | (16:0/16:1) | 728060 | 235649 | 568002 | 3565582 | 3195954 | 3075828 | 4942848 | 6561468 | 5130558 |
| PS(33:1) - H | PS(33:1) - H | PS | (33:1) | 499826 | 405674 | 283691 | 4401113 | 5524904 | 2387274 | 2958538 | 3100594 | 1489335 |
| PS(18:0/16:1) - H | PS(34:1) - H | PS | (18:0/16:1) | 1055749 | 548738 | 684137 | 3216582 | 2835107 | 3319316 | 3827580 | 3654067 | 4668131 |
| PS(34:3p) - H | PS(34:3p) - H | PS | (34:3p) | 153507 | 21797 | 41263 | 198436 | 98526 | 367469 | 722045 | 457006 | 312790 |
| PS(35:0) - H | PS(35:0) - H | PS | (35:0) | 11891104 | 7835215 | 7431554 | 59353871 | 68314802 | 52272315 | 85687569 | 86949801 | 81080831 |
| PS(17:0/18:1) - H | PS(35:1) - H | PS | (17:0/18:1) | 1307641 | 275623 | 497854 | 7336355 | 5700796 | 2616582 | 7552859 | 1167330 | 1726211 |
| PS(35:1) - H | PS(35:1) - H | PS | (35:1) | 848351 | 757585 | 414645 | 4454321 | 4979022 | 3822279 | 3571141 | 4806042 | 2964179 |
| PS(35:2) - H | PS(35:2) - H | PS | (35:2) | 3415928 | 2242822 | 1598013 | 34883266 | 36475561 | 24156246 | 17252639 | 19458459 | 11929743 |
| PS(18:0/18:2) - H | PS(36:2) - H | PS | (18:0/18:2) | 2201906 | 1098564 | 1372590 | 8751952 | 5914013 | 10784726 | 11546559 | 9446142 | 10329044 |
| PS(16:0/20:3) - H | PS(36:3) - H | PS | (16:0/20:3) | 334321 | 185257 | 202550 | 1772472 | 1390975 | 1484428 | 2026197 | 1917175 | 1847899 |
| PS(18:1/18:2) - H | PS(36:3) - H | PS | (18:1/18:2) | 285503 | 38926 | 96427 | 1161619 | 883620 | 1197986 | 2051319 | 1271760 | 1100368 |
| PS(36:3) - H | PS(36:3) - H | PS | (36:3) | 856597 | 537999 | 391845 | 2349840 | 2065038 | 2484307 | 4013435 | 3709721 | 3775290 |
| PS(36:3p) - H | PS(36:3p) - H | PS | (36:3p) | 1785308 | 961455 | 880839 | 4932449 | 3706720 | 4723479 | 4655192 | 5670664 | 5512313 |
| PS(16:0/20:4) - H | PS(36:4) - H | PS | (16:0/20:4) | 336875 | 75210 | 152969 | 1793993 | 1503983 | 1231651 | 2493720 | 1831652 | 1787382 |
| PS(36:4) - H | PS(36:4) - H | PS | (36:4) | 2097741 | 1103090 | 1282076 | 6739204 | 3862077 | 6358071 | 5643547 | 4649414 | 8285398 |
| PS(37:1) - H | PS(37:1) - H | PS | (37:1) | 4922567 | 2295692 | 2782683 | 28551029 | 24264289 | 19901449 | 30741768 | 29733958 | 25818331 |
| PS(37:2) - H | PS(37:2) - H | PS | (37:2) | 581557 | 461162 | 307952 | 4041114 | 4606071 | 2742459 | 2628164 | 3564788 | 1791980 |
| PS(38:1) - H | PS(38:1) - H | PS | (38:1) | 119029 | 88780 | 139751 | 636909 | 486060 | 845525 | 553894 | 730622 | 913435 |
| PS(20:1/18:1) - H | PS(38:2) - H | PS | (20:1/18:1) | 682040 | 256270 | 365044 | 1439149 | 1314610 | 2090937 | 2117005 | 930228 | 2366094 |
| PS(18:0/20:3) - H | PS(38:3) - H | PS | (18:0/20:3) | 2132736 | 1403886 | 1679340 | 8519606 | 7565340 | 9227315 | 12239549 | 11672688 | 9127945 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PS(38:3) - H | PS(38:3) - H | PS | (38:3) | 303414 | 254363 | 212408 | 1012883 | 908749 | 1120841 | 1194372 | 1746140 | 1675591 |
| PS(18:0/20:4) - H | PS(38:4) - H | PS | (18:0/20:4) | 5071910 | 2766460 | 3001663 | 15129170 | 10456168 | 13919549 | 18462765 | 17593909 | 9290622 |
| PS(18:3/20:3) - H | PS(38:4) - H | PS | (18:3/20:3) | 298626 | 79786 | 145696 | 1957206 | 1133429 | 1494316 | 2248184 | 1564366 | 1492944 |
| PS(16:0/22:5) - H | PS(38:5) - H | PS | (16:0/22:5) | 631783 | 264480 | 374479 | 3800992 | 2890287 | 2781598 | 4853679 | 3717065 | 3093176 |
| PS(18:0/20:5) - H | PS(38:5) - H | PS | (18:0/20:5) | 94722 | 20015 | 40398 | 562024 | 452681 | 479599 | 749689 | 610233 | 520897 |
| PS(18:1/20:4) - H | PS(38:5) - H | PS | (18:1/20:4) | 838980 | 263611 | 422542 | 3422104 | 1488738 | 2276767 | 2961791 | 2468318 | 3377401 |
| PS(38:5p) - H | PS(38:5p) - H | PS | (38:5p) | 439142 | 327919 | 234062 | 1530658 | 1573139 | 1511334 | 1625738 | 1865422 | 1770846 |
| PS(16:0/22:6) - H | PS(38:6) - H | PS | (16:0/22:6) | 501663 | 107194 | 37689 | 2985399 | 3010170 | 2363829 | 5145432 | 4645671 | 2908666 |
| PS(38:6) - H | PS(38:6) - H | PS | (38:6) | 190530 | 116195 | 73015 | 1150058 | 737999 | 556878 | 2223577 | 1819388 | 743138 |
| PS(38:6p) - H | PS(38:6p) - H | PS | (38:6p) | 3058936 | 1743299 | 1491375 | 11124637 | 10406271 | 9116870 | 12830113 | 12351643 | 9161699 |
| PS(39:1) - H | PS(39:1) - H | PS | (39:1) | 21872680 | 7500910 | 8866920 | 95030677 | 55056388 | 80746806 | 113680900 | 77726111 | 88499517 |
| PS(39:2) - H | PS(39:2) - H | PS | (39:2) | 1701928 | 574271 | 809532 | 7955388 | 7889742 | 9098386 | 9509874 | 8905576 | 8072334 |
| PS:39:3) - H | PS(39:3) - H | PS | (39:3) | 7562192 | 2893484 | 4314539 | 39378240 | 26194377 | 30330579 | 34724630 | 20359292 | 19099215 |
| PS(39:4) - H | PS(39:4) - H | PS | (39:4) | 174727 | 137788 | 52371 | 751861 | 993695 | 787691 | 923285 | 1390819 | 853288 |
| PS(18:1/22:1) - H | PS(40:2) - H | PS | (18:2/22:1) | 211765 | 131163 | 105038 | 906808 | 629577 | 1053062 | 1004361 | 1014675 | 1314302 |
| PS(18:0/22:3) - H | PS(40:3) - H | PS | (18:0/22:3) | 117790 | 97259 | 86093 | 319668 | 380740 | 347432 | 556349 | 545886 | 711212 |
| PS(18:0/22:4) - H | PS(40:4) - H | PS | (18:0/22:4) | 1059849 | 759626 | 644472 | 4483430 | 3452818 | 3593518 | 5363200 | 4875192 | 3881488 |
| PS(18:0/22:5) - H | PS(40:5) - H | PS | (18:0/22:5) | 4009613 | 1637162 | 2078516 | 18696559 | 12150436 | 15059529 | 21740311 | 17737498 | 16812537 |
| PS(18:3/22:3) - H | PS(40:6) - H | PS | (18:1/22:5) | 400712 | 160981 | 244435 | 2799589 | 2059668 | 2503137 | 3013450 | 2259542 | 2186611 |
| PS(20:3/20:3) - H | PS(40:6) - H | PS | (20:3/20:3) | 389400 | 191995 | 232757 | 1710663 | 883861 | 1305603 | 1812219 | 2230930 | 1801707 |
| PS(40:6) - H | PS(40:6) - H | PS | (40:6) | 494268 | 248494 | 234205 | 1966240 | 1411806 | 1424032 | 2098029 | 2298978 | 1936260 |
| PS(40:6p) - H | PS(40:6p) - H | PS | (40:6p) | 707637 | 454905 | 358939 | 29775 | 2390393 | 2262508 | 2398545 | 2804321 | 2134177 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PS(40:7) − H | PS(40:7) − H | PS | (40:7) | 713739 | 257615 | 320733 | 3279013 | 2087894 | 2629185 | 3657706 | 3494664 | 3004160 |
| PS(40:7p) − H | PS(40:7p) − H | PS | (40:7p) | 3404289 | 1681403 | 1688420 | 14272302 | 12030497 | 11620051 | 14088569 | 13169645 | 10420450 |
| PS(40:8p) − H | PS(40:8p) − H | PS | (40:8p) | 1158661 | 586133 | 600767 | 6251230 | 5583727 | 4875480 | 5065880 | 5810101 | 4726658 |
| PS(41:3) − H | PS(41:3) − H | PS | (41:3) | 951865 | 448118 | 576995 | 6334791 | 4490267 | 4931429 | 5021684 | 4904387 | 3341605 |
| PS(41:6) − H | PS(41:6) − H | PS | (41:6) | 22049 | 50058 | 32814 | 595444 | 859340 | 309582 | 1355926 | 1290654 | 348166 |
| PS(18:1/24:0) − H | PS(18:1/24:0) − H | PS | (18:1/24:0) | 0 | 0 | 0 | 78009 | 92103 | 135517 | 62221 | 168266 | 125115 |
| PS(42:8) − H | PS(42:8) − H | PS | (42:8) | 528806 | 186309 | 250649 | 2764970 | 1593369 | 2156639 | 2975047 | 2475408 | 2258198 |
| PS(42:9) − H | PS(42:9) − H | PS | (42:9) | 655042 | 310004 | 343129 | 3220608 | 465873 | 777565 | 3104689 | 4127216 | 2719050 |
| PS(43:5) − H | PS(43:5) − H | PS | (43:5) | 399617 | 80990 | 126503 | 6515173 | 2668871 | 686037 | 2153097 | 1749608 | 2124165 |
| SM(d30:1) + H | SM(d30:1) + H | SM | (d30:1) | 184761 | 5382 | 14779 | 866346 | 781539 | 209443 | 1130358 | 416195 | 4283 |
| SM(d31:1) + H | SM(d31:1) + H | SM | (d31:1) | 427008 | 150855 | 466 | 2270811 | 2533152 | 943006 | 2538922 | 2311377 | 668695 |
| SM(d32:0) + H | SM(d32:0) + H | SM | (d32:0) | 473741 | 370664 | 111987 | 1735887 | 1305533 | 32890 | 1208742 | 946996 | 278128 |
| SM(d18:1/14:0) + H | SM(d18:1/14:0) + H | SM | (d18:1/14:0) | 7818523 | 20504 | 6262040 | 32366470 | 27041416 | 27014979 | 173448 | 21930898 | 23043602 |
| SM(d32:2) + H | SM(d32:2) + H | SM | (d32:2) | 600410 | 243608 | 168444 | 3212485 | 2749113 | 656289 | 3608219 | 2578234 | 586473 |
| SM(d33:0) + H | SM(d33:0) + H | SM | (d33:0) | 12151 | 16349 | 0 | 206379 | 121587 | 0 | 70774 | 72621 | 0 |
| SM(d33:1) + H | SM(d33:1) + H | SM | (d33:1) | 5596588 | 5691769 | 2079406 | 23071331 | 17330654 | 6221359 | 13635154 | 13910253 | 4679777 |
| SM(d33:2) + H | SM(d33:2) + H | SM | (d33:2) | 119774 | 27949 | 129727 | 92682 | 121048 | 913068 | 67553 | 39101 | 954329 |
| SM(d34:0) + H | SM(d34:0) + H | SM | (d34:0) | 531968 | 1060649 | 191806 | 2776677 | 1677349 | 462776 | 1387235 | 1737559 | 140360 |
| SM(d18:1/16:0) + H | SM(d18:1/16:0) + H | SM | (d18:1/16:0) | 35824469 | 959523 | 40846729 | 210739888 | 159212544 | 283052883 | 131241569 | 116668495 | 91200639 |
| SM(d34:1) + H | SM(d34:1) + H | SM | (d34:1) | 4014190 | 5945051 | 871296 | 22959034 | 16691791 | 3042523 | 14311776 | 14729234 | 1573077 |
| SM(d16:1/18:1) + H | SM(d16:1/18:1) + H | SM | (d16:1/18:1) | 42333904 | 22114632 | 17789107 | 190952103 | 166808400 | 362476304 | 175300054 | 131907407 | 132613919 |
| SM(d34:3) + H | SM(d34:3) + H | SM | (d34:3) | 232532 | 60609 | 136666 | 388860 | 346762 | 703869 | 508118 | 255949 | 698658 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| SM(d34:4) + H | SM(d34:4) + H | SM | (d34:4) | 559956 | 376400 | 154329 | 1521461 | 1760738 | 1100388 | 1117836 | 1644385 | 746223 |
| SM(d35:1) + H | SM(d35:1) + H | SM | (d35:1) | 180977 | 391534 | 136733 | 1481697 | 726060 | 489660 | 442998 | 811736 | 241385 |
| SM(d35:2) + H | SM(d35:2) + H | SM | (d35:2) | 798449 | 449549 | 75756 | 3315470 | 2435349 | 475610 | 2569022 | 1768462 | 1291097 |
| SM(d35:4) + H | SM(d35:4) + H | SM | (d35:4) | 247304 | 248559 | 55237 | 1113039 | 1198834 | 576193 | 650921 | 907564 | 201684 |
| SM(d18:1/18:0) + H | SM(d18:1/18:0) + H | SM | (d18:1/18:0) | 330872 | 1193973 | 1424333 | 22431 | 2204929 | 5098132 | 1453730 | 11135 | 941319 |
| SM(d36:2) + H | SM(d36:2) + H | SM | (d18:1/18:1) | 16207446 | 10582364 | 9335930 | 70591061 | 52734427 | 99978698 | 50039781 | 34951530 | 21926216 |
| SM(d36:4) + H | SM(d36:4) + H | SM | (d36:4) | 1746122 | 3294399 | 588684 | 21429659 | 21737861 | 3800110 | 7934140 | 12147626 | 1774308 |
| SM(d36:5) + H | SM(d36:5) + H | SM | (d36:5) | 1394701 | 744751 | 358246 | 8490499 | 11206161 | 648707 | 6617846 | 7894908 | 1119755 |
| SM(d38:2) + H | SM(d38:2) + H | SM | (d38:2) | 548044 | 647588 | 8751 | 1338183 | 1034372 | 323671 | 3030639 | 321318 | 33557 |
| SM(d39:7) + H | SM(d39:7) + H | SM | (d39:7) | 927702 | 33649 | 0 | 187082 | 25244 | 0 | 727460 | 301859 | 0 |
| SM(d40:1) + H | SM(d40:1) + H | SM | (d40:1) | 10422 | 20394 | 130448 | 150910 | 118922 | 15393 | 179294 | 132116 | 44245 |
| SM(d40:2) + H | SM(d40:2) + H | SM | (d40:2) | 783199 | 1207674 | 643999 | 893349 | 680653 | 1587991 | 509401 | 449195 | 520464 |
| SM(d41:2) + H | SM(d41:2) + H | SM | (d41:2) | 101925 | 449159 | 58179 | 247523 | 178194 | 138603 | 113268 | 128450 | 16754 |
| SM(d18:1/24:1) + H | SM(d18:1/24:1) + H | SM | (d18:1/24:1) | 810831 | 2310964 | 1211292 | 2221901 | 975598 | 2461500 | 1085621 | 1514922 | 895862 |
| SM(d42:2) + H | SM(d42:2) + H | SM | (d42:2) | 413380 | 1375280 | 320873 | 926115 | 372649 | 692412 | 698855 | 657467 | 231704 |
| SM(d22:0/20:3) + H | SM(d22:0/20:3) + H | SM | (d22:0/20:3) | 4379800 | 5429055 | 2431167 | 5152508 | 4866803 | 7141033 | 3732288 | 3045049 | 3307694 |
| SM(d42:5) + H | SM(d42:5) + H | SM | (d42:5) | 22257 | 114243 | 0 | 0 | 0 | 0 | 0 | 0 | 0 |
| SM(d43:3) + H | SM(d43:3) + H | SM | (d43:3) | 9359 | 27348 | 4137 | 167426 | 25219 | 71679 | 46618 | 17132 | 8872 |
| SM(d44:2) + H | SM(d44:2) + H | SM | (d44:2) | 0 | 0 | 0 | 0 | 0 | 0 | 0 | 0 | 0 |
| SM(d44:3) + H | SM(d44:3) + H | SM | (d44:3) | 0 | 0 | 0 | 0 | 0 | 0 | 0 | 0 | 0 |
| SM(d44:5) + H | SM(d44:5) + H | SM | (d44:5) | 135954 | 100436 | 6363 | 153592 | 52620 | 6770 | 0 | 0 | 0 |
| SM(d44:6) + H | SM(d44:6) + H | SM | (d44:6) | 657626 | 487421 | 148152 | 565599 | 267374 | 15924 | 232068 | 212798 | 318887 |

TABLE 6-continued

| Lipid Ion | Lipid Group | Lipid Class | Fatty Acid Chain | B16-F10 Exomere replicate 1 | B16-F10 Exomere replicate 2 | B16-F10 Exomere replicate 3 | B16-F10 Exo-S replicate 1 | B16-F10 Exo-S replicate 2 | B16-F10 Exo-S replicate 3 | B16-F10 Exo-L replicate 1 | B16-F10 Exo-L replicate 2 | B16-F10 Exo-L replicate 3 |
|---|---|---|---|---|---|---|---|---|---|---|---|---|
| TG(8:0/8:0/8:0) + NH4 | TG(24:0) + NH4 | TG | (8:0/8:0/8:0) | 1242314 | 3209402 | 276628 | 1668652 | 2213903 | 145003 | 949093 | 5710411 | 23079 |
| TG(8:0/8:0/10:0) + NH4 | TG(26:0) + NH4 | TG | (8:0/8:0/10:0) | 1318270 | 4557273 | 176287 | 2382874 | 3207039 | 379462 | 1175973 | 10295214 | 53577 |
| TG(8:0/10:0/10:0) + NH4 | TG(28:0) + NH4 | TG | (8:0/10:0/10:0) | 980514 | 5169872 | 41175 | 2380979 | 3560819 | 53139 | 343546 | 12759725 | 38818 |
| TG(10:0/10:0/10:0) + NH4 | TG(30:0) + NH4 | TG | (10:0/10:0/10:0) | 55030 | 651568 | 112134 | 81597 | 108823 | 30295 | 86425 | 1053795 | 8762 |
| TG(16:0/8:0/8:0) + NH4 | TG(32:0) + NH4 | TG | (16:0/8:0/8:0) | 96036 | 486150 | 104161 | 117254 | 179479 | 150507 | 93300 | 403362 | 136769 |
| TG(16:0/9:0/9:0) + NH4 | TG(34:0) + NH4 | TG | (16:0/9:0/9:0) | 604664 | 901783 | 82022 | 683116 | 536194 | 33185 | 649749 | 1187702 | 246282 |
| TG(8:0/8:0/18:1) + NH4 | TG34:2) + NH4 | TG | (8:0/8:0/18:1) | 324371 | 672784 | 36583 | 348459 | 396874 | 152647 | 259133 | 765937 | 56363 |
| TG(15:0/14:0/15:0) + NH4 | TG(44:0) + NH4 | TG | (15:0/14:0/15:0) | 1618712 | 1135131 | 286008 | 1525824 | 1995121 | 268843 | 1619431 | 1331287 | 279788 |
| TG(44:5p) + NH4 | TG(44:5p) + NH4 | TG | (44:5p) | 25543551 | 3986465 | 0 | 12597022 | 2446009 | 0 | 16349391 | 18607921 | 0 |
| TG(15:0/14:0/16:0) + NH4 | TG(45:0) + NH4 | TG | (15:0/14:0/16:0) | 4118381 | 3720750 | 2541428 | 3930797 | 1343349 | 1475096 | 3565070 | 4164813 | 1675552 |
| TG(16:0/14:0/16:0) + NH4 | T6(46:0) + NH4 | TG | (16:0/14:0/16:0) | 6795037 | 5052665 | 2878349 | 6022438 | 6242181 | 2016110 | 5937839 | 5877263 | 4336876 |
| TG(46:1) + NH4 | TG(46:1) + NH4 | TG | (46:1) | 4768439 | 4079835 | 1473258 | 4479206 | 6299514 | 1142516 | 5959002 | 7292691 | 1431422 |
| TG(15:0/16:0/16:0) + NH4 | TG(47:0) + NH4 | TG | (15:0/16:0/16:0) | 6090749 | 8838655 | 3231549 | 6335618 | 7647977 | 2156161 | 5507524 | 5972182 | 2732225 |
| TG(16:0/16:0/16:0) + NH4 | TG(48:0) + NH4 | TG | (16:0/16:0/16:0) | 8140830 | 5972302 | 2771992 | 7304466 | 7413730 | 4021792 | 7229802 | 6299631 | 3277730 |
| TG(16:0/16:0/16:1) + NH4 | TG(48:1) + NH4 | TG | (16:0/16:0/16:1) | 6248878 | 5074336 | 2682659 | 5508672 | 5837385 | 1721460 | 5661303 | 11138979 | 229768 |
| TG(18:0/16:0/16:0) + NHA | TG(50:0) + NHA | TG | (18:0/16:0/16:0) | 11403968 | 9758925 | 1882255 | 10674644 | 11498263 | 1366220 | 10672750 | 11306892 | 1668406 |
| TG(16:0/16:0/18:1) + NH4 | TG(50:1) + NH4 | TG | (16:0/16:0/18:1) | 12279240 | 8130914 | 2969720 | 11354171 | 6912034 | 1356077 | 6511148 | 5494692 | 3212002 |
| TG(18:0/16:0/18:1) + NH4 | TG(52:1) + NH4 | TG | (18:0/16:0/18:1) | 5819358 | 4864513 | 1634976 | 5557327 | 5378670 | 1096755 | 5506420 | 5373435 | 1335435 |
| TG(16:0/18:/18:1) + NH4 | TG(52:2) + NH4 | TG | (16:0/18:/18:1) | 9061242 | 100072579 | 2244070 | 8249171 | 8874213 | 1748260 | 10205374 | 11992060 | 1732428 |
| TG(16:1/18:1/18:1) + NH4 | TG(52:3) + NH4 | TG | (16:1/18:1/18:1) | 4725098 | 2738900 | 643761 | 2902454 | 4511770 | 452722 | 2861650 | 3029603 | 581059 |
| TG(18:0/18:1/18:1) + NH4 | TG(54:2) + NH4 | TG | (18:0/18:1/18:1) | 5654594 | 4489151 | 979908 | 5202267 | 5196027 | 709183 | 5389810 | 5130435 | 810488 |
| TG(8:1/18:1/18:1) + NH4 | TG(54:3) + NH4 | TG | (18:1/18:1/18:1) | 11724150 | 8431628 | 1404204 | 14224033 | 14670275 | 991967 | 10211213 | 9201560 | 1610674 |

TABLE 6-continued

| Lipid Ion | Lipid Group | Lipid Class | Fatty Acid Chain | B16-F10 Exomere | | | B16-F10 Exo-S | | | B16-F10 Exo-L | | |
|---|---|---|---|---|---|---|---|---|---|---|---|---|
| | | | | Exomere replicate 1 | Exomere replicate 2 | Exomere replicate 3 | replicate 1 | replicate 2 | replicate 3 | replicate 1 | replicate 2 | replicate 3 |
| TG(18:1/18:1/ 18:2) + NH4 | TG(54:4) + NH4 | TG | (18:1/18:1/ 18:2) | 4680624 | 3917537 | 621665 | 4058915 | 4707413 | 505091 | 3930835 | 4407087 | 590330 |
| TG(18:1/18:2/ 18:2) + NH4 | TG(54:5) + NH4 | TG | (18:1/18:2/ 18:2) | 2507239 | 3032444 | 297703 | 2273173 | 2380920 | 261082 | 2921273 | 2359582 | 259348 |
| TG(18:2/18:2/ 18:2) + NH4 | TG(54:6) + NH4 | TG | (18:2/18:2/ 18:2) | 1746477 | 1389870 | 74698 | 1991526 | 1796868 | 49971 | 1894205 | 1709018 | 44805 |
| TOTAL | | | | 3.829E+09 | 3.116E+09 | 2.416E+09 | 2.059E+10 | 1.748E+10 | 2.482E+10 | 2.240E+10 | 1.886E+10 | 1.810E+10 |

The values in the table are relative signal response (signal's peak area count is normalized to sample weight and peak area count of the internal standard signal)

TABLE 7

| Lipid Ion | Lipid Group | Lipid Class | Fatty Acid Chain | MDA-MB-4175 Exomere replicate 1 | MDA-MB-4175 Exomere replicate 2 | MDA-MB-4175 Exomere replicate 3 | MDA-MB-4175 Exo-S replicate 1 | MDA-MB-4175 Exo-S replicate 2 | MDA-MB-4175 Exo-S replicate 3 | MDA-MB-4175 Exo-L replicate 1 | MDA-MB-4175 Exo-L replicate 2 | MDA-MB-4175 Exo-L replicate 3 |
|---|---|---|---|---|---|---|---|---|---|---|---|---|
| AcCa(14:0) + H | AcCa(14:0) + H | AcCa | (14:0) | 236921 | 60280 | 40369 | 126480 | 157838 | 152846 | 1834630 | 284936 | 421408 |
| AcCa(16:0) + H | AcCa(16:0) + H | AcCa | (16:0) | 173132 | 115487 | 99632 | 290548 | 540773 | 602220 | 2904828 | 842170 | 1601012 |
| AcCa(18:0) + H | AcCa(18:0) + H | AcCa | (18:0) | 130334 | 141303 | 32252 | 253192 | 333198 | 458510 | 3139944 | 678326 | 130103 |
| AcCa(18:1) + H | AcCa(18:1) + H | AcCa | (18:1) | 262216 | 178530 | 181058 | 384403 | 477005 | 418190 | 3551080 | 722892 | 775428 |
| Cer(d28:1) + H | Cer(d18:1/10:0) + H | Cer | (d18:1/10:0) | 2655983 | 2717474 | 3068942 | 2245269 | 3685342 | 3417381 | 43785352 | 7453770 | 10821114 |
| Cer(d29:1) + H | Cer(d17:1/12:0) + H | Cer | (d17:1/12:0) | 2207505 | 1985339 | 2087242 | 2100964 | 2174159 | 2042473 | 33378548 | 4186857 | 7247456 |
| Cer(d30:0) + H | Cer(d18:0/12:0) + H | Cer | (d18:0/12:0) | 5662075 | 4936509 | 5593158 | 4329811 | 4729504 | 5127001 | 91609934 | 12484096 | 19337026 |
| Cer(d31:1) + H | Cer(d18:1/13:0) + H | Cer | (d18:1/13:0) | 2422764 | 2096279 | 2465362 | 2107474 | 2288184 | 2188704 | 43488083 | 6183718 | 9429952 |
| Cer(d32:1) + H | Cer(d18:1/14:0) + H | Cer | (d18:1/14:0) | 11477831 | 12948297 | 13238862 | 20733298 | 19005688 | 24257680 | 552120875 | 103925661 | 151641948 |
| Cer(d33:1) + H | Cer(d17:1/16:0) + H | Cer | (d17:1/16:0) | 7509 | 21555 | 78579 | 105088 | 78637 | 118214 | 3460630 | 595755 | 714338 |
| Cer(d34:1) + H | Cer(d18:1/16:0) + H | Cer | (d18:1/16:0) | 1117353 | 955878 | 661319 | 1287571 | 834189 | 1375069 | 105933055 | 20713069 | 12389874 |
| Cer(d34:2) + H | Cer(d18:2/16:0) + H | Cer | (d18:2/16:0) | 52597 | 95208 | 87456 | 722863 | 663076 | 1096538 | 8685089 | 2242095 | 4531503 |
| Cer(d36:1) + H | Cer(d18:1/18:0) + H | Cer | (d18:1/18:0) | 0 | 0 | 0 | 0 | 0 | 0 | 0 | 0 | 0 |
| Cer(d36:2) + H | Cer(d18:2/18:0) + H | Cer | (d18:2/18:0) | 0 | 0 | 0 | 132962 | 135786 | 231728 | 1894280 | 654766 | 816443 |
| Cer(d40:0) + H | Cer(d18:2/22:0) + H | Cer | (d18:2/22:0) | 0 | 0 | 0 | 30277 | 18349 | 77779 | 3095047 | 813500 | 480540 |
| Cer(d42:1) + H | Cer(d18:1/24:1) + H | Cer | (d18:1/24:1) | 8852 | 7438 | 10947 | 29671 | 40745 | 44239 | 14047924 | 4203440 | 659553 |
| Cer(d42:2) + H | Cer(d18:2/24:0) + H | Cer | (d18:2/24:0) | 0 | 0 | 0 | 6450 | 32143 | 62391 | 16020443 | 3580326 | 1286726 |
| Cer(d42:3) + H | Cer(d18:2/24:1) + H | Cer | (d18:2/24:1) | 194539 | 104065 | 155166 | 692323 | 276902 | 427271 | 21410849 | 2070555 | 2387340 |
| CerG1(d34:1) + H | CerG1(d18:1/16:0) + H | CerG1 | (d18:1/16:0) | 698553 | 626375 | 657261 | 1463831 | 1176889 | 1258903 | 82287509 | 18156168 | 8437858 |
| CerG1(d34:2) + H | CerG1(d18:2/16:1) + H | CerG1 | (d18:2/16:1) | 3242 | 3156 | 11881 | 483819 | 412033 | 377232 | 4663727 | 1388424 | 1738013 |
| CerG1(d42:2) + H | CerG1(d42:2) + H | CerG1 | (d42:2) | 19156 | 38663 | 69825 | 199891 | 124949 | 159067 | 23002018 | 6801232 | 2282490 |
| CerG1(d42:3) + H | CerG1(d42:3) + H | CerG1 | (d42:3) | 8267 | 28320 | 19495 | 312700 | 408677 | 349795 | 8310956 | 2537848 | 2515903 |
| CerG2(d42:2) + H | CerG2(d42:2) + H | CerG2 | (d42:2) | 194539 | 104065 | 132010 | 164952 | 0 | 52049 | 4684460 | 1084666 | 642286 |
| CerG3(d34:1) + H | CerG3(d18:1/16:0) + H | CerG3 | (d34:1) | 82694 | 93825 | 71653 | 89390 | 81669 | 186557 | 644833 | 1077241 | 342845 |
| CL(14:0/14:0/14:0/14:0) - H | CL(56:0) - H | CL | (14:0/14:0/14:0/14:0) | 0 | 0 | 0 | 0 | 0 | 0 | 281420 | 135313 | 346310 |
| CL(18:2/14:0/14:0/14:0) - H | CL(60:2) - H | CL | (18:2/14:0/14:0/14:0) | 2113997 | 2158943 | 2979313 | 1583175 | 1872591 | 2024747 | 49191055 | 6044383 | 13647980 |
| CL(63:3) - H | CL(63:3) - H | CL | (63:3) | 26567573 | 21638964 | 23018821 | 22393188 | 15475284 | 19590970 | 400846638 | 64364027 | 87152106 |
| cPA(18:0) - H | cPA(18:0) - H | cPA | (18:0) | 0 | 0 | 0 | 0 | 0 | 0 | 0 | 0 | 0 |
| DG(9:0/9:0) + NH4 | DG(9:0/9:0) + NH4 | DG | (9:0/9:0) | 220351 | 708397 | 661717 | 384894 | 2224405 | 1359115 | 3427027 | 4147519 | 7516632 |
| DG(10:0/10:0) + NH4 | DG(10:0/10:0) + NH4 | DG | (10:0/10:0) | 71305 | 204318 | 238931 | 163071 | 549574 | 429392 | 1582819 | 1280889 | 2030563 |
| DG(16:0/14:0) + NH4 | DG(16:0/14:0) + NH4 | DG | (16:0/14:0) | 98618 | 116865 | 122307 | 190236 | 29748 | 75232 | 12666456 | 10303377 | 662173 |
| DG(16:0/16:0) + NH4 | DG(16:0/16:0) + NH4 | DG | (16:0/16:0) | 514614 | 516721 | 656759 | 1139209 | 275352 | 405462 | 344533948 | 281069758 | 2244319 |
| DG(18:0/16:0) + NH4 | DG(18:0/16:0) + NH4 | DG | (18:0/16:0) | 523401 | 401524 | 547006 | 1034357 | 749350 | 472075 | 282519224 | 197608752 | 2857014 |
| DG(16:0/18:1) + NH4 | DG(16:0/18:1) + NH4 | DG | (16:0/18:1) | 503615 | 210946 | 434667 | 610589 | 252986 | 290973 | 32916503 | 10441702 | 664591 |
| DG(16:0/18:2) + NH4 | DG(16:0/18:2) + NH4 | DG | (16:0/18:2) | 459485 | 142139 | 292571 | 374868 | 117960 | 263493 | 10967709 | 3507411 | 498989 |
| DG(16:1/18:1) + NH4 | DG(16:1/18:1) + NH4 | DG | (16:1/18:1) | 116274 | 14653 | 51648 | 244903 | 80962 | 113728 | 4036728 | 690883 | 230487 |
| DG(18:0/18:0) + NH4 | DG(18:0/18:0) + NH4 | DG | (18:0/18:0) | 423894 | 417786 | 374555 | 362393 | 534468 | 357479 | 36801516 | 21585066 | 1702063 |
| DG(18:0/18:1) + NH4 | DG(18:0/18:1) + NH4 | DG | (18:0/18:1) | 178324 | 112775 | 162706 | 212795 | 145109 | 187325 | 15156412 | 3941484 | 458267 |
| DG(18:1/18:1) + NH4 | DG(18:1/18:1) + NH4 | DG | (18:1/18:1) | 920441 | 325775 | 574502 | 836183 | 394846 | 392394 | 32608125 | 11438424 | 1054671 |
| DG(18:2/18:0) + NH4 | DG(18:2/18:0) + NH4 | DG | (18:2/18:0) | 7822 | 18131 | 84842 | 797163 | 56090 | 66050 | 21574088 | 4067784 | 106538 |
| DG(18:0/20:4) + NH4 | DG(18:0/20:4) + NH4 | DG | (18:0/20:4) | 0 | 0 | 0 | 67179 | 98416 | 73714 | 313125 | 111830 | 377480 |
| LPA(16:0) - H | LPA(16:0) - H | LPA | (16:0) | 0 | 0 | 0 | 45473 | 25422 | 17533 | 0 | 0 | 0 |
| LPA(18:0) - H | LPA(18:0) - H | LPA | (18:0) | 23790298 | 22254886 | 24392408 | 29863151 | 27665994 | 29303338 | 361686129 | 44332937 | 75970404 |
| LPC(12:0) + H | LPC(12:0) + H | LPC | (12:0) | 258413 | 269648 | 257370 | 640244 | 613158 | 604231 | 8167030 | 1968034 | 2947532 |
| LPC(14:0) + H | LPC(14:0) + H | LPC | (14:0) |  |  |  |  |  |  |  |  |  |

TABLE 7-continued

| Lipid Ion | Lipid Group | Lipid Class | Fatty Acid Chain | MDA-MB-4175 Exomere replicate 1 | MDA-MB-4175 Exomere replicate 2 | MDA-MB-4175 Exomere replicate 3 | MDA-MB-4175 Exo-S replicate 1 | MDA-MB-4175 Exo-S replicate 2 | MDA-MB-4175 Exo-S replicate 3 | MDA-MB-4175 Exo-L replicate 1 | MDA-MB-4175 Exo-L replicate 2 | MDA-MB-4175 Exo-L replicate 3 |
|---|---|---|---|---|---|---|---|---|---|---|---|---|
| LPC(15:9) + H | LPC(15:0) + H | LPC | (15:0) | 0 | 0 | 0 | 145644 | 162622 | 131006 | 945377 | 287920 | 557726 |
| LPC(16:0) + H | LPC(16:0) + H | LPC | (16:0) | 511142 | 1092870 | 1012735 | 11212410 | 1799189 | 1235571 | 17922295 | 4817545 | 7379930 |
| LPC(16:0e) + H | LPC(16:0e) + H | LPC | (16:0e) | 0 | 0 | 0 | 874804 | 908642 | 859413 | 7751597 | 2571194 | 4345836 |
| LPC(16:0p) + H | LPC(16:0p) + H | LPC | (16:0p) | 0 | 0 | 0 | 392879 | 421352 | 451399 | 2760657 | 909709 | 1887498 |
| LPC(16:1) + H | LPC(16:1) + H | LPC | (16:1) | 19507 | 33259 | 27441 | 549700 | 675184 | 313464 | 4116434 | 983238 | 1243586 |
| LPC(17:0) + H | LPC(17:0) + H | LPC | (17:0) | 0 | 0 | 0 | 346485 | 295634 | 350623 | 2818005 | 786339 | 1280303 |
| LPC(17:1) + H | LPC(17:1) + H | LPC | (17:1) | 231456 | 223932 | 251852 | 184051 | 244014 | 283861 | 2109653 | 63059 | 722448 |
| LPC(18:0) + H | LPC(18:0) + H | LPC | (18:0) | 19387 | 50326 | 49929 | 1201301 | 892073 | 924000 | 9518868 | 2775978 | 4052148 |
| LPC(18:0e) + H | LPC(18:0e) + H | LPC | (18:0e) | 15738 | 5452 | 26816 | 817225 | 668857 | 717703 | 6971758 | 2424788 | 3234886 |
| LPC(18:0p) + H | LPC(18:0p) + H | LPC | (18:0p) | 0 | 0 | 0 | 227445 | 197809 | 273952 | 2086704 | 421383 | 1034629 |
| LPC(18:1) + H | LPC(18:1) + H | LPC | (18:1) | 78091 | 682864 | 127626 | 721046 | 4981691 | 5413606 | 6909206 | 1415971 | 2577564 |
| LPC(18:1p) + H | LPC(18:1p) + H | LPC | (18:1p) | 0 | 0 | 0 | 67857 | 74595 | 66462 | 587746 | 39423 | 164326 |
| LPC(18:3) + H | LPC(18:3) + H | LPC | (18:3) | 13452 | 19986 | 26017 | 557398 | 539676 | 653872 | 3604766 | 831154 | 2385132 |
| LPC(19:0) + H | LPC(19:0) + H | LPC | (19:0) | 0 | 0 | 0 | 57278 | 36508 | 56391 | 170840 | 127841 | 228556 |
| LPC(19:1) + H | LPC(19:1) + H | LPC | (19:1) | 0 | 0 | 0 | 162478 | 53902 | 73923 | 1910635 | 138093 | 313977 |
| LPC(20:0) + H | LPC(20:0) + H | LPC | (20:0) | 0 | 0 | 0 | 293411 | 211624 | 240786 | 2453147 | 715073 | 743929 |
| LPC(20:0e) + H | LPC(20:0e) + H | LPC | (20:0e) | 0 | 0 | 0 | 234902 | 111226 | 78719 | 1168978 | 566868 | 429543 |
| LPC(20:1) + H | LPC(20:1) + H | LPC | (20:1) | 0 | 0 | 0 | 335575 | 286950 | 340239 | 3264208 | 819246 | 1361028 |
| LPC(20:2) + H | LPC(20:2) + H | LPC | (20:2) | 0 | 0 | 0 | 36382 | 13892 | 29190 | 168153 | 59093 | 171380 |
| LPC(20:3) + H | LPC(20:3) + H | LPC | (20:3) | 34037 | 58818 | 13333 | 328124 | 309797 | 384235 | 2021632 | 745731 | 1282454 |
| LPC(20:4) + H | LPC(20:4) + H | LPC | (20:4) | 11590 | 15703 | 64811 | 338945 | 247493 | 292033 | 1318615 | 238225 | 417465 |
| LPC(22:0) + H | LPC(22:0) + H | LPC | (22:0) | 0 | 0 | 0 | 223020 | 442232 | 167871 | 2068227 | 245694 | 376881 |
| LPC(22:3) + H | LPC(22:3) + H | LPC | (22:3) | 0 | 0 | 0 | 0 | 0 | 0 | 0 | 0 | 0 |
| LPC(22:4) + H | LPC(22:4) + H | LPC | (22:4) | 0 | 0 | 0 | 80883 | 49136 | 74257 | 232824 | 62682 | 142827 |
| LPC(22:5) + H | LPC(22:5) + H | LPC | (22:5) | 65136 | 81601 | 116317 | 250836 | 124532 | 197416 | 1004195 | 180428 | 615367 |
| LPC(22:6) + H | LPC(22:6) + H | LPC | (22:6) | 18278 | 57941 | 24093 | 200822 | 131690 | 137944 | 668379 | 126365 | 210287 |
| LPC(24:0) + H | LPC(24:0) + H | LPC | (24:0) | 0 | 0 | 0 | 295991 | 79870 | 102461 | 4693934 | 832912 | 215834 |
| LPC(24:1) + H | LPC(24:1) + H | LPC | (24:1) | 31659 | 31216 | 41679 | 173287 | 174716 | 123822 | 1326615 | 233447 | 479517 |
| LPC(26:1) + H | LPC(26:1) + H | LPC | (26:1) | 0 | 0 | 0 | 549956 | 257896 | 326456 | 3384573 | 828026 | 966603 |
| LPC(28:0) + H | LPC(28:0) + H | LPC | (28:0) | 157867 | 164827 | 158659 | 277434 | 285209 | 257965 | 4174619 | 532864 | 792395 |
| LPE(16:0p) - H | LPE(16:0p) - H | LPE | (16:0p) | 0 | 0 | 0 | 305679 | 283786 | 221726 | 2656494 | 966481 | 1258679 |
| LPE(18:0) - H | LPE(18:0) - H | LPE | (18:0) | 0 | 0 | 0 | 94595 | 80165 | 48211 | 587544 | 266583 | 302159 |
| LPE(20:1) - H | LPE(20:1) - H | LPE | (20:1) | 0 | 0 | 0 | 0 | 0 | 0 | 0 | 0 | 0 |
| LPE(20:4) - H | LPE(20:4) - H | LPE | (20:4) | 0 | 0 | 0 | 109524 | 0 | 227902 | 686252 | 143917 | 92179 |
| LPG(14:0) + H | LPG(14:0) + H | LPG | (14:0) | 841382 | 533465 | 723427 | 781822 | 969793 | 697483 | 9507672 | 1709038 | 1682271 |
| LPG(16:0) + H | LPG(16:0) + H | LPG | (16:0) | 0 | 0 | 0 | 0 | 0 | 0 | 0 | 0 | 0 |
| LPG(18:0) + H | LPG(18:0) + H | LPG | (18:0) | 0 | 0 | 0 | 0 | 0 | 0 | 0 | 0 | 0 |
| LPI(16:0) - H | LPI(16:0) - H | LPI | (16:0) | 0 | 0 | 0 | 181523 | 120996 | 114373 | 922878 | 249061 | 286788 |
| LPI(18:0) - H | LPI(18:0) - H | LPI | (18:0) | 0 | 0 | 0 | 41923 | 58531 | 37030 | 45212 | 29766 | 77178 |
| LPI(18:1) - H | LPI(18:1) - H | LPI | (18:1) | 80142 | 261874 | 286521 | 242666 | 1084836 | 793557 | 1650270 | 2004628 | 3872438 |
| MG(14:0) + H | MG(14:0) + H | MG | (14:0) | 12869069 | 31337664 | 31311812 | 34428216 | 112543180 | 89476091 | 302124878 | 207870963 | 391306257 |
| MG(16:0) + H | MG(16:0) + H | MG | (16:0) | 26759010 | 56344973 | 50203262 | 58402624 | 149507750 | 119903599 | 569548694 | 299981609 | 543660516 |
| MG(18:0) + H | MG(18:0) + H | MG | (18:0) | 84627 | 419296 | 473167 | 329588 | 1072455 | 1095516 | 22286684 | 2207664 | 4669714 |
| MG(18:1) + H | MG(18:1) + H | MG | (18:1) | 1228472 | 3913705 | 4429676 | 2302455 | 9738060 | 7108632 | 23436433 | 14762001 | 40048238 |
| MG(18:2) + H | MG(18:2) + H | MG | (18:2) | 159813 | 369824 | 444858 | 417350 | 1360358 | 985683 | 5947641 | 4715563 | 5555721 |
| MG(20:0) + H | MG(20:0) + H | MG | (20:0) | 0 | 0 | 0 | 128304 | 44768 | 22112 | 11676449 | 3075195 | 822160 |
| PA(34:1) - H | PA(34:1) - H | PA | (16:0/18:1) | 0 | 0 | 0 | 0 | 0 | 0 | 5255963 | 836174 | 41319 |
| PA(36:1) - H | PA(36:1) - H | PA | (18:0/18:1) | | | | | | | | | |

TABLE 7-continued

| Lipid Ion | Lipid Group | Lipid Class | Fatty Acid Chain | MDA-MB-4175 Exomere | | | MDA-MB-4175 Exo-S | | | MDA-MB-4175 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PA(18:1/18:1) − H | PA(36:2) − H | PA | (18:1/18:1) | 0 | 0 | 0 | 24916 | 6261 | 18636 | 495065 | 203516 | 31337 |
| PA(18:0/20:3) − H | PA(38:3) − H | PA | (18:0/20:3) | 0 | 0 | 0 | 0 | 0 | 0 | 0 | 0 | 0 |
| PA(18:0/20:4) − H | PA(38:4) − H | PA | (18:0/20:4) | 0 | 0 | 35757 | 116156 | 236214 | 150452 | 3350436 | 1066561 | 462363 |
| PC(16:1) + H | PC(16:1) | PC | (16:1) | 19591 | 5480 | 63718 | 70629 | 48755 | 50862 | 830071 | 129709 | 424885 |
| PC(19:1) + H | PC(19:1) | PC | (19:1) | 66872 | 44171 | 0 | 131408 | 143675 | 157187 | 737794 | 28089 | 480361 |
| PC(19:3) + H | PC(19:3) | PC | (19:3) | 0 | 0 | 0 | 1437283 | 1984186 | 2284747 | 406932 | 200393 | 346421 |
| PC(22:0) + H | PC(22:0) | PC | (22:0) | 1209573 | 1094999 | 1354462 | 4517013 | 5053785 | 5620807 | 22643890 | 5455915 | 10269555 |
| PC(23:0) + H | PC(23:0) | PC | (23:0) | 5339351 | 4669007 | 4487087 | 254420 | 175844 | 149650 | 98412130 | 14078728 | 2431643 |
| PC(14:0e/10:1) + H | PC(14:0e/10:1) | PC | (14:0e/10:1) | 18927 | 34312 | 17817 | 4646389 | 5384415 | 5397486 | 397945 | 331104 | 495352 |
| PC(25:0) + H | PC(25:0) | PC | (25:0) | 4795944 | 4771963 | 4689231 | 10007300 | 10956431 | 11269836 | 82455880 | 14723232 | 24993078 |
| PC(26:0) + H | PC(26:0) | PC | (26:0) | 8275985 | 9665322 | 9866029 | 10343330 | 9318637 | 10191677 | 178564980 | 31653172 | 51208899 |
| PC(28:0) + H | PC(28:0) | PC | (28:0) | 1106432 | 1564248 | 1283876 | 99913 | 237367 | 276974 | 120894036 | 36202735 | 40883521 |
| PC(28:1) + H | PC(28:1) | PC | (28:1) | 0 | 0 | 0 | 1855491 | 1088262 | 1528313 | 1513235 | 845586 | 744729 |
| PC(29:0) + H | PC(29:0) | PC | (29:0) | 97319 | 156901 | 123794 | 710799 | 54443 | 105836 | 26081981 | 8107306 | 8222932 |
| PC(29:0e) + H | PC(29:0e) | PC | (29:0e) | 0 | 0 | 0 | 437930 | 287908 | 436551 | 13485470 | 4110747 | 769984 |
| PC(11:0/18:1) + H | PC(11:0/18:1) | PC | (11:0/18:1) | 0 | 0 | 0 | 835680 | 638711 | 785531 | 11237279 | 4296388 | 3999681 |
| PC(29:1) + H | PC(29:1) | PC | (29:1) | 62112 | 48118 | 51039 | 80540 | 44239 | 15226 | 18447079 | 6478900 | 7145525 |
| PC(29:2) + H | PC(29:2) | PC | (29:2) | 0 | 0 | 0 | 79234042 | 32584150 | 42966990 | 691827 | 139225 | 281986 |
| PC(16:0/14:0) + H | PC(30:0) | PC | (16:0/14:0) | 4602771 | 5817623 | 5767028 | 3779659 | 1251994 | 1715938 | 1508181733 | 424951699 | 322438613 |
| PC(30:0e) + H | PC(30:0e) | PC | (30:0e) | 304701 | 316988 | 226846 | 2345472 | 971311 | 1283197 | 118766002 | 26689414 | 15498310 |
| PC(14:0p/16:0) + H | PC(14:0p/16:0) | PC | (14:0p/16:0) | 93264 | 143555 | 110028 | 10532736 | 9075411 | 11430108 | 52865186 | 16180389 | 10403201 |
| PC(16:1/14:0) + H | PC(30:1) | PC | (16:1/14:0) | 407718 | 849085 | 1082984 | 194714 | 44585 | 30466 | 102121238 | 32513960 | 45150121 |
| PC(30:1e) + H | PC(30:1e) | PC | (30:1e) | 0 | 0 | 0 | 91216 | 72114 | 11601 | 538629 | 133688 | 391370 |
| PC(30:2) + H | PC(30:2) | PC | (30:2) | 0 | 0 | 0 | 411483 | 241471 | 318855 | 100994 | 82363 | 99437 |
| PC(30:3) + H | PC(30:3) | PC | (30:3) | 0 | 0 | 0 | 7354254 | 3551647 | 4512756 | 3584986 | 979753 | 984458 |
| PC(31:0) + H | PC(31:0) | PC | (31:0) | 562500 | 627388 | 559937 | 49923 | 88484 | 128105 | 208041413 | 47825353 | 32844338 |
| PC(13:0e) + H | PC(13:0e) | PC | (31:0e) | 0 | 0 | 0 | 444680 | 169613 | 327796 | 9698835 | 2094762 | 514492 |
| PC(31:0p) + H | PC(31:0p) | PC | (31:0p) | 18256 | 28763 | 21665 | 6727970 | 6636680 | 4282044 | 21283193 | 6617157 | 3517941 |
| PC(31:1) + H | PC(31:1) | PC | (31:1) | 593255 | 949941 | 862657 | 2400815 | 2395224 | 2729234 | 17179788 | 6946787 | 15305665 |
| PC(31:2) + H | PC(31:2) | PC | (31:2) | 243432 | 226001 | 203058 | 55491 | 101513 | 122586 | 29484643 | 9514034 | 13869594 |
| PC(31:3) + H | PC(31:3) | PC | (31:3) | 0 | 0 | 0 | 41137504 | 10567863 | 16394058 | 960142 | 388584 | 807060 |
| PC(16:0/16:0) + H | PC(32:0) | PC | (16:0/16:0) | 4452214 | 2889246 | 2375948 | 1737991 | 483328 | 487339 | 2087207816 | 347790235 | 169800028 |
| PC(32:0e) + H | PC(32:0e) | PC | (32:0e) | 307077 | 147749 | 118830 | 529609443 | 433380858 | 542241915 | 139262430 | 19947233 | 9190125 |
| PC(32:1) + H | PC(32:1) | PC | (32:1) | 14353042 | 28328769 | 26110626 | 25413205 | 6266129 | 24022660 | 5381708408 | 2063475962 | 3055296955 |
| PC(16:0/16:1) + H | PC(16:0/16:1) | PC | (16:0/16:1) | 1078010 | 1712709 | 1981262 | 2906868 | 2478844 | 3294616 | 345203508 | 106814263 | 136122307 |
| PC(14:0p/18:1) + H | PC(14:0p/18:1) | PC | (14:0p/18:1) | 583540 | 789904 | 785394 | 628969 | 185957 | 1198006 | 27864431 | 11846874 | 15056673 |
| PC(16:1/16:1) + H | PC(16:1/16:1) | PC | (16:1/16:1) | 0 | 0 | 0 | 5724137 | 6037716 | 11659556 | 6309128 | 1354212 | 3441281 |
| PC(18:1/14:1) + H | PC(18:1/14:1) | PC | (18:1/14:1) | 235289 | 894714 | 789383 | 4643474 | 3896380 | 4635801 | 54210287 | 22696729 | 44333826 |
| PC(21:1/11:1) + H | PC(21:1/11:1) | PC | (21:1/11:1) | 265285 | 403424 | 382575 | 918661 | 988226 | 1104863 | 37184531 | 11008614 | 18631916 |
| PC(32:2) + H | PC(32:2) | PC | (32:2) | 72433 | 115745 | 80056 | 4872181 | 1947270 | 3036516 | 14177352 | 4586534 | 7158142 |
| PC(32:3) + H | PC(32:3) | PC | (32:3) | 150303 | 208901 | 176005 | 3892036 | 2881155 | 4444185 | 99696800 | 34888565 | 22920925 |
| PC(33:0) + H | PC(33:0) | PC | (33:0) | 299515 | 449912 | 377067 | 0 | 0 | 0 | 130248419 | 40153652 | 41041615 |
| PC(33:0e) + H | PC(33:0e) | PC | (33:0e) | 18466 | 108597 | 230880 | 2084485 | 1917217 | 2388961 | 8841852 | 2396748 | 410486 |
| PC(33:0p) + H | PC(33:0p) | PC | (33:0p) | 3413139 | 5449602 | 5653190 | 32372315 | 43970587 | 34366470 | 28996703 | 14237415 | 9002347 |
| PC(17:1/16:0) + H | PC(17:1/16:0) | PC | (17:1/16:0) | 3143910 | 460149 | 390434 | 2541014 | 2769235 | 3468141 | 384333956 | 125506096 | 267487377 |
| PC(33:1) + H | PC(33:1) | PC | (33:1) | 761232 | 2090402 | 1559426 | 18403227 | 20292111 | 24424599 | 42665807 | 15482314 | 19700029 |
| PC(33:2) + H | PC(33:2) | PC | (33:2) | 72710 | 194838 | 177564 | 3107071 | 3361698 | 3945206 | 43629291 | 15720761 | 21568498 |
| PC(33:3) + H | PC(33:3) | PC | (33:3) | | | | | | | | | |

TABLE 7-continued

| Lipid Ion | Lipid Group | Lipid Class | Fatty Acid Chain | MDA-MB-4175 Exomere Exomere replicate 1 | MDA-MB-4175 Exomere Exomere replicate 2 | MDA-MB-4175 Exomere Exomere replicate 3 | MDA-MB-4175 Exo-S Exo-S replicate 1 | MDA-MB-4175 Exo-S Exo-S replicate 2 | MDA-MB-4175 Exo-S Exo-S replicate 3 | MDA-MB-4175 Exo-L Exo-L replicate 1 | MDA-MB-4175 Exo-L Exo-L replicate 2 | MDA-MB-4175 Exo-L Exo-L replicate 3 |
|---|---|---|---|---|---|---|---|---|---|---|---|---|
| PC(33:5) + H | PC(33:5) | PC | (33:5) | 0 | 0 | 0 | 298512 | 308865 | 334620 | 3269444 | 1121079 | 1639091 |
| PC(34:0) + H | PC(34:0) | PC | (18:0/16:0) | 359178 | 138684 | 116188 | 2875745 | 379151 | 455950 | 16419583 | 23179515 | 10404795 |
| PC(34:0e) + H | PC(34:0e) | PC | (34:0e) | 0 | 0 | 0 | 258427 | 0 | 0 | 128258 | 2004318 | 974019 |
| PC(34:1) + H | PC(34:1) | PC | (16:0/18:1) | 57137534 | 98672207 | 107106161 | 795131990 | 572739671 | 756829498 | 1178901288 | 4335104749 | 3983319960 |
| PC(34:2) + H | PC(34:2) | PC | (16:1/18:1) | 10629527 | 19254471 | 18577229 | 171372963 | 149702675 | 191866057 | 1476657263 | 559485361 | 919564135 |
| PC(34:2e) + H | PC(34:2e) | PC | (34:2e) | 471190 | 661956 | 796266 | 5739580 | 4765008 | 6466545 | 61371776 | 19953333 | 3053824 |
| PC(16:1p/18:1) + H | PC(16:1p/18:1) | PC | (16:1p/18:1) | 348115 | 445260 | 450255 | 1314342 | 1782390 | 2065504 | 16487697 | 4256385 | 8290040 |
| PC(12:0/22:3) + H | PC(12:0/22:3) | PC | (12:0/22:3) | 207158 | 391727 | 370405 | 3588907 | 3207816 | 4182560 | 33314570 | 9789081 | 16389868 |
| PC(16:1/18:2) + H | PC(16:1/18:2) | PC | (16:1/18:2) | 303230 | 592858 | 570302 | 3533522 | 3247461 | 3848673 | 28631133 | 8520327 | 14523682 |
| PC(34:3) + H | PC(34:3) | PC | (34:3) | 80962 | 88993 | 72423 | 2591499 | 2591689 | 502094 | 105092248 | 26409680 | 9652776 |
| PC(34:p3) + H | PC(34:p3) | PC | (34:3p) | 87579 | 58778 | 12971 | 45418 | 35989 | 26470 | 6555518 | 212250 | 1794458 |
| PC(34:4) + H | PC(34:4) | PC | (34:4) | 421603 | 1081928 | 1026392 | 24732541 | 17463581 | 2472382 | 242010300 | 126604844 | 126424875 |
| PC(34:4p) + H | PC(34:4p) | PC | (34:4p) | 0 | 0 | 0 | 192902 | 202640 | 230415 | 556467 | 317251 | 716708 |
| PC(35:0) + H | PC(35:0) | PC | (35:0) | 0 | 0 | 0 | 196324 | 9486 | 61320 | 19014704 | 5747836 | 2095895 |
| PC(35:0p) + H | PC(35:0p) | PC | (35:0p) | 0 | 0 | 0 | 418255 | 354606 | 853138 | 14203794 | 4259540 | 3307349 |
| PC(19:1/16:0) + H | PC(19:1/16:0) | PC | (19:1/16:0) | 3139288 | 3555178 | 3893050 | 13215816 | 9084072 | 11886536 | 260862746 | 89727407 | 68046608 |
| PC(17:0/18:1) + H | PC(17:0/18:1) | PC | (17:0/18:1) | 2782400 | 1047864 | 4954808 | 5958611 | 5798727 | 8972067 | 93757582 | 44071513 | 44071513 |
| PC(35:1p) + H | PC(35:1p) | PC | (35:1p) | 139966 | 33378 | 127542 | 369383 | 214242 | 469772 | 4355549 | 1415727 | 2022928 |
| PC(19:1/16:1) + H | PC(19:1/16:1) | PC | (19:1/16:1) | 747200 | 2278320 | 1495286 | 7672831 | 6006169 | 6978198 | 60291353 | 21889342 | 31838541 |
| PC(24:1/11:1) + H | PC(24:1/11:1) | PC | (24:1/11:1) | 1292254 | 3034693 | 3387131 | 8385675 | 9318449 | 11591575 | 91610347 | 25851589 | 45034606 |
| PC(35:2) + H | PC(35:2) | PC | (35:2) | 141960 | 130151 | 141313 | 305530 | 224042 | 278553 | 9095747 | 1881723 | 1732148 |
| PC(35:2p) + H | PC(35:2p) | PC | (35:2p) | 0 | 0 | 0 | 134779 | 90719 | 68046 | 869637 | 47608 | 217366 |
| PC(35:3) + H | PC(35:3) | PC | (35:3) | 35879 | 134764 | 136385 | 765021 | 709713 | 883674 | 5599691 | 1713948 | 3176495 |
| PC(35:4) + H | PC(35:4) | PC | (35:4) | 806222 | 2113943 | 1934974 | 25307595 | 24489607 | 30362405 | 530262258 | 185381102 | 208972036 |
| PC(35:5) + H | PC(35:5) | PC | (35:5) | 612374 | 965134 | 858495 | 11032586 | 11108646 | 14167399 | 133092399 | 42870576 | 69639718 |
| PC(35:6) + H | PC(35:6) | PC | (35:6) | 69916 | 137340 | 135718 | 3344582 | 2825816 | 8996555 | 36094208 | 14513254 | 58654585 |
| PC(18:0/18:1) + H | PC(18:0/18:1) | PC | (18:0/18:1) | 14354613 | 23074082 | 21222962 | 106232599 | 52856440 | 79634742 | 267636291 | 87717929 | 526965795 |
| PC(36:1e) + H | PC(36:1e) | PC | (36:1e) | 142639 | 268436 | 289657 | 2872654 | 942616 | 1605243 | 135322709 | 35375263 | 16657216 |
| PC(20:1p/16:0) + H | PC(20:1p/16:0) | PC | (20:1p/16:0) | 1149625 | 1349211 | 1178245 | 5773630 | 4422143 | 6031619 | 82452717 | 31737314 | 35955504 |
| PC(18:1/18:1) + H | PC(18:1/18:1) | PC | (18:1/18:1) | 12347664 | 21045862 | 22975327 | 147346375 | 137578739 | 174502375 | 1425739272 | 36108764 | 733903650 |
| PC(36:2e) + H | PC(36:2e) | PC | (36:2e) | 995383 | 379485 | 316803 | 1002762 | 962875 | 1250333 | 48894919 | 15312247 | 7197236 |
| PC(18:2p/18:0) + H | PC(18:2p/18:0) | PC | (18:2p/18:0) | 37748 | 143970 | 116727 | 830809 | 986409 | 1259345 | 4209807 | 2265577 | 4214776 |
| PC(36:2p) + H | PC(36:2p) | PC | (36:2p) | 351335 | 638617 | 847840 | 3237954 | 2583674 | 3249846 | 46290306 | 11480192 | 13324388 |
| PC(16:0/20:3) + H | PC(16:0/20:3) | PC | (16:0/20:3) | 1690448 | 3193987 | 3015638 | 17836489 | 15541315 | 21796250 | 143920100 | 51635572 | 88458918 |
| PC(18:2p/18:1) + H | PC(18:2p/18:1) | PC | (18:2p/18:1) | 691197 | 1451070 | 1251471 | 6962543 | 6461936 | 8420711 | 68087446 | 23446875 | 42920697 |
| PC(16:0/20:4) + H | PC(16:0/20:4) | PC | (16:0/20:4) | 9394271 | 20097905 | 19564301 | 152665192 | 129101686 | 165501686 | 1209501671 | 477832927 | 789596316 |
| PC(36:4e) + H | PC(36:4e) | PC | (36:4e) | 219433 | 254367 | 351759 | 1569224 | 1206603 | 1500749 | 34148260 | 9926038 | 8671422 |
| PC(36:4p) + H | PC(36:4p) | PC | (36:4p) | 9437 | 61315 | 46368 | 342578 | 341984 | 391212 | 1614369 | 749413 | 1101011 |
| PC(18:4/18:1) + H | PC(18:4/18:1) | PC | (18:4/18:1) | 53274 | 145234 | 154703 | 2725178 | 1945785 | 2328049 | 18298553 | 6366793 | 13937647 |
| PC(36:5) + H | PC(36:5) | PC | (36:5) | 177514 | 410206 | 493593 | 8713623 | 6888474 | 8218716 | 63955426 | 22288016 | 55888048 |
| PC(16:0e/20:5) + H | PC(16:0e/20:5) | PC | (16:0e/20:5) | 834024 | 1544292 | 1633714 | 6935415 | 6895680 | 7951932 | 59953983 | 21782986 | 36822222 |
| PC(36:5e) + H | PC(36:5e) | PC | (36:5e) | 1320 | 26285 | 11034 | 299606 | 296764 | 387818 | 1253127 | 657998 | 982420 |
| PC(36:5p) + H | PC(36:5p) | PC | (36:5p) | 0 | 0 | 0 | 287913 | 289054 | 264226 | 1514897 | 471056 | 1197797 |
| PC(36:6) + H | PC(36:6) | PC | (36:6) | 0 | 0 | 0 | 522516 | 529248 | 588457 | 1372048 | 911732 | 666167 |
| PC(36:6p) + H | PC(36:6p) | PC | (36:6p) | 326333 | 641380 | 621942 | 1088926 | 1129462 | 1495669 | 35558474 | 11785222 | 5959811 |
| PC(37:1) + H | PC(37:1) | PC | (37:1) | 1113462 | 1742791 | 1816241 | 6255028 | 4749550 | 7379115 | 92279827 | 26237587 | 32341794 |
| PC(37:2) + H | PC(37:2) | PC | (37:2) | 397112 | 804738 | 786513 | 2556994 | 2071053 | 2755874 | 24785467 | 8123931 | 10947225 |
| PC(37:3) + H | PC(37:3) | PC | (37:3) | 676997 | 1381302 | 1391308 | 3766460 | 3736291 | 4733406 | 32341740 | 10867211 | 15524541 |

TABLE 7-continued

| Lipid Ion | Lipid Group | Lipid Class | Fatty Acid Chain | MDA-MB-4175 Exomere | | | MDA-MB-4175 Exo-S | | | MDA-MB-4175 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(15:0/22:5) + H | PC(37:5) + H | PC | (15:0/22:5) | 156900 | 344526 | 342675 | 1523155 | 1484416 | 1617145 | 9727396 | 3101276 | 5148944 |
| PC(37:5) + H | PC(37:5) + H | PC | (37:5) | 318105 | 423021 | 409321 | 4047165 | 3850702 | 4738137 | 75095817 | 28898880 | 31154457 |
| PC(37:6) + H | PC(37:6) + H | PC | (37:6) | 136541 | 390953 | 363517 | 7394508 | 6542390 | 7276105 | 134391160 | 43437543 | 50721848 |
| PC(38:1) + H | PC(38:1) + H | PC | (38:1) | 541951 | 374505 | 1068409 | 2008647 | 1392397 | 1447825 | 94746198 | 29174352 | 11662458 |
| PC(16:0/22:2) + H | PC(38:2) + H | PC | (16:0/22:2) | 1023062 | 3746088 | 2833811 | 15860475 | 13910180 | 17935763 | 254078121 | 94809394 | 100011137 |
| PC(38:2e) + H | PC(38:2e) + H | PC | (38:2e) | 0 | 0 | 0 | 565336 | 178521 | 364565 | 9718490 | 5538982 | 2886988 |
| PC(28:1/10:2) + H | PC(38:3) + H | PC | (28:1/10:2) | 1217945 | 2009628 | 264703 | 8205689 | 6275382 | 7778534 | 120878165 | 42671315 | 39116391 |
| PC(18:0/20:3) + H | PC(38:3) + H | PC | (18:0/20:3) | 5608615 | 10179956 | 11780551 | 24550013 | 19834404 | 25375969 | 249200358 | 92388362 | 89148939 |
| PC(38:3e) + H | PC(38:3e) + H | PC | (38:3e) | 36942 | 69567 | 74682 | 1135142 | 699972 | 832972 | 20927578 | 5423967 | 6070033 |
| PC(24:0/14:4) + H | PC(38:4) + H | PC | (24:0/14:4) | 2221230 | 4362980 | 4738731 | 14991589 | 14373161 | 17962577 | 119704699 | 41215604 | 66433405 |
| PC(18:0/20:4) + H | PC(38:4) + H | PC | (18:0/20:4) | 17483958 | 34897014 | 39831332 | 110336870 | 103353337 | 126598098 | 912804948 | 367123332 | 456219389 |
| PC(38:4e) + H | PC(38:4e) + H | PC | (38:4e) | 455091 | 426209 | 482502 | 6176603 | 4995887 | 7130835 | 90639464 | 25480228 | 36083224 |
| PC(38:4p) + H | PC(38:4p) + H | PC | (38:4p) | 713157 | 1404646 | 1298517 | 5623064 | 5918103 | 7547131 | 46811765 | 16829415 | 33283941 |
| PC(18:1/20:4) + H | PC(38:5) + H | PC | (18:1/20:4) | 11449628 | 24490329 | 23673925 | 155745407 | 138651176 | 138651176 | 1079658231 | 443320655 | 705120020 |
| PC(16:0/22:6) + H | PC(38:6) + H | PC | (16:0/22:6) | 0 | 0 | 0 | 334908 | 344130 | 431665 | 3301071 | 1396051 | 2013185 |
| PC(18:1/20:5) + H | PC(38:6) + H | PC | (18:1/20:5) | 6779923 | 12734088 | 12128090 | 40965770 | 41881252 | 49101290 | 299592871 | 96385480 | 147209871 |
| PC(38:6e) + H | PC(38:6e) + H | PC | (38:6e) | 168670 | 302465 | 337779 | 1306540 | 1244633 | 1528541 | 9693004 | 4337657 | 6028592 |
| PC(38:6p) + H | PC(38:6p) + H | PC | (38:6p) | 995876 | 2511086 | 2389073 | 8313063 | 5999773 | 8096177 | 48793626 | 19073302 | 32073670 |
| PC(38:7) + H | PC(38:7) + H | PC | (38:7) | 1106556 | 2335929 | 2559792 | 11284696 | 9874598 | 14138543 | 68137931 | 31562996 | 50812002 |
| PC(39:3) + H | PC(39:3) + H | PC | (39:3) | 469376 | 787255 | 762519 | 7278466 | 5528504 | 7748374 | 48359785 | 18183225 | 33060843 |
| PC(39:4) + H | PC(39:4) + H | PC | (39:4) | 60048 | 253399 | 236247 | 825124 | 664776 | 857006 | 10074118 | 4042324 | 3359834 |
| PC(39:5) + H | PC(39:5) + H | PC | (39:5) | 106623 | 311653 | 363814 | 583769 | 831288 | 1181466 | 3764668 | 2681453 | 4488329 |
| PC(39:6) + H | PC(39:6) + H | PC | (39:6) | 460907 | 847895 | 846817 | 2199359 | 2246591 | 2734654 | 14849064 | 5472785 | 8094852 |
| PC(39:7) + H | PC(39:7) + H | PC | (39:7) | 363776 | 688682 | 690252 | 2120943 | 2091226 | 2458762 | 13242595 | 5115345 | 7263732 |
| PC(40:1) + H | PC(40:1) + H | PC | (40:1) | 56257 | 18932 | 57154 | 245885 | 159847 | 114030 | 1740294 | 275171 | 460596 |
| PC(40:2) + H | PC(40:2) + H | PC | (40:2) | 0 | 0 | 0 | 223423 | 12228 | 122727 | 24758649 | 8035527 | 2770742 |
| PC(40:3) + H | PC(40:3) + H | PC | (40:3) | 11471 | 58462 | 98252 | 1628851 | 1362984 | 1752107 | 37550967 | 14319920 | 11884426 |
| PC(40:3p) + H | PC(40:3p) + H | PC | (40:3p) | 95201 | 157022 | 297187 | 1240209 | 1228392 | 1520557 | 17158437 | 5881270 | 7057461 |
| PC(40:4) + H | PC(40:4) + H | PC | (40:4) | 13777 | 45386 | 99017 | 608956 | 383896 | 658993 | 11065763 | 2675669 | 3684100 |
| PC(18:1/22:4) + H | PC(40:5) + H | PC | (18:1/22:4) | 2038465 | 4097217 | 5521298 | 13079879 | 8503255 | 14253766 | 115203954 | 40789419 | 55358204 |
| PC(40:5) + H | PC(40:5) + H | PC | (40:5) | 7147724 | 14103713 | 15191629 | 34009226 | 32683347 | 41313293 | 248040907 | 101126845 | 119844944 |
| PC(40:5e) + H | PC(40:5e) + H | PC | (40:5e) | 105343 | 320868 | 410181 | 1292640 | 1589237 | 1339751 | 16333641 | 4669949 | 5591935 |
| PC(18:0/22:6) + H | PC(40:6) + H | PC | (18:0/22:6) | 1156960 | 2571737 | 2677364 | 13913706 | 13529273 | 22356511 | 104912863 | 52151880 | 81789080 |
| PC(20:3/20:3) + H | PC(40:6) + H | PC | (20:3/20:3) | 7293565 | 14518867 | 14889706 | 36636027 | 35270303 | 41922413 | 245243158 | 94456000 | 118046565 |
| PC(40:6e) + H | PC(40:6e) + H | PC | (40:6e) | 315472 | 724752 | 836623 | 4084783 | 2781592 | 1567767 | 28123198 | 10080132 | 12676041 |
| PC(40:6p) + H | PC(40:6p) + H | PC | (40:6p) | 223556 | 772277 | 734407 | 2371860 | 1954178 | 2622667 | 17136802 | 6721238 | 7738071 |
| PC(20:3/20:4) + H | PC(40:7) + H | PC | (20:3/20:4) | 1282401 | 2591495 | 2408340 | 8872549 | 8657668 | 10811380 | 55079478 | 19577905 | 31892380 |
| PC(40:7) + H | PC(40:7) + H | PC | (40:7) | 57115 | 139379 | 162919 | 475980 | 579759 | 704352 | 3751728 | 1296351 | 2219531 |
| PC(40:7p) + H | PC(40:7p) + H | PC | (40:7p) | 373074 | 864902 | 783967 | 3833467 | 3640745 | 4767614 | 19587132 | 8605721 | 14529135 |
| PC(40:8) + H | PC(40:8) + H | PC | (40:8) | 18393 | 32255 | 17394 | 308734 | 469715 | 469742 | 866539 | 1113470 | 606524 |
| PC(40:9) + H | PC(40:9) + H | PC | (40:9) | 250728 | 494056 | 437201 | 118333 | 140654 | 2212508 | 12556276 | 1169429 | 76071 |
| PC(41:5) + H | PC(41:5) + H | PC | (41:5) | 5389 | 48601 | 99717 | 223947 | 184873 | 279181 | 465955 | 611325 | 541978 |
| PC(41:6) + H | PC(41:6) + H | PC | (41:6) | 40175 | 177451 | 194621 | 484153 | 300102 | 320600 | 1584945 | 1116418 | 796995 |
| PC(41:7) + H | PC(41:7) + H | PC | (41:7) | 16601 | 68343 | 127215 | 327811 | 347996 | 297400 | 1446872 | 574323 | 460063 |
| PC(42:1) + H | PC(42:1) + H | PC | (42:1) | 0 | 0 | 0 | 104336 | 60000 | 12157 | 12214976 | 5859261 | 1589612 |
| PC(42:10) + H | PC(42:10) + H | PC | (42:10) | 75400 | 91965 | 102256 | 324751 | 244027 | 371237 | 2711854 | 597427 | 1111573 |
| PC(42:2) + H | PC(42:2) + H | PC | (42:2) | 8057 | 9377 | 27272 | 775882 | 666964 | 809519 | 27301630 | 12167560 | 7553855 |
| PC(42:3p) + H | PC(42:3p) + H | PC | (42:3p) | 0 | 0 | 0 | 71738 | 21793 | 55290 | 688883 | 516737 | 225527 |

TABLE 7-continued

| Lipid Ion | Lipid Group | Lipid Class | Fatty Acid Chain | MDA-MB-4175 Exomere | | | MDA-MB-4175 Exo-S | | | MDA-MB-4175 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PC(42:4p) + H | PC(42:4p) + H | PC | (42:4p) | 43717 | 215862 | 205533 | 539284 | 390398 | 485673 | 4705712 | 1897518 | 1503785 |
| PC(42:6) + H | PC(42:6) + H | PC | (42:6) | 63862 | 177219 | 265448 | 827589 | 526664 | 1053065 | 2148818 | 2324189 | 2943310 |
| PC(42:6e) + H | PC(42:6e) + H | PC | (42:6e) | 922337 | 712128 | 557875 | 1133591 | 1180121 | 2608847 | 11602850 | 2922275 | 2228431 |
| PC(42:7) + H | PC(42:7) + H | PC | (42:7) | 148736 | 288245 | 310230 | 826301 | 887737 | 1177085 | 6471063 | 2309885 | 8580354 |
| PC(42:7p) + H | PC(42:7p) + H | PC | (42:7p) | 0 | 0 | 0 | 0 | 0 | 0 | 0 | 0 | 0 |
| PC(42:8) + H | PC(42:8) + H | PC | (42:8) | 13084 | 44531 | 64376 | 363119 | 276813 | 535165 | 1175356 | 669385 | 1410597 |
| PC(42:9) + H | PC(42:9) + H | PC | (42:9) | 0 | 0 | 0 | 529808 | 97790 | 425505 | 531716 | 253268 | 437388 |
| PC(44:1) + H | PC(44:1) + H | PC | (44:1) | 0 | 0 | 0 | 0 | 0 | 0 | 7277079 | 3453354 | 132204 |
| PC(44:2) + H | PC(44:2) + H | PC | (44:2) | 0 | 0 | 0 | 216407 | 176688 | 339912 | 13242236 | 7068657 | 2775961 |
| PE(12:0/14:0) − H | PE(12:0/14:0) − H | PE | (12:0/14:0) | 835307 | 539707 | 679586 | 252112 | 998694 | 279666 | 9383820 | 1583508 | 3187973 |
| PE(26:0) − H | PE(26:0) − H | PE | (26:0) | 11173607 | 10466733 | 11364016 | 15551617 | 16650782 | 11779956 | 197251294 | 35467547 | 40448099 |
| PE(32:0p) − H | PE(32:0p) − H | PE | (32:0p) | 0 | 0 | 0 | 0 | 0 | 0 | 0 | 0 | 0 |
| PE(16:0/16:1) − H | PE(16:0/16:1) − H | PE | (16:0/16:1) | 94951 | 37124 | 17572 | 1065144 | 660921 | 558596 | 10308810 | 3058037 | 3321271 |
| PE(16:0p/16:1) − H | PE(16:0p/16:1) − H | PE | (16:0p/16:1) | 0 | 0 | 0 | 290319 | 201459 | 198653 | 4399204 | 1633435 | 1276485 |
| PE(16:1/16:1) − H | PE(16:1/16:1) − H | PE | (16:1/16:1) | 0 | 0 | 0 | 0 | 0 | 0 | 0 | 0 | 0 |
| PE(17:1/16:01) − H | PE(17:1/16:01) − H | PE | (17:1/16:01) | 0 | 0 | 0 | 23380 | 36474 | 78191 | 1133848 | 212068 | 1105410 |
| PE(33:1p) − H | PE(33:1p) − H | PE | (33:1p) | 0 | 0 | 0 | 0 | 0 | 0 | 318858 | 323710 | 144975 |
| PE(16:0/18:1) − H | PE(16:0/18:1) − H | PE | (16:0/18:1) | 206504 | 334455 | 310634 | 5617754 | 2995755 | 3694359 | 113349997 | 32998453 | 23003406 |
| PE(16:0p/18:1) − H | PE(16:0p/18:1) − H | PE | (16:0p/18:1) | 142407 | 254608 | 224241 | 2690549 | 1668689 | 2211092 | 79765754 | 24986491 | 15759256 |
| PE(16:1/18:1) − H | PE(16:1/18:1) − H | PE | (16:1/18:1) | 30506 | 58033 | 40849 | 1587297 | 1142572 | 1186081 | 15456377 | 3769218 | 5161718 |
| PE(18:1p/16:1) − H | PE(18:1p/16:1) − H | PE | (18:1p/16:1) | 0 | 0 | 0 | 139831 | 144147 | 165536 | 1782364 | 543231 | 860529 |
| PE(16:0p/18:2) − H | PE(16:0p/18:2) − H | PE | (16:0p/18:2) | 0 | 0 | 0 | 33554 | 16533 | 15392 | 1223756 | 487117 | 320193 |
| PE(16:1/18:2) − H | PE(16:1/18:2) − H | PE | (16:1/18:2) | 0 | 0 | 0 | 0 | 0 | 0 | 0 | 0 | 0 |
| PE(16:0p/18:3) − H | PE(16:0p/18:3) − H | PE | (16:0p/18:3) | 2209 | 20007 | 14312 | 40998 | 24227 | 19109 | 273614 | 165267 | 188813 |
| PE(17:0/18:1) − H | PE(17:0/18:1) − H | PE | (17:0/18:1) | 0 | 0 | 0 | 262875 | 109011 | 142165 | 8120137 | 2433136 | 1169734 |
| PE(17:1/18:1) − H | PE(17:1/18:1) − H | PE | (17:1/18:1) | 0 | 0 | 0 | 586753 | 493919 | 397708 | 3719476 | 1400061 | 1829147 |
| PE(18:0/18:1) − H | PE(18:0/18:1) − H | PE | (18:0/18:1) | 191345 | 351458 | 310031 | 3036954 | 1174487 | 1895087 | 152971684 | 36247881 | 13477931 |
| PE(36:1) − H | PE(36:1) − H | PE | (36:1) | 0 | 0 | 0 | 500440 | 99027 | 104474 | 374526 | 718588 | 387728 |
| PE(18:0p/18:1) − H | PE(18:0p/18:1) − H | PE | (18:0p/18:1) | 41360 | 86530 | 51250 | 776959 | 325626 | 527579 | 54566522 | 14237459 | 4369348 |
| PE(18:1/18:1) − H | PE(18:1/18:1) − H | PE | (18:1/18:1) | 79739 | 204486 | 160651 | 2758963 | 2118188 | 2188303 | 45653047 | 11981057 | 12619870 |
| PE(18:1p/18:1) − H | PE(18:1p/18:1) − H | PE | (18:1p/18:1) | 34733 | 87099 | 85100 | 1597350 | 1410722 | 1699456 | 22484446 | 8227246 | 9609538 |
| PE(16:0/20:3) − H | PE(16:0/20:3) − H | PE | (16:0/20:3) | 0 | 0 | 0 | 328447 | 303902 | 232609 | 4341687 | 1797952 | 1447398 |
| PE(18:1/18:2) − H | PE(18:1/18:2) − H | PE | (18:1/18:2) | 7100 | 46368 | 35709 | 1490445 | 1196964 | 1111499 | 11136679 | 3198549 | 4513279 |
| PE(16:0p/20:3) − H | PE(16:0p/20:3) − H | PE | (16:0p/20:3) | 19304 | 44949 | 42032 | 1268423 | 870438 | 1020219 | 20589211 | 5949373 | 6328041 |
| PE(36:3p) − H | PE(36:3p) − H | PE | (36:3p) | 0 | 0 | 0 | 572319 | 729900 | 576361 | 6870467 | 2004004 | 3275495 |
| PE(16:0/20:4) − H | PE(16:0/20:4) − H | PE | (16:0/20:4) | 50380 | 119492 | 134119 | 4151507 | 3321396 | 3055142 | 30639960 | 11435475 | 15410484 |
| PE(16:1/20:3) − H | PE(16:1/20:3) − H | PE | (16:1/20:3) | 0 | 0 | 0 | 0 | 0 | 0 | 0 | 0 | 0 |
| PE(16:0p/20:4) − H | PE(16:0p/20:4) − H | PE | (16:0p/20:4) | 449635 | 942082 | 748609 | 28906215 | 21933749 | 21043073 | 274931065 | 84010230 | 109932723 |
| PE(16:0/20:5) − H | PE(16:0/20:5) − H | PE | (16:0/20:5) | 0 | 0 | 0 | 126255 | 112308 | 92195 | 810145 | 276599 | 407791 |
| PE(16:1/20:4) − H | PE(16:1/20:4) − H | PE | (16:1/20:4) | 0 | 0 | 0 | 68330 | 37926 | 48663 | 31917 | 65750 | 75139 |
| PE(18:0/20:2) − H | PE(18:0/20:2) − H | PE | (18:0/20:2) | 9179 | 00 | 8871 | 232491 | 69821 | 117203 | 7924892 | 1739209 | 1172649 |
| PE(16:0p/22:2) − H | PE(16:0p/22:2) − H | PE | (16:0p/22:2) | 18783 | 3624 | 34658 | 82701 | 65923 | 96853 | 3443986 | 3591328 | 2518852 |
| PE(18:0/20:3) − H | PE(18:0/20:3) − H | PE | (18:0/20:3) | 0 | 42202 | 0 | 1044458 | 449921 | 608800 | 28252412 | 6814471 | 4377476 |
| PE(18:1/20:2) − H | PE(18:1/20:2) − H | PE | (18:1/20:2) | 0 | 0 | 0 | 610637 | 511182 | 451475 | 6939566 | 2406010 | 2393191 |
| PE(16:0p/22:3) − H | PE(16:0p/22:3) − H | PE | (16:0p/22:3) | 39875 | 90868 | 63938 | 1987937 | 930503 | 1070084 | 34481880 | 9303204 | 7516530 |
| PE(38:3p) − H | PE(38:3p) − H | PE | (38:3p) | 19051 | 29963 | 30405 | 630524 | 301635 | 387666 | 19467240 | 5106644 | 3168267 |
| PE(18:0/20:4) − H | PE(18:0/20:4) − H | PE | (18:0/20:4) | 405290 | 885331 | 777260 | 19075195 | 14174694 | 15495000 | 267184606 | 74663348 | 76291857 |
| PE(18:1/20:3) − H | PE(18:1/20:3) − H | PE | (18:1/20:3) | 0 | 0 | 0 | 2108646 | 2060060 | 1889938 | 35755830 | 5695213 | 7573573 |

TABLE 7-continued

| Lipid Ion | Lipid Group | Lipid Class | Fatty Acid Chain | MDA-MB-4175 Exomere Exomere replicate 1 | MDA-MB-4175 Exomere Exomere replicate 2 | MDA-MB-4175 Exomere Exomere replicate 3 | MDA-MB-4175 Exo-S Exo-S replicate 1 | MDA-MB-4175 Exo-S Exo-S replicate 2 | MDA-MB-4175 Exo-S Exo-S replicate 3 | MDA-MB-4175 Exo-L Exo-L replicate 1 | MDA-MB-4175 Exo-L Exo-L replicate 2 | MDA-MB-4175 Exo-L Exo-L replicate 3 |
|---|---|---|---|---|---|---|---|---|---|---|---|---|
| PE(38:4e) − H | PE(38:4e) − H | PE | (38:4e) | 12581 | 44768 | 48122 | 499125 | 427049 | 496021 | 8606627 | 2422792 | 2636873 |
| PE(16:0p/22:4) − H | PE(38:4p) − H | PE | (16:0p/22:4) | 151270 | 294349 | 257827 | 6786173 | 5264637 | 5345856 | 106540361 | 28801033 | 33997114 |
| PE(18:0p/20:4) − H | PE(38:4p) − H | PE | (18:0p/20:4) | 479623 | 952310 | 840565 | 17498934 | 13054619 | 14200003 | 262698265 | 84197752 | 88532563 |
| PE(38:4p) − H | PE(38:4p) − H | PE | (38:4p) | 0 | 0 | 0 | 490390 | 1202551 | 774262 | 3944790 | 2024931 | 2731247 |
| PE(18:0/20:5) − H | PE(38:5) − H | PE | (18:0/20:5) | 0 | 0 | 183672 | 1107104 | 755449 | 917099 | 9752576 | 2991200 | 3408702 |
| PE(18:1/20:4) − H | PE(38:5) − H | PE | (18:1/20:4) | 123816 | 228908 | 97024 | 6641324 | 4927459 | 5540034 | 54661096 | 16512000 | 26062282 |
| PE(16:0p/22:5) − H | PE(38:5p) − H | PE | (16:0p/22:5) | 50814 | 121783 | 630017 | 3372903 | 2325193 | 2416725 | 34245607 | 9331589 | 11576069 |
| PE(18:1p/20:4) − H | PE(38:5p) − H | PE | (18:1p/20:4) | 381469 | 819881 | 41714 | 24437101 | 18622450 | 18857868 | 191478808 | 56117605 | 82006414 |
| PE(16:0/22:6) − H | PE(38:6) − H | PE | (16:0/22:6) | 13771 | 54424 | 0 | 2116853 | 1468262 | 1602887 | 16018589 | 4647496 | 6464006 |
| PE(16:1/22:5) − H | PE(38:6) − H | PE | (16:1/22:5) | 0 | 0 | 0 | 0 | 0 | 0 | 0 | 0 | 0 |
| PE(18:0/22:3) − H | PE(40:3) − H | PE | (18:0/22:3) | 0 | 0 | 0 | 272443 | 88099 | 177541 | 10417001 | 2484548 | 1206377 |
| PE(18:0p/22:3) − H | PE(40:3p) − H | PE | (18:0p/22:3) | 24540 | 63366 | 92585 | 455346 | 212622 | 292005 | 18035611 | 4014990 | 2343446 |
| PE(18:0/22:4) − H | PE(40:4) − H | PE | (18:0/22:4) | 35382 | 121013 | 91387 | 2004137 | 1562228 | 1803772 | 39779114 | 12796498 | 10745717 |
| PE(18:0p/22:4) − H | PE(40:4p) − H | PE | (18:0p/22:4) | 61500 | 206627 | 205977 | 2758411 | 1944884 | 2289797 | 64276841 | 19859786 | 16876343 |
| PE(40:4p) − H | PE(40:4p) − H | PE | (40:4p) | 92698 | 59537 | 50475 | 548298 | 368519 | 433752 | 9157475 | 2145907 | 2592482 |
| PE(18:0/22:5) − H | PE(40:5) − H | PE | (18:0/22:5) | 45634 | 118396 | 95194 | 3869623 | 2888128 | 2869796 | 37421032 | 13739126 | 12316101 |
| PE(18:1/22:4) − H | PE(40:5) − H | PE | (18:1/22:4) | 0 | 0 | 0 | 1569018 | 1627205 | 1278158 | 14695125 | 4102260 | 5804913 |
| PE(18:0p/22:5) − H | PE(40:5p) − H | PE | (18:0p/22:5) | 157299 | 337815 | 277143 | 6790956 | 4972075 | 5471298 | 91297210 | 28760281 | 31407034 |
| PE(40:5p) − H | PE(40:5p) − H | PE | (40:5p) | 25753 | 108558 | 79567 | 2462095 | 2273855 | 2408565 | 29093596 | 8725776 | 11101220 |
| PE(18:0/22:6) − H | PE(40:6) − H | PE | (18:0/22:6) | 59238 | 140868 | 117954 | 5238826 | 3569772 | 3883856 | 56312579 | 14746047 | 17878948 |
| PE(18:1/22:5) − H | PE(40:6) − H | PE | (18:1/22:5) | 0 | 0 | 0 | 889236 | 63031 | 251098 | 3642796 | 2001033 | 2376216 |
| PE(18:0p/22:6) − H | PE(40:6p) − H | PE | (18:0p/22:6) | 166678 | 345040 | 287739 | 8309820 | 5910984 | 6060502 | 103751941 | 30759033 | 30452499 |
| PE(18:1p/22:5) − H | PE(40:6p) − H | PE | (18:1p/22:5) | 8409 | 53482 | 67277 | 2314717 | 1952777 | 2123023 | 17862011 | 5902815 | 9449441 |
| PE(18:1/22:6) − H | PE(40:7) − H | PE | (18:1/22:6) | 11085 | 72340 | 28437 | 2185913 | 1607630 | 1761904 | 12967591 | 4420414 | 6910775 |
| PE(18:1p/22:6) − H | PE(40:7p) − H | PE | (18:1p/22:6) | 32343 | 110093 | 93609 | 3689468 | 2948804 | 3075709 | 27896860 | 7085740 | 11040470 |
| PE(16:0/16:1) − H | PEt(32:1) − H | PEt | (16:0/16:1) | 0 | 0 | 0 | 128304 | 39382 | 35309 | 1107104 | 3401896 | 115566 |
| PEt(32:4) − H | PEt(32:4) − H | PEt | (32:4) | 279069077 | 278343754 | 271228360 | 396595593 | 398286346 | 297179039 | 5018214562 | 759502356 | 1098284317 |
| PEt(18:0/16:1) − H | PEt(34:1) − H | PEt | (18:0/16:1) | 0 | 0 | 0 | 116156 | 236214 | 0 | 5241098 | 871252 | 52438 |
| PEt(18:2/18:2) − H | PEt(36:4) − H | PEt | (18:2/18:2) | 2500 | 12347 | 20658 | 3509108 | 3360390 | 150452 | 3350436 | 1066561 | 462363 |
| PG(12:0/14:0) − H | PG(2600) − H | PG | (12:0/14:0) | 2996776 | 3034456 | 3078805 | 197723 | 174778 | 3108790 | 52042151 | 7349663 | 12209703 |
| PG(16:0/14:0) − H | PG(30:0) − H | PG | (16:0/14:0) | 331753 | 313756 | 323116 | 0 | 0 | 271719 | 6298537 | 620232 | 1265644 |
| PG(32:1) − H | PG(32:1) − H | PG | (32:1) | 0 | 0 | 0 | 0 | 0 | 0 | 0 | 0 | 0 |
| PG(17:1/16:0) − H | PG(33:1) − H | PG | (17:1/16:0) | 0 | 0 | 0 | 159437 | 16537 | 208936 | 411800 | 325227 | 455332 |
| PG(16:0/18:1) − H | PG(34:1) − H | PG | (16:0/18:1) | 0 | 0 | 0 | 430603 | 313435 | 339642 | 8614846 | 2313954 | 1858741 |
| PG(16:1/18:1) − H | PG(34:2) − H | PG | (16:1/18:1) | 21746 | 37325 | 27360 | 56595 | 37085 | 42525 | 582042 | 143033 | 236520 |
| PG(17:0/18:1) − H | PG(35:1) − H | PG | (17:0/18:1) | 0 | 0 | 0 | 1016441 | 964046 | 1046676 | 6363266 | 2399116 | 4766762 |
| PG(17:1/18:1) − H | PG(35:2) − H | PG | (17:1/18:1) | 0 | 0 | 0 | 163448 | 223055 | 139385 | 2448112 | 727509 | 2369852 |
| PG(18:1/18:1) − H | PG(36:1) − H | PG | (18:1/18:1) | 0 | 0 | 0 | 12323 | 15255 | 16153 | 0 | 0 | 0 |
| PG(18:1/18:2) − H | PG(36:2) − H | PG | (18:1/18:2) | 0 | 0 | 0 | 0 | 0 | 0 | 0 | 0 | 0 |
| PG(20:1/18:1) − H | PG(36:3) − H | PG | (20:1/18:1) | 0 | 0 | 0 | 0 | 0 | 0 | 0 | 0 | 0 |
| PG(18:1/20:2) − H | PG(38:2) − H | PG | (18:1/20:2) | 21801 | 25235 | 21324 | 151709 | 71063 | 68036 | 7717501 | 1554686 | 570911 |
| PG(18:0/20:4) − H | PG(38:3) − H | PG | (18:0/20:4) | 0 | 0 | 0 | 0 | 0 | 0 | 0 | 0 | 0 |
| PG(18:3/18:4) − H | PG(38:4) − H | PG | (18:3/18:4) | 0 | 0 | 0 | 0 | 0 | 0 | 0 | 0 | 0 |
| PG(18:1/20:3) − H | PG(38:5) − H | PG | (18:1/20:3) | 0 | 0 | 0 | 0 | 0 | 0 | 0 | 0 | 0 |
| PG(18:1/20:4) − H | PG(38:6) − H | PG | (18:1/20:4) | 0 | 0 | 0 | 0 | 0 | 0 | 0 | 0 | 0 |
| PG(16:0/22:6) − H | PG(38:8) − H | PG | (16:0/22:6) | 0 | 0 | 0 | 97613 | 99608 | 76825 | 276833 | 20025 | 25349 |
| PG(18:1/22:4) − H | PG(40:5) − H | PG | (18:1/22:4) | 0 | 0 | 0 | 18359 | 12885 | 17817 | 0 | 0 | 0 |
| PG(18:0/22:6) − H | PG(40:6) − H | PG | (18:0/22:6) | 0 | 0 | 0 | 80771 | 72399 | 66510 | 0 | 0 | 0 |

TABLE 7-continued

| Lipid Ion | Lipid Group | Lipid Class | Fatty Acid Chain | MDA-MB-4175 Exomere Exomere replicate 1 | MDA-MB-4175 Exomere Exomere replicate 2 | MDA-MB-4175 Exomere Exomere replicate 3 | MDA-MB-4175 Exo-S Exo-S replicate 1 | MDA-MB-4175 Exo-S Exo-S replicate 2 | MDA-MB-4175 Exo-S Exo-S replicate 3 | MDA-MB-4175 Exo-L Exo-L replicate 1 | MDA-MB-4175 Exo-L Exo-L replicate 2 | MDA-MB-4175 Exo-L Exo-L replicate 3 |
|---|---|---|---|---|---|---|---|---|---|---|---|---|
| PG(18:1/22:5) – H | PG(40:6) – H | PG | (18:1/22:5) | 0 | 0 | 0 | 18976 | 6070 | 8874 | 0 | 0 | 0 |
| PG(18:1/22:6) – H | PG(40:7) – H | PG | (18:1/22:6) | 0 | 0 | 0 | 862230 | 778194 | 782003 | 973979 | 347757 | 591283 |
| PG(20:1/22:6) – H | PG(42:7) – H | PG | (20:1/22:6) | 0 | 0 | 0 | 0 | 0 | 0 | 0 | 0 | 0 |
| PG(20:2/22:6) – H | PG(42:8) – H | PG | (20:2/22:6) | 0 | 0 | 0 | 0 | 0 | 0 | 0 | 0 | 0 |
| PI(16:0/18:1) – H | PI(34:1) – H | PI | (16:0/18:1) | 207265 | 403469 | 326785 | 1666070 | 5377187 | 6216683 | 107496050 | 31734088 | 25126566 |
| PI(16:1/18:1) – H | PI(34:2) – H | PI | (16:1/18:1) | 0 | 0 | 0 | 34339 | 24300 | 11368 | 59477 | 76990 | 129444 |
| PI(18:0/18:1) – H | PI(36:1) – H | PI | (18:0/18:1) | 123836 | 155434 | 144386 | 2550655 | 852089 | 1197680 | 73101178 | 13569781 | 5409439 |
| PI(16:0/20:3) – H | PI(36:3) – H | PI | (16:0/20:3) | 0 | 0 | 0 | 125921 | 178738 | 111964 | 972536 | 313168 | 444576 |
| PI(18:1/18:2) – H | PI(36:3) – H | PI | (18:1/18:2) | 0 | 0 | 0 | 166755 | 75972 | 152945 | 657662 | 167481 | 290916 |
| PI(16:0/20:4) – H | PI(36:4) – H | PI | (16:0/20:4) | 0 | 0 | 0 | 150229 | 100424 | 0 | 0 | 684790 | 704467 |
| PI(17:0/20:4) – H | PI(37:4) – H | PI | (17:0/20:4) | 0 | 0 | 0 | 94240 | 77828 | 80481 | 227158 | 182549 | 293712 |
| PI(20:1/18:1) – H | PI(38:2) – H | PI | (20:1/18:1) | 0 | 0 | 0 | 0 | 0 | 0 | 278494 | 132307 | 81096 |
| PI(18:0/20:3) – H | PI(38:3) – H | PI | (18:0/20:3) | 76367 | 100481 | 97880 | 2117265 | 837601 | 1015849 | 28117369 | 6105706 | 4678508 |
| PI(18:1/20:3) – H | PI(38:4) – H | PI | (18:1/20:3) | 5237 | 31011 | 16173 | 593889 | 492634 | 465764 | 10496166 | 2294116 | 2055798 |
| PI(18:0/20:5) – H | PI(38:5) – H | PI | (18:0/20:5) | 0 | 0 | 0 | 162798 | 119010 | 160884 | 781145 | 382314 | 467393 |
| PI(18:1/20:4) – H | PI(38:5) – H | PI | (18:1/20:4) | 0 | 0 | 0 | 1066944 | 1133842 | 709902 | 440501 | 1267290 | 981722 |
| PI(18:0/22:4) – H | PI(40:4) – H | PI | (18:0/22:4) | 0 | 0 | 0 | 938473 | 539919 | 655085 | 10271169 | 3056243 | 3723958 |
| PMe(14:0/14:0) – H | PMe(28:0) – H | PMe | (14:0/14:0) | 197233 | 186704 | 197921 | 233689 | 185238 | 197160 | 3102192 | 415794 | 650827 |
| PMe(34:5) – H | PMe(34:5) – H | PMe | (34:5) | 217296466 | 220166027 | 191306985 | 206143596 | 192082882 | 182843648 | 3509160915 | 489928236 | 692043430 |
| PMe(34:6) – H | PMe(42:6) – H | PMe | (42:6) | 445198 | 687639 | 616907 | 9188019 | 3439530 | 4622705 | 30771285 | 55136066 | 24483243 |
| PS(12:0/14:0) – H | PS(26:0) – H | PS | (12:0/14:0) | 1614543 | 1496858 | 1622028 | 2032182 | 1992144 | 1914011 | 28345507 | 3516088 | 6713480 |
| PS(16:0/16:1) – H | PS(32:1) – H | PS | (16:0/16:1) | 0 | 0 | 0 | 709341 | 440595 | 1551648 | 4883070 | 1785540 | 2550206 |
| PS(33:1) – H | PS(33:1) – H | PS | (33:1) | 0 | 0 | 0 | 0 | 0 | 0 | 0 | 0 | 0 |
| PS(18:0/16:1) – H | PS(34:1) – H | PS | (18:0/16:1) | 97442 | 177311 | 158102 | 2907496 | 1967089 | 2337056 | 64986325 | 16745343 | 12735657 |
| PS(34:3p) – H | PS(34:3p) – H | PS | (34:3p) | 0 | 0 | 0 | 0 | 0 | 0 | 0 | 0 | 0 |
| PS(35:0) – H | PS(35:0) – H | PS | (35:0) | 538666 | 997297 | 827237 | 17896669 | 16069304 | 15753705 | 120092087 | 34487043 | 53222088 |
| PS(17:0/18:1) – H | PS(35:1) – H | PS | (17:0/18:1) | 31744 | 72837 | 67051 | 1172966 | 1168309 | 741564 | 22190294 | 6860227 | 1750383 |
| PS(35:1) – H | PS(35:1) – H | PS | (35:1) | 0 | 0 | 0 | 56732 | 40007 | 142128 | 1062434 | 396446 | 948516 |
| PS(35:2) – H | PS(35:2) – H | PS | (35:2) | 0 | 0 | 0 | 0 | 0 | 0 | 0 | 0 | 0 |
| PS(18:0/18:2) – H | PS(36:2) – H | PS | (18:0/18:2) | 159698 | 297725 | 309362 | 5530936 | 3866723 | 4266397 | 66482481 | 18498648 | 22120371 |
| PS(16:0/20:3) – H | PS(36:3) – H | PS | (16:0/20:3) | 0 | 0 | 0 | 493697 | 394704 | 451184 | 3608732 | 959942 | 1466983 |
| PS(18:1/18:2) – H | PS(36:3) – H | PS | (18:1/18:2) | 0 | 0 | 0 | 457286 | 369805 | 414584 | 3219733 | 837026 | 1521022 |
| PS(36:3) – H | PS(36:3) – H | PS | (36:3) | 12858 | 39203 | 37556 | 695047 | 554855 | 475378 | 18794108 | 4205650 | 3460278 |
| PS(36:3p) – H | PS(36:3p) – H | PS | (36:3p) | 5987 | 32847 | 28797 | 401345 | 273130 | 306407 | 12147615 | 3764508 | 2312891 |
| PS(16:0/20:4) – H | PS(36:4) – H | PS | (16:0/20:4) | 0 | 0 | 0 | 504066 | 518995 | 539917 | 3728026 | 1291304 | 2254419 |
| PS(36:4) – H | PS(36:4) – H | PS | (36:4) | 25147 | 57619 | 40780 | 1546353 | 1123863 | 1205590 | 22348538 | 5254145 | 5302937 |
| PS(37:1) – H | PS(37:1) – H | PS | (37:1) | 103925 | 202624 | 279931 | 2153303 | 1878319 | 1896115 | 14650703 | 3433156 | 7796187 |
| PS(37:2) – H | PS(37:2) – H | PS | (37:2) | 0 | 0 | 0 | 38551 | 6857 | 23932 | 93052 | 68361 | 202167 |
| PS(38:1) – H | PS(38:1) – H | PS | (38:1) | 0 | 0 | 0 | 131682 | 38421 | 87348 | 9647588 | 1900465 | 606454 |
| PS(20:1/18:1) – H | PS(38:2) – H | PS | (20:1/18:1) | 0 | 0 | 0 | 619467 | 710257 | 822693 | 11620755 | 2317125 | 3558461 |
| PS(18:0/20:3) – H | PS(38:3) – H | PS | (18:0/20:3) | 124012 | 227219 | 216689 | 4604588 | 3285498 | 3016987 | 71377509 | 20263566 | 20164143 |
| PS(18:3) – H | PS(38:3) – H | PS | (38:3) | 18158 | 50225 | 47308 | 526136 | 255058 | 382293 | 28884312 | 6181587 | 2638371 |
| PS(18:0/20:4) – H | PS(38:4) – H | PS | (18:0/20:4) | 80422 | 337987 | 305279 | 3498645 | 2639132 | 2196641 | 124069072 | 19908644 | 24987487 |
| PS(18:1/20:3) – H | PS(38:4) – H | PS | (18:1/20:3) | 0 | 0 | 0 | 493488 | 441954 | 460899 | 3498990 | 937986 | 1731247 |
| PS(16:0/22:5) – H | PS(38:5) – H | PS | (16:0/22:5) | 0 | 0 | 0 | 1003868 | 974808 | 848464 | 6483253 | 1514751 | 3327651 |
| PS(18:0/20:5) – H | PS(38:5) – H | PS | (18:0/20:5) | 0 | 0 | 0 | 538951 | 431797 | 506824 | 4234705 | 1134025 | 2139227 |
| PS(18:1/20:4) – H | PS(38:5) – H | PS | (18:1/20:4) | 0 | 0 | 0 | 1170057 | 942290 | 972128 | 8853041 | 2651403 | 4753546 |
| PS(38:5p) – H | PS(38:5p) – H | PS | (38:5p) | 0 | 0 | 0 | 236574 | 164874 | 161078 | 4083243 | 980936 | 1287805 |

TABLE 7-continued

| Lipid Ion | Lipid Group | Lipid Class | Fatty Acid Chain | MDA-MB-4175 Exomere | | | MDA-MB-4175 Exo-S | | | MDA-MB-4175 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| PS(16:0/22:6) − H | PS(16:0/22:6) − H | PS | (16:0/22:6) | 0 | 0 | 0 | 270747 | 359955 | 311336 | 1601519 | 755752 | 1053010 |
| PS(38:6) − H | PS(38:6) − H | PS | (38:6) | 1400 | 2242 | 1751 | 625536 | 497739 | 538392 | 6058304 | 1405830 | 2302998 |
| PS(38:6p) − H | PS(38:6p) − H | PS | (38:6p) | 46150 | 115567 | 100964 | 4545355 | 3712660 | 3847072 | 44270610 | 12373809 | 21403878 |
| PS(39:1) − H | PS(39:1) − H | PS | (39:1) | 632737 | 1169704 | 1237962 | 13169394 | 11288740 | 13799910 | 96013550 | 25615901 | 42391171 |
| PS(39:2) − H | PS(39:2) − H | PS | (39:2) | 48913 | 180273 | 168408 | 1827523 | 1366200 | 1466328 | 9475552 | 2265026 | 4469531 |
| PS(39:3) − H | PS(39:3) − H | PS | (39:3) | 455644 | 1035957 | 936332 | 8581795 | 6720518 | 7079635 | 36227939 | 11577047 | 21463136 |
| PS(39:4) − H | PS(39:4) − H | PS | (39:4) | 0 | 0 | 0 | 325492 | 249540 | 390643 | 3228058 | 1330179 | 2173109 |
| PS(18:1/22:1) − H | PS(18:1/22:1) − H | PS | (18:1/22:1) | 0 | 0 | 0 | 399045 | 278443 | 412582 | 12622421 | 3528113 | 3159688 |
| PS(18:0/22:3) − H | PS(18:0/22:3) − H | PS | (18:0/22:3) | 105924 | 249253 | 213426 | 515829 | 190865 | 326068 | 15123603 | 2782564 | 2036074 |
| PS(18:0/22:4) − H | PS(18:0/22:4) − H | PS | (18:0/22:4) | 146606 | 332309 | 312213 | 5380454 | 4319323 | 4997892 | 74157592 | 23847958 | 25983626 |
| PS(18:0/22:5) − H | PS(18:0/22:5) − H | PS | (18:0/22:5) | 0 | 0 | 0 | 10408121 | 8221687 | 8462113 | 98727320 | 27994819 | 37323768 |
| PS(18:1/22:5) − H | PS(18:1/22:5) − H | PS | (18:1/22:5) | 0 | 0 | 0 | 472766 | 500458 | 375232 | 3453673 | 872529 | 1990946 |
| PS(20:3/20:3) − H | PS(20:3/20:3) − H | PS | (20:3/20:3) | 61297 | 120647 | 131804 | 762938 | 497252 | 628108 | 10402954 | 3179957 | 2786238 |
| PS(40:6) − H | PS(40:6) − H | PS | (40:6) | 4899 | 39528 | 36501 | 3380755 | 2766864 | 2842966 | 43140475 | 11633277 | 15731032 |
| PS(40:6p) − H | PS(40:6p) − H | PS | (40:6p) | 30049 | 103106 | 84358 | 1247587 | 920284 | 1258763 | 17653104 | 5071904 | 7497451 |
| PS(40:7) − H | PS(40:7) − H | PS | (40:7) | 36328 | 102896 | 92165 | 2473682 | 2240180 | 2439584 | 26615648 | 6819779 | 10425179 |
| PS(40:7p) − H | PS(40:7p) − H | PS | (40:7p) | 11019 | 47088 | 43527 | 3598766 | 3152882 | 3094159 | 28421479 | 8287972 | 14217323 |
| PS(40:8p) − H | PS(40:8p) − H | PS | (40:8p) | 63894 | 168426 | 166946 | 1889102 | 1678944 | 1718199 | 17592428 | 4535674 | 7409624 |
| PS(41:3) − H | PS(41:3) − H | PS | (41:3) | 0 | 0 | 0 | 1023016 | 990598 | 1006077 | 5369528 | 1270858 | 3264903 |
| PS(41:6) − H | PS(41:6) − H | PS | (41:6) | 0 | 0 | 0 | 85844 | 62171 | 78130 | 235119 | 525658 | 227692 |
| PS(18:1/24:0) − H | PS(18:1/24:0) − H | PS | (18:1/24:0) | 0 | 0 | 0 | 1464832 | 1257884 | 1518317 | 1225623 | 295963 | 0 |
| PS(42:8) − H | PS(42:8) − H | PS | (42:8) | 18485 | 59321 | 66432 | 2183237 | 1799535 | 1710184 | 14565124 | 3699847 | 5231179 |
| PS(42:9) − H | PS(42:9) − H | PS | (42:9) | 7144 | 78406 | 120590 | 473049 | 192901 | 447790 | 20608914 | 4278020 | 7010451 |
| PS(43:5) − H | PS(43:5) − H | PS | (43:5) | 0 | 0 | 0 | 615719 | 631109 | 706314 | 372283 | 437908 | 163301 |
| SM(d30:1) + H | SM(d30:1) + H | SM | (d30:1) | 59798 | 147569 | 122434 | 1347188 | 837142 | 1012924 | 3874423 | 1510201 | 2740728 |
| SM(d31:1) + H | SM(d31:1) + H | SM | (d31:1) | 1108812 | 1843673 | 1730073 | 869251 | 580700 | 773451 | 14414899 | 2724618 | 3640860 |
| SM(d32:0) + H | SM(d32:0) + H | SM | (d32:0) | 88181 | 199227 | 188339 | 13790596 | 10293325 | 38165 | 23835547 | 4601133 | 4964988 |
| SM(d18:1/14:0) + H | SM(d18:1/14:0) + H | SM | (d18:1/14:0) | 0 | 0 | 0 | 1845386 | 1607297 | 1712799 | 827380 | 38866734 | 48372637 |
| SM(d32:2) + H | SM(d32:2) + H | SM | (d32:2) | 1265735 | 1658083 | 1491116 | 0 | 0 | 0 | 12711829 | 2468275 | 4436539 |
| SM(d33:0) + H | SM(d33:0) + H | SM | (d33:0) | 90044 | 19403 | 53726 | 8515714 | 5175910 | 6484024 | 4282150 | 852481 | 648658 |
| SM(d33:1) + H | SM(d33:1) + H | SM | (d33:1) | 836958 | 692120 | 449173 | 76483 | 58515 | 35559 | 214903255 | 41780873 | 34028177 |
| SM(d33:2) + H | SM(d33:2) + H | SM | (d33:2) | 18307271 | 523327 | 596877 | 2178600 | 899902 | 1467732 | 11728869 | 62959 | 120133 |
| SM(d34:0) + H | SM(d34:0) + H | SM | (d34:0) | 1307895 | 1582630 | 1278876 | 86186422 | 1574211 | 50388936 | 253094120 | 34639587 | 139974017 |
| SM(d18:1/16:0) + H | SM(d18:1/16:0) + H | SM | (d18:1/16:0) | 25065 | 7050024 | 6809144 | 15109596 | 6342158 | 9158968 | 4274137129 | 761578752 | 379912703 |
| SM(d34:1) + H | SM(d34:1) + H | SM | (d34:1) | 0 | 0 | 0 | 66462167 | 57496045 | 62349821 | 665606026 | 146205846 | 86089783 |
| SM(d16:1/18:1) + H | SM(d16:1/18:1) + H | SM | (d16:1/18:1) | 34521 | 134939 | 154759 | 105094 | 235189 | 302699 | 671063320 | 149729965 | 220490415 |
| SM(d34:3) + H | SM(d34:3) + H | SM | (d34:3) | 247968 | 184095 | 114466 | 794716 | 638889 | 656125 | 880943 | 341502 | 840518 |
| SM(d34:4) + H | SM(d34:4) + H | SM | (d34:4) | 48150 | 106033 | 120968 | 506334 | 214959 | 225096 | 11690213 | 2568360 | 2945863 |
| SM(d35:1) + H | SM(d35:1) + H | SM | (d35:1) | 43594 | 79926 | 27139 | 1050795 | 937930 | 994361 | 39671655 | 6028091 | 1974718 |
| SM(d35:2) + H | SM(d35:2) + H | SM | (d35:2) | 629637 | 12300 | 195989 | 491640 | 258966 | 304051 | 11489940 | 2772515 | 4023233 |
| SM(d35:4) + H | SM(d35:4) + H | SM | (d35:4) | 1765732 | 3344285 | 3379071 | 615028 | 111917 | 93344 | 12156988 | 2319433 | 1850319 |
| SM(d18:1/18:0) + H | SM(d18:1/18:0) + H | SM | (d18:1/18:0) | 994807 | 1005077 | 839513 | 21409555 | 5364100 | 7847110 | 30348283 | 220310 | 3411614 |
| SM(d18:1/18:1) + H | SM(d18:1/18:1) + H | SM | (d18:1/18:1) | 297164 | 295012 | 319403 | 4586442 | 1678318 | 2342663 | 294109613 | 92989524 | 115325271 |
| SM(d36:4) + H | SM(d36:4) + H | SM | (d36:4) | 54214 | 146906 | 297379 | 2163920 | 1717689 | 1990882 | 18367470 | 61473943 | 18141979 |
| SM(d36:5) + H | SM(d36:5) + H | SM | (d36:5) | 0 | 0 | 0 | 522298 | 328078 | 495458 | 6403489 | 4400627 | 6902944 |
| SM(d38:2) + H | SM(d38:2) + H | SM | (d38:2) | 0 | 0 | 0 | 0 | 270310 | 884517 | 0 | 681309 | 2148728 |
| SM(d39:7) + H | SM(d39:7) + H | SM | (d39:7) | 0 | 0 | 0 | 79805 | 23955 | 0 | 26547071 | 3398222 | 1750601 |
| SM(d40:1) + H | SM(d40:1) + H | SM | (d40:1) | 0 | 0 | 0 | 0 | 0 | 0 | 0 | 0 | 722860 |

TABLE 7-continued

| Lipid Ion | Lipid Group | Lipid Class | Fatty Acid Chain | MDA-MB-4175 Exomere | | | MDA-MB-4175 Exo-S | | | MDA-MB-4175 Exo-L | | |
|---|---|---|---|---|---|---|---|---|---|---|---|---|
| | | | | Exomere replicate 1 | Exomere replicate 2 | Exomere replicate 3 | Exo-S replicate 1 | Exo-S replicate 2 | Exo-S replicate 3 | Exo-L replicate 1 | Exo-L replicate 2 | Exo-L replicate 3 |
| SM(d40:2) + H | SM(d40:2) + H | SM | (d40:2) | 753188 | 561975 | 887099 | 893095 | 720769 | 778773 | 48584542 | 11488146 | 7168405 |
| SM(d41:2) + H | SM(d41:2) + H | SM | (d41:2) | 215875 | 294435 | 350164 | 276787 | 129588 | 227992 | 32278155 | 6183741 | 2228561 |
| SM(d18:1/24:1) + H | SM(d18:1/24:1) + H | SM | (d18:1/24:1) | 1625404 | 1629174 | 1821544 | 2188269 | 1410509 | 1368023 | 442748344 | 85798660 | 20143857 |
| SM(d42:2) + H | SM(d42:2) + H | SM | (d42:2) | 1477469 | 2347652 | 2528121 | 4200414 | 3059142 | 3681665 | 360071978 | 93337240 | 34821089 |
| SM(d22:0/20:3) + H | SM(d42:3) + H | SM | (d22:0/20:3) | 2310406 | 5232438 | 5683793 | 11679202 | 12661396 | 12795722 | 235300942 | 84914349 | 63611365 |
| SM(d42:5) + H | SM(d42:5) + H | SM | (d42:5) | 30185 | 63739 | 132957 | 153193 | 60884 | 115125 | 6166808 | 2526148 | 1151755 |
| SM(d43:3) + H | SM(d43:3) + H | SM | (d43:3) | 19195 | 107388 | 126659 | 210701 | 181102 | 363854 | 5998722 | 2459182 | 1694580 |
| SM(d44:2] + H | SM(d44:2) + H | SM | (d44:2) | 0 | 0 | 0 | 155768 | 39339 | 27387 | 14665416 | 4883880 | 1036712 |
| SM(d44:3) + H | SM(d44:3) + H | SM | (d44:3) | 232986 | 486935 | 384438 | 801404 | 996177 | 1334532 | 52172136 | 15175888 | 8646236 |
| SM(d44:5) + H | SM(d44:5) + H | SM | (d44:5) | 98025 | 306566 | 328238 | 653603 | 714749 | 810959 | 2877078 | 1336496 | 1357844 |
| SM(d44:6) + H | SM(d44:6) + H | SM | (d44:6) | 125004 | 342163 | 431832 | 873569 | 1222537 | 1100198 | 26141105 | 7759675 | 6006034 |
| TG(8:0/8:0/8:0) + NH4 | TG(24:0) + NH4 | TG | (8:0/8:0/8:0) | 3965811 | 797256 | 1476350 | 1896834 | 2535680 | 14707218 | 60690014 | 23530427 | 18048952 |
| TG(8:0/8:0/10:0) + NH4 | TG(26:0) + NH4 | TG | (8:0/8:0/10:0) | 6559548 | 573706 | 2153442 | 2932146 | 1997854 | 16154403 | 70751794 | 36506807 | 12530641 |
| TG(8:0/10:0/10:0) + NH4 | TG(28:0) + NH4 | TG | (8:0/10:0/10:0) | 2342790 | 432826 | 1314501 | 3392028 | 941790 | 8740681 | 77221691 | 55368425 | 6075965 |
| TG(10:0/10:0/10:0) + NH4 | TG(30:0) + NH4 | TG | (10:0/10:0/10:0) | 266416 | 47127 | 79600 | 182075 | 31480 | 41853 | 6743274 | 3168680 | 122003 |
| TG(16:0/8:0/8:0) + NH4 | TG(32:0) + NH4 | TG | (16:0/8:0/8:0) | 167145 | 73331 | 141206 | 123244 | 102925 | 71211 | 3755974 | 1433263 | 282992 |
| TG(16:0/9:0/9:0) + NH4 | TG(34:0) + NH4 | TG | .(16:0/9:0/9:0) | 381580 | 466967 | 731092 | 838300 | 459850 | 667295 | 14125951 | 8628510 | 2357855 |
| TG(8:0/8:0/18:1) + NH4 | TG(34:1) + NH4 | TG | (8:0/8:0/18:1) | 251726 | 288316 | 368907 | 273798 | 313742 | 234995 | 7130788 | 3378372 | 1289724 |
| TG(15:0/14:0/15:0) + NH4 | TG(44:0) + NH4 | TG | (15:0/14:0/15:0) | 1469265 | 1351220 | 1511143 | 1219858 | 1652197 | 1338090 | 18523461 | 277117 | 4691112 |
| TG(44:5p) + NH4 | TG(44:5p) + NH4 | TG | (44:5p) | 4535937 | 15262064 | 18607564 | 16764338 | 11357362 | 23614638 | 105316939 | 57814262 | 95944906 |
| TG(15:0/14:0/16:0) + NH4 | TG(45:0) + NH4 | TG | (15:0/14:0/16:0) | 4242570 | 3545451 | 4058101 | 4398708 | 4761167 | 4015965 | 57774139 | 7439883 | 11538391 |
| TG(16:0/14:0/16:0) + NH4 | TG(46:0) + NH4 | TG | (16:0/14:0/16:0) | 5598020 | 5491304 | 5740841 | 12961236 | 12433442 | 6066611 | 91201311 | 14934132 | 17853551 |
| TG(46:1) + NH4 | TG(46:1) + NH4 | TG | (46:1) | 4535191 | 3566419 | 3822725 | 3849498 | 6655554 | 4088181 | 59982626 | 7728002 | 12991948 |
| TG(15:0/16:0/16:0) + NH4 | TG(47:0) + NH4 | TG | (15:0/16:0/16:0) | 6014432 | 5475226 | 3911054 | 7677815 | 8650709 | 6115645 | 94128965 | 10564714 | 16907993 |
| TG(16:0/16:0/16:0) + NH4 | TG(48:0) + NH4 | TG | (16:0/16:0/16:0) | 13215849 | 7342566 | 9280311 | 9210184 | 10219013 | 11944126 | 126876794 | 17516384 | 23203629 |
| TG(16:0/16:0/16:1) + NH4 | TG(48:1) + NH4 | TG | (16:0/16:0/16:1) | 7167337 | 9384379 | 9164578 | 6488288 | 7035808 | 5850627 | 113045336 | 10346750 | 31796586 |
| TG(18:0/16:0/16:0) + NH4 | TG(50:0) + NH4 | TG | (18:0/16:0/16:0) | 10886254 | 9827643 | 10291485 | 9795707 | 12440452 | 10621227 | 155760042 | 19004297 | 30876653 |
| TG(16:0/16:0/18:1) + NH4 | TG(50:1) + NH4 | TG | (16:0/16:0/18:1) | 12797301 | 11948320 | 11868663 | 10238770 | 15749855 | 13016257 | 175512959 | 20929309 | 37775864 |
| TG(18:0/16:0/18:1) + NH4 | TG(52:1) + NH4 | TG | (18:0/16:0/18:1) | 5543436 | 4792621 | 4939364 | 4904924 | 6207580 | 5483708 | 81536378 | 9679591 | 15175364 |
| TG(16:0/18:1/18:1) + NH4 | TG(52:2) + NH4 | TG | (16:0/18:1/18:1) | 11155612 | 9475346 | 10146783 | 8652307 | 11401260 | 10267952 | 169800206 | 17824084 | 32126335 |
| TG(16:1/18:1/18:1) + NH4 | TG(52:3) + NH4 | TG | (16:1/18:1/18:1) | 3426569 | 3780301 | 2696421 | 4518607 | 3413526 | 3080318 | 39668886 | 6703732 | 8320377 |
| TG(18:0/18:1/18:1) + NH4 | TG(54:2) + NH4 | TG | (18:0/18:1/18:1) | 5548113 | 4798377 | 5110804 | 4945345 | 6063474 | 5205137 | 80452150 | 10110102 | 15282425 |
| TG(18:1/18:1/18:1) + NH4 | TG(54:3) + NH4 | TG | (18:1/18:1/18:1) | 13490074 | 10791203 | 12914132 | 12217457 | 13097620 | 9435764 | 178846144 | 23630828 | 38109977 |
| TG(18:1/18:1/18:2) + NH4 | TG(54:4) + NH4 | TG | (18:1/18:1/18:2) | 4370798 | 3844782 | 4120196 | 4044172 | 4899610 | 4325095 | 64491431 | 7551802 | 11839565 |
| TG(18:1/18:2/18:2) + NH4 | TG(54:5) + NH4 | TG | (18:1/18:2/18:2) | 2129330 | 2134585 | 2098042 | 1890230 | 2384790 | 2093424 | 31554468 | 4111277 | 6377519 |
| TG(18:2/18:2/18:2) + NH4 | TG(54:6) + NH4 | TG | (18:2/18:2/18:2) | 1634749 | 1308316 | 1632192 | 1291751 | 1805935 | 1569949 | 25320674 | 3118308 | 4816398 |
| TOTAL | | | | 1.067E+09 | 1.286E+09 | 1.278E+09 | 4.515E+09 | 3.858E+09 | 4.478E+09 | 6.485E+10 | 1.922E+10 | 2.134E+10 |

The values in the table are relative signal response (signal's peak area count is normalized to sample weight and peak area count of the internal standard signal)

TABLE 8

| Lipid Ion | Lipid Group | Lipid Class | Fatty Acid Chain | AsPC-1 Exomere Exomere replicate 1 | Exomere replicate 2 | Exomere replicate 3 |
|---|---|---|---|---|---|---|
| Cer(d18:1/10:0) + H | Cer(d28:1) + H | Cer | (d18:1/10:0) | 922714 | 731280 | 588136 |
| Cer(d18:0/12:0) + H | Cer(d30:0) + H | Cer | (d18:0/12:0) | 433299 | 379876 | 642277 |
| Cer(d18:1/13:0) + H | Cer(d31:1) + H | Cer | (d18:1/13:0) | 739433 | 804300 | 724615 |
| Cer(d18:1/14:0) + H | Cer(d32:1) + H | Cer | (d18:1/14:0) | 3355483 | 1035085 | 3512941 |
| Cer(d17:1/16:0) + H | Cer(d33:1) + H | Cer | (d17:1/16:0) | 111097 | 86765 | 101162 |
| Cer(d18:0/16:0) + H | Cer(d34:0) + H | Cer | (d18:0/16:0) | 475984 | 215732 | 127355 |
| Cer(d18:1/16:0) + H | Cer(d34:1) + H | Cer | (d18:1/16:0) | 1884993 | 1962653 | 2259029 |
| Cer(d18:2/16:0) + H | Cer(d34:2) + H | Cer | (d18:2/16:0) | 0 | 0 | 0 |
| Cer(d35:4) + H | Cer(d35:4) + H | Cer | (d35:4) | 30075019 | 22790952 | 18212913 |
| Cer(d18:1/18:0) + H | Cer(d36:1) + H | Cer | (d18:1/18:0) | 723102 | 876411 | 741514 |
| Cer(d36:4) + H | Cer(d36:4) + H | Cer | (d36:4) | 1739037 | 1282484 | 1030974 |
| Cer(d18:0/20:0) + H | Cer(d38:0) + H | Cer | (d18:0/20:0) | 1024850 | 396750 | 688157 |
| Cer(d18:1/20:0) + H | Cer(d38:1) + H | Cer | (d18:1/20:0) | 782329 | 603911 | 456780 |
| Cer(d18:0/22:0) + H | Cer(d40:0) + H | Cer | (d18:0/22:0) | 1145918 | 799985 | 654517 |
| Cer(d18:1/22:0) + H | Cer(d40:1) + H | Cer | (d18:1/22:0) | 1272049 | 832318 | 801555 |
| Cer(d18:2/22:0) + H | Cer(d40:2) + H | Cer | (d18:2/22:0) | 790415 | 139469 | 61759 |
| Cer(d40:2) + H | Cer(d40:2) + H | Cer | (d40:2) | 73301 | 109610 | 36883 |
| Cer(d18:1/23:0) + H | Cer(d41:1) + H | Cer | (d18:1/23:0) | 1344840 | 815327 | 677163 |
| Cer(d18:1/23:1) + H | Cer(d41:2) + H | Cer | (d18:1/23:1) | 442846 | 460976 | 361945 |
| Cer(d18:0/24:0) + H | Cer(d42:0) + H | Cer | (d18:0/24:0) | 1807119 | 1314270 | 930309 |
| Cer(d18:1/24:0) + H | Cer(d42:1) + H | Cer | (d18:1/24:0) | 2697504 | 2278243 | 1370820 |
| Cer(d42:2) + H | Cer(d42:2) + H | Cer | (d42:2) | 256524 | 219449 | 157660 |
| Cer(d18:1/24:1) + H | Cer(d42:2) + H | Cer | (d18:1/24:1) | 876326 | 1125299 | 1167028 |
| Cer(d18:2/24:1) + H | Cer(d42:3) + H | Cer | (d18:2/24:1) | 568391 | 643582 | 672065 |
| Cer(d18:1/24:2) + H | Cer(d42:3) + H | Cer | (d18:1/24:2) | 0 | 0 | 0 |
| Cer(d18:1/25:1) + H | Cer(d43:2) + H | Cer | (d18:1/25:1) | 488430 | 362169 | 225244 |
| Cer(d18:1/26:0) + H | Cer(d44:1) + H | Cer | (d18:1/26:0) | 1136492 | 862823 | 743784 |
| Cer(d18:1/26:1) + H | Cer(d44:2) + H | Cer | (d18:1/26:1) | 242162 | 185654 | 156839 |
| Cer(d20:0/26:0) + H | Cer(d46:0) + H | Cer | (d20:0/26:0) | 1635975 | 1712563 | 1476686 |
| CerG1(d18:0/16:0) + H | CerG1(d34:0) + H | CerG1 | (d18:0/16:0) | 0 | 0 | 0 |
| CerG1(d34:1) + H | CerG1(d34:1) + H | CerG1 | (d34:1) | 1351687 | 1012105 | 257971 |
| CerG1(d18:1/16:1) + H | CerG1(d34:2) + H | CerG1 | (d18:1/16:1) | 0 | 0 | 0 |
| CerG1(d18:0/22:0) + H | CerG1(d40:0) + H | CerG1 | (d18:0/22:0) | 364522 | 47776 | 34953 |
| CerG1(d40:1) + H | CerG1(d40:1) + H | CerG1 | (d40:1) | 823991 | 744770 | 372644 |

TABLE 8-continued

| | | | | | | |
|---|---|---|---|---|---|---|
| CerG1(d40:2) + H | CerG1(d40:2) + H | CerG1 | (d40:2) | 2839228 | 1492021 | 1193354 |
| CerG1(d41:1) + H | CerG1(d41:1) + H | CerG1 | (d41:1) | 764164 | 806908 | 542801 |
| CerG1(d41:2) + H | CerG1(d41:2) + H | CerG1 | (d41:2) | 89410 | 276065 | 109846 |
| CerG1(d18:0/24:0) + H | CerG1(d42:0) + H | CerG1 | (d18:0/24:0) | 0 | 0 | 0 |
| CerG1(d18:0/24:1) + H | CerG1(d42:1) + H | CerG1 | (d18:0/24:1) | 788807 | 631057 | 454415 |
| CerG1(d18:1/24:0) + H | CerG1(d42:1) + H | CerG1 | (d18:1/24:0) | 1557377 | 1337767 | 1049977 |
| CerG1(d18:1/24:1) + H | CerG1(d42:2) + H | CerG1 | (d18:1/24:1) | 925349 | 672135 | 566679 |
| CerG1(d18:1/24:2) + H | CerG1(d42:3) + H | CerG1 | (d18:1/24:2) | 801368 | 459987 | 393780 |
| CerG1(d42:3) + H | CerG1(d42:3) + H | CerG1 | (d42:3) | 226214 | 176624 | 108803 |
| CerG1(d43:1) + H | CerG1(d43:1) + H | CerG1 | (d43:1) | 5239817 | 4204259 | 3347078 |
| CerG2(d34:1) + H | CerG2(d34:1) + H | CerG2 | (d34:1) | 0 | 0 | 0 |
| CerG2(d42:1) + H | CerG2(d42:1) + H | CerG2 | (d42:1) | 0 | 0 | 0 |
| CerG2(d42:2) + H | CerG2(d42:2) + H | CerG2 | (d42:2) | 96147 | 16943 | 24405 |
| CerG3(d18:1/16:0) + H | CerG3(d34:1) + H | CerG3 | (d18:1/16:0) | 0 | 0 | 0 |
| CerG3(d40:1) + H | CerG3(d40:1) + H | CerG3 | (d40:1) | 0 | 0 | 0 |
| CerG3(d18:1/24:0) + H | CerG3(d42:1) + H | CerG3 | (d18:1/24:0) | 101864 | 57543 | 85153 |
| CerG3(d18:1/24:1) + H | CerG3(d42:2) + H | CerG3 | (d18:1/24:1) | 0 | 0 | 0 |
| ChE(18:1) + NH4 | ChE(18:1) + NH4 | ChE | (18:1) | 983008 | 946225 | 868231 |
| ChE(20:4) + NH4 | Che(20:4) + NH4 | ChE | (20:4) | 3982391 | 3632500 | 2741401 |
| CL(65:6) − H | CL(65:6) − H | CL | (65:6) | 0 | 0 | 0 |
| DG(16:0/14:0) + NH4 | DG(30:0) + NH4 | DG | (16:0/14:0) | 584979 | 556763 | 475330 |
| DG(16:0/16:0) + NH4 | DG(32:0) + NH4 | DG | (16:0/16:0) | 28029721 | 27287300 | 24519117 |
| DG(18:0/16:0) + NH4 | DG(34:0) + NH4 | DG | (18:0/16:0) | 160330793 | 150546977 | 121630016 |
| DG(16:0/18:1) + NH4 | DG(34:1) + NHA | DG | (16:0/18:1) | 3632172 | 2822252 | 2470031 |
| DG(18:0/18:0) + NH4 | DG(36:0) + NH4 | DG | (18:0/18:0) | 113870656 | 102936251 | 85807125 |
| DG(18:0/18:1) + NH4 | DG(36:1) + NH4 | DG | (18:0/18:1) | 1063008 | 1652304 | 1230277 |
| DG(18:1/18:1) + NH4 | DG(36:2) + NH4 | DG | (18:1/18:1) | 2184985 | 1723649 | 2463802 |
| DG(38:4) + NH4 | DG(38:4) + NH4 | DG | (38:4) | 0 | 0 | 0 |
| LPC(12:0) + H | LPC(12:0) + H | LPC | (12:0) | 30343631 | 23220962 | 18423149 |
| LPC(14:0) + H | LPC(14:0) + H | LPC | (14:0) | 312936 | 153702 | 124001 |
| LPC(16:0) + H | LPC(16:0) + H | LPC | (16:0) | 795149 | 691995 | 25605 |
| LPC(16:0e) + H | LPC(16:0e) + H | LPC | (16:0e) | 0 | 0 | 0 |
| LPC(16:1) + H | LPC(16:1) + H | LPC | (16:1) | 0 | 0 | 0 |
| LPC(17:0) + H | LPC(17:0) + H | LPC | (17:0) | 0 | 0 | 0 |
| LPC(18:0) + H | LPC(18:0) + H | LPC | (18:0) | 400591 | 288773 | 267154 |
| LPC(18:0p) + H | LPC(18:0p) + H | LPC | (18:0p) | 0 | 0 | 0 |
| LPC(18:1) + H | LPC(18:1) + H | LPC | (18:1) | 113490 | 94404 | 51393 |
| LPC(18:2) + H | LPC(18:2) + H | LPC | (18:2) | 426612 | 372635 | 277702 |
| LPC(20:4) + H | LPC(20:4) + H | LPC | (20:4) | 0 | 0 | 0 |
| LPC(22:5) + H | LPC(22:5) + H | LPC | (22:5) | 0 | 0 | 0 |

TABLE 8-continued

| | | | | | | |
|---|---|---|---|---|---|---|
| LPC(22:6) + H | LPC(22:6) + H | LPC | (22:6) | 0 | 0 | 0 |
| LPE(18:1) − H | LPE(18:1) − H | LPE | (18:1) | 0 | 0 | 0 |
| LPE(20:3) − H | LPE(20:3) − H | LPE | (20:3) | 0 | 0 | 0 |
| LPE(20:4) − H | LPE(20:4) − H | LPE | (20:4) | 0 | 0 | 0 |
| LPG(14:0) − H | LPG(14:0) − H | LPG | (14:0) | 2357456 | 1668521 | 608968 |
| LPG(18:1) − H | LPG(18:1) − H | LPI | (18:1) | 0 | 0 | 0 |
| LPG(18:0) − H | LPG(18:0) − H | LPS | (18:0) | 0 | 0 | 0 |
| LPG(18:1) − H | LPG(18:1) − H | LPS | (18:1) | 0 | 0 | 0 |
| LPG(19:1) − H | LPS(19:1) − H | LPS | (19:1) | 0 | 0 | 0 |
| MG(16:0) + H | MG(16:0) + H | MG | (16:0) | 14143724 | 10172586 | 5817578 |
| MG(18:0) + H | MG(18:0) + H | MG | (18:0) | 4367977 | 3317133 | 2317922 |
| PC(19:1) + H | PC(19:1) + H | PC | (19:1) | 84259 | 62866 | 193858 |
| PC(23:0) + H | PC(23:0) + H | PC | (23:0) | 1281742 | 1045112 | 1050288 |
| PC(25:0) + H | PC(25:0) + H | PC | (25:0) | 653226 | 859218 | 815950 |
| PC(26:0) + H | PC(26:0) + H | PC | (26:0) | 164278 | 240402 | 305841 |
| PC(29:0e) + H | PC(29:0e) + H | PC | (29:0e) | 0 | 0 | 0 |
| PC(30:0) + H | PC(30:0) + H | PC | (30:0) | 0 | 0 | 0 |
| PC(30:0e) + H | PC(30:0e) + H | PC | (30:0e) | 0 | 0 | 0 |
| PC(30:1e) + H | PC(30:1e) + H | PC | (30:1e) | 0 | 0 | 0 |
| PC(31:0) + H | PC(31:0) + H | PC | (31:0) | 32936 | 91914 | 136126 |
| PC(31:0e) + H | PC(31:0e) + H | PC | (31:0e) | 0 | 0 | 0 |
| PC(31:1) + H | PC(31:1) + H | PC | (31:1) | 500377 | 352524 | 1407330 |
| PC(31:2) + H | PC(31:2) + H | PC | (31:2) | 18434 | 55350 | 119105 |
| PC(32:0) + H | PC(32:0) + H | PC | (32:0) | 4203748 | 6634160 | 9559867 |
| PC(32:0e) + H | PC(32:0e) + H | PC | (16:0e/16:0) | 4180999 | 6545060 | 7882185 |
| PC(32:1) + H | PC(32:1) + H | PC | (32:1) | 278801 | 300378 | 524287 |
| PC(32:1e) + H | PC(32:1e) + H | PC | (32:1e) | 0 | 0 | 0 |
| PC(32:1p) + H | PC(32:1p) + H | PC | (32:1p) | 0 | 0 | 0 |
| PC(32:3) + H | PC(32:3) + H | PC | (32:3) | 0 | 0 | 0 |
| PC(33:0) + H | PC(33:0) + H | PC | (33:0) | 33618 | 199395 | 300228 |
| PC(33:0e) + H | PC(33:0e) + H | PC | (33:0e) | 63572 | 186964 | 237328 |
| PC(33:0p) + H | PC(33:0p) + H | PC | (33:0p) | 0 | 0 | 0 |
| PC(15:0/18:1) + H | PC(33:1) + H | PC | (15:0/18:1) | 209392 | 322296 | 506948 |
| PC(33:1p) + H | PC(33:1p) + H | PC | (33:1p) | 66058 | 846230 | 85808 |
| PC(33:2) + H | PC(33:2) + H | PC | (33:2) | 415422 | 2012692 | 1805737 |
| PC(11:0/22:2) + H | PC(33:2) + H | PC | (11:0/22:2) | 200582 | 274147 | 165613 |
| PC(33:3) + H | PC(33:3) + H | PC | (33:3) | 0 | 0 | 0 |
| PC(34:0) + H | PC(34:0) + H | PC | (34:0) | 4121693 | 6223644 | 6771436 |
| PC(34:0e) + H | PC(34:0e) + H | PC | (18:0e/16:0) | 7150592 | 8261064 | 11354670 |
| PC(34:1) + H | PC(34:1) + H | PC | (16:0/18:1) | 3730178 | 5307082 | 11620462 |

TABLE 8-continued

| | | | | | | |
|---|---|---|---|---|---|---|
| PC(34:1e) + H | PC(34:1e) + H | PC | (16:0e/18:1) | 1212041 | 2036509 | 4798753 |
| PC(34:2) + H | PC(34:2) + H | PC | (34:2) | 1072380 | 873593 | 1129504 |
| PC(34:2e) + H | PC(34:2e) + H | PC | (34:2e) | 125308 | 444773 | 424157 |
| PC(34:2p) + H | PC(34:2p) + H | PC | (34:2p) | 64077 | 287277 | 291967 |
| PC(34:3) + H | PC(34:3) + H | PC | (34:3) | 0 | 0 | 0 |
| PC(34:3p) + H | PC(34:3p) + H | PC | (34:3p) | 387366 | 831234 | 334851 |
| PC(35:0) + H | PC(35:0) + H | PC | (35:0) | 0 | 0 | 0 |
| PC(35:0p) + H | PC(35:0p) + H | PC | (35:0p) | 35538 | 27787 | 36860 |
| PC(17:0/18:1) + H | PC(35:1) + H | PC | (17:0/18:1) | 3835758 | 4031186 | 4927640 |
| PC(35:1p) + H | PC(35:1p) + H | PC | (35:1p) | 0 | 0 | 0 |
| PC(35:2) + H | PC(35:2) + H | PC | (35:2) | 1675917 | 2001719 | 2156091 |
| PC(35:3) + H | PC(35:3) + H | PC | (35:3) | 0 | 0 | 0 |
| PC(35:4) + H | PC(35:4) + H | PC | (35:4) | 0 | 0 | 0 |
| PC(35:5) + H | PC(35:5) + H | PC | (35:5) | 356462 | 364034 | 384169 |
| PC(35:6) + H | PC(35:6) + H | PC | (35:6) | 0 | 0 | 0 |
| PC(36:0e) + H | PC(36:0e) + H | PC | (36:0e) | 79388 | 149892 | 194133 |
| PC(36:1) + H | PC(36:1) + H | PC | (18:0/18:1) | 5112511 | 6497046 | 14742392 |
| PC(36:1e) + H | PC(36:1e) + H | PC | (18:0e/18:1) | 1771544 | 3519641 | 6392630 |
| PC(36:2) + H | PC(36:2) + H | PC | (18:1/18:1) | 9310826 | 10328068 | 13038034 |
| PC(36:2e) + H | PC(36:2e) + H | PC | (36:2e) | 785677 | 1391854 | 375522 |
| PC(36:2p) + H | PC(36:2p) + H | PC | (36:2p) | 0 | 0 | 0 |
| PC(24:0/12:3) + H | PC(36:3) + H | PC | (24:0/12:3) | 164735 | 139799 | 256712 |
| PC(36:3) + H | PC(36:3) + H | PC | (36:3) | 269683 | 270909 | 201161 |
| PC(36:4) + H | PC(36:4) + H | PC | (36:4) | 0 | 0 | 0 |
| PC(36:4e) + H | PC(36:4e) + H | PC | (36:4e) | 0 | 0 | 0 |
| PC(36:4p) + H | PC(36:4p) + H | PC | (36:4p) | 0 | 0 | 0 |
| PC(36:5) + H | PC(36:5) + H | PC | (36:5) | 0 | 0 | 0 |
| PC(37:1) + H | PC(37:1) + H | PC | (37:1) | 50846 | 144950 | 220004 |
| PC(19:1/18:1) + H | PC(37:2) + H | PC | (19:1/18:1) | 6949122 | 5440153 | 8273071 |
| PC(37:3) + H | PC(37:3) + H | PC | (37:3) | 0 | 0 | 0 |
| PC(37:4) + H | PC(37:4) + H | PC | (37:4) | 0 | 0 | 0 |
| PC(37:5) + H | PC(37:5) + H | PC | (37:5) | 0 | 0 | 0 |
| PC(37:6) + H | PC(37:6) + H | PC | (37:6) | 0 | 0 | 0 |
| PC(38:0e) + H | PC(38:0e) + H | PC | (38:0e) | 108496 | 166253 | 117810 |
| PC(38:1e) + H | PC(38:1e) + H | PC | (38:1e) | 87765 | 98939 | 280764 |
| PC(38:2) + H | PC(38:2) + H | PC | (38:2) | 342595 | 893920 | 1083926 |
| PC(38:2e) + H | PC(38:2e) + H | PC | (38:2e) | 156710 | 180106 | 182506 |
| PC(38:3) + H | PC(38:3) + H | PC | (38:3) | 0 | 0 | 0 |
| PC(38:3e) + H | PC(38:3e) + H | PC | (38:3e) | 0 | 0 | 0 |
| PC(38:4) + H | PC(38:4) + H | PC | (38:4) | 149067 | 90719 | 379869 |

TABLE 8-continued

| | | | | | | |
|---|---|---|---|---|---|---|
| PC(38:4e) + H | PC(38:4e) + H | PC | (38:4e) | 0 | 0 | 0 |
| PC(38:4p) + H | PC(38:4p) + H | PC | (38:4p) | 59228 | 240250 | 343852 |
| PC(27:1/11:4) + H | PC(38:5) + H | PC | (27:1/11:4) | 0 | 0 | 0 |
| PC(38:5) + H | PC(38:5) + H | PC | (38:5) | 305262 | 236785 | 505916 |
| PC(38:6) + H | PC(38:6) + H | PC | (38:6) | 0 | 0 | 0 |
| PC(38:6e) + H | PC(38:6e) + H | PC | (38:6e) | 0 | 0 | 0 |
| PC(38:7) + H | PC(38:7) + H | PC | (38:7) | 0 | 0 | 0 |
| PC(39:5) + H | PC(39:5) + H | PC | (39:5) | 0 | 0 | 0 |
| PC(39:6) + H | PC(39:6) + H | PC | (39:6) | 0 | 0 | 0 |
| PC(40:1e) + H | PC(40:1e) + H | PC | (40:1e) | 168705 | 477182 | 303757 |
| PC(40:2) + H | PC(40:2) + H | PC | (40:2) | 0 | 0 | 0 |
| PC(40:2e) + H | PC(40:2e) + H | PC | (40:2e) | 1056476 | 1307641 | 1555495 |
| PC(40:3) + H | PC(40:3) + H | PC | (40:3) | 0 | 0 | 0 |
| PC(40:4) + H | PC(40:4) + H | PC | (40:4) | 2363346 | 2333289 | 964621 |
| PC(40:5) + H | PC(40:5) + H | PC | (40:5) | 0 | 0 | 0 |
| PC(40:5e) + H | PC(40:5e) + H | PC | (40:5e) | 0 | 0 | 0 |
| PC(18:0/22:6) + H | PC(40:6) + H | PC | (18:0/22:6) | 0 | 0 | 0 |
| PC(40:6) + H | PC(40:6) + H | PC | (40:6) | 0 | 0 | 0 |
| PC(40:6e) + H | PC(40:6e) + H | PC | (40:6e) | 0 | 0 | 0 |
| PC(40:6p) + H | PC(40:6p) + H | PC | (40:6p) | 0 | 0 | 0 |
| PC(40:7) + H | PC(40:7) + H | PC | (40:7) | 0 | 0 | 0 |
| PC(42:1) + H | PC(42:1) + H | PC | (42:1) | 19564 | 87575 | 145919 |
| PC(42:1e) + H | PC(42:1e) + H | PC | (42:1e) | 200433 | 166531 | 298280 |
| PC(42:2) + H | PC(42:2) + H | PC | (42:2) | 14940 | 20915 | 13240 |
| PC(42:2e) + H | PC(42:2e) + H | PC | (42:2e) | 25323 | 92239 | 19366 |
| PC(42:3p) + H | PC(42:3p) + H | PC | (42:3p) | 0 | 0 | 0 |
| PC(44:1) + H | PC(44:1) + H | PC | (44:1) | 0 | 0 | 0 |
| PC(44:2) + H | PC(44:2) + H | PC | (44:2) | 0 | 0 | 0 |
| PE(32:1p) − H | PE(32:1p) − H | PE | (16:0p/16:1) | 0 | 0 | 0 |
| PE(33:1p) − H | PE(33:1p) − H | PE | (33:1p) | 0 | 0 | 0 |
| PE(16:0/18:1) − H | PE(34:1) − H | PE | (16:0/18:1) | 601756 | 200276 | 219181 |
| PE(34:1e) − H | PE(34:1e) − H | PE | (34:1e) | 0 | 0 | 0 |
| PE(16:0p/18:1) − H | PE(34:1p) − H | PE | (16:0p/18:1) | 114895 | 145950 | 281241 |
| PE(16:1/18:1) − H | PE(34:2) − H | PE | (16:1/18:1) | 0 | 0 | 0 |
| PE(34:2p) − H | PE(34:2p) − H | PE | (18:1p/16:1) | 0 | 0 | 0 |
| PE(16:0/18:2) − H | PE(34:2p) − H | PE | (16:0p/18:2) | 0 | 0 | 0 |
| PE(18:0/18:1) − H | PE(36:1) − H | PE | (18:0/18:1) | 153814 | 93203 | 171083 |
| PE(18:0e/18:1) − H | PE(36:1e) − H | PE | (18:0e/18:1) | 28588 | 33260 | 43901 |
| PE(18:0p/18:1) − H | PE(36:1p) − H | PE | (18:0p/18:1) | 680151 | 522948 | 730742 |
| PE(18:1/18:1) − H | PE(36:2) − H | PE | (18:1/18:1) | 1173527 | 447335 | 395702 |

TABLE 8-continued

| | | | | | | |
|---|---|---|---|---|---|---|
| PE(18:1p/18:1) – H | PE(36:2p) – H | PE | (18:1p/18:1) | 0 | 0 | 0 |
| PE(18:0p/18:2) – H | PE(36:2p) – H | PE | (18:0p/18:2) | 0 | 0 | 0 |
| PE(18:1/18:2) – H | PE(36:3) – H | PE | (18:1/18:2) | 0 | 0 | 0 |
| PE(16:0p/20:3) – H | PE(36:3p) – H | PE | (16:0p/20:3) | 0 | 0 | 0 |
| PE(16:0p/20:4) – H | PE(36:4p) – H | PE | (16:0p/20:4) | 0 | 0 | 0 |
| PE(36:5p) – H | PE(38:5p) – H | PE | (16:0p/20:5) | 0 | 0 | 0 |
| PE(20:1/18:1) – H | PE(38:2) – H | PE | (20:1/18:1) | 0 | 0 | 0 |
| PE(18:0/20:2) – H | PE(38:2) – H | PE | (18:0/20:2) | 0 | 0 | 0 |
| PE(18:0p/20:2) – H | PE(38:2p) – H | PE | (18:0p/20:2) | 0 | 0 | 0 |
| PE(18:1/20:2) – H | PE(38:3) – H | PE | (18:1/20:2) | 0 | 0 | 0 |
| PE(18:0/20:3) – H | PE(38:3) – H | PE | (18:0/20:3) | 0 | 0 | 0 |
| PE(18:0p/20:3) – H | PE(38:3p) – H | PE | (18:0p/20:3) | 0 | 0 | 0 |
| PE(38:3p) – H | PE(38:3p) – H | PE | (18:0p/20:3) | 0 | 0 | 0 |
| PE(18:0/20:4) – H | PE(38:4) – H | PE | (18:0/20:4) | 0 | 0 | 0 |
| PE(18:1p/20:3) – H | PE(38:4p) – H | PE | (18:1p/20:3) | 0 | 0 | 0 |
| PE(18:0p/20:4) – H | PE(38:4p) – H | PE | (18:0p/20:4) | 0 | 0 | 0 |
| PE(18:1/20:4) – H | PE(38:5) – H | PE | (18:1/20:4) | 0 | 0 | 0 |
| PE(18:1p/20:4) – H | PE(38:5p) – H | PE | (18:1p/20:4) | 0 | 0 | 0 |
| PE(38:5p) – H | PE(38:5p) – H | PE | (38:5p) | 0 | 0 | 0 |
| PE(16:0p/22:6) – H | PE(38:6p) – H | PE | (16:0p/22:6) | 0 | 0 | 0 |
| PE(40:4p) – H | PE(40:4p) – H | PE | (18:0p/22:4) | 0 | 0 | 0 |
| PE(18:0p/22:5) – H | PE(40:5p) – H | PE | (18:0p/22:5) | 0 | 0 | 0 |
| PE(40:5p) – H | PE(40:5p) – H | PE | (18:0p/22:5) | 0 | 0 | 0 |
| PE(18:1p/22:5) – H | PE(40:6p) – H | PE | (18:1p/22:5) | 0 | 0 | 0 |
| PE(18:0p/22:6) – H | PE(40:6p) – H | PE | (18:0p/22:6) | 0 | 0 | 0 |
| PE(18:1/24:0) – H | PE(42:1) – H | PE | (18:1/24:0) | 0 | 0 | 0 |
| PE(50:2) – H | PE(50:2) – H | PE | (50:2) | 0 | 0 | 0 |
| PG(12:0/14:0) – H | PG(26:0) – H | PG | (12:0/14:0) | 2289790 | 1297380 | 747348 |
| PG(18:1/18:1) – H | PG(36:2) – H | PG | (18:1/18:1) | 671672 | 355189 | 227011 |
| PI(16:0/18:1) – H | PI(34:1) – H | PI | (16:0/18:1) | 0 | 0 | 0 |
| PI(18:0/18:1) – H | PI(36:1) – H | PI | (18:0/18:1) | 513756 | 828168 | 529957 |
| PI(18:1/18:1) – H | PI(36:2) – H | PI | (18:1/18:1) | 0 | 0 | 0 |
| PI(18:0/20:2) – H | PI(38:2) – H | PI | (18:0/20:2) | 0 | 0 | 0 |
| PI(18:1/20:2) – H | PI(38:3) – H | PI | (18:1/20:2) | 0 | 0 | 0 |
| PI(18:0/20:3) – H | PI(38:3) – H | PI | (18:0/20:3) | 0 | 0 | 0 |
| PI(18:0/20:4) – H | PI(38:4) – H | PI | (18:0/20:4) | 0 | 0 | 0 |
| PI(18:1/20:4) – H | PI(38:5) – H | PI | (18:1/20:4) | 0 | 0 | 0 |
| PI(18:0/22:4) – H | PI(40:4) – H | PI | (18:0/22:4) | 0 | 0 | 0 |
| PI(18:0/22:5) – H | PI(40:5) – H | PI | (18:0/22:5) | 0 | 0 | 0 |
| PS(12:0/14:0) – H | PS(26:0) – H | PS | (12:0/14:0) | 714575 | 346586 | 294597 |
| PS(18:0/16:1) – H | PS(34:1) – H | PS | (18:0/16:1) | 0 | 0 | 0 |
| PS(35:1) – H | PS(35:1) – H | PS | (35:1) | 0 | 0 | 0 |
| PS(17:1/18:0) – H | PS(35:1) – H | PS | (17:1/18:0) | 0 | 0 | 0 |
| PS(18:0/18:1) – H | PS(36:1) – H | PS | (18:0/18:1) | 5033800 | 3921496 | 3947054 |

TABLE 8-continued

| | | | | | | |
|---|---|---|---|---|---|---|
| PS(18:0e/18:1) – H | PS(36:1e) – H | PS | (18:0e/18:1) | 0 | 0 | 0 |
| PS(18:1/18:1) – H | PS(36:2) – H | PS | (18:1/18:1) | 0 | 0 | 0 |
| PS(18:0/18:2) – H | PS(36:2) – H | PS | (18:0/18:2) | 0 | 0 | 0 |
| PS(36:3p) – H | PS(36:3p) – H | PS | (36:3p) | 0 | 0 | 0 |
| PS(37:0) – H | PS(37:0) – H | PS | (37:0) | 760780 | 1021200 | 860070 |
| PS(19:0/18:1) – H | PS(37:1) – H | PS | (19:0/18:1) | 759832 | 604079 | 391985 |
| PS(37:1) – H | PS(37:1) – H | PS | (37:1) | 0 | 0 | 0 |
| PS(37:2) – H | PS(37:2) – H | PS | (37:2) | 156968 | 148413 | 131555 |
| PS(20:0/18:1) – H | PS(38:1) – H | PS | (20:0/18:1) | 0 | 0 | 0 |
| PS(20:1/18:1) – H | PS(38:2) – H | PS | (20:1/18:1) | 0 | 0 | 0 |
| PS(18:0/20:2) – H | PS(38:2) – H | PS | (18:0/20:2) | 0 | 0 | 0 |
| PS(38:2p) – H | PS(38:2p) – H | PS | (38:2p) | 0 | 0 | 0 |
| PS(18:0/20:3) – H | PS(38:3) – H | PS | (18:0/20:3) | 0 | 0 | 0 |
| PS(18:0/20:4) – H | PS(38:4) – H | PS | (18:0/20:4) | 649164 | 763006 | 512449 |
| PS(38:6p) – H | PS(38:6p) – H | PS | (38:6p) | 499022 | 80779 | 72098 |
| PS(39:1) – H | PS(39:1) – H | PS | (39:1) | 1337394 | 688759 | 467218 |
| PS(39:2) – H | PS(39:2) – H | PS | (39:2) | 0 | 0 | 0 |
| PS(39:3) – H | PS(39:3) – H | PS | (39:3) | 0 | 0 | 0 |
| PS(39:4) – H | PS(39:4) – H | PS | (39:4) | 0 | 0 | 0 |
| PS(18:1/22:0) – H | PS(40:1) – H | PS | (18:1/22:0) | 298959 | 265951 | 213382 |
| PS(18:1/22:1) – H | PS(40:2) – H | PS | (18:1/22:1) | 0 | 0 | 0 |
| PS(18:1/22:2) – H | PS(40:3) – H | PS | (18:1/22:2) | 0 | 0 | 0 |
| PS(18:0/22:4) – H | PS(40:4) – H | PS | (18:0/22:4) | 0 | 0 | 0 |
| PS(18:0/22:5) – H | PS(40:5) – H | PS | (18:0/22:5) | 0 | 0 | 0 |
| PS(40:5) – H | PS(40:5) – H | PS | (40:5) | 0 | 0 | 0 |
| PS(18:1/24:0) – H | PS(42:1) – H | PS | (18:1/24:0) | 304095 | 175928 | 112391 |
| PS(18:1/24:1) – H | PS(42:2) – H | PS | (18:1/24:1) | 0 | 0 | 0 |
| SM(d31:1) + H | SM(d31:1) + H | SM | (d31:1) | 0 | 0 | 0 |
| SM(d32:0) + H | SM(d32:0) + H | SM | (d32:0) | 0 | 0 | 0 |
| SM(d32:1) + H | SM(d32:1) + H | SM | (d32:1) | 0 | 0 | 0 |
| SM(d32:2) + H | SM(d32:2) + H | SM | (d32:2) | 0 | 0 | 0 |
| SM(d33:1) + H | SM(d33:1) + H | SM | (d33:1) | 0 | 0 | 0 |
| SM(d33:5) + H | SM(d33:5) + H | SM | (d33:5) | 13767217 | 7353865 | 5205066 |
| SM(d34:0) + H | SM(d34:0) + H | SM | (d34:0) | 968701 | 762450 | 1218142 |
| SM(d34:1) + H | SM(d34:1) + H | SM | (d18:1/16:0) | 5647889 | 7474945 | 9598049 |
| SM(d34:2) + H | SM(d34:2) + H | SM | (d18:1/16:1) | 0 | 0 | 0 |
| SM(d35:1) + H | SM(d35:1) + H | SM | (d35:1) | 0 | 0 | 0 |
| SM(d35:2) + H | SM(d35:2) + H | SM | (d35:2) | 0 | 0 | 0 |
| SM(d35:4) + H | SM(d35:4) + H | SM | (d35:4) | 0 | 0 | 0 |
| SM(d36:0) + H | SM(d36:0) + H | SM | (d20:0/16:0) | 277558 | 245117 | 232802 |

TABLE 8-continued

| | | | | | | |
|---|---|---|---|---|---|---|
| SM(d36:1) + H | SM(d36:1) + H | SM | (d18:0/18:1) | 1693696 | 1847623 | 1767849 |
| SM(d36:2) + H | SM(d36:2) + H | SM | (d18:1/18:1) | 0 | 0 | 0 |
| SM(d36:4) + H | SM(d36:4) + H | SM | (d36:4) | 144312 | 410617 | 402904 |
| SM(d38:1) + H | SM(d38:1) + H | SM | (d38:1) | 629163 | 1171614 | 641719 |
| SM(d40:0) + H | SM(d40:0) + H | SM | (d40:0) | 831110 | 694245 | 576019 |
| SM(d40:1) + H | SM(d40:1) + H | SM | (d40:1) | 29722 | 17597 | 41575 |
| SM(d17:1/23:0) + H | SM(d40:1) + H | SM | (d17:1/23:0) | 8002552 | 7469383 | 6186988 |
| SM(d40:2) + H | SM(d40:2) + H | SM | (d40:2) | 249009 | 428289 | 225202 |
| SM(d41:1) + H | SM(d41:1) + H | SM | (d41:1) | 2217904 | 2152799 | 1219236 |
| SM(d41:2) + H | SM(d41:2) + H | SM | (d41:2) | 519481 | 377538 | 271016 |
| SM(d18:1/24:0) | SM(d42:1) + H | SM | (d18:1/24:0) | 1403775 | 1329722 | 1375161 |
| SM(d42:1) + H | SM(d42:1) + H | SM | (d42:1) | 20063175 | 15292830 | 12264345 |
| SM(d18:1/24:1) + H | SM(d42:2) + H | SM | (d18:1/24:1) | 10177555 | 10775373 | 13484127 |
| SM(d18:1/24:2) + H | SM(d42:3) + H | SM | (d18:1/24:2) | 100418 | 221234 | 596242 |
| SM(d42:5) + H | SM(d42:5) + H | SM | (d42:5) | 0 | 0 | 0 |
| SM(d43:1) + H | SM(d43:1) + H | SM | (d43:1) | 328738 | 498963 | 163191 |
| SM(d18:2/25:0) + H | SM(d43:2) + H | SM | (d18:2/25:0) | 432950 | 328433 | 217142 |
| SM(d43:3) + H | SM(d43:3) + H | SM | (d43:3) | 0 | 0 | 0 |
| SM(d43:4) + H | SM(d43:4) + H | SM | (d43:4) | 71421 | 79867 | 29898 |
| SM(d44:1) + H | SM(d44:1) + H | SM | (d44:1) | 99170 | 26271 | 53968 |
| SM(d44:2) + H | SM(d44:2) + H | SM | (d16:1/28:1) | 408391 | 331363 | 542864 |
| SM(d44:3) + H | SM(d44:3) + H | SM | (d44:3) | 0 | 0 | 0 |
| SM(d44:4) + H | SM(d44:4) + H | SM | (d44:4) | 1756037 | 1561280 | 1165937 |
| SM(d44:5) + H | SM(d44:5) + H | SM | (d44:5) | 397723 | 404998 | 1273342 |
| SM(d44:6) + H | SM(d44:6) + H | SM | (d44:6) | 0 | 0 | 0 |
| TG(16:0/14:0/14:0) + NH4 | TG(44:0) + NH4 | TG | (16:0/14:0/14:0) | 5303660 | 4167352 | 3263212 |
| TG(44:5p) + NH4 | TG(44:5p) + NH4 | TG | (44:5p) | 1849254 | 2918445 | 1219107 |
| TG(15:0/14:0/16:0) + NH4 | TG(45:0) + NH4 | TG | (15:0/14:0/16:0) | 15559462 | 10888195 | 12475767 |
| TG(16:0/14:0/16:0) + NH4 | TG(46:0) + NH4 | TG | (16:0/14:0/16:0) | 12694392 | 9433598 | 7845824 |
| TG(15:0/16:0/16:0) + NH4 | TG(47:0) + NH4 | TG | (15:0/16:0/16:0) | 21832045 | 18085839 | 12610089 |
| TG(16:0/16:0/16:0) + NH4 | TG(48:0) + NH4 | TG | (16:0/16:0/16:0) | 26521769 | 20001891 | 17929239 |
| TG(16:0/16:0/16:1) + NH4 | TG(48:1) + NH4 | TG | (16:0/16:0/16:1) | 12412377 | 9353767 | 7694661 |
| TG(16:0/16:0/17:0) + NH4 | TG(49:0) + NH4 | TG | (16:0/16:0/17:0) | 13887670 | 10159264 | 8261798 |
| TG(18:0/16:0/16:0) + NH4 | TG(50:0) + NH4 | TG | (18:0/16:0/16:0) | 22287169 | 19441382 | 14565244 |
| TG(16:0/16:0/18:1) + NH4 | TG(50:1) + NH4 | TG | (16:0/16:0/18:1) | 14395579 | 11314658 | 10220305 |
| TG(18:0/16:0/18:0) + NH4 | TG(52:0) + NH4 | TG | (18:0/16:0/18:0) | 30196361 | 24602915 | 18880481 |
| TG(18:0/16:0/18:1) + NH4 | TG(52:1) + NH4 | TG | (18:0/16:0/18:1) | 8767125 | 6675705 | 6023037 |
| TG(16:0/18:1/18:1) + NH4 | TG(52:2) + NH4 | TG | (16:0/18:1/18:1) | 14399280 | 10801174 | 9022808 |
| TG(18:0/18:0/18:0) + NH4 | TG(54:0) + NH4 | TG | (18:0/18:0/18:0) | 13232227 | 15433611 | 9540723 |
| TG(18:0/18:1/18:1) + NH4 | TG(54:2) + NH4 | TG | (18:0/18:1/18:1) | 6466612 | 4735583 | 4070103 |

TABLE 8-continued

| TG(18:1/18:1/18:1) + NH4 | TG(54:3) + NH4 | TG | (18:1/18:1/18:1) | 10995098 | 11297342 | 8798428 |
|---|---|---|---|---|---|---|
| TG(18:1/18:1/18:2) + NH4 | TG(54:4) + NH4 | TG | (18:1/18:1/18:2) | 3984880 | 3595645 | 4091756 |
| | | | sum | 8.28E+08 | 7.39E+08 | 6.62E+08 |

| | AsPC-1 Exo-S | | | AsPC-1 Exo-L | | |
|---|---|---|---|---|---|---|
| Lipid Ion | Exo-S replicate 1 | Exo-S replicate 2 | Exo-S replicate 3 | Exo-L replicate 1 | Exo-L replicate 2 | Exo-L replicate 3 |
| Cer(d18:1/10:0) + H | 1161226 | 1104881 | 1080798 | 1009806 | 970265 | 1019853 |
| Cer(d18:0/12:0) + H | 1487628 | 1400270 | 1360991 | 1328204 | 1348430 | 1431742 |
| Cer(d18:1/13:0) + H | 710091 | 727948 | 646497 | 691943 | 734274 | 672348 |
| Cer(d18:1/14:0) + H | 15028983 | 10756351 | 12788017 | 11837058 | 13185164 | 17142365 |
| Cer(d17:1/16:0) + H | 379140 | 281638 | 284626 | 294461 | 333111 | 675879 |
| Cer(d18:0/16:0) + H | 3199021 | 2170628 | 2182341 | 1908614 | 2413209 | 6114505 |
| Cer(d18:1/16:0) + H | 30384987 | 18029692 | 17991061 | 16808869 | 20310534 | 49842138 |
| Cer(d18:2/16:0) + H | 843471 | 433831 | 601831 | 464028 | 719898 | 2103409 |
| Cer(d35:4) + H | 26319798 | 39255398 | 33728028 | 32453953 | 32665201 | 31914933 |
| Cer(d18:1/18:0) + H | 1412875 | 1266895 | 1230538 | 948796 | 1065738 | 2469847 |
| Cer(d36:4) + H | 2490620 | 3453773 | 3082102 | 3179130 | 3200308 | 2943881 |
| Cer(d18:0/20:0) + H | 558221 | 750178 | 724697 | 477538 | 650722 | 593305 |
| Cer(d18:1/20:0) + H | 740000 | 699573 | 731853 | 567302 | 694776 | 788387 |
| Cer(d18:0/22:0) + H | 1121869 | 1105527 | 942368 | 991968 | 1038308 | 1156820 |
| Cer(d18:1/22:0) + H | 3416578 | 3333647 | 3005547 | 2442580 | 2996249 | 5201654 |
| Cer(d18:2/22:0) + H | 1069304 | 923098 | 858943 | 770839 | 965341 | 1376478 |
| Cer(d40:2) + H | 528227 | 488293 | 496723 | 330455 | 403122 | 646014 |
| Cer(d18:1/23:0) + H | 1502701 | 1633233 | 1468462 | 1376976 | 1460770 | 2052176 |
| Cer(d18:1/23:1) + H | 1015675 | 969892 | 820092 | 682008 | 931279 | 1370667 |
| Cer(d18:0/24:0) + H | 3184280 | 2823858 | 2154463 | 2737526 | 2510675 | 2760974 |
| Cer(d18:1/24:0) + H | 8271652 | 8929382 | 7674317 | 6102411 | 6961716 | 11310964 |
| Cer(d42:2) + H | 1536223 | 1036262 | 955659 | 1041349 | 1277473 | 1516394 |
| Cer(d18:1/24:1) + H | 17012350 | 12558081 | 13636203 | 13992651 | 13806383 | 21927440 |
| Cer(d18:2/24:1) + H | 2506551 | 2252357 | 2314338 | 1654686 | 1934877 | 3114050 |
| Cer(d18:1/24:2) + H | 481704 | 451615 | 492035 | 310218 | 427242 | 714094 |
| Cer(d18:1/25:1) + H | 683789 | 534379 | 404730 | 538777 | 584311 | 861871 |
| Cer(d18:1/26:0) + H | 597931 | 883146 | 637774 | 578080 | 619969 | 729993 |
| Cer(d18:1/26:1) + H | 1016476 | 699431 | 1098185 | 457425 | 742659 | 1061528 |
| Cer(d20:0/26:0) + H | 708722 | 868500 | 765557 | 718766 | 819701 | 574516 |
| CerG1(d18:0/16:0) + H | 864168 | 506638 | 609843 | 553861 | 832616 | 1432924 |
| CerG1(d34:1) + H | 7021599 | 3688081 | 4458304 | 3677552 | 3456609 | 13273493 |
| CerG1(d18:1/16:1) + H | 1018845 | 378416 | 668961 | 859960 | 785304 | 2817295 |
| CerG1(d18:0/22:0) + H | 628338 | 650900 | 612148 | 474909 | 575159 | 858877 |

TABLE 8-continued

| | | | | | | |
|---|---|---|---|---|---|---|
| CerG1(d40:1) + H | 3052629 | 3270582 | 3204884 | 2599195 | 3459299 | 4077409 |
| CerG1(d40:2) + H | 1626853 | 3387723 | 1536495 | 1988983 | 2509258 | 2777076 |
| CerG1(d41:1) + H | 1692484 | 1838120 | 1850641 | 1652466 | 1936847 | 2397855 |
| CerG1(d41:2) + H | 930620 | 993643 | 1181784 | 754978 | 1200394 | 1394143 |
| CerG1(d18:0/24:0) + H | 286005 | 335772 | 233098 | 272549 | 249176 | 348811 |
| CerG1(d18:0/24:1) + H | 1347692 | 1371485 | 1352479 | 1062879 | 1364555 | 1724422 |
| CerG1(d18:1/24:0) + H | 11027272 | 11234757 | 10945107 | 8532979 | 9834946 | 14096107 |
| CerG1(d18:1/24:1) + H | 10337681 | 10431503 | 10034066 | 7372647 | 7652274 | 11279492 |
| CerG1(d18:1/24:2) + H | 2792122 | 2494495 | 2245846 | 2027476 | 2376374 | 3649090 |
| CerG1(d42:3) + H | 763634 | 754435 | 672905 | 490811 | 646572 | 907412 |
| CerG1(d43:1) + H | 1744932 | 3094670 | 1778420 | 2204296 | 2159863 | 2140945 |
| CerG2(d34:1) + H | 642664 | 394912 | 547028 | 210517 | 329480 | 997227 |
| CerG2(d42:1) + H | 444004 | 559695 | 522116 | 224790 | 312103 | 529451 |
| CerG2(d42:2) + H | 363978 | 386598 | 391621 | 364937 | 522104 | 635200 |
| CerG3(d18:1/16:0) + H | 1373647 | 1156975 | 1202804 | 871826 | 1506591 | 3563338 |
| CerG3(d40:1) + H | 614765 | 752731 | 728724 | 523409 | 893840 | 1312598 |
| CerG3(d18:1/24:0) + H | 1065963 | 1287090 | 1345598 | 970774 | 1487985 | 1822581 |
| CerG3(d18:1/24:1) + H | 1649962 | 1982943 | 1952014 | 1287818 | 2043444 | 3161386 |
| ChE(18:1) + NH4 | 244470 | 334002 | 466805 | 4256 | 26349 | 21028 |
| ChE(20:4) + NH4 | 916434 | 1627716 | 1352287 | 218337 | 315787 | 374468 |
| CL(65:6) − H | 702956 | 552776 | 339214 | 421191 | 247887 | 424130 |
| DG(16:0/14:0) + NH4 | 973603 | 1158921 | 1174666 | 679157 | 616636 | 1121200 |
| DG(16:0/16:0) + NH4 | 61921183 | 68407427 | 76083764 | 24020977 | 22806431 | 38878778 |
| DG(18:0/16:0) + NH4 | 230841669 | 280004469 | 270615121 | 86899288 | 71714323 | 119350648 |
| DG(16:0/18:1) + NH4 | 5330915 | 5580228 | 5683906 | 2482229 | 3806795 | 5541844 |
| DG(18:0/18:0) + NH4 | 148057137 | 181162446 | 202969267 | 53698985 | 48750456 | 69243389 |
| DG(18:0/18:1) + NH4 | 13092850 | 7393824 | 7041699 | 3960275 | 4899353 | 11105058 |
| DG(18:1/18:1) + NH4 | 3398696 | 3475896 | 3375059 | 1848013 | 2473660 | 5223812 |
| DG(38:4) + NH4 | 2710444 | 2416677 | 2784049 | 1019162 | 1626647 | 4373355 |
| LPC(12:0) + H | 6875148 | 15237499 | 11335390 | 14641381 | 14103549 | 10268177 |
| LPC(14:0) + H | 64246 | 180518 | 79870 | 378594 | 305649 | 127215 |
| LPC(16:0) + H | 601713 | 3672654 | 3446154 | 5882972 | 4860845 | 3275044 |
| LPC(16:0e) + H | 243209 | 292626 | 414534 | 958148 | 742665 | 456908 |
| LPC(16:1) + H | 5785 | 396438 | 298862 | 668287 | 1013889 | 1032464 |
| LPC(17:0) + H | 70542 | 69075 | 63959 | 44774 | 60125 | 49923 |
| LPC(18:0) + H | 1927402 | 2299656 | 2103428 | 1827748 | 1489634 | 1855024 |
| LPC(18:0p) + H | 207965 | 581189 | 448823 | 1212508 | 1085489 | 577963 |
| LPC(18:1) + H | 395707 | 643028 | 828394 | 1931504 | 1011218 | 1224900 |
| LPC(18:2) + H | 179810 | 283973 | 196460 | 406567 | 363529 | 411191 |
| LPC(20:4) + H | 49823 | 225843 | 255573 | 689835 | 486941 | 632133 |

TABLE 8-continued

| | | | | | | |
|---|---|---|---|---|---|---|
| LPC(22:5) + H | 80675 | 143231 | 178404 | 316426 | 293360 | 293471 |
| LPC(22:6) + H | 0 | 0 | 0 | 86510 | 232105 | 208305 |
| LPE(18:1) − H | 139448 | 325069 | 344966 | 367619 | 394221 | 250340 |
| LPE(20:3) − H | 111547 | 222401 | 208878 | 370133 | 3644009 | 246116 |
| LPE(20:4) − H | 216557 | 274736 | 267947 | 628875 | 568699 | 494027 |
| LPG(14:0) − H | 274890 | 153355 | 180713 | 311235 | 243986 | 138531 |
| LPG(18:1) − H | 87027 | 181641 | 99964 | 246331 | 223662 | 144567 |
| LPG(18:0) − H | 169089 | 134254 | 166002 | 201245 | 164475 | 166604 |
| LPG(18:1) − H | 98760 | 213048 | 177159 | 729058 | 573819 | 375246 |
| LPG(19:1) − H | 68019 | 113820 | 70263 | 394183 | 217347 | 131259 |
| MG(16:0) + H | 5899502 | 13145688 | 12085848 | 10489087 | 10194685 | 9503516 |
| MG(18:0) + H | 12732909 | 10535058 | 11683798 | 9733769 | 8411484 | 14989788 |
| PC(19:1) + H | 122926 | 555836 | 486515 | 353299 | 632150 | 454546 |
| PC(23:0) + H | 496786 | 263827 | 326499 | 376003 | 316583 | 274788 |
| PC(25:0) + H | 38200 | 310715 | 298325 | 291393 | 536801 | 301964 |
| PC(26:0) + H | 998129 | 825300 | 807520 | 1199487 | 1147117 | 1418367 |
| PC(29:0e) + H | 1328872 | 250142 | 389003 | 260507 | 365739 | 2364802 |
| PC(30:0) + H | 63943542 | 23370942 | 34507465 | 21699367 | 26794604 | 93096918 |
| PC(30:0e) + H | 10114487 | 3331109 | 5098548 | 3783590 | 4224563 | 12140025 |
| PC(30:1e) + H | 1025759 | 429715 | 578419 | 378541 | 629557 | 1730399 |
| PC(31:0) + H | 5492878 | 2611494 | 3358798 | 1673558 | 2388076 | 7241760 |
| PC(31:0e) + H | 4080802 | 1568609 | 1948575 | 1311610 | 1663829 | 6970217 |
| PC(31:1) + H | 6011892 | 3305120 | 2855380 | 3426604 | 3830843 | 10886160 |
| PC(31:2) + H | 1276901 | 777935 | 857771 | 771724 | 910353 | 2150286 |
| PC(32:0) + H | 222463088 | 73885024 | 103573737 | 54969035 | 72787383 | 299526790 |
| PC(32:0e) + H | 157924876 | 66726205 | 83052912 | 52829339 | 71874784 | 265148202 |
| PC(32:1) + H | 163964056 | 62072430 | 95532316 | 65253343 | 86138840 | 277506868 |
| PC(32:1e) + H | 47258395 | 18758432 | 27062064 | 20165414 | 29575036 | 85804351 |
| PC(32:1p) + H | 3616382 | 2130448 | 3237822 | 1995523 | 2466831 | 8302859 |
| PC(32:3) + H | 3043031 | 624002 | 1562553 | 974509 | 1007768 | 2506956 |
| PC(33:0) + H | 5008317 | 2448474 | 3276320 | 2097658 | 2556923 | 8080469 |
| PC(33:0e) + H | 8189510 | 2678103 | 4082465 | 2067407 | 2869997 | 9251867 |
| PC(33:0p) + H | 6397448 | 3614457 | 5354263 | 3315323 | 5213227 | 13839753 |
| PC(15:0/18:1) + H | 13728709 | 8024142 | 10367415 | 6489996 | 7833478 | 23435505 |
| PC(33:1p) + H | 1601956 | 919262 | 506235 | 761065 | 455790 | 4502564 |
| PC(33:2) + H | 18052045 | 12291802 | 13081911 | 10187182 | 13373854 | 30000402 |
| PC(11:0/22:2) + H | 2267403 | 1862264 | 2225879 | 1889345 | 1931937 | 5281977 |
| PC(33:3) + H | 1027039 | 723191 | 925158 | 739632 | 904388 | 2124102 |
| PC(34:0) + H | 83132810 | 44647806 | 52253530 | 29513711 | 37605970 | 120581424 |
| PC(34:0e) + H | 148548027 | 79146970 | 94349458 | 62492086 | 78166918 | 262828420 |

TABLE 8-continued

| | | | | | | |
|---|---|---|---|---|---|---|
| PC(34:1) + H | 879077540 | 342271124 | 515629960 | 271405044 | 374571523 | 1222348694 |
| PC(34:1e) + H | 429796059 | 213607792 | 294219626 | 182594040 | 259325783 | 819615632 |
| PC(34:2) + H | 103666480 | 27739950 | 41819777 | 47595261 | 62731171 | 207685629 |
| PC(34:2e) + H | 32855363 | 17844060 | 28402773 | 16462324 | 23447065 | 78892513 |
| PC(34:2p) + H | 20792235 | 3406653 | 5366602 | 2977466 | 4086870 | 20524193 |
| PC(34:3) + H | 15792697 | 5429109 | 8623407 | 4658898 | 6390042 | 20994718 |
| PC(34:3p) + H | 3582997 | 920913 | 1979741 | 1407326 | 2005150 | 6383460 |
| PC(35:0) + H | 1734535 | 1270945 | 1224689 | 603898 | 1099443 | 3902983 |
| PC(35:0p) + H | 12025612 | 6318554 | 10202029 | 4259749 | 8172861 | 27656575 |
| PC(17:0/18:1) + H | 31280319 | 17547139 | 22758164 | 13605271 | 16063303 | 47602977 |
| PC(35:1p) + H | 2945064 | 1901246 | 2534803 | 1761623 | 2427471 | 8412815 |
| PC(35:2) + H | 9468768 | 7036386 | 8657409 | 5322675 | 7203421 | 18903749 |
| PC(35:3) + H | 1036383 | 480327 | 483676 | 455052 | 957129 | 1529499 |
| PC(35:4) + H | 5013103 | 3145516 | 4224496 | 2622638 | 2878708 | 8523382 |
| PC(35:5) + H | 1201973 | 926920 | 1187038 | 822205 | 1013364 | 2508421 |
| PC(35:6) + H | 1573743 | 1751103 | 876983 | 574233 | 432246 | 1841804 |
| PC(36:0e) + H | 3902025 | 2912032 | 3624892 | 2099787 | 2860392 | 7737745 |
| PC(36:1) + H | 474400334 | 237173016 | 317062368 | 154373907 | 212240303 | 715131037 |
| PC(36:1e) + H | 169591121 | 91320975 | 121158842 | 67761706 | 96009736 | 356456609 |
| PC(36:2) + H | 324666678 | 166775194 | 242131812 | 141046062 | 192670417 | 628039448 |
| PC(36:2e) + H | 97167630 | 64719454 | 86759273 | 57974614 | 85255206 | 258144537 |
| PC(36:2p) + H | 17222343 | 8050609 | 13465033 | 8143532 | 12746039 | 42746990 |
| PC(24:0/12:3) + H | 27092292 | 15772942 | 21768455 | 11076757 | 15766577 | 44703253 |
| PC(36:3) + H | 22911621 | 13362379 | 13646157 | 10181077 | 9496648 | 52059855 |
| PC(36:4) + H | 110189529 | 49588882 | 78576258 | 35415317 | 50297707 | 169256945 |
| PC(36:4e) + H | 38069521 | 15576770 | 24673031 | 13316096 | 22319102 | 73379638 |
| PC(36:4p) + H | 2756595 | 1621421 | 2048603 | 1182737 | 1741625 | 5461028 |
| PC(36:5) + H | 4857625 | 1164977 | 1738395 | 1194229 | 1649032 | 9973998 |
| PC(37:1) + H | 5304541 | 3115622 | 3885020 | 2035884 | 2456141 | 7811462 |
| PC(19:1/18:1) + H | 10817575 | 8676144 | 10426351 | 7418812 | 8565635 | 20790315 |
| PC(37:3) + H | 1317492 | 436963 | 738382 | 770785 | 671578 | 2512843 |
| PC(37:4) + H | 1793297 | 1081559 | 1438550 | 513421 | 881156 | 2902676 |
| PC(37:5) + H | 438600 | 333449 | 379787 | 112158 | 211023 | 685896 |
| PC(37:6) + H | 11368778 | 864920 | 6598599 | 4309772 | 9144234 | 14451472 |
| PC(38:0e) + H | 962497 | 828723 | 1192211 | 548438 | 821886 | 2314833 |
| PC(38:1e) + H | 4748876 | 2261374 | 5431443 | 2278222 | 3264407 | 12824060 |
| PC(38:2) + H | 34125965 | 21280872 | 27187219 | 15335018 | 18679914 | 57870214 |
| PC(38:2e) + H | 3818221 | 4501763 | 5303514 | 2094512 | 3911259 | 15442890 |
| PC(38:3) + H | 24010539 | 15620616 | 20829185 | 8215146 | 12265718 | 39116728 |
| PC(38:3e) + H | 3587391 | 2515178 | 3466725 | 1942637 | 3010984 | 9560628 |

TABLE 8-continued

| | | | | | | |
|---|---|---|---|---|---|---|
| PC(38:4) + H | 75591644 | 39154589 | 49192201 | 22831255 | 31486336 | 109458253 |
| PC(38:4e) + H | 13218272 | 5783361 | 6021199 | 4736207 | 7437737 | 33065247 |
| PC(38:4p) + H | 5819383 | 2721201 | 4471814 | 2815866 | 4860563 | 17618545 |
| PC(27:1/11:4) + H | 97295656 | 52924138 | 71975188 | 31312601 | 45819149 | 146213524 |
| PC(38:5) + H | 23628994 | 12356472 | 19405208 | 10808692 | 16371303 | 46459934 |
| PC(38:6) + H | 18810629 | 9749474 | 13899646 | 5722454 | 8560641 | 25258911 |
| PC(38:6e) + H | 2427286 | 2079964 | 2721481 | 1354677 | 1977902 | 5503233 |
| PC(38:7) + H | 3087577 | 1540326 | 2842895 | 1255838 | 1853276 | 6723691 |
| PC(39:5) + H | 1020470 | 1082619 | 871351 | 445031 | 840162 | 2093480 |
| PC(39:6) + H | 747698 | 424200 | 426959 | 215079 | 367974 | 864086 |
| PC(40:1e) + H | 3884757 | 3006051 | 3225138 | 2089874 | 2866312 | 7385477 |
| PC(40:2) + H | 3684092 | 2396213 | 2789114 | 1530716 | 2002747 | 5797455 |
| PC(40:2e) + H | 21597550 | 15602090 | 15705062 | 14040184 | 14623827 | 30631508 |
| PC(40:3) + H | 1365862 | 1009399 | 1290362 | 770109 | 881906 | 2508288 |
| PC(40:4) + H | 7279839 | 4805786 | 6050261 | 2919457 | 4100939 | 9004000 |
| PC(40:3) + H | 24484856 | 12247208 | 16650322 | 7234538 | 9777885 | 31592139 |
| PC(40:5e) + H | 1350707 | 687572 | 1713199 | 869781 | 878835 | 2174102 |
| PC(18:0/22:6) + H | 9863904 | 4518368 | 8459785 | 3770019 | 4383755 | 16982380 |
| PC(40:6) + H | 15959856 | 8768453 | 12263365 | 4851447 | 6729448 | 21167408 |
| PC(40:6e) + H | 1533314 | 1013363 | 1247103 | 640465 | 1006167 | 3681620 |
| PC(40:6p) + H | 455558 | 475649 | 398468 | 237876 | 704771 | 2287725 |
| PC(40:7) + H | 3139185 | 2870450 | 3222294 | 1346363 | 1744917 | 5947286 |
| PC(42:1) + H | 2690383 | 1705651 | 1913714 | 1330900 | 1393883 | 2948525 |
| PC(42:1e) + H | 1098437 | 887955 | 1060519 | 832552 | 1048504 | 1929601 |
| PC(42:2) + H | 2255144 | 1444606 | 2317659 | 1326718 | 1604104 | 3559083 |
| PC(42:2e) + H | 1855766 | 1700702 | 3051695 | 1324034 | 1575294 | 3915372 |
| PC(42:3p) + H | 381684 | 341452 | 384422 | 301856 | 371096 | 631483 |
| PC(44:1) + H | 1742298 | 861037 | 1098095 | 653008 | 825915 | 1534289 |
| PC(44:2) + H | 2528570 | 1283888 | 1096267 | 829378 | 1064444 | 2243455 |
| PE(32:1p) − H | 2618424 | 1659248 | 1315766 | 2321072 | 2099928 | 3372313 |
| PE(33:1p) − H | 903743 | 496539 | 705154 | 679063 | 710887 | 1119170 |
| PE(16:0/18:1) − H | 3674815 | 2620161 | 2406102 | 2484273 | 2912718 | 4582132 |
| PE(34:1e) − H | 3930789 | 2940532 | 2474440 | 3132362 | 3487901 | 6300910 |
| PE(16:0p/18:1) − H | 55642480 | 39253682 | 35950078 | 40694139 | 41661111 | 72631371 |
| PE(16:1/18:1) − H | 1079465 | 582126 | 547000 | 749387 | 762330 | 1180379 |
| PE(34:2p) − H | 1839730 | 1207904 | 1354935 | 1652512 | 1924765 | 2984746 |
| PE(16:0p/18:2) − H | 4227446 | 2685483 | 3085951 | 3395463 | 3886736 | 5547793 |
| PE(18:0/18:1) − H | 11340890 | 7811024 | 7961603 | 6938323 | 7334625 | 13314806 |
| PE(18:0e/18:1) − H | 4316902 | 3518076 | 2792821 | 3240904 | 3735407 | 6075437 |
| PE(18:0p/18:1) − H | 54066906 | 36260521 | 32597299 | 35285393 | 40334232 | 70748309 |

TABLE 8-continued

| | | | | | | |
|---|---|---|---|---|---|---|
| PE(18:1/18:1) – H | 11670295 | 9231838 | 8898946 | 8511974 | 9914551 | 15091442 |
| PE(18:1p/18:1) – H | 26808491 | 22917708 | 18908008 | 21821759 | 28678381 | 41213892 |
| PE(18:0/18:2) – H | 10135135 | 7837039 | 7172352 | 7760336 | 9253548 | 14886682 |
| PE(18:1/18:2) – H | 605983 | 353804 | 358398 | 464863 | 528073 | 728493 |
| PE(16:0/20:3) – H | 7055940 | 6380755 | 5433122 | 5443765 | 6793168 | 12925825 |
| PE(16:0p/20:4) – H | 8750192 | 7231959 | 8800934 | 7424227 | 8737467 | 14671467 |
| PE(36:5p) – H | 583346 | 147901 | 427459 | 214610 | 434422 | 1391145 |
| PE(20:1/18:1) – H | 843611 | 845936 | 829466 | 613446 | 470787 | 1084624 |
| PE(18:0/20:2) – H | 977179 | 1001059 | 705111 | 661540 | 774746 | 1227265 |
| PE(18:0p/20:2) – H | 3147747 | 3298923 | 3096878 | 3134453 | 3328251 | 5755997 |
| PE(18:1/20:2) – H | 644606 | 831645 | 729447 | 571635 | 741194 | 1087995 |
| PE(18:0/20:3) – H | 822655 | 704189 | 1094886 | 575801 | 981705 | 1080121 |
| PE(18:0p/20:3) – H | 8459059 | 7275978 | 7770000 | 6440927 | 7674115 | 12883313 |
| PE(38:3p) – H | 1941455 | 1832068 | 1455014 | 1569157 | 1749962 | 3371718 |
| PE(18:0/20:4) – H | 3101405 | 2666193 | 2834578 | 2173039 | 2086309 | 5223388 |
| PE(18:1p/20:3) – H | 3923194 | 3515701 | 3275846 | 2736430 | 4721849 | 5885507 |
| PE(18:0p/20:4) – H | 16780935 | 13978386 | 15402870 | 13548809 | 14239309 | 31132615 |
| PE(18:1/20:4) – H | 689015 | 670541 | 695704 | 639850 | 678666 | 1251839 |
| PE(18:1p/20:4) – H | 8309135 | 8501259 | 8196929 | 7289834 | 9364385 | 15176212 |
| PE(38:5p) – H | 1997401 | 1394232 | 2059438 | 1523582 | 1680179 | 3412340 |
| PE(16:0p/22:6) – H | 3008957 | 2368636 | 2575277 | 2259033 | 1822695 | 5717519 |
| PE(40:4p) – H | 1285881 | 1175993 | 1075705 | 963090 | 1237635 | 2112065 |
| PE(18:0p/22:5) – H | 6341812 | 3949646 | 5236486 | 3722745 | 4914949 | 10481870 |
| PE(40:5p) – H | 1099314 | 984994 | 913846 | 647611 | 884381 | 1577766 |
| PE(18:1p/22:5) – H | 1338473 | 1488843 | 1684049 | 1200405 | 1353040 | 2516287 |
| PE(18:0p/22:6) – H | 3972438 | 3382531 | 4093363 | 2825394 | 3236022 | 7810302 |
| PE(18:1/24:0) – H | 311901 | 238088 | 228092 | 232206 | 215615 | 365493 |
| PE(50:2) – H | 1005524 | 954836 | 600499 | 840041 | 829035 | 954214 |
| PG(12:0/14:0) – H | 778862 | 751787 | 786034 | 886930 | 722802 | 684809 |
| PG(18:1/18:1) – H | 679359 | 639578 | 1624713 | 2197066 | 3214381 | 1367647 |
| PI(16:0/18:1) – H | 9424925 | 6626824 | 8703877 | 4371912 | 6004310 | 10841649 |
| PI(18:0/18:1) – H | 18101102 | 16364444 | 19666540 | 9088733 | 13020178 | 18097026 |
| PI(18:1/18:1) – H | 13751746 | 10787284 | 14167932 | 7131297 | 11284150 | 19000924 |
| PI(18:0/20:2) – H | 4946120 | 3287562 | 4387715 | 1912738 | 4403415 | 2778679 |
| PI(18:1/20:2) – H | 2618637 | 2212748 | 2484554 | 1781400 | 2169038 | 3190556 |
| PI(18:0/20:3) – H | 6943837 | 6228542 | 8075780 | 4483756 | 5798218 | 10751576 |
| PI(18:0/20:4) – H | 17035253 | 10708750 | 16861168 | 8148968 | 13076195 | 24840850 |
| PI(18:1/20:4) – H | 287961 | 1266010 | 607255 | 733593 | 1006391 | 1894491 |
| PI(18:0/22:4) – H | 1080406 | 1115417 | 1299789 | 630077 | 811852 | 1337280 |
| PI(18:0/22:5) – H | 1120507 | 764545 | 942205 | 465617 | 779390 | 1137390 |
| PS(12:0/14:0) – H | 446810 | 362690 | 365026 | 407321 | 374932 | 359106 |
| PS(18:0/16:1) – H | 8268715 | 4949134 | 6550191 | 4779166 | 7728863 | 10374329 |
| PS(35:1) – H | 2924351 | 1496904 | 1470006 | 1339749 | 1516361 | 1964229 |

TABLE 8-continued

| | | | | | | |
|---|---|---|---|---|---|---|
| PS(17:1/18:0) − H | 2471947 | 2147249 | 2440076 | 1451199 | 1576367 | 3397779 |
| PS(18:0/18:1) − H | 167102689 | 119649760 | 143690425 | 90644014 | 116354851 | 197535824 |
| PS(18:0e/18:1) − H | 4853460 | 3820314 | 4839820 | 2919212 | 3519713 | 6837569 |
| PS(18:1/18:1) − H | 9194266 | 6754491 | 8027641 | 5640061 | 5875839 | 9680330 |
| PS(18:0/18:2) − H | 7880013 | 5801947 | 7222412 | 5220068 | 5742639 | 10402688 |
| PS(36:3p) − H | 7633078 | 6703107 | 7416310 | 6323698 | 6492904 | 10986258 |
| PS(37:0) − H | 66650314 | 48250113 | 70052193 | 35212504 | 46133049 | 80874243 |
| PS(19:0/18:1) − H | 36339253 | 21526885 | 18947113 | 16597452 | 19390253 | 26717642 |
| PS(37:1) − H | 1490285 | 1230200 | 1235925 | 1091459 | 1106377 | 1765735 |
| PS(37:2) − H | 2442618 | 1570682 | 1294178 | 1322160 | 1543685 | 1712773 |
| PS(20:0/18:1) − H | 4404058 | 3438353 | 3842166 | 2467943 | 3232377 | 5076280 |
| PS(20:1/18:1) − H | 4447972 | 3647879 | 3171644 | 1468351 | 2896624 | 4625348 |
| PS(18:0/20:2) − H | 7301485 | 6132980 | 6804179 | 4283064 | 6532851 | 10844537 |
| PS(38:2p) − H | 868292 | 557395 | 539300 | 591168 | 509697 | 1082727 |
| PS(18:0/20:3) − H | 7291099 | 5913557 | 6277321 | 3075230 | 4133649 | 8275825 |
| PS(18:0/20:4) − H | 16230081 | 13766920 | 15571875 | 7992582 | 13196623 | 12118691 |
| PS(38:6p) − H | 1128932 | 979481 | 1380585 | 1009252 | 1217181 | 2419377 |
| PS(39:1) − H | 24120671 | 22985681 | 29804384 | 17316401 | 24036311 | 39411959 |
| PS(39:2) − H | 2186666 | 3356194 | 1539822 | 1142790 | 1149598 | 1675487 |
| PS(39:3) − H | 347503 | 2594189 | 3858644 | 1551287 | 103153 | 1098989 |
| PS(39:4) − H | 5368112 | 2963524 | 3154200 | 2495422 | 3334581 | 4466299 |
| PS(18:1/22:0) − H | 4064467 | 3910947 | 3839662 | 2517450 | 3511624 | 5597790 |
| PS(18:1/22:1) − H | 3408770 | 3588086 | 3990233 | 2412607 | 3464760 | 3787527 |
| PS(18:1/22:2) − H | 1900591 | 1419299 | 1770545 | 1001745 | 1410861 | 1663921 |
| PS(18:0/22:4) − H | 439453 | 24375 | 1323084 | 733550 | 83798 | 235578 |
| PS(18:0/22:5) − H | 2505071 | 1868756 | 1987230 | 1119427 | 1353943 | 2677997 |
| PS(40:5) − H | 918647 | 782875 | 799605 | 438104 | 636444 | 1227835 |
| PS(18:1/24:0) − H | 1779094 | 1588676 | 1707118 | 1285165 | 1539504 | 2224250 |
| PS(18:1/24:1) − H | 1309327 | 1699668 | 1528903 | 817297 | 1296234 | 2146994 |
| SM(d31:1) + H | 661321 | 39442 | 320879 | 242393 | 432634 | 801486 |
| SM(d32:0) + H | 2126244 | 1150012 | 1461213 | 1264922 | 1557618 | 2827620 |
| SM(d32:1) + H | 20813576 | 9887653 | 13209613 | 9420803 | 13501642 | 26642009 |
| SM(d32:2) + H | 458904 | 420542 | 479445 | 322512 | 460479 | 1013558 |
| SM(d33:1) + H | 20176171 | 12082191 | 15165424 | 9881287 | 33816429 | 22692799 |
| SM(d33:5) + H | 6655681 | 10365948 | 5994543 | 5789838 | 6753033 | 6067349 |
| SM(d34:0) + H | 74348703 | 38343858 | 42519960 | 32268555 | 43803065 | 99339303 |
| SM(d34:1) + H | 720958003 | 316727747 | 485339516 | 278121991 | 391114186 | 1145239538 |
| SM(d34:2) + H | 46429259 | 24835983 | 33744528 | 22937733 | 34010155 | 62982988 |
| SM(d35:1) + H | 9805746 | 5698520 | 7181681 | 4112566 | 5511952 | 13770024 |
| SM(d35:2) + H | 1022318 | 469336 | 783310 | 366076 | 438517 | 1396268 |

TABLE 8-continued

| | | | | | | |
|---|---|---|---|---|---|---|
| SM(d35:4) + H | 1219039 | 605454 | 847635 | 521359 | 700116 | 1618402 |
| SM(d36:0) + H | 7328963 | 4292407 | 5027560 | 3365397 | 4533780 | 9924313 |
| SM(d36:1) + H | 54907427 | 27142651 | 32516465 | 17480858 | 26319513 | 73609304 |
| SM(d36:2) + H | 73447874 | 36400065 | 51621875 | 29077068 | 41004005 | 92640203 |
| SM(d36:4) + H | 129364326 | 36073210 | 64720825 | 25862014 | 44697675 | 189484155 |
| SM(d38:1) + H | 10928751 | 8448664 | 8192737 | 4663660 | 5920079 | 14480605 |
| SM(d40:0) + H | 6777251 | 6240481 | 6467063 | 4250276 | 5850613 | 7784881 |
| SM(d40:1) + H | 5321195 | 3301180 | 3456980 | 2931700 | 2960577 | 5389633 |
| SM(d17:1/23:0) + H | 77647589 | 57935569 | 56954593 | 36365164 | 48256698 | 96592883 |
| SM(d40:2) + H | 20148273 | 12043372 | 16079145 | 9871827 | 10367643 | 24131468 |
| SM(d41:1) + H | 29502586 | 21030836 | 20205698 | 20637081 | 23624592 | 29878221 |
| SM(d41:2) + H | 24595173 | 17713926 | 20309327 | 9317081 | 16938431 | 18494247 |
| SM(d18:1/24:0) + H | 32414981 | 25623789 | 29154664 | 20909991 | 23987512 | 34003673 |
| SM(d42:1) + H | 166038798 | 165707986 | 149865103 | 125824271 | 138966875 | 238445675 |
| SM(d18:1/24:1) + H | 506599392 | 378706422 | 418698134 | 249048472 | 323643458 | 726366870 |
| SM(d18:1/24:2) + H | 72319308 | 51039170 | 59775725 | 31725892 | 40856511 | 81325582 |
| SM(d42:5) + H | 3304635 | 1559076 | 2157023 | 827924 | 1384270 | 4405363 |
| SM(d43:1) + H | 6820186 | 4921753 | 4122241 | 5040782 | 5337809 | 7556288 |
| SM(d18:2/25:0) + H | 17119825 | 11991050 | 12580046 | 10240012 | 12843064 | 16158271 |
| SM(d43:3) + H | 2864266 | 2367593 | 2485033 | 1532869 | 1866262 | 3096500 |
| SM(d43:4) + H | 2486363 | 2400248 | 2112193 | 1914779 | 2254701 | 4635707 |
| SM(d44:1) + H | 4289607 | 3697676 | 3704597 | 2665198 | 2898206 | 4652818 |
| SM(d44:2) + H | 18273013 | 14139423 | 14425244 | 10407028 | 11349422 | 21240496 |
| SM(d44:3) + H | 10419505 | 7020260 | 8225159 | 4954560 | 5508703 | 16922243 |
| SM(d44:4) + H | 22148591 | 18165758 | 17943939 | 14457717 | 16811064 | 27270177 |
| SM(d44:5) + H | 76471759 | 47687528 | 58666392 | 33031699 | 49433776 | 118380147 |
| SM(d44:6) + H | 11507445 | 6706391 | 7295208 | 3601424 | 5492228 | 12759843 |
| TG(16:0/14:0/14:0) + NH4 | 1520012 | 2642041 | 2166017 | 2045191 | 1966742 | 1871033 |
| TG(44:5p) + NH4 | 10866658 | 11424737 | 12368285 | 7563479 | 10164188 | 14413003 |
| TG(15:0/14:0/16:0) + NH4 | 4376313 | 6379941 | 6680392 | 5753912 | 5320679 | 4772871 |
| TG(16:0/14:0/16:0) + NH4 | 3287947 | 5879047 | 4773183 | 4417473 | 4360536 | 3798349 |
| TG(15:0/16:0/16:0) + NH4 | 5817155 | 9760490 | 7353934 | 6660437 | 7230331 | 7362384 |
| TG(16:0/16:0/16:0) + NH4 | 8610155 | 13960240 | 11763798 | 9318170 | 9654277 | 8493829 |
| TG(16:0/16:0/16:1) + NH4 | 3634548 | 5632293 | 4785307 | 4086280 | 4105906 | 3643224 |
| TG(16:0/16:0/17:0) + NH4 | 3563345 | 6092571 | 5302713 | 4686056 | 4723196 | 4083586 |
| TG(18:0/16:0/16:0) + NH4 | 12997842 | 21828186 | 19306947 | 7698317 | 6909395 | 8532186 |
| TG(16:0/16:0/18:1) + NH4 | 4723975 | 6972172 | 6228199 | 5303522 | 5453287 | 4920543 |
| TG(18:0/16:0/18:0) + NH4 | 24098293 | 29381643 | 29176733 | 10602096 | 8673417 | 11135253 |
| TG(18:0/16:0/18:1) + NH4 | 3041252 | 4863162 | 3889854 | 2613999 | 2985202 | 2793863 |
| TG(16:0/18:1/18:1) + NH4 | 4355829 | 8429628 | 5769497 | 5502647 | 4773535 | 5666641 |

TABLE 8-continued

| | | | | | | |
|---|---|---|---|---|---|---|
| TG(18:0/18:0/18:0) + NH4 | 10143089 | 17446411 | 14178580 | 6393429 | 5741955 | 6201394 |
| TG(18:0/18:1/18:1) + NH4 | 2453354 | 3672295 | 3070653 | 2003892 | 2259814 | 2201605 |
| TG(18:1/18:1/18:1) + NH4 | 3815697 | 5370092 | 4497556 | 5050375 | 5521008 | 4612804 |
| TG(18:1/18:1/18:2) + NH4 | 1817698 | 1933037 | 1684654 | 2111086 | 1645265 | 1672020 |
| | 8.12E+09 | 4.90E+09 | 6.03E+09 | 3.57E+09 | 4.61E+09 | 1.20E+10 |

Figures 1A, 1B, 1C:
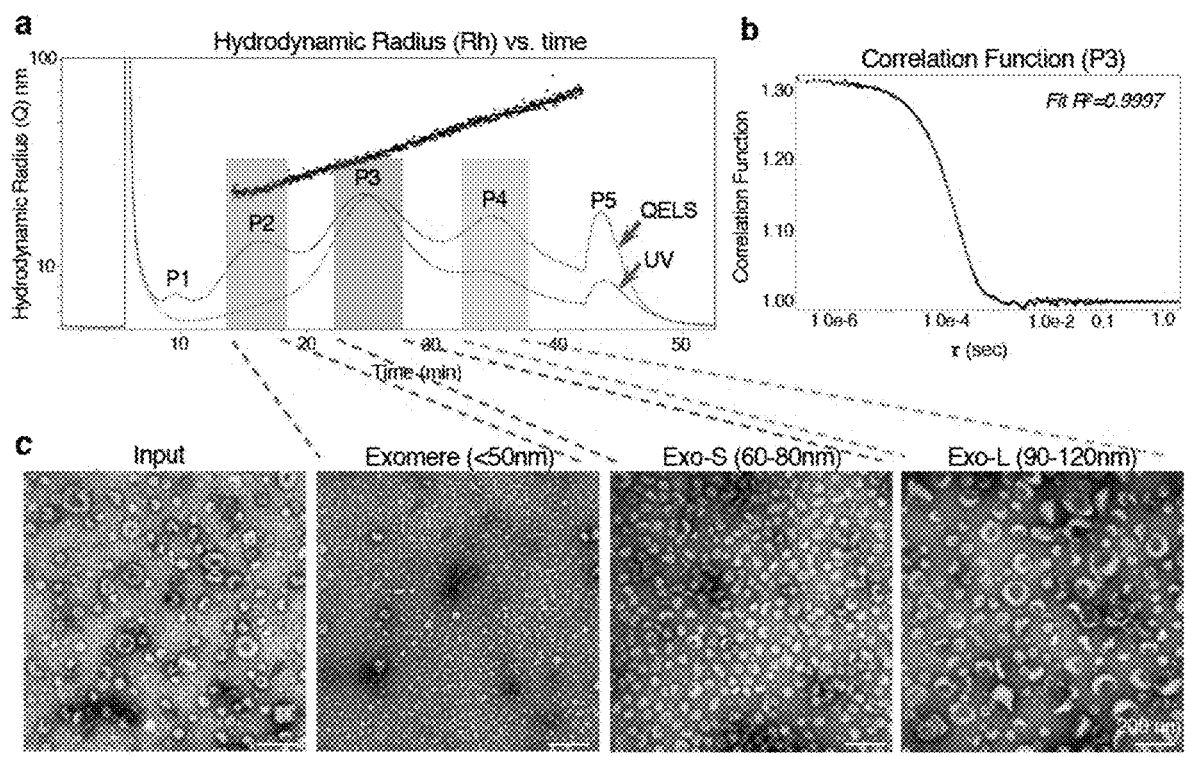
FIGS. 1A-1G show the identification, via AF4 and EM imaging analysis, of exomeres and two distinct subpopulations of exosomes released by tumor cells.

Example 1—Identification of a Distinct Nanoparticle Population and Subsets of Exosomes B16-F10 melanoma-derived sEVs were first fractionated by AF4 (see Methods). A linear separation of the sEV mixture was achieved based on the hydrodynamic radius (black dots, Y axis) along the time course (X axis) (FIG. 1A). The online QELS monitor for real-time dynamic light scattering (DLS) measurement (red trace) determined the hydrodynamic radius of particles. UV absorbance (blue trace) measured protein concentration and abundance of particles at specific time points for corresponding particle sizes. Particles with a 35-150 nm diameter were successfully separated by AF4 (FIG. 1A). Five peaks (P1-P5) were identified, corresponding to the time and particle size, at which most abundant particles were detected. P1 represented the void peak, a mixture of all types of nanoparticles. P5 was composed of individual or aggregated particles and protein aggregates with much larger sizes, which are outside the separation range of the current AF4 protocol, and eluted when crossflow dropped to zero (FIG. 2A). The hydrodynamic diameters of peaks P2, P3 and P4 were 47 nm, 62 nm and 101 nm, respectively. To infer the hydrodynamic radius, correlation functions were fitted to single exponentials (FIG. 1B, representative P3 fraction graph).

Individual fractions were measured using Nanosight Tracking Analysis (NIA), validating consistent particle size for each fraction between 60 nm and 140 nm (FIG. 2B). DLS combined with AF4 showed a broader dynamic range than NTA for those particles with a smaller (~70 nm) or larger (~160 nm) particle size (FIG. 2C). Moreover, NTA of each individual fraction in the range of 60-160 nm revealed a monomodal profile with a peak of ~77 nm (FIG. 2D).

Transmission electron microscopy (TEM) with negative staining of AF4 input and representative fractions across the full dynamic range revealed three populations of particles (P2, P3, P4; FIG. 1A) with distinct morphology and size (FIG. 1C). P2 represented a distinct population of nanoparticles not previously described, which were smaller than 50 nm (~35 nm) and clearly lacked an external membrane structure (FIG. 1C); these structures were therefore named "exomeres". The other two nanoparticle subpopulations are referred to as small exosomes (Exo-S; 60-80 nm [P3]) and large exosomes (Exo-L; 90-120 nm [P4]) (FIG. 1C). All three particle types were readily detected in the input TEM image (FIG. 1C). Western blot analysis confirmed exosome markers Tsg101 and Alix for Exo-S and Exo-L, and heat shock protein 90 (Hsp90) for exomeres (FIG. 1D). The sizes of each particle type measured in batch mode showed consistent results (FIG. 1E).

In summary, a single run of AF4 can efficiently discern exomeres and two distinct exosome subpopulations in a robust and highly reproducible manner (FIG. 2E, 2F). Freeze-thawing of samples led to inconsequential differences (FIG. 2G). However, changes in culture conditions led to differences in relative abundance of each particle type (FIG. 2H-2I).

Importantly, only a minor peak eluted in the time range similar to exomeres in a blank media control compared to CM of B16-F10 and MDA-MB-4175 when processed in parallel (FIG. 2J, 2K), thereby confirming that exomeres are indeed actively secreted by cultured cells and not mere aggregates present in media.

Figure 3A:
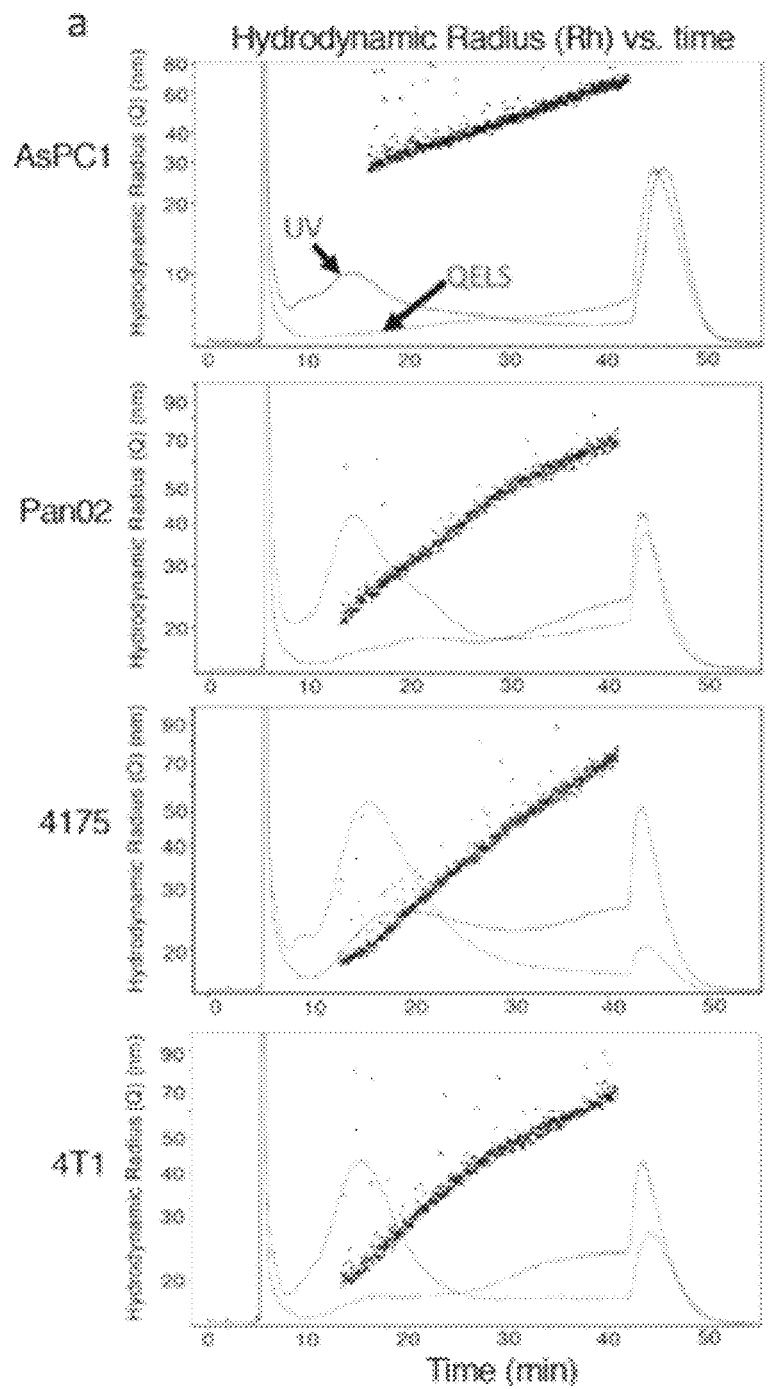
FIGS. 3A-3B show identification of exomeres and exosome subpopulations released by multiple cancer cell lines. Shown are AF4 profiles (FIG. 3A) and representative TEM images (FIG. 38) of unfractionated input samples and pooled fractions of exomeres, Exo-S and Exo-L that derived from various cancer cell lines, including AsPC-1, Pan02, MDA-MB-231-4175, and 4T1. Multiple independent experiments were conducted with similar results for (FIG. 3A) (repeated times: AsPC-1, 9×; Pan02, 16×; 4175, 17×; 4T1, 10×) and (FIG. 3B) (AsPC-1, 3×; Pan02, 2×; 4175, 1×; 4T1, 4×). Scale bar, 200 nm. x-axis, time (minutes); y-axis (scale) and black dots, hydrodynamic radius (nm); Red and blue lines illustrate the QELS (DLS) intensity and UV absorbance (shown on a relative scale), respectively.
Figure 3B:
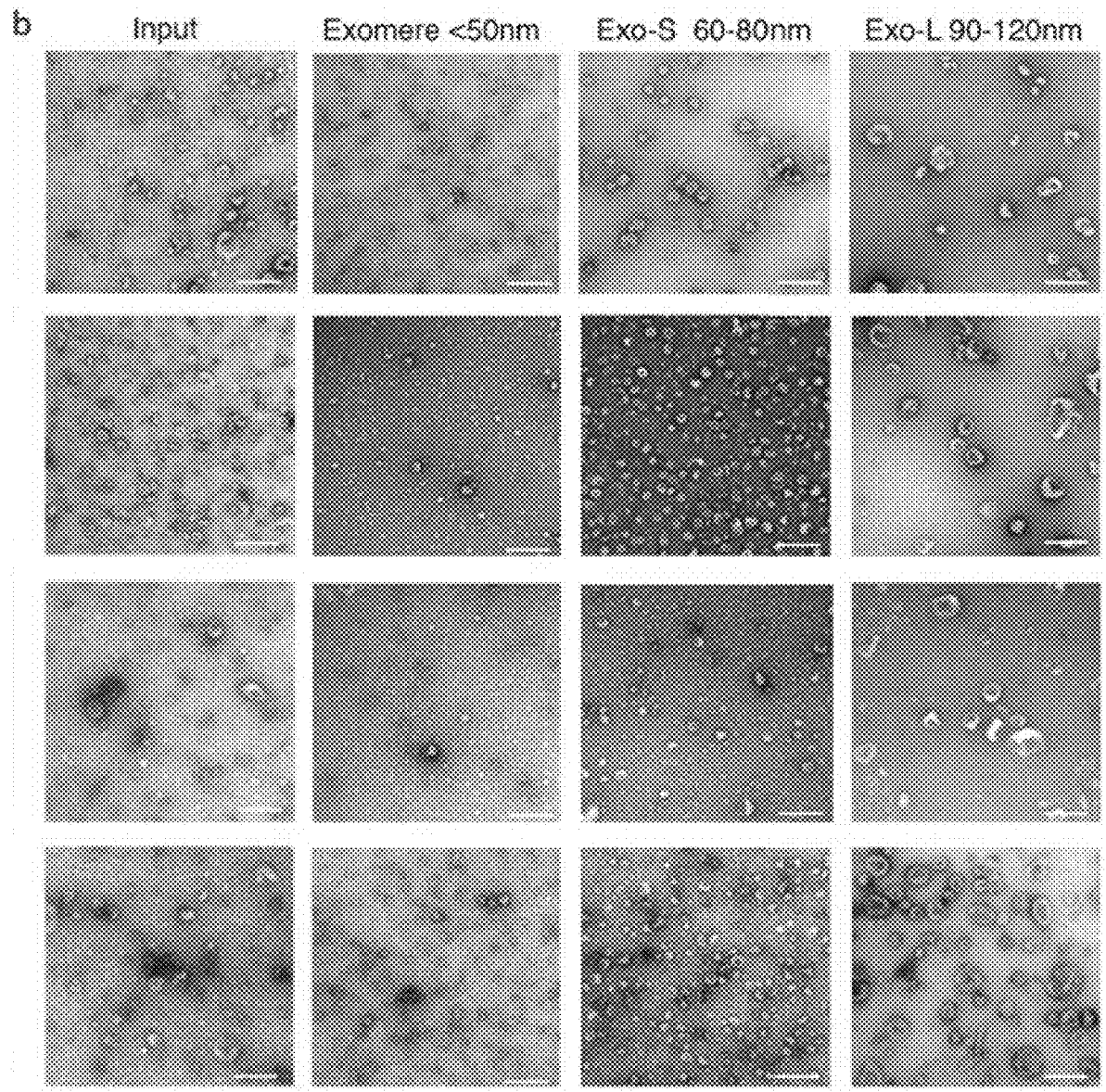

Using AF4, distinct particles were detected with diameters corresponding to exomeres and Exo-S/L in more than 20 cell lines analyzed (Table 9, FIG. 3A), findings confirmed by TEM analysis of pooled fractions from selected cell lines (FIG. 3B).

TABLE 9

| Cancer | Cell lines | Species |
|---|---|---|
| Melanoma | B16-F10 | m |
| | B16-F1 | m |
| | SK-Mel113 | h |
| | A375M | h |
| | A375P | h |
| Pancreatic Cancer | AsPC-1 | h |
| | Pan02 | m |
| | PANC1 | h |
| | HPAPII | h |
| | BxPC3 | h |
| CRC | HCT116 | h |
| | SW620 | h |
| NSCLC | PC9 | h |
| | LLC | m |
| Prostate Cancer | DU145 | h |
| | PC3 | h |
| Breast Cancer | 4TI | m |
| | MDA-MB-231 | h |
| | MDA-MB-1833 | h |
| | MDA-MB-4175 | h |
| | MDA-MB-831 | h |
| Leukemia | K562 | h |
| | NB4 | h |
| Transformed Non-cancer cells | NIH3T3 | m |
| | ET2B | h |

Based on UV absorbance and TEM analysis, all cells secreted higher amounts of exomeres relative to Exo-S/L, except for B16-F10 and 816-F1 where Exo-S were relatively more abundant (FIG. 3A and FIG. 1A, 1B). Measurement of the hydrodynamic diameter of each of these particles using Zetasizer showed sizes similar to the B16-F10 preparations (FIG. 1E).

Figures 4A, 4B:
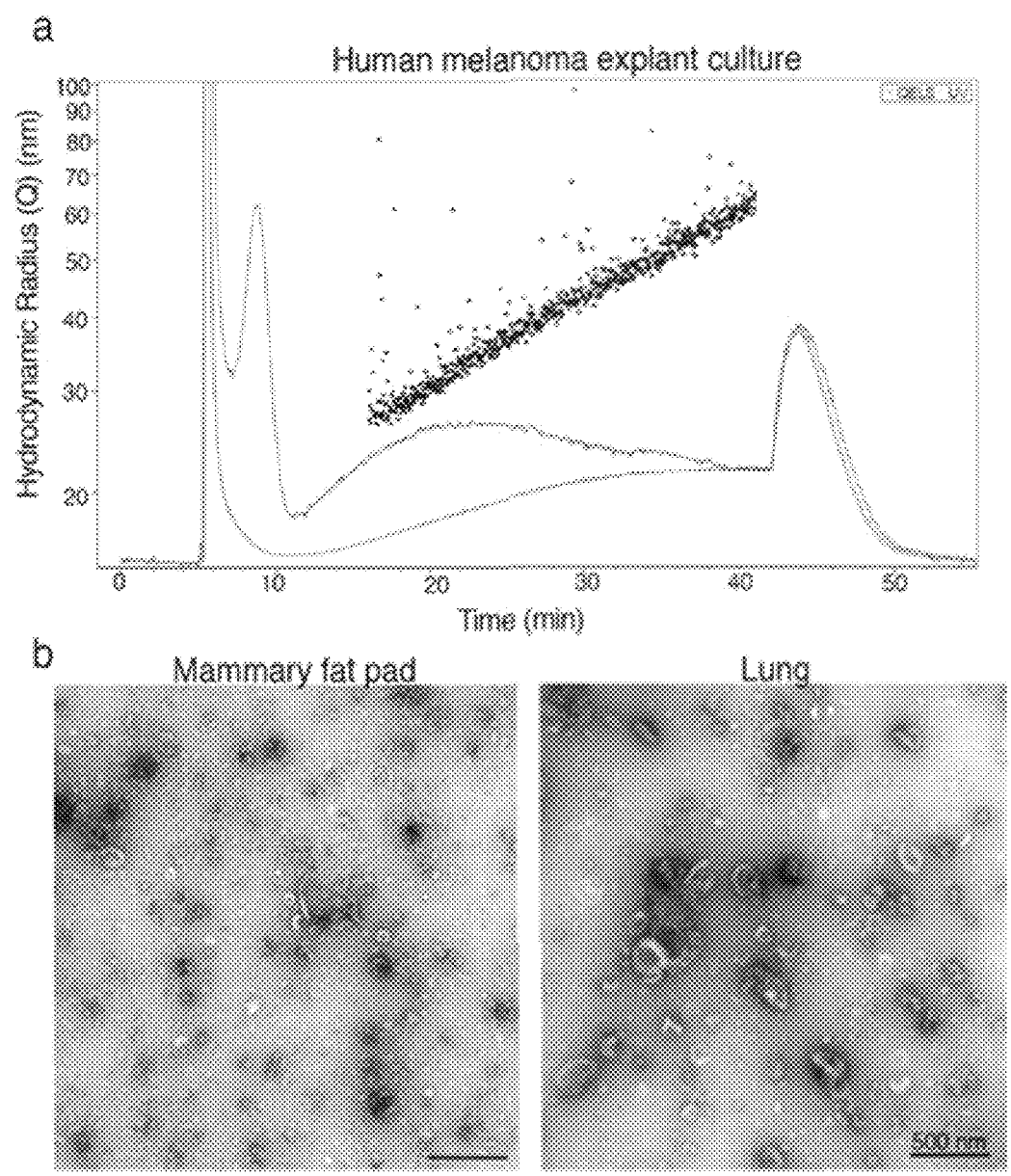
FIGS. 4A-4B show detection of exomeres, Exo-S and Exo-L in samples isolated from the tissue explant cultures.
Figure 10A:
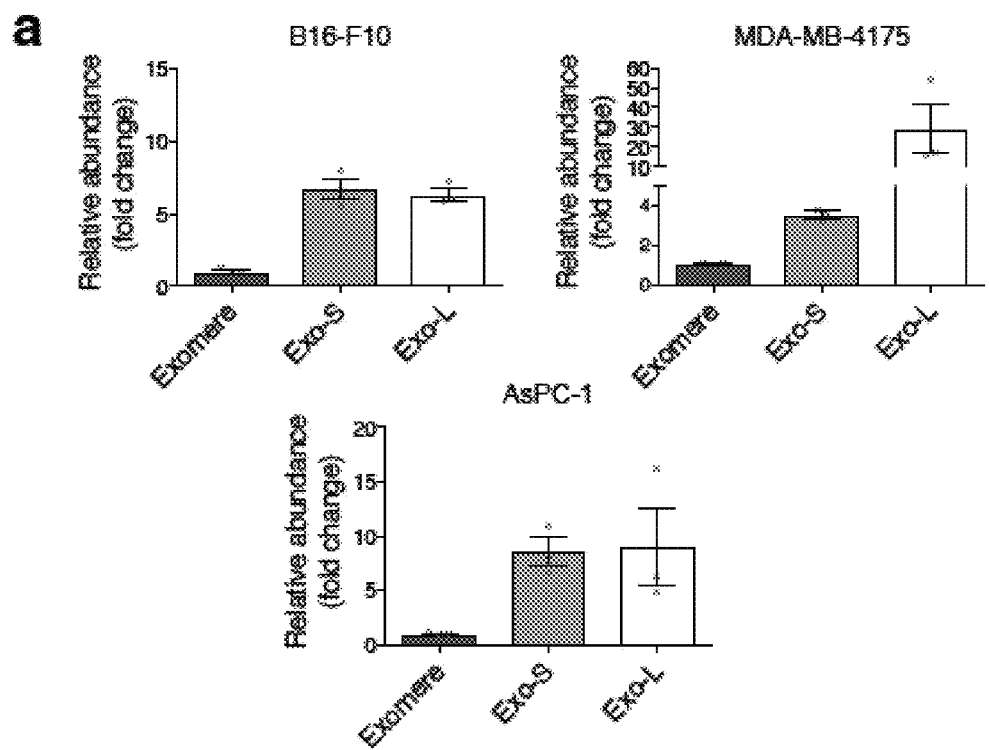
FIGS. 10A-10C show characterization of lipid composition in exomeres and exosome subsets.

Exomeres and Exo-S/L were also detected in AF4-fractionated sEVs from CM of human melanoma tumor explants by TEM (FIG. 1F, arrows; FIG. 4A). Exomere and Exo-S size, measured in batch mode using Zetasizer, was comparable to results from tumor cell lines (FIG. 10). AF4 profiting and TEM imaging analysis showed that the normal mouse tissue explants (mammary fat pad and lung) also secreted exomeres, and Exo-S/L nanoparticles (FIG. 4B).

Example 2—Biophysical Characterization of Exomeres and Exosome Subpopulations

Figure 5A:
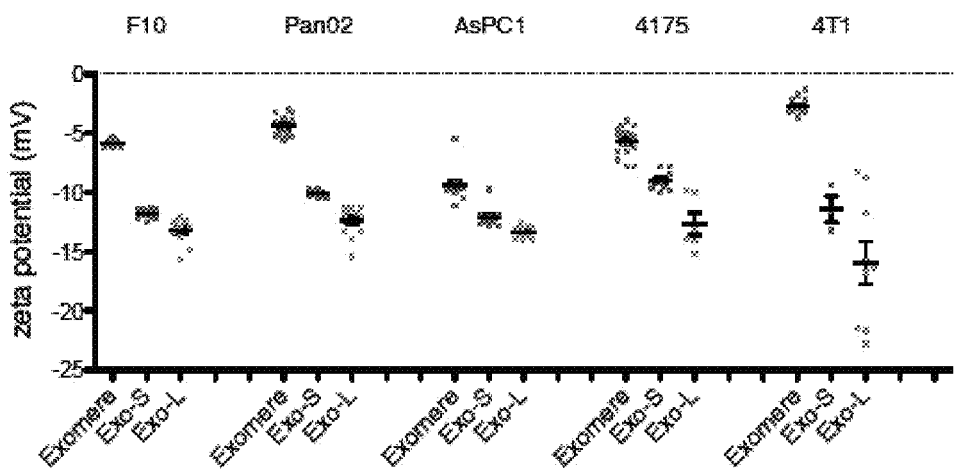
FIGS. 5A-5D show characterization of physical and mechanical properties of exomeres and exosome subpopulations. Zeta potential (FIG. 5A) and stiffness (FIG. 5B) of exomeres and exosome subpopulations derived from various cancer cells were measured using Zetasizer and AFM indentation, respectively. Young's modulus was used to express particle stiffness. At least 3 and 5 replicates for each group of particles was measured for zeta potential and stiffness, respectively. Data are presented as mean±SEM. For FIG. 5A, in the order of exomere, Exo-S and Exo-L: B16-F10 (n=8, 10, and 12 independent measurements, respectively); Pan02 (n=13, 11, 13); AsPC-1 (n=12, 12, 12); 4175 (n=17, 9, 6); 4T1 (n=13, 3, 9); for FIG. 5B, B16-F10 (n=6, 6, 6 particles measured); Pan02 (n=6, 6, 6); AsPC-1 (n=21, 19, 16); 4175 (n=11, 10, 5); 4T1 (n=9, 8, 9)).
Figure 5B:
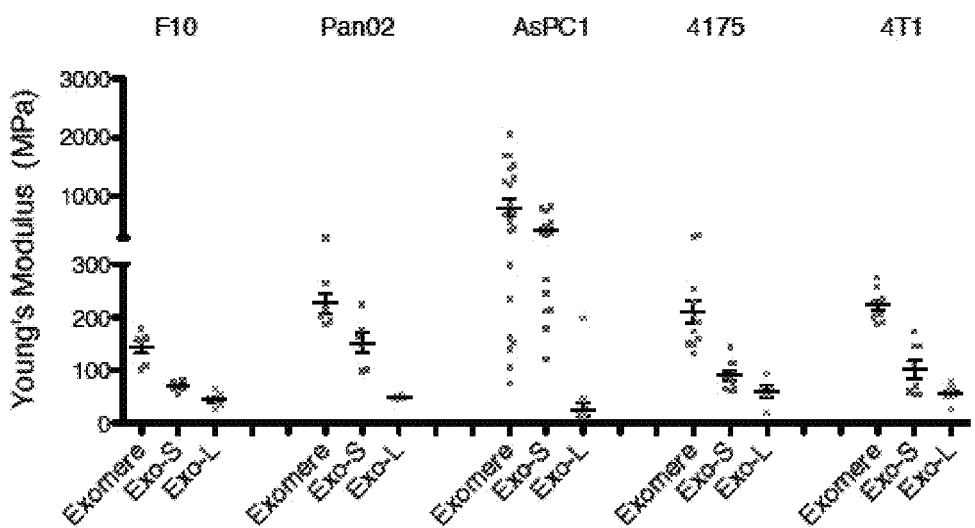

Given the structural differences between exomeres and Exo-S1L, their biophysical properties, such as zeta potential and stiffness, were examined. Measuring zeta potential, an average surface charge, using Zetasizer, revealed all particles were negatively charged, with exomeres being the weakest negatively charged (−2.7 mV to −9.7 mV); Exo-L, the strongest (−12.3 mV to −16.0 mV); and Exo-S, intermediate (−9.0 mV to −12.3 mV) (FIG. 5A).

For particle stiffness, atomic force microscopy (AFM) was performed in solution (see Methods). Exomeres demonstrated the highest stiffness (145-816 mPa) and Exo-L the lowest (26-73 mPa), with Exo-S stiffness being intermediate (70-420 mPa).

Figure 5C:
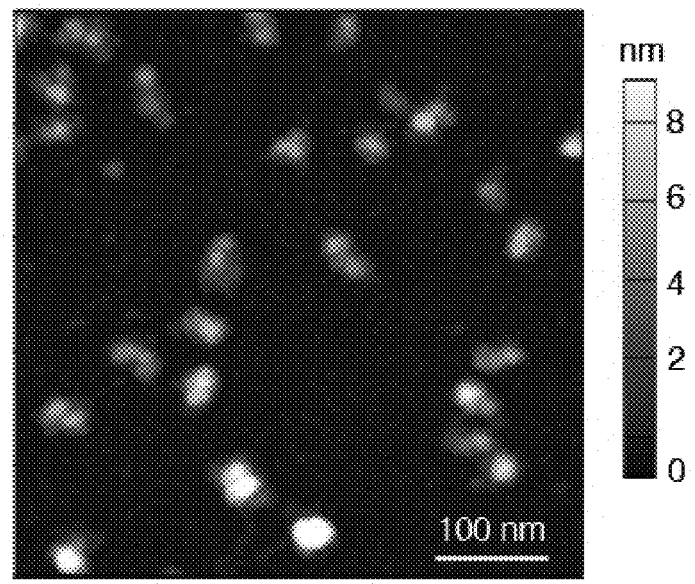
Figure 5D:
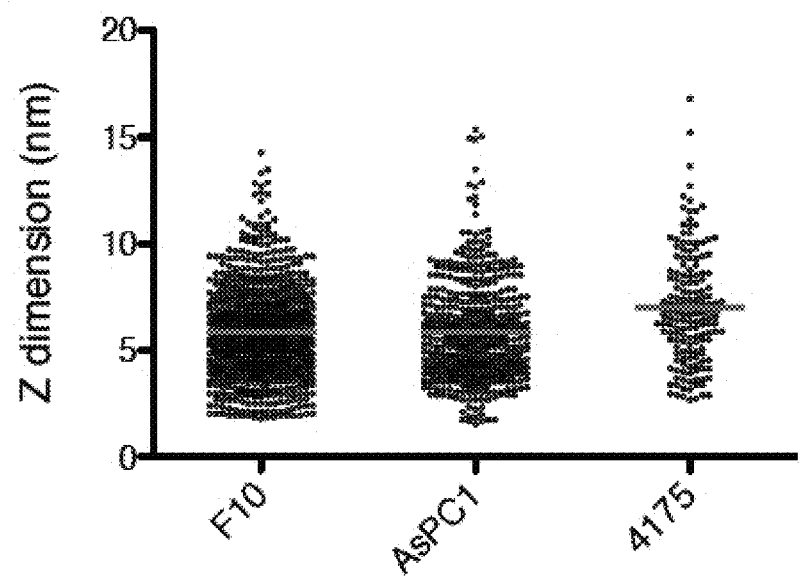

AFM analysis of exomeres derived from 1316-F10, MDA-MB-4175, and AsPC-1 cell lines demonstrated exomere structural heterogeneity and average exomere heights of 5.9 nm, 7.0 nm and 5.8 nm, respectively (FIG. 5C, 5D).

Collectively, these findings demonstrate the diverse biophysical properties exhibited by exomeres versus distinct exosome subpopulations. How size, charge, and mechanical properties influence the differential stability, trafficking and uptake of the nanoparticles in viva requires further investigation (Beningo et al., "Fc-Receptor-Mediated Phagocytosis is Regulated by Mechanical Properties of the Target," *Journal of Cell Science* 115:849-856 (2002); Key et al., "Soft Discoidal Polymeric Nanoconstructs Resist Macrophage Uptake and Enhance Vascular Targeting in Tumors," *ACS Nano* 9:11628-11641 (2015), which are hereby incorporated by reference in their entirety).

Example 3—Distinct Proteomic Content and Cellular Functions Among Exomeres and Exosome Subpopulations To characterize the molecular composition of exomeres and distinct exosome subpopulations, proteomic profiling of nanoparticles derived from B16-F10, Pan02, 4T1, AsPC-1, MDA-MB-4175 cells was conducted using label-free mass spectrometry. A range of 165-483 proteins were identified in exomeres, 433-1004 proteins in Exo-S, and 247-1127 proteins in Exo-L. Moreover, unique proteins were detected in each nanoparticle subtype (FIG. 6A), suggesting exomeres are unique entities released by cells rather than debris or fragments of exosomes.

Examination of the subcellular localization annotation of proteins revealed the specific enrichment of Exo-S/L in membrane-associated proteins, which were relatively depleted in exomeres (Table 10), consistent with the structural studies identifying Exo-S/L as membrane-encapsulated particles and exomeres as non-encapsulated particles.

TABLE 10

| EXOMERE | | EXO-S | | EXO-L | |
|---|---|---|---|---|---|
| Pathways | FDR q-val | Pathways | FDR q-val | Pathways | FDR q-val |
| Proteasame accessory complex | <0.001 | Intrinsic component of plasma membrane | <0.001 | Escrt complex | <0.001 |
| Endoplasmic reticulum lumen | <0.001 | Late endosome membrane | <0.001 | Cytoplasmic side of membrane | 0.001 |
| Cytosolic part | 0.001 | Endosomal part | <0.001 | Intercalated disc | 0.001 |
| Vesicle lumen | 0.001 | Phagocytic vesicle | <0.001 | Basolateral plasma membrane | 0.002 |
| Proteasome complex | 0.001 | Secretory granule membrane | <0.001 | Extrinsic component of cytoplasmic side of plasma membrane | 0.002 |
| Secretory granule lumen | 0.002 | Vacuolar membrane | <0.001 | midbody | 0.002 |
| microtubule | 0.004 | Phagocytic vesicle membrane | 0.001 | Heterotrimeric g protein complex | 0.002 |
| sarcoplasm | 0.029 | Late endosome | 0.001 | Cell cell contact zone | 0.002 |
| Inclusion body | 0.030 | Lytic vacuole membrane | 0.001 | Apical junction complex | 0.004 |
| Myelin sheath | 0.031 | endosome | 0.001 | Cell division site | 0.005 |
| Platelet alpha granule lumen | 0.032 | Vacuolar part | 0.001 | Extrinsic component of plasma membrane | 0.005 |
| Blood microparticle | 0.032 | vacuole | 0.007 | Late endosome membrane | 0.006 |
| Extracellular matrix | 0.033 | Multivesicular body | 0.008 | Extrinsic component of membrane | 0.010 |
| Chromosome centromeric region | 0.070 | Lytic vacuole | 0.010 | filopodium | 0.011 |
| mitochondrion | 0.071 | Endocytic vesicle | 0.010 | Side of membrane | 0.012 |
| Supramolecular fiber | 0.074 | Recycling endosome | 0.011 | Plasma membrane protein complex | 0.012 |
| Proteinaceous extracellular matrix | 0.083 | Extracellular matrix_component | 0.011 | synapse | 0.013 |
| Extracellular space | 0.087 | escrt_complex | 0.013 | postsynapse | 0.015 |
| Dna packaging complex | 0.114 | early_endosome | 0.013 | Synapse part | 0.016 |
| Microtubule cytoskeleton | 0.146 | snare_complex | 0.013 | Snare complex | 0.016 |
| Methyltransferase complex | 0.151 | plasma_membrane_raft | 0.013 | Cell junction | 0.017 |
| Cytosketetal part | 0.166 | membrane_protein_complex | 0.014 | Anchoring junction | 0.017 |
| microbody | 0.186 | cell_cell_adherens_junction | 0.016 | ruffle | 0.017 |
| Motile cilium | 0.236 | basement_membrane | 0.022 | Membrane region | 0.018 |
| polysome | 0.238 | proton_transporting_two_sector_atpase_complex | 0.024 | Trans Golgi network transport vesicle | 0.018 |

TABLE 10-continued

| EXOMERE | | EXO-S | | EXO-L | |
|---|---|---|---|---|---|
| Pathways | FDR q-val | Pathways | FDR q-val | Pathways | FDR q-val |
| Ciliary part | 0.238 | dna_packaging_complex | 0.025 | Neuron spine | 0.018 |
| Nuclear pore | 0.246 | endacytic_vesicle_membrane | 0.025 | Plasma membrane receptor complex | 0.018 |
| podosome | 0.257 | secretory_vesicle | 0.025 | Cell leading edge | 0.019 |
| Sperm part | 0.258 | Plasma membrane protein complex | 0.032 | Intrinsic component of plasma membrane | 0.023 |

ESCRT- and Snare-related proteins, involved in vesicle budding, membrane fusion and exosome biogenesis (Colombo et al., "Biogenesis, Secretion, and Intercellular Interactions of Exosomes and Other Extracellular Vesicles," Annu Rev Cell Dev Biol 30:255-289 (2014); Hessvik et al., "Current Knowledge on Exosome Biogenesis and Release," Cell Mol Life Sci (2017), which are hereby incorporated by reference in their entirety), were identified within Exo-S/L. In particular, proteins associated with endosomes, multivesicular bodies, vacuoles, and phagocytic vesicles were enriched in Exo-S. Plasma membrane, cell-cell contact/junction, late-endosome, and trans-Golgi network proteins were enriched in Exo-L. Notably, proteins associated with extracellular matrix and space, proteasome accessory complex, endoplasmic reticulum, mitochondrion, and microtubule/cytoskeleton were packaged in exomeres. These findings imply possible fundamental differences in exomeres, Exo-S, and Exo-L biogenesis.

Figures 6A, 6B:
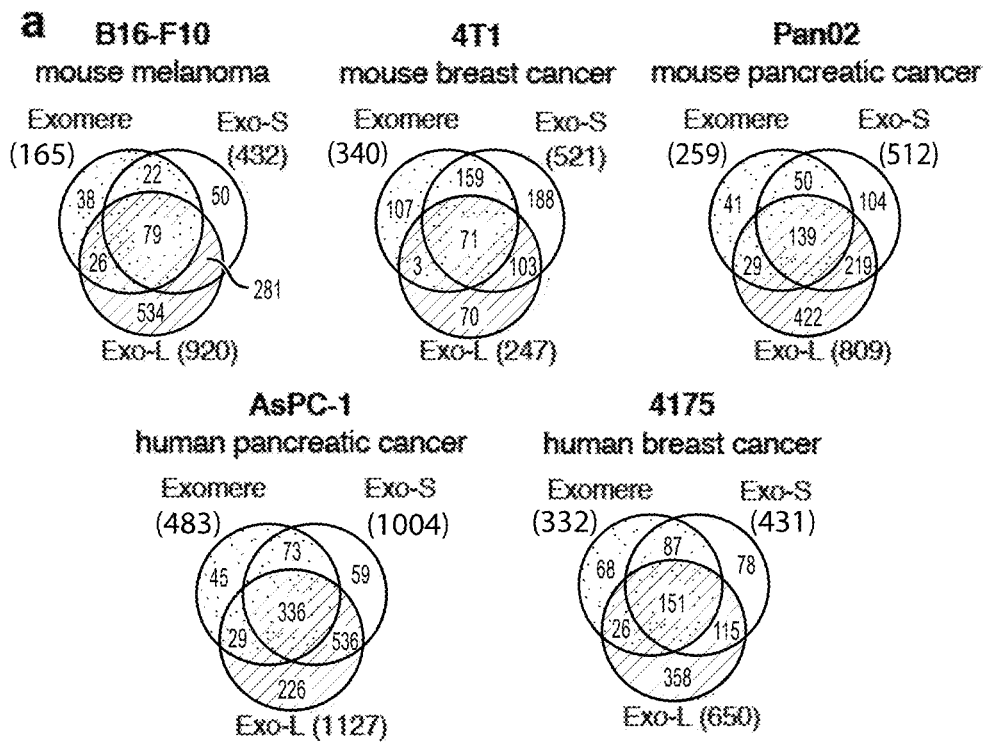
FIGS. 6A-6G show proteomic profiling of exomeres and exosome subpopulations derived from various cancer cells.
Figure 6C:
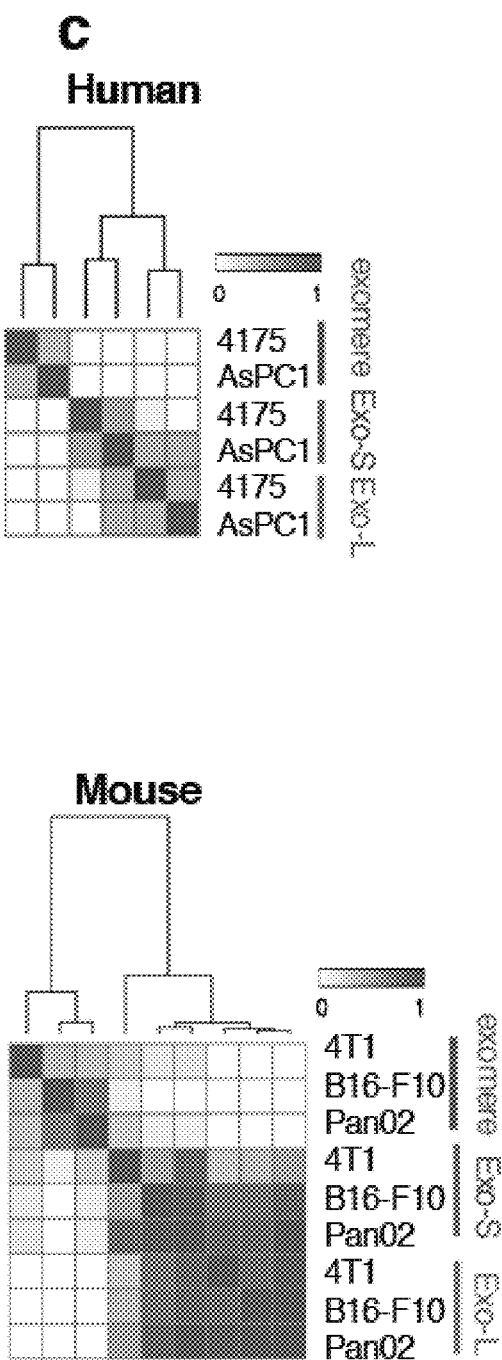
Figures 7A, 7B, 7C:
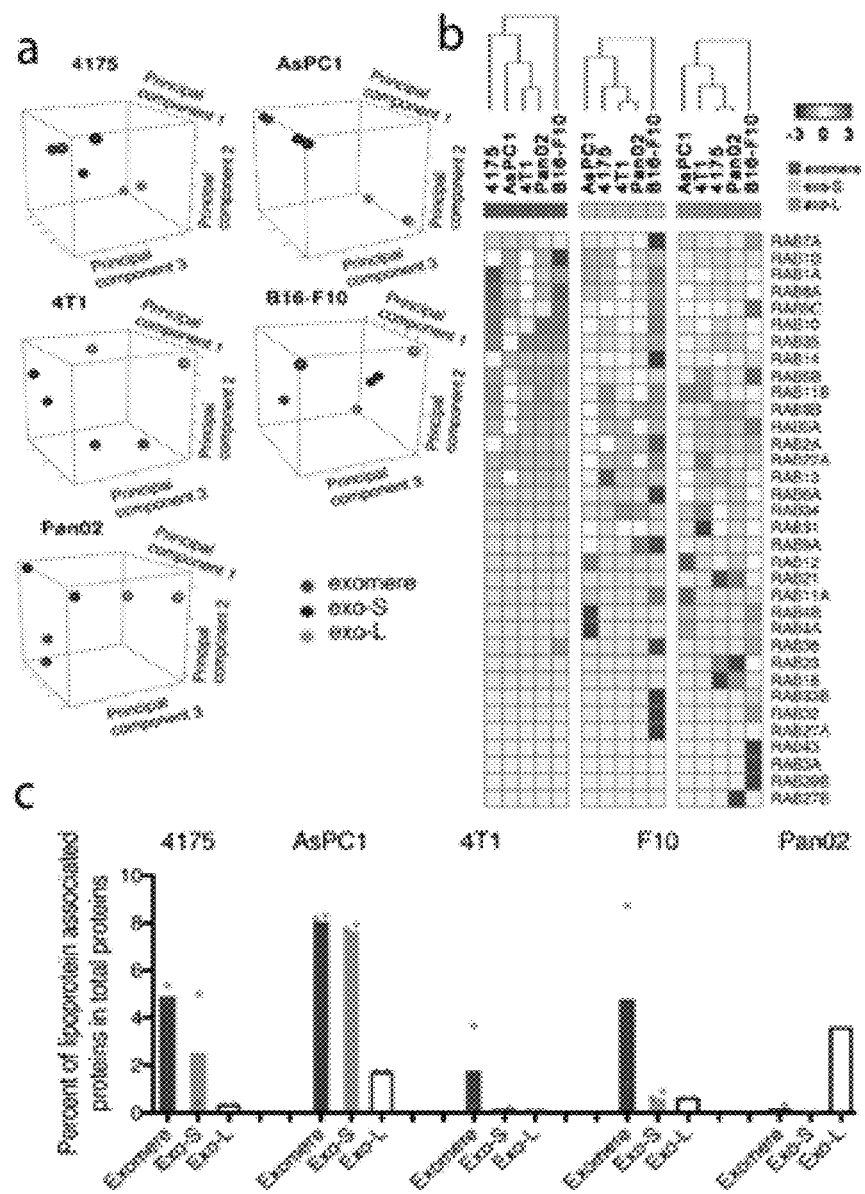
FIGS. 7A-7E show proteomic profiling of exomeres and exosome subpopulations derived from multiple cancer cell lines.

Principal component analysis (PCA) demonstrated closer correlation of protein expression for Exo-S and Exo-L compared to exomeres from the same cell-type (FIG. 7A). According to RCA and consensus clustering analysis, exomeres from different cell types exhibited a higher degree of similarity to each other than to Exo-S and Exo-L from the same cell type (FIG. 6B, 6C).

To identify the signature proteins in each particle subset, statistical analysis was performed on the expression levels of proteins identified in these datasets. 64 proteins were pinpointed for exomeres and 99 proteins for Exo-S/L (Tables 11-14), with a false discovery rate (FDR)<0.05, positive enrichment in each particle subset of interest, and detection frequency of >80% (i.e., a particular protein was positively enriched in at least 4/5 samples for each subtype of nanoparticles derived from 5 different cell lines).

TABLE 11

| Symbol | Average expression in exomere | Frequency (%, n = 5) | Fold change exomere vs Exo-S | Fold change exomere vs Exo-L |
|---|---|---|---|---|
| PPID | 1.83E+08 | 80% | Inf | 21.5 |
| GANAB | 3.03E+08 | 80% | 16.4 | Inf |
| MAT1A | 9.11E+08 | 100% | 10.4 | Inf |
| DPYD | 1.61E+08 | 80% | 10.1 | Inf |
| FAT4 | 3.48E+08 | 100% | 9.3 | 91.9 |
| GMPPB | 1.15E+08 | 80% | 8.3 | Inf |
| ERP44 | 2.64E+08 | 100% | 7.5 | Inf |
| CALR | 5.71E+08 | 100% | 8.8 | 48.4 |
| GPD1 | 2.93E+08 | 100% | 7.1 | Inf |
| BZW1 | 1.86E+08 | 100% | 9.5 | 24.3 |
| PFKL | 5.34E+08 | 100% | 6.4 | 134.6 |
| OLFML3 | 1.98E+08 | 80% | 6.1 | Inf |
| HGD | 4.03E+08 | 100% | 5.9 | Inf |
| LGALS3BP | 3.40E+09 | 100% | 7.9 | 21.2 |
| GCLC | 3.87E+08 | 100% | 5.6 | Inf |
| PEPD | 8.00E+08 | 100% | 5.8 | 87.6 |
| MTHFD1 | 6.17E+08 | 100% | 8.1 | 15.4 |
| PGD | 1.01E+09 | 80% | 7.0 | 16.2 |
| ACTR3 | 3.54E+08 | 100% | 12.7 | 7.6 |
| XPNPEP1 | 3.68E+08 | 100% | 5.3 | 43.6 |
| UGP2 | 8.77E+08 | 100% | 5.8 | 24.6 |
| SNX2 | 1.89E+08 | 80% | 4.7 | 214.1 |
| ALDOC | 4.03E+08 | 80% | 6.2 | 17.2 |
| SEPT11 | 2.14E+08 | 80% | 29.0 | 5.3 |
| HSPA13 | 8.68E+08 | 100% | 5.6 | 22.4 |
| AARS | 1.67E+08 | 80% | 15.4 | 6.3 |
| SERPINH1 | 6.42E+08 | 100% | 4.7 | 48.8 |
| CNDP2 | 4.63E+08 | 100% | 4.4 | 76.7 |
| PDE5A | 2.22E+08 | 80% | 4.4 | 79.7 |
| AGL | 3.14E+08 | 100% | 4.4 | 72.8 |
| EXT1 | 8.34E+08 | 100% | 4.2 | 146.4 |
| IDH1 | 4.82E+08 | 100% | 5.1 | 20.6 |
| SERPINC1 | 3.95E+09 | 80% | 4.0 | 1601.2 |
| RRM1 | 5.00E+08 | 100% | 4.0 | Inf |
| CKB | 3.61E+08 | 80% | 3.8 | 97.1 |
| HMGCS1 | 4.25E+08 | 100% | 4.4 | 17.9 |
| HPD | 1.10E+09 | 100% | 3.9 | 38.6 |
| PSMC4 | 3.13E+08 | 100% | 3.9 | 35.6 |
| NPEPPS | 2.09E+08 | 80% | 4.0 | 24.4 |

TABLE 11-continued

| Symbol | Average expression in exomere | Frequency (%, n = 5) | Fold change exomere vs Exo-S | Fold change exomere vs Exo-L |
|---|---|---|---|---|
| CAT | 4.57E+08 | 100% | 3.9 | 32.2 |
| EXT2 | 6.05E+08 | 100% | 3.8 | 38.6 |
| CORO1C | 6.60E+08 | 100% | 3.9 | 26.1 |
| B4GAT1 | 6.53E+08 | 100% | 3.5 | 63.7 |
| RACK1 | 3.10E+08 | 100% | 4.4 | 13.3 |
| MAPRE1 | 2.46E+08 | 80% | 4.6 | 11.1 |
| PGM1 | 1.12E+09 | 100% | 3.5 | 37.8 |
| PDIA3 | 6.64E+08 | 80% | 4.4 | 11.2 |
| ADK | 1.23E+09 | 100% | 3.6 | 25.9 |
| SHMT1 | 2.30E+08 | 80% | 3.6 | 24.5 |
| ACO1 | 1.72E+09 | 100% | 3.3 | 65.1 |
| GSN | 1.29E+10 | 100% | 3.2 | 96.9 |
| ESD | 4.15E+08 | 80% | 5.0 | 6.3 |
| PPP2R1A | 6.38E+08 | 100% | 3.7 | 10.1 |
| ALDH1L1 | 1.73E+09 | 100% | 2.9 | 36.4 |
| OLA1 | 2.81E+08 | 80% | 5.0 | 5.8 |
| ACLY | 8.92E+08 | 100% | 3.1 | 20.8 |
| EEF1G | 7.95E+08 | 100% | 3.3 | 13.6 |
| FLNB | 3.08E+08 | 80% | 4.0 | 7.9 |
| PSMD11 | 2.26E+08 | 80% | 3.1 | 17.8 |
| ANGPTL3 | 3.01E+08 | 80% | 2.8 | 31.7 |
| FERMT3 | 7.54E+08 | 80% | 2.8 | 27.6 |
| PYGL | 1.60E+09 | 100% | 2.8 | 28.6 |
| MDH1 | 3.34E+08 | 80% | 8.0 | 3.7 |
| EIF4A2 | 5.83E+08 | 80% | 2.6 | 86.4 |

"inf" stands for "infinity", indicating proteins that are absent in Exo-S or Exo-L.

TABLE 12

| Symbol | Average expression in Exosome | Frequency (%, n = 20) | Fold change Exosome vs exomere |
|---|---|---|---|
| GNA13 | 1.16E+09 | 80% | Inf |
| DNAJA1 | 9.79E+08 | 100% | Inf |
| SLC38A2 | 9.48E+08 | 90% | Inf |
| TFRC | 9.06E+08 | 100% | Inf |
| BSG | 8.57E+08 | 80% | Inf |
| LAMP1 | 6.77E+08 | 90% | Inf |
| EHD2 | 6.74E+08 | 80% | Inf |
| ANXA5 | 6.56E+08 | 80% | Inf |
| SLC1A5 | 5.89E+08 | 90% | Inf |
| NRAS | 5.84E+08 | 100% | Inf |
| CHMP5 | 5.69E+08 | 90% | Inf |
| DNAJA2 | 5.51E+08 | 90% | Inf |
| ANXA1 | 5.46E+08 | 90% | Inf |
| ANXA11 | 5.28E+08 | 80% | Inf |
| ATP1B3 | 5.28E+08 | 90% | Inf |
| SH3GL1 | 5.01E+08 | 90% | Inf |
| FLOT2 | 4.92E+08 | 100% | Inf |
| RAP2B | 4.83E+08 | 90% | Inf |
| FLOT1 | 4.31E+08 | 100% | Inf |
| RALA | 4.26E+08 | 80% | Inf |
| RAP2C | 4.23E+08 | 80% | Inf |
| CEP55 | 4.18E+08 | 90% | Inf |
| STOM | 4.13E+08 | 100% | Inf |
| MMP14 | 3.60E+08 | 90% | Inf |
| CHMP2A | 3.59E+08 | 90% | Inf |
| TM9SF2 | 3.04E+08 | 80% | Inf |
| MYO1C | 3.02E+08 | 80% | Inf |
| DIP2B | 3.01E+08 | 90% | Inf |
| GNA11 | 3.00E+08 | 90% | Inf |
| MET | 2.91E+08 | 80% | Inf |
| CTNNB1 | 2.78E+08 | 90% | Inf |
| ANXA4 | 2.78E+08 | 80% | Inf |
| LYN | 2.58E+08 | 90% | Inf |
| ATP2B1 | 2.54E+08 | 80% | Inf |
| GNG12 | 2.54E+08 | 80% | Inf |
| GNAQ | 2.24E+08 | 90% | Inf |
| YES1 | 2.22E+08 | 100% | Inf |
| RRAS | 2.16E+08 | 80% | Inf |
| ITCH | 1.86E+08 | 90% | Inf |
| ANTXR2 | 1.86E+08 | 90% | Inf |
| RRAS2 | 1.84E+08 | 80% | Inf |
| TGFBR2 | 1.81E+08 | 80% | Inf |
| ARF4 | 1.64E+08 | 90% | Inf |
| TOLLIP | 1.60E+08 | 90% | Inf |
| ANXA7 | 1.59E+08 | 90% | Inf |
| SNAP23 | 1.58E+08 | 80% | Inf |
| VPS25 | 1.49E+08 | 80% | Inf |
| SLC12A2 | 1.46E+08 | 80% | Inf |
| CD2AP | 1.44E+08 | 90% | Inf |
| STXBP3 | 1.40E+08 | 90% | Inf |
| EPS8 | 1.37E+08 | 80% | Inf |
| CHMP1A | 1.36E+08 | 80% | Inf |
| JAK1 | 1.30E+08 | 90% | Inf |
| GRB2 | 1.20E+08 | 80% | Inf |
| MAP4K4 | 1.19E+08 | 80% | Inf |
| STX4 | 1.18E+08 | 80% | Inf |
| NEDD4L | 1.15E+08 | 80% | Inf |
| RAB22A | 1.04E+08 | 80% | Inf |
| ANXA2 | 1.08E+09 | 80% | 54.6 |
| MYOF | 6.20E+08 | 100% | 48.6 |
| VPS4B | 6.85E+08 | 90% | 47.3 |
| PDCD6 | 7.87E+08 | 90% | 39.5 |
| VPS37C | 1.09E+09 | 90% | 34.7 |
| VPS4A | 4.66E+08 | 90% | 31.9 |
| ITGAV | 5.61E+08 | 100% | 30.6 |
| TSPAN14 | 4.39E+08 | 80% | 26.6 |
| TSPAN4 | 1.24E+09 | 80% | 26.5 |
| CHMP4B | 8.65E+08 | 100% | 26.1 |
| ITGB5 | 2.93E+08 | 80% | 19.5 |
| IST1 | 1.03E+09 | 80% | 19.0 |
| EPHA2 | 9.45E+08 | 80% | 16.5 |
| GNAI3 | 2.15E+09 | 90% | 12.5 |
| RAB5B | 2.99E+08 | 90% | 11.6 |
| GNAS | 1.75E+09 | 100% | 10.8 |
| VPS37B | 6.71E+08 | 100% | 10.8 |
| ITGA3 | 5.46E+09 | 80% | 9.7 |
| TSG101 | 1.11E+09 | 100% | 9.5 |
| CTNNA1 | 8.46E+08 | 90% | 9.4 |
| MVB12A | 9.08E+08 | 90% | 9.1 |
| RDX | 8.18E+08 | 80% | 9.0 |
| ATP1A1 | 1.96E+09 | 100% | 8.9 |
| PACSIN2 | 1.37E+08 | 80% | 8.8 |
| ITGB1 | 8.77E+09 | 100% | 8.7 |
| SLC3A2 | 2.39E+09 | 100% | 8.6 |

TABLE 12-continued

| Symbol | Average expression in Exosome | Frequency (%, n = 20) | Fold change Exosome vs exomere |
|---|---|---|---|
| RAB8B | 5.71E+08 | 80% | 8.6 |
| ITGA6 | 8.84E+08 | 80% | 8.6 |
| RAB14 | 6.00E+08 | 100% | 8.6 |
| VPS28 | 1.37E+09 | 100% | 8.0 |
| CD9 | 8.89E+09 | 100% | 7.9 |
| LAMP2 | 3.95E+08 | 90% | 7.8 |
| RAB35 | 7.70E+08 | 100% | 7.5 |
| BROX | 4.16E+08 | 90% | 7.2 |
| CD44 | 9.51E+08 | 90% | 7.0 |
| MFGE8 | 5.72E+09 | 90% | 6.9 |
| CTNND1 | 3.39E+08 | 80% | 6.8 |
| ITM2B | 5.79E+08 | 80% | 6.7 |
| GNAI2 | 2.49E+09 | 100% | 6.3 |
| ARRDC1 | 1.11E+09 | 80% | 5.9 |
| PDCD6IP | 8.05E+09 | 100% | 5.8 |

"inf" stands for "infinity", indicating proteins that are absent in exomere.

TABLE 13

| Symbol | Average expression in Exo-S | Frequency (%, n = 5) | Fold change Exo-S vs exomere | Fold change Exo-S vs Exo-L |
|---|---|---|---|---|
| TTYH3 | 2.66E+08 | 100% | Inf | 7.8 |
| FLOT1 | 7.46E+08 | 100% | Inf | 6.4 |
| FLOT2 | 8.39E+08 | 100% | Inf | 5.8 |
| TSPAN14 | 7.39E+08 | 100% | 44.8 | 5.3 |
| LAMC1 | 1.44E+08 | 80% | 6.8 | 11.4 |
| CD63 | 5.95E+09 | 100% | Inf | 3.3 |
| MVB12A | 1.44E+09 | 80% | 14.5 | 3.8 |
| ZDHHC20 | 1.56E+08 | 80% | Inf | 3.0 |
| VAMP3 | 1.08E+08 | 80% | Inf | 2.8 |
| VPS37B | 1.03E+09 | 100% | 16.6 | 3.3 |
| ARRDC1 | 1.75E+09 | 80% | 9.3 | 3.7 |
| TGFBR2 | 2.60E+08 | 80% | Inf | 2.6 |

"inf" stands for "infinity", indicating proteins that are absent in Exomere or Exo-L.

TABLE 14

| Symbol | Average expression in Exo-L | Frequency (%, n = 5) | Fold change Exo-L vs exomere | Fold change Exo-L vs Exo-S |
|---|---|---|---|---|
| SQSTM1 | 2.34E+08 | 80% | Inf | Inf |
| STIP1 | 1.99E+08 | 100% | Inf | Inf |
| HINT1 | 1.68E+08 | 80% | Inf | Inf |
| WASF2 | 1.58E+08 | 80% | Inf | Inf |
| RASA3 | 1.48E+08 | 80% | Inf | Inf |
| EPB41L2 | 1.45E+08 | 80% | Inf | Inf |
| GIPC1 | 1.29E+08 | 80% | Inf | Inf |
| S100A10 | 3.76E+08 | 80% | Inf | 89.7 |
| MPP6 | 1.70E+08 | 100% | Inf | 42.1 |
| KIF23 | 3.38E+08 | 80% | Inf | 35.8 |
| RACGAP1 | 2.43E+08 | 80% | Inf | 24.8 |
| ANXA5 | 1.23E+09 | 100% | Inf | 14.9 |
| CASK | 1.24E+08 | 80% | Inf | 14.8 |
| DLG1 | 2.18E+08 | 100% | Inf | 14.4 |
| TJP1 | 1.02E+08 | 80% | Inf | 13.4 |
| BAG5 | 1.36E+08 | 80% | Inf | 12.3 |
| TXN | 4.79E+08 | 80% | Inf | 12.3 |
| ABI1 | 1.91E+08 | 100% | Inf | 11.5 |
| ANXA1 | 1.00E+09 | 100% | Inf | 11.0 |
| CAPG | 1.17E+08 | 80% | Inf | 9.9 |
| DBI | 2.68E+08 | 80% | Inf | 9.0 |
| S100A6 | 3.22E+09 | 80% | 33.2 | 12.1 |
| CHMP2B | 1.78E+08 | 80% | Inf | 8.6 |
| CHMP3 | 1.76E+08 | 86% | Inf | 7.9 |
| ANXA2 | 1.91E+09 | 80% | 96.7 | 7.7 |
| MYO1C | 5.24E+08 | 100% | Inf | 6.6 |
| ANXA4 | 4.79E+08 | 100% | Inf | 6.2 |
| SNX12 | 1.23E+08 | 80% | Inf | 5.8 |
| LIN7C | 1.97E+08 | 80% | Inf | 5.3 |
| STXBP3 | 2.32E+08 | 100% | Inf | 4.9 |
| CEP55 | 6.92E+08 | 80% | Inf | 4.8 |
| ALCAM | 2.93E+08 | 80% | Inf | 4.7 |
| VCL | 2.95E+08 | 80% | 20.0 | 6.0 |
| CHMP1A | 2.21E+08 | 100% | Inf | 4.3 |
| FARP1 | 3.59E+08 | 80% | 14.1 | 6.2 |
| ACSL4 | 1.64E+08 | 80% | Inf | 4.3 |
| BAIAP2 | 2.28E+08 | 80% | Inf | 4.3 |
| SH3GL1 | 8.10E+08 | 100% | Inf | 4.2 |
| DSTN | 2.41E+08 | 100% | 4.8 | 36.4 |

TABLE 14-continued

| Symbol | Average expression in Exo-L | Frequency (%, n = 5) | Fold change Exo-L vs exomere | Fold change Exo-L vs Exo-S |
|---|---|---|---|---|
| LGALS1 | 1.74E+09 | 80% | 13.0 | 5.9 |
| CYFIP1 | 1.66E+08 | 100% | 9.4 | 7.1 |
| CTNNA1 | 1.43E+09 | 100% | 15.9 | 5.4 |
| RAB31 | 2.28E+08 | 80% | Inf | 4.0 |
| ARF6 | 2.05E+08 | 80% | Inf | 3.9 |
| SLC1A5 | 9.38E+08 | 100% | Inf | 3.9 |
| EPS8 | 2.18E+08 | 80% | Inf | 3.9 |
| FMNL2 | 2.11E+08 | 100% | Inf | 3.9 |
| PGAM1 | 5.42E+08 | 100% | 4.3 | 26.8 |
| CNP | 1.37E+08 | 80% | Inf | 3.7 |
| CHMP4B | 1.39E+09 | 100% | 41.9 | 4.0 |
| ANXA3 | 4.14E+08 | 80% | Inf | 3.7 |
| VPS4B | 1.09E+09 | 100% | 75.0 | 3.9 |
| GNG12 | 3.99E+08 | 100% | Inf | 3.6 |
| PACSIN3 | 1.20E+08 | 100% | Inf | 3.4 |
| GLG1 | 1.25E+08 | 80% | Inf | 3.2 |
| VTA1 | 3.19E+08 | 80% | Inf | 3.2 |
| LYN | 3.91E+08 | 100% | Inf | 3.1 |
| VPS37C | 1.68E+09 | 100% | 53.2 | 3.3 |
| CHMP5 | 8.59E+08 | 100% | Inf | 3.1 |
| F3 | 8.48E+08 | 80% | 28.6 | 3.4 |
| DNAJA1 | 1.47E+09 | 100% | Inf | 3.0 |
| RHOC | 1.09E+09 | 80% | 26.0 | 3.4 |
| GNA13 | 1.72E+09 | 100% | Inf | 2.9 |
| CHMP2A | 5.33E+08 | 100% | Inf | 2.9 |
| ATP2B1 | 3.74E+08 | 100% | Inf | 2.8 |
| RDX | 1.26E+09 | 100% | 13.9 | 3.4 |
| ATP1B1 | 3.67E+08 | 80% | Inf | 2.7 |
| CAPZB | 1.29E+08 | 80% | 3.2 | 15.3 |
| EHD1 | 4.39E+09 | 100% | 6.2 | 4.5 |
| DNAJA2 | 7.91E+08 | 80% | Inf | 2.5 |
| CTNND1 | 5.21E+08 | 100% | 10.4 | 3.3 |

"inf" stands for "infinity", indicating proteins that are absent in Exomere or Exo-S.

Figure 6D:
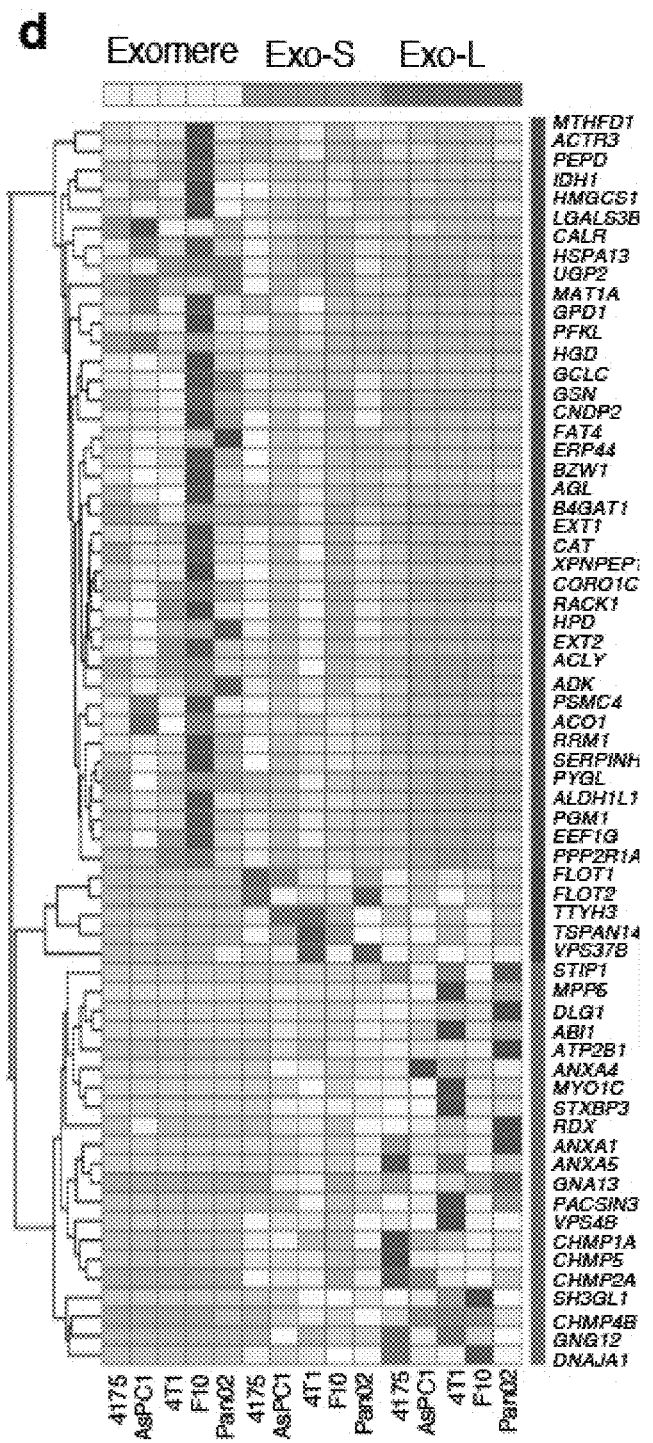
Figure 6E:
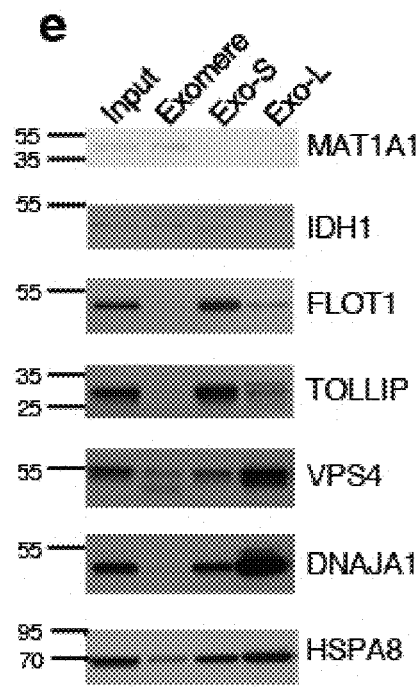

Remarkably, exomeres were significantly enriched in proteins involved in metabolism (see gene set enrichment analysis [GSEA] analysis below), including MAT1A, IDH1, GMPPB, UGP2, EXT1, and PFKL. The sialoglycoprotein galectin-3-binding protein (LGALS3BP) and key proteins controlling glycan-mediated protein folding control (CALR) (Molinari et al., "Chaperone Selection During Glycoprotein Translocation into the Endoplasmic Reticulum," Science 288:331-333 (2000), which is hereby incorporated by reference in its entirety) and glycan processing (MAN2A1, HEXB, GANAB) (Fukuda et al., "Incomplete Synthesis of N Glycans in Congenital Dyserythropoietic Anemia Type II Caused by a Defect in the Gene Encoding Alpha-Mannosidase II," Proc Natl Acad Sci USA 87:7443-7447 (1990); Yang et al., "An Intrinsic Mechanism of Secreted Protein Aging and Turnover," Proc Natl Acad Sci USA 112:13657-13662 (2015); Martiniuk et al., "Identity of Neutral Alpha-Glucosidase AB and the Glycoprotein Processing Enzyme Glucosidase II. Biochemical and Genetic Studies," The Journal of Biological Chemistry 260:1238-1242 (1985), which are hereby incorporated by reference in their entirety) are also enriched in exomeres, suggesting exomere cargo may mediate the targeting of recipient cells through specific glycan recognition and modulate glycosylation in recipient cells. Among proteins uniquely represented in Exo-S/L were annexins, ESCRT components (charged multivesicular body proteins/CHMPs, vacuolar protein-sorting proteins, HGS, Alix1/PDCD6IP, and Tsg101), Hsp40 (DnaJ) family proteins, signaling transducer G protein subunits, integrins, Rab proteins, and solute carrier family members. Members of key signaling pathways, such as JAK1, TGFBR2, and MET, were also enriched in Exo-S/L. To evaluate the unique markers of Exo-S and Exo-L subpopulations, protein expression was compared between these two sample sets and exomeres separately using t-test. A second set of filters (protein intensity/area>$10^8$ and fold change≥5.0) was applied to the identified signature for exomeres and Exo-L, but not for Exo-S(FIG. 6D). Fewer signature proteins were identified for Exo-S compared to exomeres and Exo-L, most likely due to similarity of Exo-S to the other particles. Representative signature proteins identified by proteomics in each subset were validated by western blot analysis (FIG. 6E).

Figure 6F:
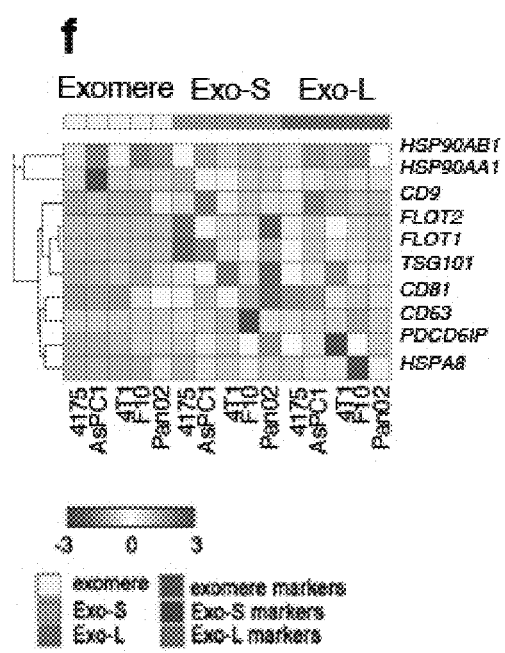

These proteomic datasets were further mined for conventional exosome markers, including flotillins, CD9, CD63, CD81, Alix1, Tsg101, HSC70 (HSPA8) and Hsp90 (FIG. 6F). Among the five cell lines, flotillins (FLOT1 and FLOT2) represented bona fide markers of Exo-S, while HSP90ABI was preferentially associated with exomeres. Although CD9, CD63 and CD81 all demonstrated specific association with Exo-S/L subsets, they all showed a cell type- and particle-dependent preferential expression. Consistent with Kowal et al, "Proteomic Comparison Defines Novel Markers to Characterize Heterogeneous Populations of Extracellular Vesicle Subtypes," Proc Natl Acad Sci USA 113:E968-977 (2016), which is hereby incorporated by reference in its entirety, combining CD63, CD9 or CD81 will be necessary to isolate/label exosomes.

Numerous Rab proteins were found in Exo-S/L subsets, but few of them in exomeres (FIG. 7B), suggesting critical roles of Rab proteins for Exo-S/L formation and trafficking, but not for exomere biogenesis.

Next, the most abundant proteins in each subset of nanoparticles were examined. Hemoglobin, histones, cytoskeleton proteins (actins and tubulins), peptidylprolyl isomerase A (PPIA) and HSP ranked as the most abundant top 50 proteins in all three nanoparticle subpopulations (Table 1). Hsp40/DnaJ family (HSP70 co-chaperones) members were also found in the top 50 proteins for Exo-L. Interestingly, HSP90AB1 was preferentially packaged in exomeres, while HSP70 members (HSPA8, HSPA2 and HSPA5) were more abundant in Exo-S/L. Other proteins relatively enriched in exomeres included inter-alpha-trypsin inhibitor heavy chain family members (ITIH), gelsolin (GSN), talin 1 (TLN1), WD repeat domain 1 (WDR1), and proteins involved in metabolism, such as phosphoglycerate kinase 1 (PGK1), pyruvate kinase muscle (PKM), and enolase 1 (ENO1). Consistent with the analysis above, SDCBP, PDCD6IP/Alix, tetraspanins (CD9, CD63, CD81 and others), G protein family proteins and integrins were highly represented in both Exo-S and Exo-L. Tetraspanins were preferentially enriched in Exo-S while G proteins and integrins were more prominent in Exo-L. Eukaryotic translation elongation factor 1 alpha 1 (EEF1A1) was most often present in exomeres and Exo-L. Other proteins preferentially associated with Exo-S included immunoglobulin superfamily member 8 (IGSF8) and its paralog prostaglandin F2 receptor inhibitor (PTGFRN), milk fat globule-EGF factor 8 protein (MFGE8), and components of the ESCRT-1 complex. Notably, annexins and S100 proteins were only represented in the top 50 proteins of Exo-L.

Furthermore, to exclude the possibility of lipoprotein contamination in exomeres, proteins that are typically associated with purified lipoprotein particles (high-, low-, and very low-density lipoproteins, i.e., HDL, LDL, and VLDL) were examined by proteomic MS analysis and then evaluated their presence in exomeres and Exo-S/L. Much fewer proteins were found in lipoproteins (Table 2) and only some of these proteins were detected in exomeres and Exo-S/L, suggesting most nanoparticle proteins are distinct from lipoproteins. A rough estimation showed that the lipoprotein-associated proteins account for 0-8% of total nanoparticle proteins (FIG. 7C). Moreover, EM analysis revealed that lipoprotein morphology/structure was clearly distinct from exomeres and Exo-S/L (FIG. 7D). Taken together, these analyses ruled out the possibility that exomeres were mere lipoprotein contaminants.

The possible contamination of exomeres with other types of protein complexes with high molecular weights was also ruled out when exomere proteins were surveyed for subunits of known complexes. The co-existence of multiple subunits of protein complexes of similar size to exomeres were not detected (Table 2) except for 10 out of 59 subunits of Parvulin-associated pre-rRNP complex in 4T1 exomeres, 17 subunits of ribosomes in AsPC-1 exomeres, and 7 out of 16 subunits of Kinase maturation complex 1 in MDA-MB-4175 exomeres. However, these proteins account for only 1.8%, 2.1% and 1.8% of total exomere proteins in each case, respectively, suggesting their contribution diminishes the purity of exomeres by ~2%.

Figure 6G:
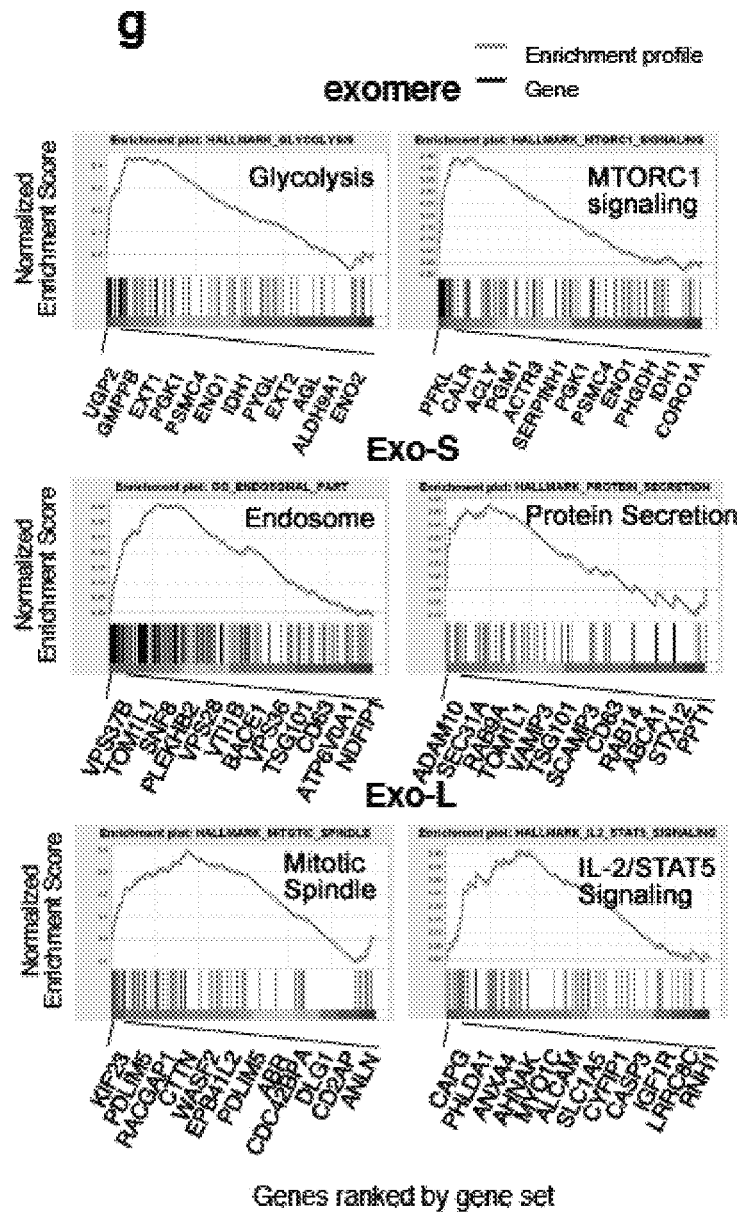
Figure 7E:
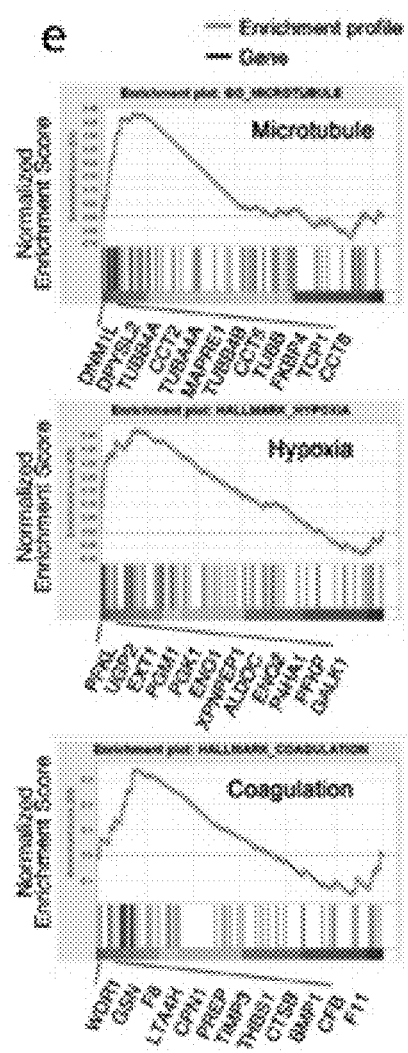
Figure 7E:
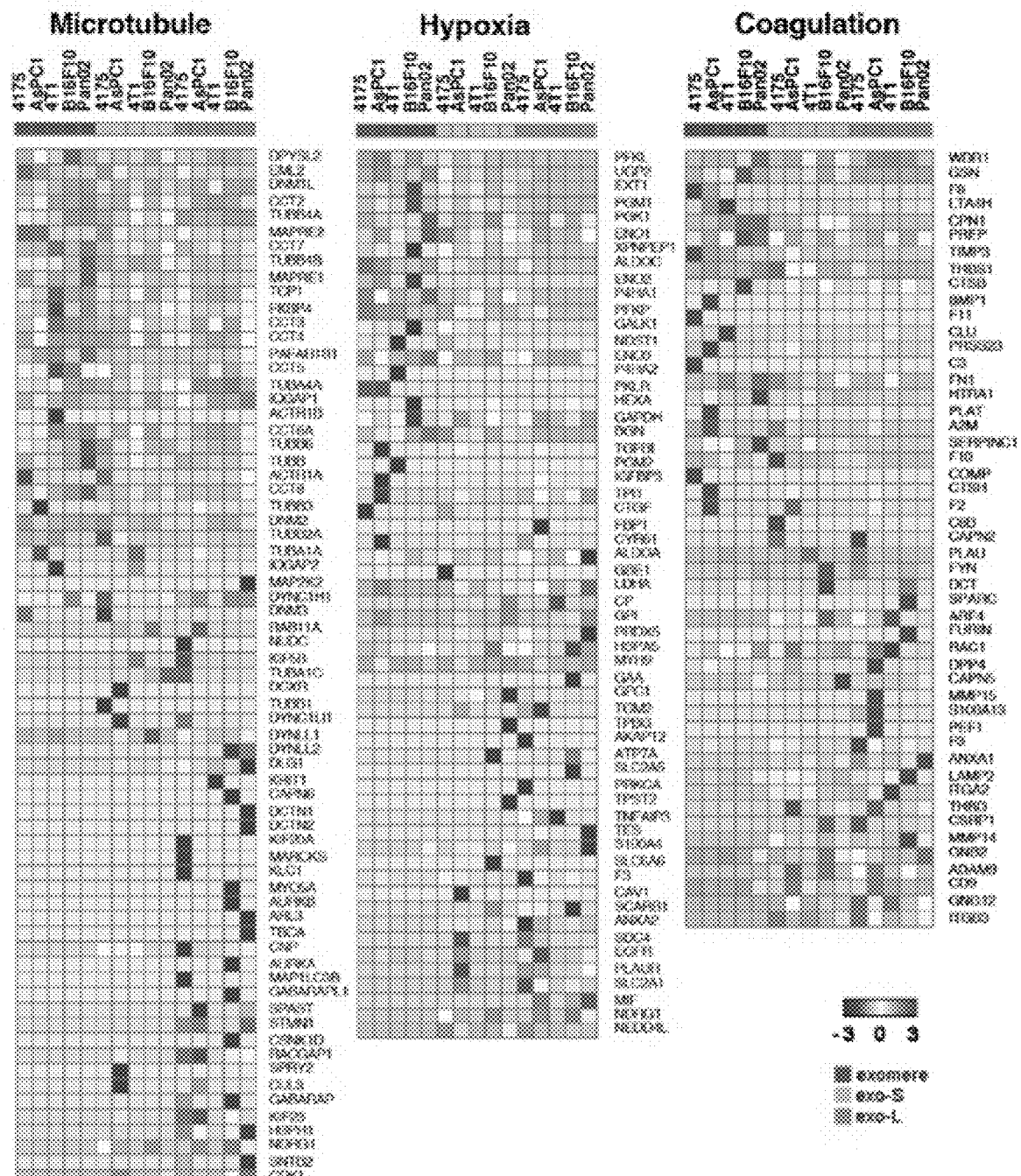

To gain insight into the function of these particle subsets, °SEA was conducted utilizing gene ontology (GO), Kyoto Encyclopedia of Genes and Genomes (KEGG) and hallmark databases (Tables 3-5). Strikingly, GSEA demonstrated that exomere-specific proteins were selectively enriched in metabolic processes, including carbohydrate metabolism, protein synthesis, and small-molecules. At least 36 of the top 50 "GO-biological processes" pathways identified metabolic processes associated with exomeres in contrast to no metabolic processes associated with Exo-S/L (Tables 3-5). Genes encoding proteins involved in hypoxia, microtubule and coagulation were identified in exomeres (FIG. 7E). Exo-S were enriched in membrane vesicle biogenesis and transport, protein secretion and receptor signaling gene sets. For Exo-L, enriched gene sets included mitotic spindle, IL-2/Stat5 signaling, multi-organism organelle organization, and G-protein signaling. Profiles of top rank gene sets enriched in exomeres (glycolysis and mTORC1 signaling), Exo-S (endosome and protein secretion) and Exo-L (mitotic spindle and IL-2/Stat5 signaling) are displayed in FIG. 6G.

Example 4—Distinct N-Glycan Profiles of Exomeres and Exosome Subpopulations

Aberrant glycosylation is involved in pathological processes, including cancer (Pinho et al., "Glycosylation in Cancer: Mechanisms and Clinical Implications," Nature Reviews Cancer 15:540-555 (2015), which is hereby incorporated by reference in its entirety). Here, the aim was to determine the N-glycan profiles of each particle subset in three cell lines by conducting lectin blotting analysis (FIG. 8A) and glycomic mass spectrometry.

E-PHA recognizing bisected N-glycans detected a major band at approximately 75 kDa in both Exo-S and Exo-L of B16-F10 and AsPC-1, with faint detection in exomeres across the three cell lines and Exo-S of MDA-MB-4175. E-PHA detected a high molecular-weight glycoprotein (240 kDa) in MDA-MB-4175 exomeres and a high molecular weight glycoprotein (150 kDa) in AsPC-1 and MDA-MB-4175 exomeres. L-PHA recognizing branched N-glycans detected a predominant band at 75 kDa in both Exo-S and Exo-L of B16F-10 and AsPC-1. Multiple bands ranging from 50 to 70 kDa were also detected in all exomeres (especially MDA-MB-4175). Using AAL, analysis of structures related to fucosylation (fucose linked α-1,6) to GlcNAc or fucose linked (α-1.3) to GlcNAc related structures revealed two abundant glycoproteins between 70 and 100 kDa in both Exo-S and Exo-L of B16-F10 and AsPC-1. Exomeres across all three cell lines and Exo-S of MDA-MB-4175 displayed strong fucosylation on high molecular-weight glycoproteins (200-280 kDa). SNA, recognizing α-2,6 linked sialic acid, detected the presence of high molecular-weight α-2,6-sialylated glycoproteins (200-250 kDa) in all exomeres. Moreover, a low molecular-weight protein (~60 kDa) displaying α-2,6-linked sialic acid modification was uniquely detected in Exo-L (but not Exo-S) from B16-F10. For AsPC-1, exomeres were the major carriers of sialylated glycoproteins, while these sialylated structures were almost absent in Exo-L. Lectin-binding profiles did not overlap with the most abundant proteins in the SDS-PAGE gel, indicating the specificity of lectin recognition independently of protein abundance (FIG. 9A). Therefore, Exo-S and Exo-L versus exomeres display distinct N-glycosylation patterns. Notably, exomere and Exo-St-associated N-glycan profiles vary by cell type. Future studies will address the identity of these glycoproteins via glycoproteomic approaches.

The next aim was to identify profiles of the glycan structures enriched in each particle subset by MALDI-TOF mass spectrometry (MS). Two independent, semi-quantitative MS analyses were conducted on B16-F10-derived exomeres and Exo-S/L (FIG. 8B). FIG. 8C depicts the quantification of the top six most abundant N-glycan structures detected in one of the representative experiments. The ubiquitous expression of certain complex N-glycans was observed in all subsets, corresponding to peaks at mix 2209.8, 2223.7, 2237.7 and 2365.5. Specifically, a complex N-glycan at m/z 2015.7 and a hybrid N-glycan at m/z 2404.8 were enriched in exomeres. Moreover, four of these six N-glycans contained sialic acid, and three of six were fucosylated. Similarly, the ions m/z 2015.7 and 2404.8 were enriched in exomeres from MDA-MB-4175 (FIG. 9B, 9D).

The ion m/z 2404.8 was slightly enriched in AsPC1 exomeres, but the ion at m/z 2015.7 was not detected in AsPC-1 samples (FIG. 9B, 9C). Instead, the ion at m/z 2012.7 was strongly detected in AsPC1 exomeres and Exo-S. Two other ions, at m/z 2117.7 and 2389.9, demonstrating Exo-S enrichment, were detected in AsPC-1 only (FIGS. 9B, 9D).

High-resolution MS analysis allowed further structural characterization of certain N-glycans (FIG. 9E-9J). This was the case of extracted ion chromatogram tut 1111.39 (2-) and 1007.38 (2-) (corresponding to m/z 2223.7 and 2015.7 in FIG. 4c, respectively). In addition, the combination of CID-MS/MS de novo sequencing and PGC-LC relative retention times for extracted ion chromatogram at 1111.39 (2-) revealed that this N-glycan from exomeres contained both α2,3-linked and α2,6-linked sialic acids, whereas the glycan from Exo-S contained exclusively α2,3-linked sialic acids. The unique presence of m/z 1007.38 (2-) in exomeres was also further confirmed.

Taken together, the glycomics study demonstrated the prevalence of complex N-glycans in all particle subsets with relatively high levels of sialylation, consistent with previous findings of complex N-glycans and sialoglycoproteins in tumor microvesicles/exosomes (Escrevente et al., "Sialoglycoproteins and N-glycans from Secreted Exosomes of Ovarian Carcinoma Cells," *PloS One* 8:e78631 (2013); Batista et al., "Identification of a Conserved Glycan Signature for Microvesicles," *Journal of Proteome Research* 10:4624-4633 (2011); Saraswat et al, "N-linked (N-) Glycoproteomics of Urinary Exosomes," *Molecular & Cellular Proteomics* 14:263-276 (2015), which are hereby incorporated by reference in their entirety). Furthermore, the study revealed differences in N-glycan composition and structures among exomeres, Exo-S, and Exo-L.

Example 5—Distinct Lipid Composition Among Exomeres and Exosome Subpopulations

To investigate the lipid composition of each subset of particles, quantitative lipidomics was performed on these nanoparticles derived from B16-F10, MDA-MB-4175 and AsPC-1. By lipid MS, it was found that Exo-S and Exo-L contained more lipids than exomeres for all cell lines (FIG. 10A, >5× fold in all subpopulations, except for Exo-S of MDA-MB-4175 (>3× fold)).

Figure 10B:
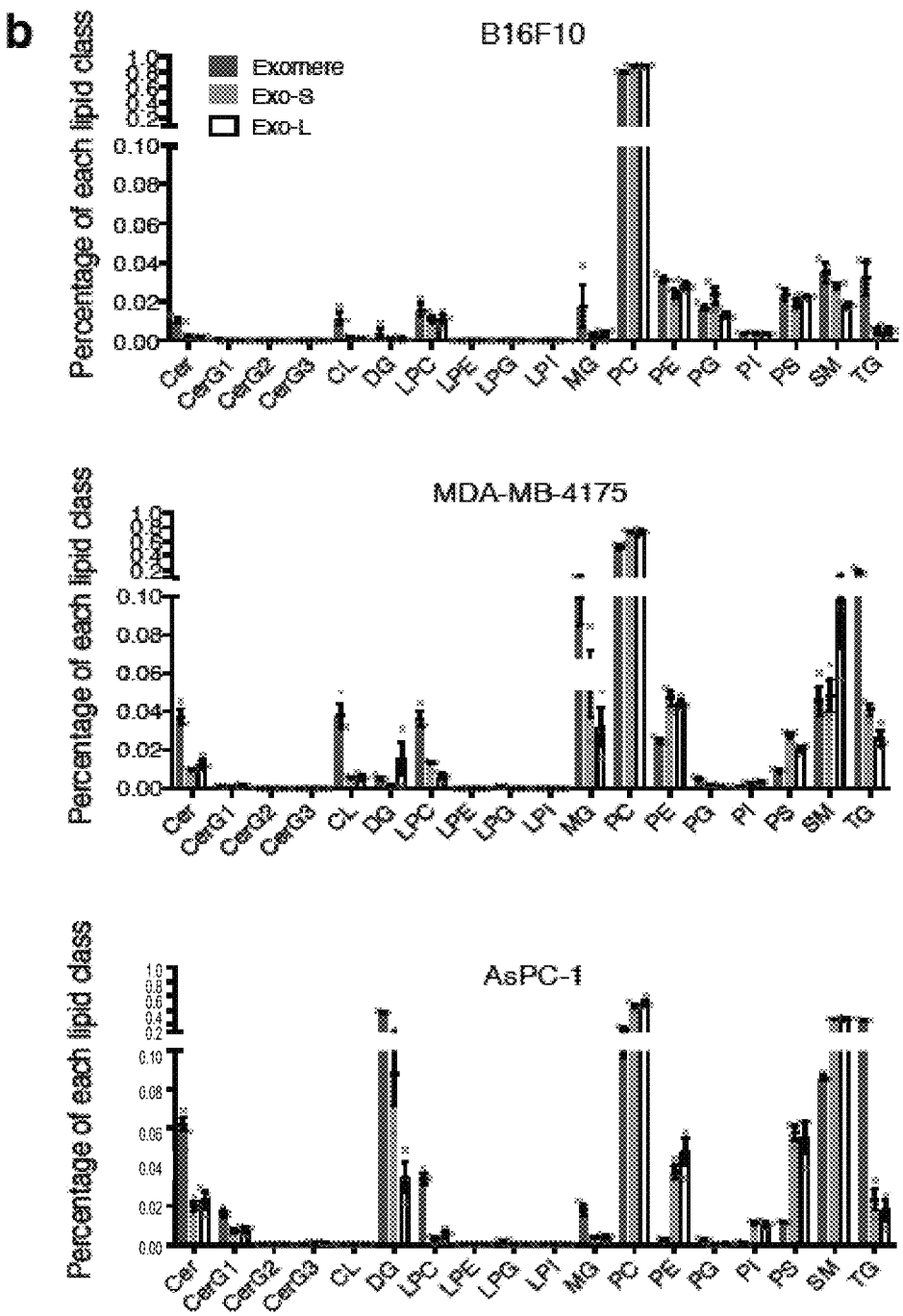
Figure 10C:
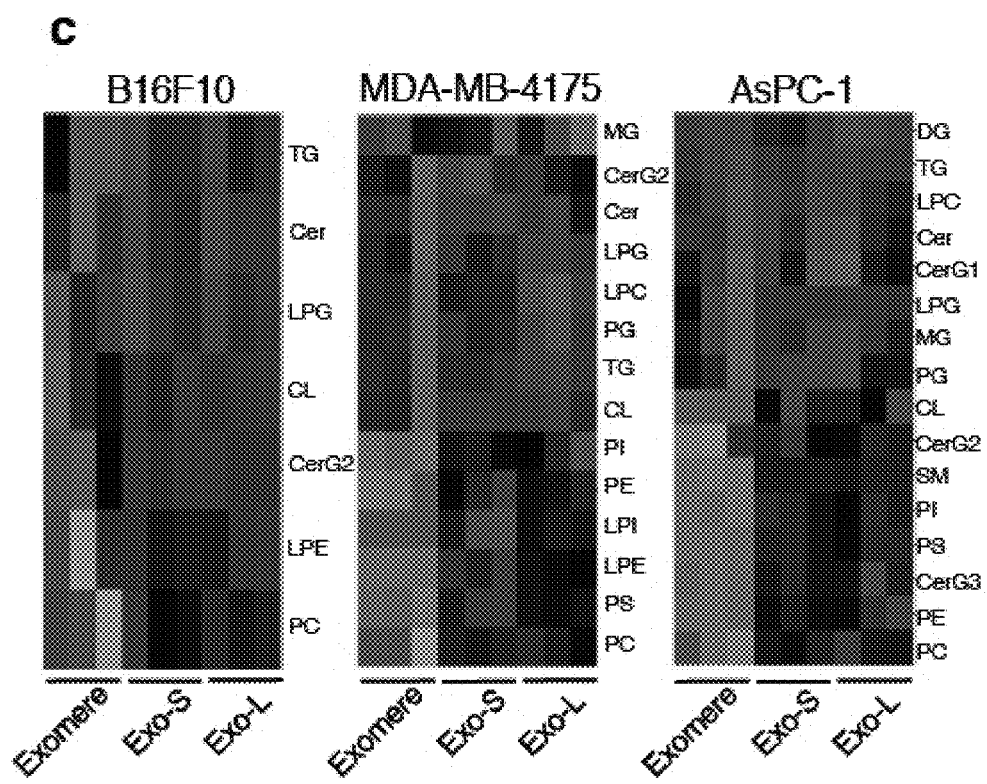

Eighteen lipid classes were commonly identified in all samples (Tables 6-8, FIG. 10B), and their relative frequency in each sample was compared. Phosphatidylcholine (PC) was the predominant lipid component in all subpopulations (46%-89%) except for AsPC-1 exomeres (13%) (FIG. 10B), which contained higher levels of diglyceride (DO, 38%) and triglyceride (TG, 26%) instead. Other phospholipids, including phosphatidylethanolamine (PE) and phosphatidylserine (PS), accounted for 2-6% of total lipids in Exo-S/L across all cell lines (FIG. 10B). However, PE and PS levels were lower in exomeres from MDA-MB-4175 and AsPC-1, but similar to Exo-S/L in B16-F10 (FIGS. 10B, 10C). Phosphatidylinositol (PI) levels were lower than other phospholipids but had a pattern of distribution across nanoparticle subsets similar to that of PE and PS (FIGS. 10B, 10C). Sphingomyelin (SM) accounts for 2-10% of the total lipid in all samples except for AsPC-1 Exo-S/L, which contained a higher level of SM (28%, FIGS. 10B, 10C). Cholesterol data were not collected in this study.

The relative levels of ceramide (Cer), TG and lysophosphatidylglycerol (LPG) varied significantly between exomeres and Exo-S/L across cell lines (ANOVA test, qβ0.05). Additionally, simple glycosphingolipid CerG2 and mitochondrion-specific cardiolipin (CL) were more abundant in exomeres of B16-F10 and MDA-MB-4175 compared to exosome subsets. In contrast, CerG2 and CL were more abundant in Exo-S/L compared to exomeres isolated from AsPC-1 cells. Monoglyceride (MG), phosphatidylglycerol (PG) and lysophosphatidylcholine (LPC) were more abundant in exomeres than in Exo-S/L from MDA-MB-4175 and AsPC-1, but present at equal levels in all three 1316-F10 nanoparticle subsets. Lastly, lysophosphatidylethanolamine (LPE) was detected at higher levels in Exo-S/L from 816-F10 and MDA-MB-4175, but not from AsPC-1. Thus, the study revealed cell type-dependent differences in the total lipid content and composition among distinct nanoparticle subsets.

Collectively, these bioinformatic analyses of the proteomic content of each particle subset revealed the predominant link between exomere-associated proteins and metabolism and the link between Exo-S/L-associated proteins and multiple signaling transduction pathways, including biogenesis-related ESCRT complexes.

Figures 11A, 11B:
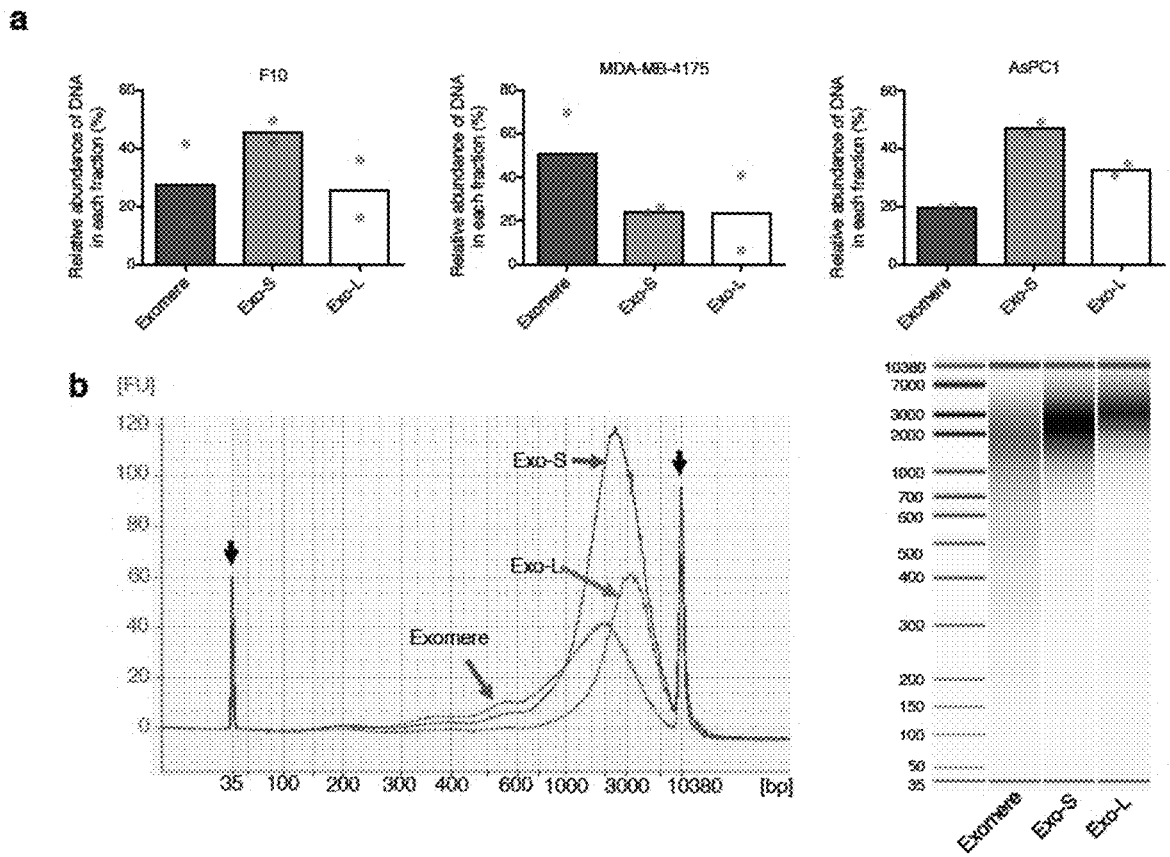
FIGS. 11A-11D show characterization of nucleic acid association with exomere and exosome subsets.
Figure 12:
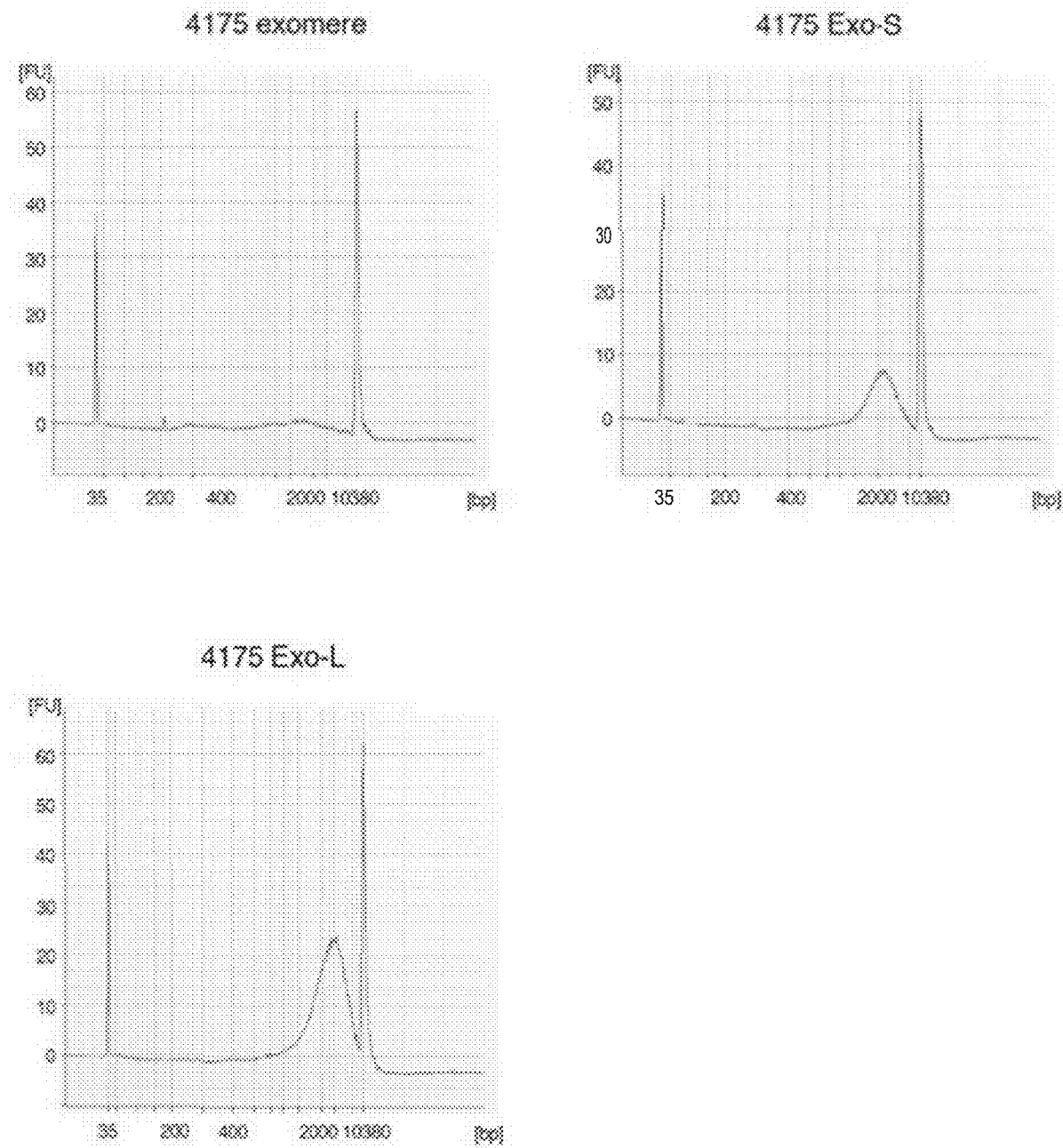
FIG. 12 shows bioanalyzer analysis of the size distribution of DNA associated with exomere, Exo-S and Exo-L derived from B16-F10 (top) and MDA-MB-231-4175 (bottom). This experiment was repeated twice independently with similar results.

Example 6—Distinct Nucleic Acid Content Among Exomeres and Exosome Subpopulations Since dsDNA was previously detected in tumor-derived exosomes (Thakur et al., "Double-Stranded DNA in Exosomes: a Novel Biomarker in Cancer Detection," Cell Research 24:766-769 (2014), which is hereby incorporated by reference in its entirety), the relative abundance of DNA in exomeres and Exo-S/L was determined. DNA was detected in all three types of nanoparticles; however, relative abundance varied by cell-type (FIG. 11A). The relative amount of DNA was highest in exomeres derived from MDA-MB-4175 and in Exo-S from B16-F10 cells and AsPC-1. Bioanalyzer (Agilent) analysis revealed distinct size distribution of DNA associated with each subset of nanoparticles (FIG. 11B and FIG. 12). Exomere DNA was relatively evenly distributed in a broad range of sizes between 100 bp and 10 kb with a slight enrichment around 2 kb in several cases. In contrast, a strong enrichment between 2 kb to 4 kb was detected for Exo-S/L DNA, and the peak size of Exo-L DNA was slightly larger than that of Exo-S DNA. This phenomenon may be due to the structural capacity and different biogenesis mechanisms of each particle subset.

Figures 11C, 11D:
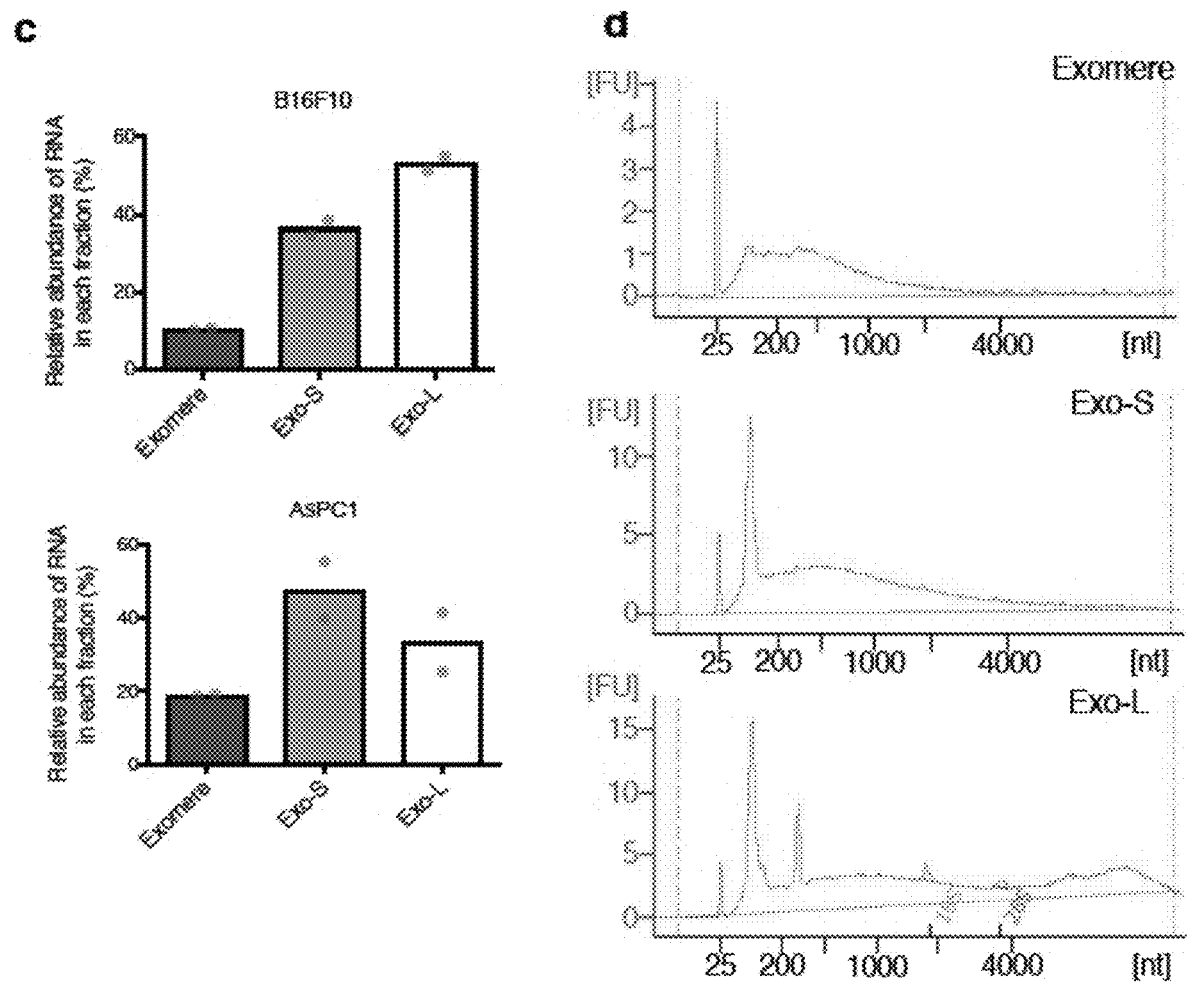

RNA was preferentially associated with Exo-S/L in both B16-F10 and AsPC-1 (FIG. 11C). RNA associated with exomeres and Faro-S showed a monomodal distribution (peak at 400 nt and 500 nt, respectively), whereas Exo-L RNA displayed a bimodal distribution (FIG. 11D) (additional peak>4000 nt). Specifically, 18S and 28S rRNAs were detected at very low levels in Exo-L, barely detected in Exo-S and absent in exomeres compared to cellular RNA. A strong small RNA peak (corresponding to tRNAs, microRNAs and other small RNAs) was detected in Exo-S and Exo-L, but not in exomeres. Remarkably, a unique RNA peak of unknown identity, of ~315 nt in size, was detected only in Exo-L.

Example 7—Distinct Organ Biodistribution of Exomeres and Exosome Subpopulations

Figure 13A:
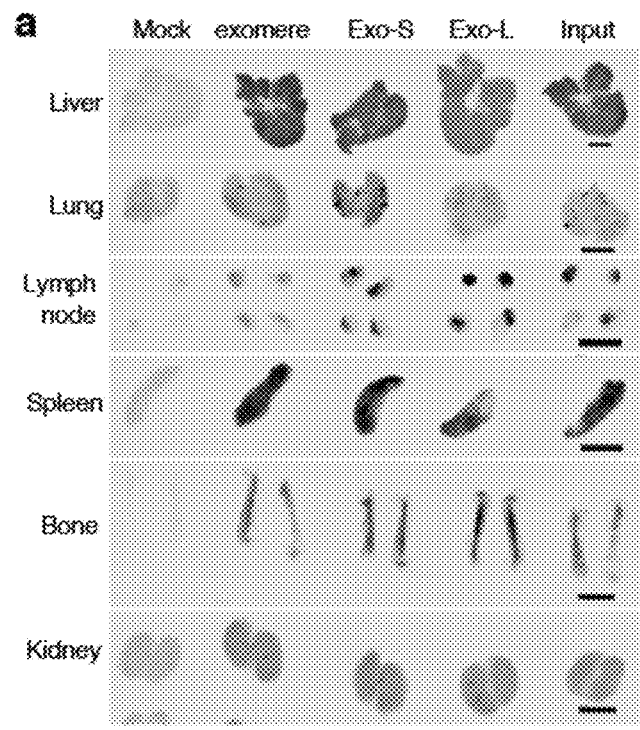
FIGS. 13A-13B show organ biodistribution of B16F10-derived exomeres and exosome subpopulations in syngeneic naïve mice.
Figure 13B:
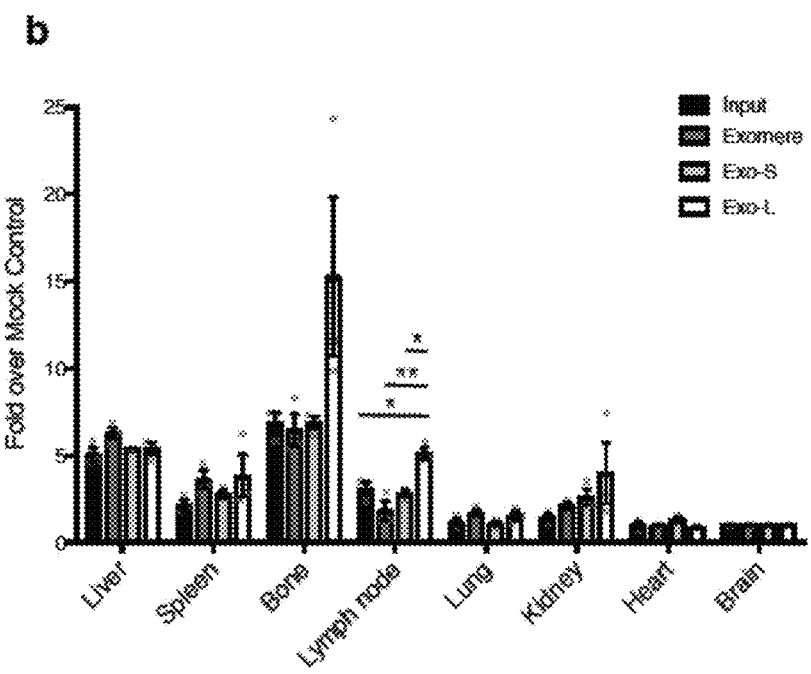
Figure 14:
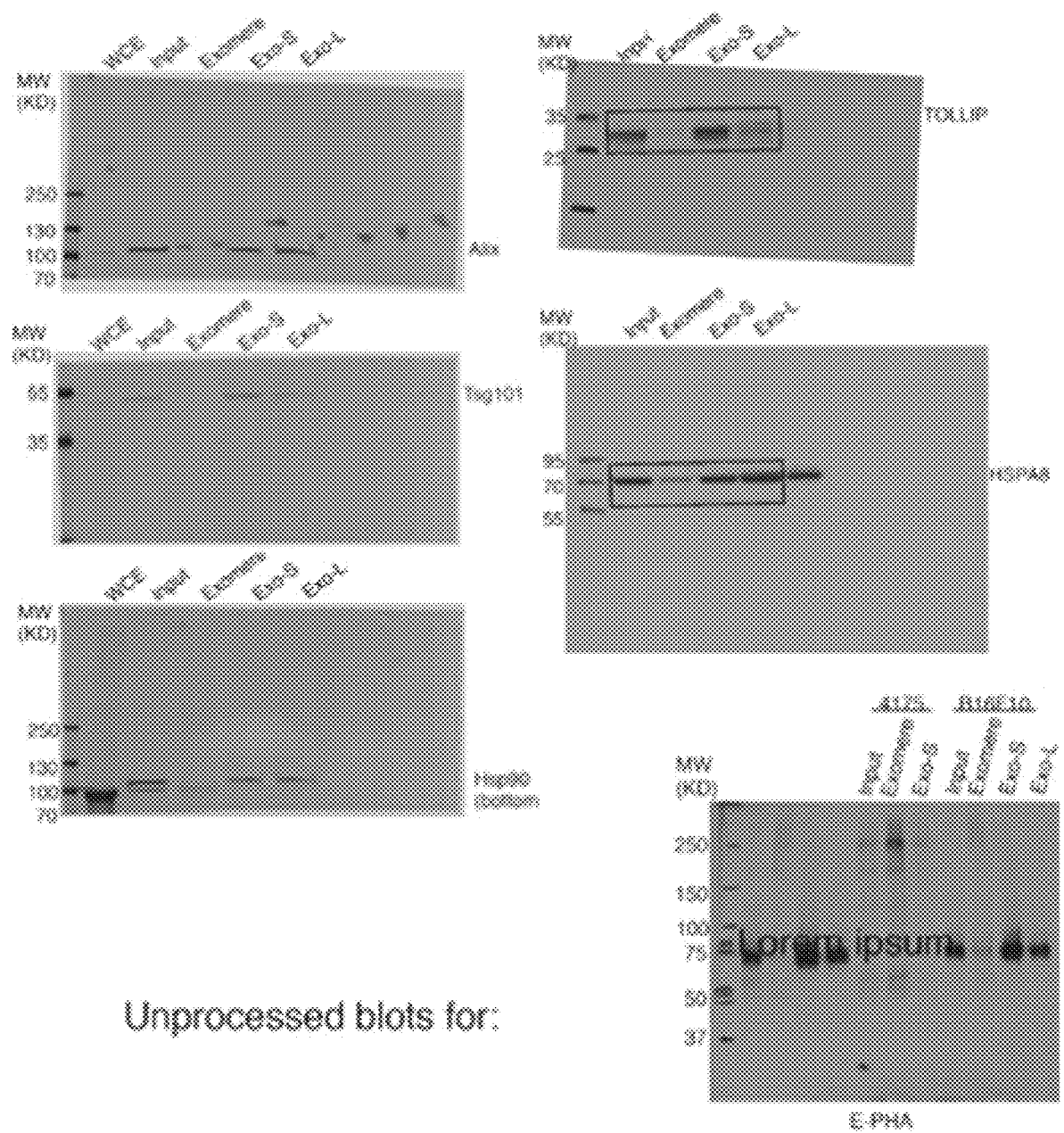
FIG. 14 shows unprocessed blots for related figures in FIG. 1, FIG. 6 and FIG. 8.
Figure 14:
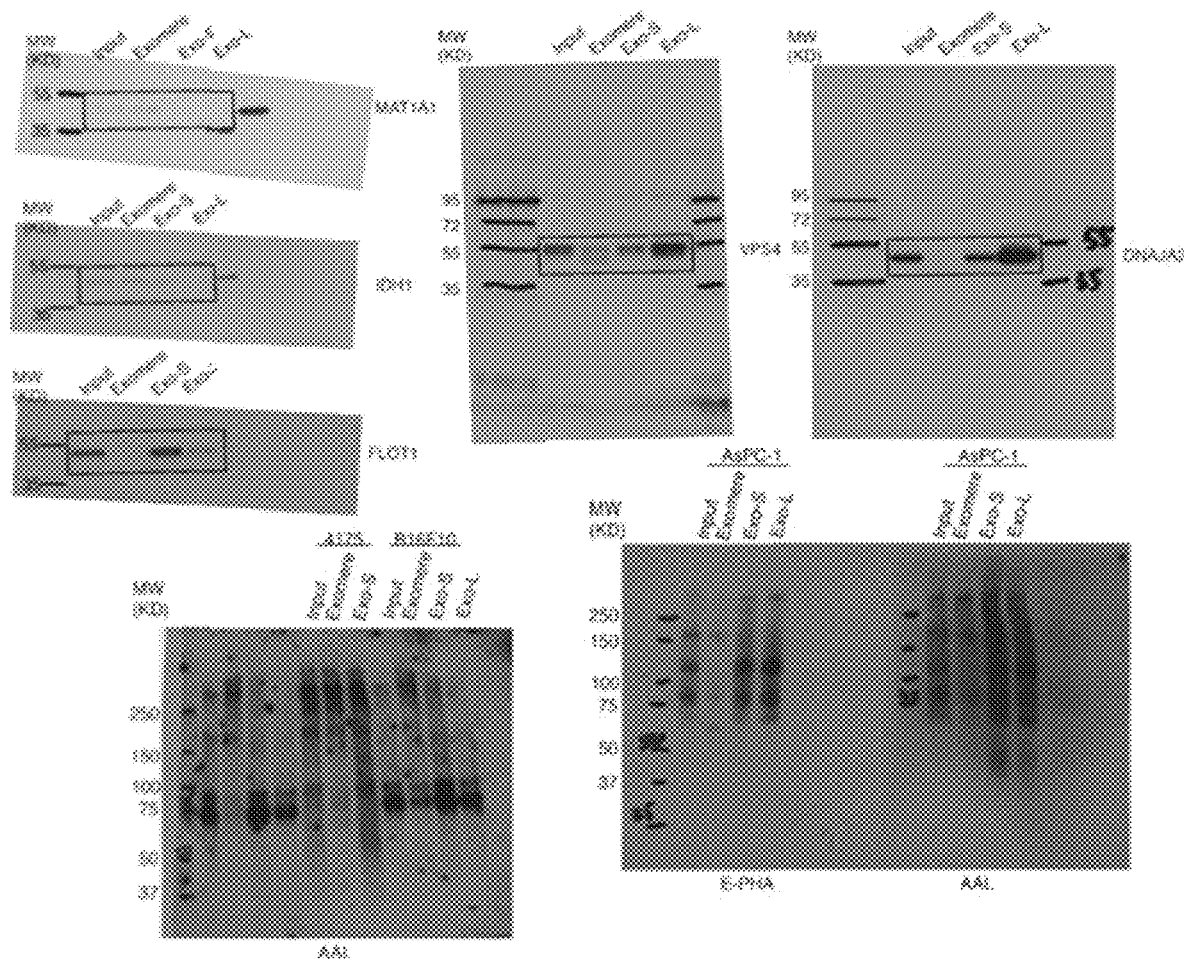
Figure 14:
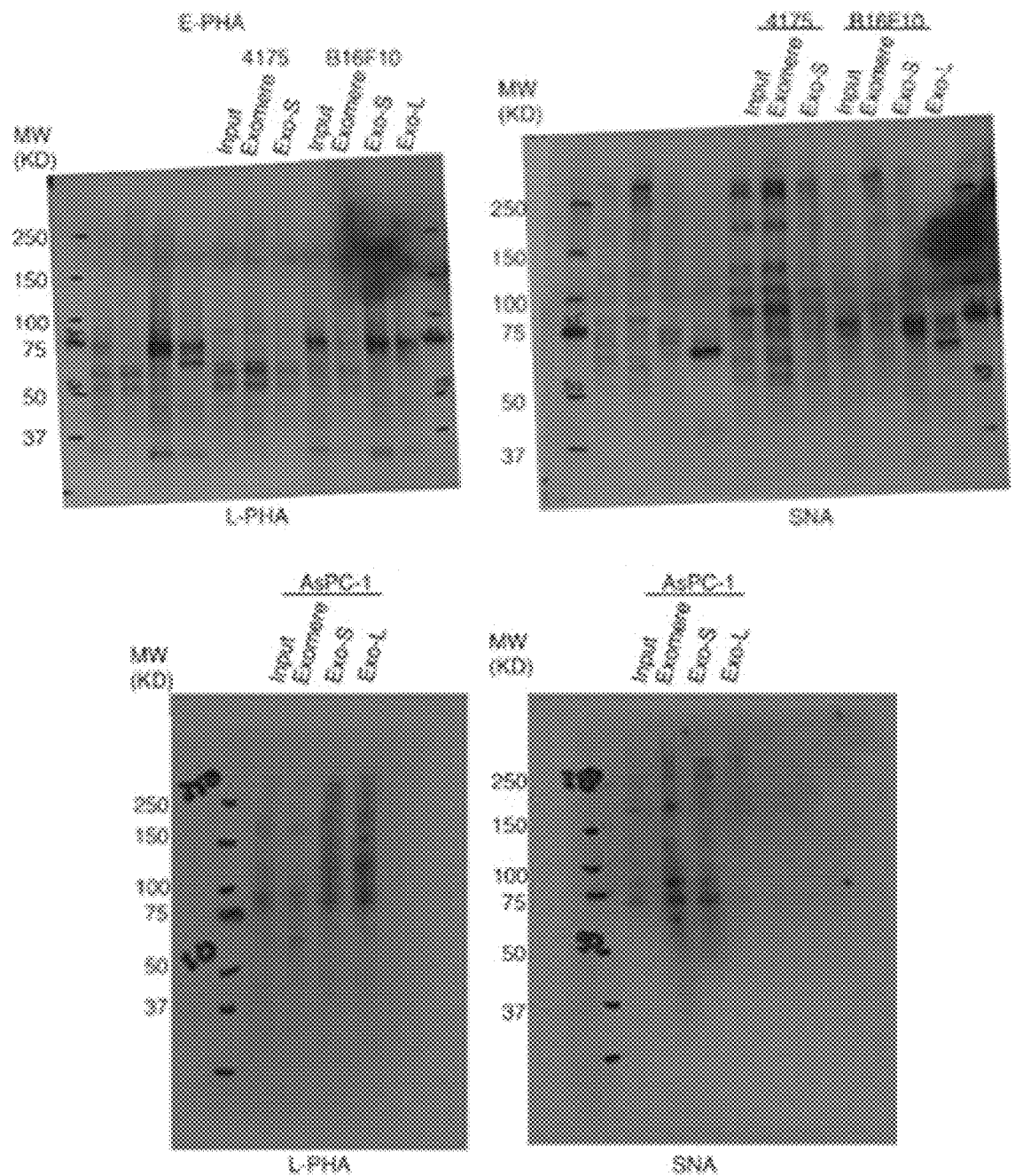

Next, the organ biodistribution of B16-F10-derived nanoparticle subsets in naïve mice was investigated. Twenty-four hours post intravenous injection of near infrared dye (NIR)-labeled exomeres, Exo-S and Exo-L into mice, organs were collected and analyzed using the Odyssey imaging system (LI-COR Biosciences; FIG. 13). Interestingly, all nanoparticles were uptaken by hematopoietic organs, such as the liver (~84% of total signals), spleen (~14%) and bone marrow (~1.6%). The lungs (~0.23%), lymph nodes (~0.07%), and kidneys (~0.08%) showed less uptake of all nanoparticle subtypes. Particle uptake was not detected in the brain. Subsequently, the dynamic range of signal intensity in each organ was adjusted to compare the uptake of each subset of nanoparticles in the same organ (FIG. 13A). Punctuated distribution patterns of nanoparticles were detected specifically in the lung and lymph nodes. This is in contrast to the homogenous distribution pattern found for all nanoparticle subsets in the liver, spleen, and bone marrow. Importantly, although exomeres and Exo-S/L were predominantly uptaken in the liver, Exo-L displayed lymph node tropism. In addition, though not statistically significant, a trend of higher uptake of exomeres in the liver was observed. Quantification is shown in FIG. 13B. Distinct organ distributions indicate that nanoparticle subsets may be involved in different aspects of tumor progression and metastasis.

Discussion of Examples 1-7

Dissecting the heterogeneity of EV populations by differential ultracentrifugation, immuno-affinity capture, ultra-filtration and size-exclusion chromatography, polymer-based precipitation, and microfluidics (Thery et al, "Isolation and Characterization of Exosomes from Cell Culture Supernatants and Biological Fluids;" *Current Protocols in Cell Biology Chapter* 3, Unit 3 22 (2006); Merchant et al., "Microfiltration Isolation of Human Urinary Exosomes for Characterization by MS," *Proteomics Clinical Applications* 4:84-96 (2010); Lasser et al., "Isolation and Characterization of RNA-Containing Exosomes," *Journal of Visualized Experiments* 59:e3037 (2012); Chen et al., "Microfluidic Isolation and Transcriptome Analysis of Serum Microvesicles," *Lab on a Chip* 10:505-511 (2010); Jorgensen et al, "Extracellular Vesicle (EV) Array: Microarray Capturing of Exosomes and Other Extracellular Vesicles for Multiplexed Phenotyping," *Journal of Extracellular Vesicles* 2 (2013); Tauro et al., "Comparison of Ultracentrifugation, Density Gradient Separation, and Immunoaffinity Capture Methods for Isolating Human Colon Cancer Cell Line LIM1863-Derived Exosomes," *Methods* 56:293-304 (2012), which are hereby incorporated by reference in their entirety) in an attempt to separate nanoparticle populations has proven daunting. By employing state-of-the-art AF4 technology, two discernible exosome subpopulations, Exo-S and Exo-L, were separated and a distinct nanoparticle, named exomere, which differs in size and content from other reported particles, was identified. Unlike labor-intensive and time-consuming gradient methods, AF4 is highly reproducible, fast, simple, label-free and gentle. Moreover, the exosome subpopulations and exomeres were able to be efficiently resolved in a single AF4 run with real-time measurements of various physical parameters of individual particles.

The analyses revealed that exomeres were selectively enriched in proteins involved in metabolism, especially "glycolysis" and "mTORC1" metabolic pathways, suggesting their potential roles in influencing the metabolic program in target organ cells, as well as in proteins associated with coagulation (e.g., Factors VIII and X) and hypoxia. The proteomic analysis also showed that exomeres were enriched in key proteins controlling glycan-mediated protein folding control (CALR) (Molinari et al., "Chaperone Selection During Glycoprotein Translocation into the Endoplasmic Reticulum," *Science* 288:331-333 (2000), which is hereby incorporated by reference in its entirety) and glycan processing (MAN2A1, HEXB, GANAB) (Fukuda et al., "Incomplete Synthesis of N-Glycans in Congenital Dyserythropoietic Anemia Type II Caused by a Defect in the Gene Encoding Alpha-Mannosidase II," *Proc Natl Acad Sci USA* 87:7443-7447 (1990); Yang et al, "An Intrinsic Mechanism of Secreted Protein Aging and Turnover," *Proc Natl Acad Sci USA* 112:13657-13662 (2015); Martiniuk et al, "Identity of Neutral Alpha-Glucosidase AB and the Glycoprotein Processing Enzyme Glucosidase II. Biochemical and Genetic Studies," *The Journal of Biological Chemistry* 260:1238-1242 (1985), which are hereby incorporated by reference in their entirety), suggesting exomere cargo may modulate glycosylation in distant recipient cells. Subcellular localization analysis of exomere-enriched proteins revealed their specific association with ER, mitochondria and microtubules, demonstrating the potential roles of these proteins in exomere biogenesis and secretion.

Proteins unique to exosomes (Exo-L and Exo-S) versus exomeres were also identified. Multiple components of ESCRT complexes were specifically associated with Exo-S and Exo-L, but not observed within exomeres, suggesting a major role for ESCRT complexes in Exo-S/L but not exomere production. Other exosome-enriched proteins included Rab proteins, annexins, Hsp40 members, and proteins involved in multiple signaling transduction pathways, such as integrins, 0-proteins, JAK1 and TGFBRs.

Further differences were found between Exo-S and Exo-L protein cargo. Flotillin 1, flotillin 2, tweety family member 3, tetraspanin 14, and ESCRT-1 subunit VPS37B were specifically enriched in Exo-S. In contrast, levels of such proteins as annexin A1/A4/A5, charged multivesicular body protein 1A/2A/4B/5, vacuolar protein sorting 4 homolog B, DnaJ heat shock protein family (Hsp40) member A1, and myosin 1C were relatively higher in Exo-L. Interestingly, tissue factor, a well-studied exosome protein (Gardiner et al., "Extracellular Vesicles, Tissue Factor, Cancer and Thrombosis—Discussion Themes of the ISEV 2014 Educational Day," *Journal of Extracellular Vesicles* 4:26901 (2015), which is hereby incorporated by reference in its entirety), was enriched in Exo-L. It is thus plausible that exomeres and Exo-L cooperate to optimize the coagulation cascade in vivo.

Exo-S were predominantly enriched in proteins associated with endosomes, multivesicular bodies, vacuoles, and phagocytic vesicles, while Exo-L were specifically enriched in plasma membrane, cell-cell contact/junction, late-endosome, and trans Golgi network proteins. These data indicate that Exo-S are most likely bona fide/canonical exosomes (i.e., derived from intraluminal vesicles of endosomal compartments), whereas Exo-L may represent non-canonical exosomes or probably sEVs of different sub-cellular origin (i.e., plasma membrane budding).

Identifying specific exosome and exomere markers to better isolate and characterize these nanoparticles is critical to advancing knowledge of EV biology. Since Flotillin 1 and 2 were specifically associated with Exo-S, these proteins may represent reliable markers of conventionally defined exosomes. Other previously reported exosome markers, including CD9, CD63, CD81, Tsg101 and Alix1, were present in Exo-S and/or Exo-L in a cell type-dependent manner, and therefore would have to be combined with size exclusion to distinguish exosome subpopulations. Notably, Hsp90-13, highly represented in exomeres, could be a potential exomere marker, whereas several Hsp70 family members, such as HSC70/HSPA8 could serve as possible markers for Exo-S/L subpopulations.

The glycomic, lipidomic, and genomic studies also revealed additional distinct molecular signatures in exomeres and exosomes. Similar to the expression in metastatic tumor cells, exosome subsets were enriched with sialylated glycoproteins, supporting the role of these structures in exosome-mediated cellular recognition. One predominant sialoglycoprotein previously identified in exosomes (Escrevente et al., "Sialoglycoproteins and N-glycans from Secreted Exosomes of Ovarian Carcinoma Cells," *PloS One* 8:e78631(2013); Liang et al., "Complex N-linked Glycans Serve as a Determinant for Exosome/Microvesicle Cargo Recruitment," *The Journal of Biological Chemistry* 289:32526-32537 (2014), which are hereby incorporated by reference in their entirety), the galectin-3-binding protein (LGALS3BP), a modulator of cell communication and immune responses (White et al., "Galectin-3 Binding Protein Secreted by Breast Cancer Cells Inhibits Monocyte-Derived Fibrocyte Differentiation" *Journal of Immunology* 195:1858-1867 (2015): Laubli et al., "Lectin Galactoside-Binding Soluble 3 Binding Protein (LGALS3BP) is a Tumor-Associated Immunomodulatory Ligand for CD33-Related Siglecs," *The Journal of Biological Chemistry* 289: 33481-33491 (2014), which are hereby incorporated by reference in their entirety), was highly enriched in exomeres. This ligand could mediate the specific interaction of exomeres with target cells through proteins, such as collagens, fibronectin, nidogen, galectin-3 and integrin beta-I (Hellstem et al., "Functional Studies on Recombinant Domains of Mac-2-Binding Protein," *The Journal of Biological Chemistry* 277:15690-15696 (2002); Sasaki et al., "Mac-2 Binding Protein is a Cell-Adhesive Protein of the Extracellular Matrix which Self-Assembles into Ring-Like Structures and Binds Beta1 Integrins, Collagens and Fibronectin," *The EMBO Journal* 17:1606-1613 (1998), which are hereby incorporated by reference in their entirety).

Interestingly, the lipidomics analyses revealed that exomeres contained fewer lipids compared to Exo-S and Exo-L. Phospholipids and SM, the major structural components of plasma lipid bilayer membrane (Van Meer et al., "Membrane Lipids: Where They are and How They Behave," *Nat Rev Mol Cell Biol* 9:112-124 (2008), which is hereby incorporated by reference in its entirety) ranked top in all nanoparticles examined. Such an observation is expected for Exo-S/L subsets due to their vesicular membrane structure, however, exomeres seem to lack external membrane structures. Yet, differences in several lipid classes distinguished exomeres from Exo-S and Exo-L. For instance, exomeres were found to contain higher levels of triglycerides and ceramides compared to exosome subpopulations and thus may serve to transport these metabolites to recipient cells. The study further revealed that DNA packaging in exomeres and exosomes varied by tumor-type, while RNA was packaged in Exo-S and Exo-L independent of tumor classification.

Collectively, the findings demonstrate that proteins, glycans, lipids, and nucleic acids are selectively packaged in exomeres, Exo-S, and Exo-L, further supporting the idea that these are distinct nanoparticle subsets.

The observation that nanoparticle subtypes have different organ biodistribution patterns suggests they mediate the pleiotropic effects of cancer. The punctate pattern of Exo-L uptake and its apparent tropism for lymph nodes implicate this nanoparticle in facilitating metastasis of disseminated tumor cells. Exomeres, along with exosomes, were uptaken by hematopoietic organs, including the liver, spleen, and bone marrow. Interestingly, the predominant exomere uptake by the liver and the exomere enrichment in protein cargo involved in metabolism lead us to speculate that exomeres may specifically target the liver for metabolic reprogramming during tumor progression. The data indicate that the size of nanoparticles, in addition to their specific cargo, may influence metastatic patterning and systemic effects of cancer.

The identification of exomeres highlights the diversity of EVs and particles secreted by cells. Elucidating their biogenesis will be essential to unravel their roles in cellular and organ function. Target cells and the functional outcomes exerted by each nanoparticle subset in organs need to be further delineated to advance the understanding of the collective, systemic effects of nanoparticles in the metastasis process. Undoubtedly, these discoveries will open avenues for translational studies of EVs and particles in diagnostic, prognostic, and therapeutic applications.

Materials and Methods for Examples 8-12

Preparation of small extracellular vesicles (sEVs) from cell culture. With the aim to separate distinct cellular nanoparticles, such as exomeres and exosome subsets, sEVs isolated using dUC as the input samples for AF4 were studied. Alternative methods, such as DGF, UF and SEC, can also be used for sEV input sampling. EVs captured by IAC can be applied, as well, if the antibody can be removed from the EVs.

This protocol has been developed and optimized using sEVs derived from cell culture model systems. Conditioned media was sequentially spun to remove cells, cell debris, and large EVs and finally pellet down the sEVs. It has been reported herein that fresh versus frozen sEV samples do not markedly differ in AF4 profiles, indicating that the structural integrity of EVs is well preserved during the freeze-thaw process. Of note, the culture conditions, such as growing cells in hypoxic conditions, and the passage of cells can influence EV production and composition (i.e. the percent of each particle type in a sample). Thus, these changes in ENP composition may require modifications of the AF4 methods for further optimization to achieve desired separation quality.

As described infra, this protocol could also be applied to sEVs prepared from other resources, such as bodily fluids, including plasma. AF4 parameters, such as the cross-flow gradient, can be further adjusted to meet the specific requirements of particular samples (for example, existence of additional types of ENPs). However, for certain sample types, the EV composition is more complicated than that derived from conditioned media of cell cultures. For example, the presence of lipoprotein particles in blood plasma may interfere with the separation of exosomes due to their partial overlap in size. In this case, other means of prior removal of lipoproteins from the plasma sample is desired before loading them onto the AF4 channel.

AF4 fractionation of sEVs and online data collection and analysis. The AF4 operative method for separation of exomeres and exosome subsets (i.e., Exo-S and Exo-L) from cell culture-derived sEVs is illustrated in FIG. 21. Based on the complexity of the EV samples and the goal of each specific study, this running method can be further adjusted, as described infra.

For real-time monitoring and analysis oldie fractionation of particles, several online detectors are usually installed immediately downstream of the AF4 channel. The laboratory has the DAWN HELEOS-11 (MALS detector) with QELS (DLS detector) installed at the detector 12 (100°) position (Wyatt Technology) and the Agilent 1260 Infinity Multiple Wavelength Detector (set at 280 nm for UV absorbance detection) in place. The DLS measurement is mainly used to determine the hydrodynamic size of the fractionated particles in real time. The primary data from a DLS measurement is the autocorrelation function, which plots the average overall changes in the scattered light intensity of molecules with time (see example in FIG. 22). The exponential decay rate of the autocorrelation function determines the translational diffusion coefficient ($D_t$) of molecules in solution based on the following equation:

| Auto correlation function | $G(\tau) = 1 + \beta\exp(-2D_t q^2 \tau)$ |
|---|---|
| $\tau$—delay time, $\beta$—intercept of the correlation function; $q$—scattering factor | $q = (4\pi n_0/\lambda_0)/\sin(\theta/2)$, $n_0$ is the refractive index of the solution; $\lambda_0$ is the laser wavelength; $G$ is the scattering angle |
| Based on the Stokes-Einstein relation, | |
| $R_h = kT/6\pi\eta D_t$ | k—Boltzmann's constant, T—temperature, $\eta$—viscosity of solvent | an effective hydrodynamic radius ($R_h$) can be further deduced from $D_t$. The assumption for this calculation is that the solute (EV, in the present case) is a sphere undergoing Brownian motion. $R_h$ is the radius of a sphere with the same translational diffusion coefficient as the analyzed solute. $R_h$ depends only on the physical size of the solute and its size-related behavior, such as diffusion and viscosity, but is not affected by its density or molecular weight. The measurement range of 0.5 nm to 1000 nm radius makes DLS an effective tool to measure the size of sEVs.

Combining AF4 with online DLS measurements is critical for accurate size determination. In a polydisperse sample, DLS measurement yields an average $R_h$ and the specific information on each compositional species in a given sample is missing. However, fractionation results in the separation of solutes with different sizes and each fraction contains only a very small admixture of different $R_h$ particles. Thus, fractionation allows the size of each species to be more accurately measured. For such monodisperse samples, the resulting autocorrelation functions are single exponentials, which are simple to interpret. Fitting the data to a single exponential function is performed in the Astra software using the Cumulants model (Wyatt Technology Corporation. DYNAMICS User's Guide. Version 7.0 (M1400 Rev.) Appendix A-2 (2010), which is hereby incorporated by reference in its entirety). By examining the ideal fitting to a single exponential, one can further evaluate the separation quality.

One requirement for accurate DLS measurement of $R_h$ is that the sample concentration must be sufficient so that the sample scatters at least three times more light than the solvent to obtain an acceptable signal/noise ratio. In particular, small molecules, such as exomeres, scatter less light and require even higher concentrations of analyte to optimize results.

Besides DLS, static light scattering (SLS) detected by MALS measures the radius of gyration ($R_g$). $R_g$ is defined as the mass averaged distance of each point in a molecule from its gravity center and is generally different from $R_h$. Comparing $R_g$ to $R_h$ can further reveal the compactness of a solute (i.e., empty versus filled particles). In general, the MALS detector is more sensitive than DLS monitoring and thus it will be of specific use when only little amount of material available for analysis.

The UV detector is used as part of the instrumentation for online concentration measurements. The intensity of UV absorbance can provide us an approximation of the relative abundance of different species in the sample, despite not having defined extinction coefficients for different species in the EV sample mixture. The peaks of UV absorbance are useful in guiding the choice of combining fractions of similar particles. However, the bicinchoninic acid assay (BCA assay) and NTA is often conducted after fraction collection for quantification purposes. Once pure EVs are obtained and further characterization can be performed, the extinction coefficients of each species for improved interpretation of the UV absorbance data to concentration can then be determined.

One key consideration for online detectors is that it must have exceptional sensitivity due to the limited amount of material passing through the detector at each single time point. Besides the detectors mentioned above, other sensors, such as differential refractive index (dRI) and fluorescence detectors (FLDs), are often included as standard parts of the instrumentation for a variety of macromolecular characterization techniques. dRI, considered a universal concentration detector, is accurate and versatile in all types of solvents and independent of chromophores or fluorophores. FLDs are useful if autofluorescent molecules or artificial fluorescent labeling are present in specific subsets of EVs. It should be noted that, with additional detectors assembled online, the fractionated particles take a longer path and more time to reach the fraction collector. As a result, diffusion of molecules will lead to broadening of peaks, dilution of fractionated samples and reduction in separation resolution. Therefore, only detectors considered essential for the real-time monitoring should be installed.

Fraction collection, concentrations and characterization. AF4 fractions can be collected automatically or manually for downstream offline characterization. The Agilent Fraction Collector (1260 series) has been installed to automatically collect fractions into 96-well plates, but similar fraction collectors can be utilized for accurate and reproducible fraction collections. Fractions can be collected either by volume or over time, and fractions of particles with the same identity based on online and offline characterization can be further pooled together for downstream analysis. For example, as described supra, to identify exomeres and distinct subsets of exosomes, representative fractions were first examined across the whole time course of fractionation by online DLS and offline transmission electron microscopy analysis and then the fractions of particles with similar size and morphology were pooled together for further characterization. This step was also guided by the peaks of UV absorbance (indicating the most abundant fraction of each type of particles). To validate that the pooled fractions are relatively pure and not contaminated significantly by other types of adjacent particles, only fractions centered around the peaks were pooled together. Depending on the resolution of the fractionation, this fraction combination step can be empirically determined. Due to the different composition of EV subpopulations in a given sample, occasionally the UV peaks are not identifiable and thus the fraction combination will rely more on other properties, such as size and morphology.

The individual or combined fractions can be directly utilized for downstream analysis or subjected to a concentration step before further characterization. The collected fractions are usually concentrated using the Amicon Ultra-series of centrifugal filter units with Ultracel-30 (30 KM cutoff) membrane (Millipore). Other alternative means of concentration, such as tangential filtration centrifugation, direct UF, UC, or IAC, can be applied depending on the need for the downstream analysis. A variety of analyses can be performed on fractionated EVs, including but not limited to: BCA assay, NTA, atomic force microscopy, electron microscopy, mass spectrometry of molecular contents (e.g., proteins, lipids, glycan, and metabolites), western blotting or the enzyme-linked immunosorbent assay, sequencing of genetic material (DNA and RNAs), DLS measurement in batch mode, and zeta potential measurement. The functional roles of the fractionated EV subpopulations can be further investigated in vitro or in vivo.

Reagents.
- B16-F10 cell line (ATCC). Cell lines should be regularly checked to ensure that they are authentic and free of mycoplasma contamination.
- DMEM (VWR, Catalog No. 45000-304)
- Premium Grade Fetal Bovine Serum (FBS) (VWR, Catalog No. 97068-085)
- L-Glutamine, 100×(Corning, Catalog No. 25-005-Cl)
- Penicillin-Streptomycin Solution, 50× (Coming, Catalog No. 30-001-Cl)
- Sterile PBS (VWR, Catalog No. 45000-446)
- TrypLE (Thermo Fisher Scientific, Catalog No. 12604-039P)
- Pierce BCA Protein Assay Kit (Thermo Fisher Scientific, Catalog No, 23225)
- ATCC Universal Mycoplasma Detection kit (ATCC, Catalog No. 30-1012K)
- Bovine serum albumin (BSA) (Sigma, Catalog No. A 1900)
- Water filtered using the Milli Q system
- Ethanol (Sigma, Catalog No. 459828)
- Contrad 70 (Decon Labs, Inc Catalog No. 1003)
- Sodium Dodecyl Sulfate (SDS) (Omnipur, Catalog No. 7910)
- Nitric Acid (Fisher Scientific, Catalog No. 7697-37-2)

Consumable Equipment.
- 150×25 mm tissue culture dish with Grid (VWR, Catalog No. 25383-103)
- 5/10/25 mL Serological pipettes (VWR, Catalog No. 82050-478/82050-482/82051-182)
- Disposable Tips (Denville, Catalog No. P1096-FR/P1121/P1122/P1126)
- 500 ml Supor machV PES Filter Units (VWR, Catalog No. 73520-984)
- 15 mL/50 mL conical tubes (VWR, Catalog No. 82050-276/82050-346)
- 1.7 ml Micmcentrifuge Tubes (VWR, Catalog No. 53550-698)
- 96-well plate (VWR, Catalog No. 62406-081)
- Blue screw caps (Agilent, Catalog No. 5182-0717)
- Screw cap vials (Agilent, Catalog No. 5182-0714)
- vial insert, 250 µl pulled point glass (Agilent, Catalog No. 5183-2085)
- 96-well plate, 1.0 ml, polypropylene (Agilent, Catalog No. 8010-0534)
- Sealing tape, clear polyolefin (Thermo Fisher Scientific, Catalog No. 232701)
- Ultracentrifuge tube (Beckman Coulter, Catalog No. 355628)
- Amicon Ultra-15 Centrifugal Filter Unit with Ultracel-30 membrane (Millipore, Catalog No. UFC903024)
- Amicon Ultra-4 Centrifugal Filter Unit with Ultracel-30 membrane (Millipore, Catalog No. UFC803024)
- Millipore Reg. Cellulose membrane 10KD SC (Wyatt technology, Catalog No. 4057)
- Nadir Polyethersulfone membrane 10KD SC (Wyatt technology, Catalog No. 1903)
- Inline filter membrane 0.1 µm (Wyatt Technology, Catalog No. 1871)
- Dry wipes (Kimtech, Catalog No. 7552)
- 2 L glass bottles (VWR, Catalog No. 10754-822)
- Hemocytometer (Weber Scientific, Catalog 3048-12)

Equipment.
- Labconco Purifier Class II biosafety cabinet
- Tissue culture incubator
- EVOS FL Microscope (Thermo Fisher Scientific)
- Optima XPN-100 Ultracentrifuge (Beckman Coulter, Catalog No. A94469)
- Type 45 Ti Rotor, Fixed-Angle, Titanium (Beckman Coulter, Catalog No. 41103909)
- Table-top Heraeus Multifuge x3R Centrifuge Series (Thermo Fisher Scientific, Catalog No. 75004501)
- Microcentrifuge (Eppendorf, 5424R)
- AccuScan GO UV/Vis Microplate Spectrophotometer (Fisher Scientific, Catalog No. 14-377-579)
- Milli Q system (Millipore)
- 4° C. Refrigerator (Thermo Fisher Scientific)
- −20° C. freezer (Thermo Fisher Scientific)
- −80° C. freezer (Thermo Fisher Scientific)
- 37° C. Incubator (Thermo Fisher Scientific)
- Autoclave (Tuttnauer)
- Dishwasher (Steelco)
- AF4 Instrument Parts.
- Agilent 1260 Infinity Analytical- and Preparative-scale Fraction Collectors (G1364C)
- Agilent 1290 Thermostat (G1330B)
- Agilent 1260 Infinity Standard Autosampler (G1329B)
- Agilent 1260 Infinity Multiple Wavelength Detector (G1365D)
- Agilent 1260 Infinity Isocratic Pump (G1310B)
- GASTORR TG-14 HPLC vacuum degasser
- Wyatt Technology DAWN HELEOS-II with QELS installed at detector 12 (100°)
- Wyatt Technology Eclipse AF4
- Wyatt Technology short channel
- Computer installed with Chemstation and Astra 6 softwares Software.
- Chemstation (Agilent Technologies) integrated with the Eclipse module (Wyatt Technology) to operate the AF4 flow
- Astra 6 (Wyatt Technology) for MALS, DLS and UV data acquisition and analysis Reagent Setup.
- B16-F10 cell culture medium 500 mL of DMEM is supplemented with 10% (vol/vol) FBS (exosome-depleted), 50 units/mL Penicillin, 50 μg/mL Streptomycin, and 2 mM L-Glutamine, and stored at 4° C. for up to a month.

Exosome-depleted FBS FBS is depleted of exosomes by ultracentrifugation at 100,000 g for 90 min and sterilized with a 0.22 μm filter unit. Aliquots of exosome-depleted FBS can be stored at −20° C. for long term. To avoid contamination, the rotor needs to be first sterilized by wiping with 70% Ethanol and all tubes for ultracentrifugation should be autoclaved. The entire FBS handling process should be carried out in a Biological Safety Cabinet for tissue culture.

20% (vol/vol) Ethanol. Milli Q filtered water is used to make the dilution of ethanol. The final solution is made freshly and filtered with a 0.22 μm filter unit.

0.5 mg/mL BSA solution. Dissolve BSA powder in PBS at a concentration of 0.5 mg/mL and store aliquot at −20° C. for long term.

1% (vol/vol) Contrad 70. Dilute Contrad 70 with Milli Q water to a final concentration of 1% (vol/vol), and store at room temperature (RT, ~22° C.) for long term.

10% (wt/vol) SDS. Dissolve SDS powder in Milli Q water at a concentration of 10% (wt/vol) (i.e. 10 g per 100 mL) and store at RT for long term. This chemical is corrosive and toxic, and can cause severe skin and eye irritation. Wear protective gloves, mask, eyeshield, faceshield, and protective clothing to handle.

10% (vol/vol) Nitric Acid. Dilute nitric acid with Milli Q water to a final concentration of 10% (vol/vol), and store at RT for long term. This chemical is highly corrosive and can cause severe eye and skin burns, severe respiratory and digestive tract burns. Wear proper protective equipment (gloves, eyeshield, faceshield, clothing, respirators) and handle it in a chemical hood. The waste should be treated as a hazardous waste following state and local hazardous waste regulations.

Instrument setup. All the parts of the AF4 instrument should be installed, configured, calibrated and certified by the manufactures (Agilent and Wyatt Technology) before utilization.

Preparation of sEVs from the conditioned media of cell culture. B16-F10 murine melanoma is used as a model system in this protocol. A schematic flow diagram summarizing the key steps of the entire procedure and the flow route of AF4 is shown in FIG. 21.

1. Seed $2.25 \times 10^6$ B16-F10 cells per P150 tissue culture plate in 25 mL of the DMEM complete medium supplemented with exosome-depleted FBS, and seed a total of 12 plates. Cell lines should be regularly checked to ensure that they are authentic and free of mycoplasma contamination. The passage number of the B16-F10 cells influences sEV composition, reflected by the changes in the relative abundance of different subsets of sEVs (7). So, avoid comparing experimental data using B16-F10 cells with a big difference in their passage numbers.
2. Keep cells in a humidified tissue culture incubator for 72 hours under standard conditions (5% $CO_2$, 37° C.). The cell culture should just reach confluence without cell death and any abnormal phenotypical changes. Cells should be allowed to reach confluence to get highest sEV yield, but no cell death and stressed phenotype should be apparent by the harvesting time to ensure the purity of the sEVs.
3. Collect the conditioned media into 50 mL conical tubes and centrifuge at 500×g at 10° C. for 10 minutes in the table-top centrifuge. The supernatant can be spun at 3000×g 10° C. for 20 minutes in the table-top centrifuge, transferred to new tubes and placed at −80° C. for long term storage.
4. Transfer the supernatant to ultracentrifuge tubes (6×50 mL/tube) and centrifuge at 12,000×g at 10° C. for 20 minutes in Type 45-Ti ultracentrifuge rotor (pre-chilled at 4° C.). For ultracentrifugation, the opposing pair of tubes across the center of rotation need to be balanced with each other. Do not load more than 50 mL per tube to avoid sample spilling. The rotors should be kept at 4° C. when not in use.
5. Transfer the supernatant to new ultracentrifuge tubes and centrifuge at 100,000×g at 10° C. for 70 minutes in the same rotor. At the end of each ultracentrifugation step, make sure the supernatant is transferred immediately to avoid the loosening of the pellet and either contaminating the supernatant or losing the pelleted samples.
6. Discard the supernatant and resuspend the pellets in one milliliters of ice-cold PBS gently. Avoid introducing air bubbles. Combine all the samples into one ultracentrifuge tube and bring the final volume to 50 mL with PBS.
7. Centrifuge at 100,000×g at 10° C. for another 70 minutes. Resuspend the final pellet in ~0.5 mL of PBS and transfer to 1.7 mL microcentrifuge tubes on ice (the sEV sample for A F4 fraction in the next section). The pellet sometimes may be hard to break and resuspended into a homogeneous suspension. If so, the samples can be kept on ice for another 15 to 30 minutes or an extra volume of PBS can be added to the sample. Then gently pipette up and down to resuspend the samples and transfer to Eppendorf tubes for quantification. Avoid introducing air bubbles.
8. Quantify the sEV yield by measuring the protein concentration using the Pierce BCA Protein Assay Kit. Follow the manufacture's instruction to mix the samples or BSA standards provided by the kit with the reagents in a 96-well plate and incubate at 37° C. for 30 minutes. Read the absorbance at 562 nm using the AccuScan GO UV/Vis Microplate Spectrophotometer and calculate the concentration of the samples based on the BSA standards included.
9. The samples can be immediately applied for AF4 fractionation, or kept on ice overnight to be processed further the next day. The samples can be frozen at −80° C. for long term storage.

AF4 Fractionation of sEVs.

Assemble the AF4 Channel

10. Before assembling the AF4 channel, one should select the membrane type and cutoff size (e.g., RC membrane with 10 KDa cutoff size) and the spacer with desired thickness (i.e. the channel height, preferably 490 μm) first.
11. Rinse all parts with Milli Q water and assemble in the order of the top plate, spacer, membrane and bottom plates with the frit/O-ring in place). Bolt the parts together using a torque wrench with 5 Nm and 73 Nm torques applied sequentially. Since the sample specimen is positioned in the channel laminae very close to the membrane, it is critical that the membrane should be smooth and unruffled. Wear gloves and do not bend the membrane during the assembly procedure. Since ethanol can cause the "membrane swelling" phenomena and reduce the effective channel height for fractionation, avoid exposing the membrane to ethanol. It is critical that the channel be tightly sealed and its height be precise and even across the whole channel. To assemble the AF4 channel, a metered wrench such as a torque wrench should be used to apply force precisely. A good practice is to tighten the two bolts in the center first and then the ones at the corners in diagonal order.

12. Connect the tubing to the inlet, crossflow and injection ports but with the outlet port unconnected. Start to run water at a channel flow rate of 1 mL/min (program the flow rate settings and operate using ChemStation) through the system for at least 30 minutes and let air in the channel run out from the outlet port first. Then connect the tubing from the outlet to the detectors. No air bubbles should be observed in the channel. The instrument can be operated in the Night Rinse mode with a constant channel flow of 0.2 mL/min overnight, up to a few days. For short term storage, keep the system running in the Night Rinse mode. Do not leave the system in still aqueous solvents for a long period. For long term storage, dissemble the membrane from the channel and maintain the system in 20% ethanol. Keep the tubing from the channel to the detectors and the fraction collector as short as possible to reduce the peak broadening and sample dilution effects and to avoid decreases in separation resolution.

Equilibrate and Coat the Membrane with BSA

Change the aqueous solvent to PBS, and keep running at a channel flow of 1 mL/min for at least 30 minutes to 1 hour. The instrument can be operated in the Night Rinse mode overnight, with a constant channel flow of 0.2 mL/min. If the system has been maintained in ethanol or isopropanol, it should be flushed completely with water first before switching to PBS. Mixing PBS with alcohol will cause salt precipitation.

13. Load 30 to 40 µg of BSA (0.5 mg/mL) onto AF4 and run the sample using the same AF4 method as for sEV fractionation except for the elution step, using a constant crossflow of 3 mL/min for 15 minutes for BSA instead. Repeat, by running BSA 1-2 more times. The instrument can be operated in the Night Rinse mode overnight, up to a few days after membrane coating. The purpose of this step is to block non-specific binding of the samples to the membrane. The sample to be analyzed, if extra sample is available, can be used for this blocking step, too. This step is only needed when a new membrane is installed. At the end of the day, after all samples have been processed, turn on the COMET of the DAWN HELEOS 11 detector for about 30 min to clean the flow cell.

AF4 Fractionation of sEVs.

14. Instrument initialization:
    (a) Open Chemstation and load the AF4 running method as described in Table 15 (The running method is programmed, edited and saved in the "Method" module of Chemstation).
    (b) Set both thermostats for the autosampler and the fraction collector at 4° C.; turn on the UV lamp for the MWD detector (280 nm) at least 30 minutes before sample analysis; turn on the laser for DAWN HELEOS II (664 nm).
    (c) Turn on the fraction collector and choose the collection mode (based on volume or time interval); install 96-well plates for fraction collection (Ensure plates are installed according to the configuration of the fraction collector). Fractions are collected based on time intervals of 0.5 minutes, so two plates are needed to collect the fractions from one sample). All operations should be done using the ChemStation software except for switching on the laser of DAWN HELEOS II using the instrument's front control panel.

15. Open Astra 6 and start a new experiment file for data collection:
    (a) For Configuration, select "PBS, aqueous" as the system solvent; specify UV wavelength at 280 nm" and enable "Band Broadening" option; for HELEOS, enable "Band Broadening" and "Temperature Control" options; and for QELS, select "Use QELS dithering".
    (b) For Procedure: specify the time interval for MALS data collection at 1 second and QELS interval at 2 seconds; set the duration for data collection at 60 minutes; select "Trigger on Auto-Inject";
    (c) Click the "Run" button and the data collection will automatically start once triggered by the signal from the autosampler.

16. Prepare the AF4 input samples by adjusting the concentration of the sEVs isolated in Step 9 to 1 µg/µl with PBS. Spin at 12,000×g 4° C. for 5 minutes to remove insoluble aggregates right before loading onto AF4.

17. Transfer the supernatant into a pre-chilled screw cap glass vial (250 µl pulled point glass vial insert can be used if the total volume of the sample is small), and put it onto the autosampler platform at the designated position from which the autosampler is set to pick up the sample automatically. Pre-spinning of the sample before loading onto AF4 is critical to avoid analyzing artifacts of aggregates formed during the high-speed ultracentrifugation.

18. In the Autosampler module of Chemstation, specify the sample volume to analyze (40 to 100 µl; i.e. 40 to 100 µg at 1 µg/µl), and then click the "Single Sample" to start the fractionation, real time data collection (MALS. DLS, and UV absorption), and fraction collection (by time slice of 0.5 mL). The pilot study has determined a range from 40 to 100 µg of B16-F10 sEVs is suitable for the current AF4 running method that has

TABLE 15

| Time (min) | Mode | Channel flow (mL/min) | Cross flow Start (mL/min) | Cross flow End (mL/min) |
|---|---|---|---|---|
| 2 | Elution | 1.0 | 0.5 | 0.5 |
| 1 | Focus | 1.0 | — | — |
| 2 | Focus + Inject | 1.0 | — | — |
| 45 | Elution | 1.0 | 0.5 | 0 |
| 5 | Elution | 1.0 | 0 | 0 |
| 5 | Elution + Inject | 1.0 | 0 | 0 |

Inject flow 0.2 mL/min: Focus fow 0.5 mL/min

Focus valve position- Focusing (%): 30 been developed. This can be further adjusted for specific samples due to their composition complexity. It is critical to avoid getting air bubbles into the system. Make sure that no air bubbles trapped in the sample vial and have a larger volume of sample in the vial than the volume to be analyzed.

19. During the running of the sample, check the real flow rates in the panel of "Wyatt Eclipse Status" and make sure they are close enough to the set flow rates. If the real flow rates are quite different from the set ones, something is wrong with the flow control and repairing/maintenance by the manufacturer is needed to ensure the fractionation quality. It is critical to keep the channel flow rate (the detector flow) constant during the fractionation. Changes in the flow rate can cause artifact signal detection by the monitors.

20. Once the fractionation is finished, take the 96-well plates out of the fraction collector and seal them using adhesive tape. Keep the plates on ice or at 4° C. for the next procedure.

21. Click "Reset the fraction collector" so that the starting position for fraction collection is reset to its original position. Otherwise, the instrument will resume the fraction collection of the next sample from the last fraction position of the previous sample.)

22. Proceed to "Online data analysis" described infra to evaluate the fractionation quality.

23. Proceed to "Fraction offline characterization" as described infra or star the fractionation of the next sample (first install new 96-well fraction collection plates and then start fractioning the next sample by repeating steps 16-23). If multiple samples need to be analyzed but the collection of separated fractions is not required, a "Sequence" (a series of methods and samples programmed to be run sequentially) can be run instead of the method for a single sample. Users can refer to the manual from the manufacturer for details.

24. A good practice includes running a PBS blank control (or other types of running buffer used to analyze the samples) using the same AF4 running method for the samples on the same day. This blank control can help evaluate the instrument performance such as background noise level and identify systemic problems than may influence sample analysis.

25. After all samples have been analyzed for the day, turn on the COMET of the DAWN HELEOS II for ~30 minutes and switch off the laser, UV lamp, thermostats and fraction collector. Change the aqueous solvent to water and run in the Night Rinse mode overnight or up to a few days. For long term storage, please refer to Step 12.

Online data analysis. Online data analysis is performed using Astra 6. First, select the experiment to be analyzed and (a) adjust the baselines: set up the baseline for the MALS signal collected from the LS 11 (90°) detector first, and then apply it to all the other detectors. Make sure to check individual detectors to ensure the baselines are set up correctly.

(b) Select peak regions to analyze: a single or multiple regions can be selected to analyze simultaneously.

(c) Examine the fractionation quality by checking upon the fitting of the autocorrelation function at representative fractions to a single exponential model. The closer of $R^2$ to 1, the better purity of the separation.

26. Open a new window of EAST Graph, and plot Hydrodynamic Radius ($R_h$), QELS (DLS) and UV signals versus time. The hydrodynamic radius ($R_h$) of particles is deduced solely from DLS signal using equations described above. The Hydrodynamic Radius ($R_h$) plot displays the size of particles eluted at each time point. The UV signal intensity can reveal the relative abundance of particles with different sizes. Based on these plots (and together with potential of pine characterizations), one can judge the AF4 separation quality and the sample composition (i.e. the relative abundance of particles with different sizes). Other types of analysis can be plotted as well by choosing different axes to display in EAS1 Graph according to the need. Besides online UV detection, other means of quantification such as BCA assay and NTA analysis can be used to measure the concentration of the fractions. The sample concentration should be high enough to scatter enough light for accurate $R_h$ determination, especially for small size particles as they scatter much less light.

Fraction Collection and Concentration for Offline Characterization.

27. Depending on the characterization to be conducted, the individual fractions can be examined directly or further concentrated before examination. Adjacent fractions with similar properties (especially from the same peak region) can be combined and concentrated for downstream analysis. If a high amount of material is required for the downstream characterization, multiple runs of the same sEV sample can be carried out following the same procedure and similar fractions from each run can be combined.

28. Individual fraction or pooled fractions are concentrated using Millipore centrifugal filter columns with Ultracel-30 membrane (30 kDa cutoff) in the following steps.

(a) The filter columns are first pre-rinsed by adding 5 mL (for Ultra-4 filter column) or 15 mL (for Ultra-15 filter column) of ice-cold PBS followed by spinning at 3,700×g at 4° C. for 5 minutes. The flow-through and liquid remaining in the top filter columns are discarded.

(b) Pooled fractionated samples are then transferred into the top filter column and spun at 3,700×g at 4° C. for 7-8 minutes. The concentrated samples are retained in the top filter columns and buffer is collected at the bottom of the collection tubes (the flow-through). Discard the flow-through.

(c) Repeat step 31 (b) until each sample is concentrated to the desired volume. For each sample, the same filter column can be repeatedly loaded and spun to concentrate the sample.

(d) Transfer the concentrated samples to 1.7 mL microcentrifuge tubes on ice. Record the volume and take an aliquot for BCA measurements to determine the protein concentration.

(e) The concentrated samples can be kept on ice for short-term storage (up to 2~3 days) or frozen at −80° C. for long term storage. Downstream molecular characterizations and functional study can be followed up on these concentrated fractionated samples. For an unknown sample that is analyzed using AF4 for the first time, check the morphology of representative individual fractions by TEM first before pooling fractions together for further analysis. It is possible that particles with same hydrodynamic size but different morphology are eluted together from AF4. Other means to separate these particles based on their distinct biophysical/biochemical properties (such as density, surface molecule expression, and charge) should be explored in combination with AF4 for further fractionation. Pool fractions together based on the hydrodynamic size, morphology and purity of representative fractions. If baseline separation of two adjacent, distinct populations of particles is not achieved, avoid collecting those fractions in the "valley" between the peaks of two populations for further characterization.

Troubleshooting. Table 16. Troubleshooting Table.

TABLE 16

| Step | Problem | Possible reason | Solution |
|---|---|---|---|
| 9 | Low sEV yield | Low cell confluence by the CM harvest time | Seed a higher number of cells per plate or a bigger number of plates, or use a longer cell culture time |
|  |  | Lost the sEV pellet of 100,000× g ultracentrifugation | Remove the supernatant immediately from the sEV pellet of 100,000× g ultracentrifugation |
|  | Abnormally high sEV yield | Contamination due to inefficient washing | Resuspend the pellet from Step 6 completely and use a large volume of PBS to wash in Step 7 |
|  |  | Too much carry over of media in Step 6 | Invert the tubes from Step 6 on paper towel to drain the leftover of media or suck it off using the vacuum system before washing with PBS |
|  |  | Contamination from the pellet of 12,000× g ultracentrifugation | Transfer the supernatant immediately to new tubes from the pellet of 12,000× g ultracentrifugation in Steps 4-5 |
| 12 | Leaking channel and/or tubing connection | The AF4 channel was not assembled properly | Reassemble the channel following Steps 11-12. Make sure the channel is assembled using the proper and precise force with a torque wrench |
|  |  | The Q-ring is damaged or not placed properly | Change to a new O-ring if it is damaged; install it evenly and smoothly in the groove along the frit on the bottom plate of the channel |
|  |  | The screw thread is damaged or worn out | Replace with new screws, or use a piece of Teflon (polytetrafluoroethylene (PTFE) film) tape to help seal the thread |
| 13 | high LS background noise | Particle contaminants in the system | Change the inline filter for mobile phase solution |
|  |  |  | Thoroughly rinse the membrane with Milli Q water before assembling; equilibrate the membrane in the AF44 channel with PBS overnight; flush the channel thoroughly before connecting to detectors. |
|  |  | Membrane installed improperly | Reassemble the channel and make sure the smooth side of the membrane facing the inside of the channel |
| 14, 19 | No signal or much lower signal than expected for the | Lost sample due to leaking channel connection | See above troubleshooting for the Step 12 "Leaking channel and/or tubing connection" |
|  |  | Lost sample due to damaged membrane | Replace with new membrane |
|  |  | Inefficient focus | Use a colored sample such as blue Dextran to test the focus efficiency. A narrow band of the sample should be located close to the inject port. If not, increase the focus time post the injection step |
| 14, 19 | High noise | Contaminant present in the mobile phase solution | Filter the buffer before use and use an inline filter (0.1 μm, and change it routinely, about once a month) If compatible with downstream analysis, include sodium azide in the mobile phase solution |
|  |  | Particle contaminants in the system | Use COMMET after running samples to clean the MALS flow channel |
|  |  |  | Flush the channel and the system thoroughly with a large volume of filter water; If flushing with water does not solve the problem, clean the detectors by running and incubating in 10% SDS, 1% Contrad 70, or 10% Nitric acid for 30 min up to overnight, then thoroughly rinse with filtered water |
| 14, 19 | Baseline drifting | Particle contaminants in the system | See above troubleshooting for the Step 14, 19 "High noise" |
|  |  |  | Collect AF4 profile of PBS blank control right before or after the AF4 fractionation of the samples of interest, and then use the PBS control profile to perform baseline subtraction from the profile of the samples. |
| 14, 19 | Sharp jump in signal intensity | Laser performance quality decreased | Replace with new laser |
|  |  | Unstable voltage | Use the power supply that provides stable voltage and current |
|  |  | Air bubble introduced into the system | Degas the buffer before use and/or use an online degaser; make sure there is no air bubble in the sample vial and have an excess of sample to inject |
| 14, 19 | Sample elutes too early or too late than expected | Aberrant flow rate | Compare the real flow rate versus the set flow rate shown in the panel of "Wyatt Eclipse Status" If the difference is big, repair by the manufacture is required. |
| 18 | Too large pellet | Insufficient resuspension of sEV pellet in Step 9. | Repeat pipetting up and down gently to resuspend the pellet, use a larger volume of PBS to resuspend the pelleted sEVs. To get more accurate loading of the sample, conduct the BCA assay upon the supernatant from the brief spin at 12,000 ×g in Step 18. |
| 19 | A shift toward late elution | Membrane used for extended period and bound non-specifically with contaminant | Replace with a new membrane |
| 19 | The signal not reaching the baseline level by the end of AF4 fractionation | Not enough elution time | Use a longer cross flow gradient time and/or a longer time for the last two steps (Elution, Elution + Inject) of the AF4 running method |

TABLE 16-continued

| | | | |
|---|---|---|---|
| 28 | Curling-up tail of the $R_h$ plot at the small $R_h$ end | Inaccurate $R_h$ determination from the DLS measurement due to insuffient amount of the sample, especially for particles of small size Insufficient separation of the particles, especially at the beginning of AF4 fractionation | Increase the amount of the sample to analyze Use other means such as EM and NTA analysis to validate the purity Increase the Focus time after the injection step Increase the initial cross flow rate and n longer time span of fractionation to allow better separation |
| 28 | Scattered $R_h$ plot | Inaccurate $R_h$ determination from the DLS measurement due to insuffient amount of the sample, especially for particles of small size High background noise | Increase the amount of the sample to analyze See above troubleshooting for the Step 14. 19 "High noise" |
| 28 | Too big P5-corresponding peak | Not enough elution time | Use a longer cross flow gradient time |
| 30 | No sample recovered | Lost sample due to damaged membrane of the filter unit | Save the flow through and apply to new filter unit for concentration |

Timing.
  I. Step 1-9, cell culture and isolation of sEVs: ~3 days.
  II. Step 10-12, the AF4 channel assembling: ~1 hour.
    Step 13-14, Equilibration and coating the membrane with BSA: 2~3 hours.
    (Step 10-14 are only needed when a new membrane is installed.)
    Step 15-26. AF4 fractionation of sEVs: 1-2 hours per sample.
  III. Step 27-28, online data analysis: ~20 minutes per sample.
  IV. Step 29-30, fraction collection and concentration for offline characterization: 1-2 hours.

Example 8—Cross-Flow

Figures 16A, 16B, 16C:
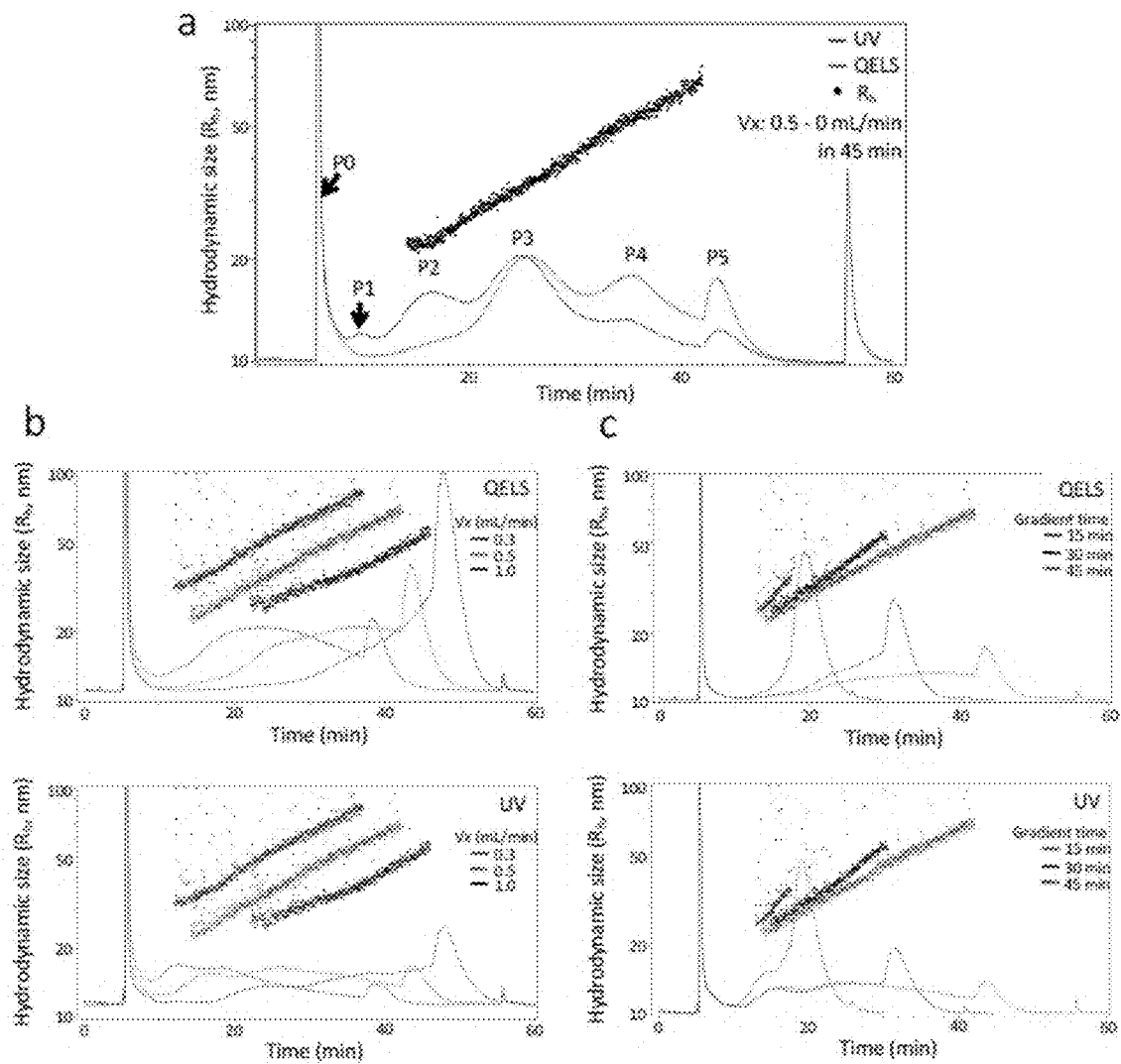
FIGS. 16A-16C show the influence of cross-flow on AF4 fractionation.

According to the AF4 theory, cross-flow is the driving force counteracting the Brownian motion of particles to resolve particles with different hydrodynamic sizes at different channel-flow laminae at steady state. Thus, cross-flow is a defining factor in AF4 fractionation quality. To determine the optimal cross-flow for exosome fractionation, various cross-flow settings were evaluated. Exosome fractionation profiles (fractograms of UV absorbance and DLS) were devised from representative cross-flow settings, as shown in FIG. 16. Specifically, linear gradients of cross-flow with different starting flow rates (at 0.3, 0.5 and 1.0 mL/min) and slopes (i.e., how fast the cross-flow drops to 0 mL/min; tested conditions: a decrease in flow rate from 0.5 to 0 mL/min within 15, 30 and 45 min) were examined. Three major peaks (P2, P3 and P4) were observed when the cross-flow decreased from 0.5 to 0 mL/min within 45 min. These peaks represented the exomeres and two exosome subsets (i.e., small exosomes [Exo-S] and large exosomes [Exo-L]), respectively, as reported supra (FIG. 16A). Among the other peaks, P0 is the void peak, resulting from flow disturbance when switching from the focus/injection mode to the elution mode. P1 is a very minor peak, generated by the concomitant elution of the void peak and species that were smaller than exomeres. Depending on the ENP preparation, P1 was sometimes barely detected. P5 was generated due to loss of control on flow rate when it decreased below ~0.08 mL/min and all retained sample components (larger microparticles and/or aggregates of small particles) were eluted out. As shown in FIG. 16B, when the initial cross-flow rate was increased to 1.0 mL/min, no additional shoulder peaks were observed to separate further from peaks P2-P4, indicating the uniformity of these three populations of particles. A delay in the elution of all three peaks was observed. Moreover, a much higher P5 peak was observed and this is due to insufficient time for elution of large particles, including Exo-L, in the given time and based on the channel size. In contrast, when the initial cross-flow rate was set to 0.3 mL/min, the samples eluted much earlier, indicating that this flow rate was not fast enough to retain the sample constituents inside the channel and resolve them efficiently. Therefore, an initial cross-flow rate of 0.5 mL/min was used throughout the procedure.

Next, the impact of different slopes of the cross-flow gradient on separation quality was evaluated. A linear decrease of the cross-flow rate from 0.5 to 0 ml, min within a time span of 15, 30 and 45 minutes were compared. Clearly, the peaks became narrower and the separation quality was compromised when shorter time spans were used (FIG. 16C). In addition, a larger P5 peak was observed when a shorter time span was used, indicating insufficient time for elution of large particles.

On the contrary, when longer time spans were used, the peaks broadened but with improved separation quality. This setting is desired when high-purity particles in discrete fractions need to be recovered for further offline characterization. However, when longer time spans are used, other practical issues, such as the dilution of samples and the sensitivity limit of online detectors for accurate measurement, have to be taken into account. Therefore, it was aimed to separate distinct subsets of exosomes (<150 nm), which were clearly separated from each other when a time span of 45 minutes was applied (longer time spans were not tested). A linear gradient of the cross-flow decreasing from 0.5 to 0 mL/min for 45 minutes was chosen for the study.

Example 9—Channel Height

Figure 17:
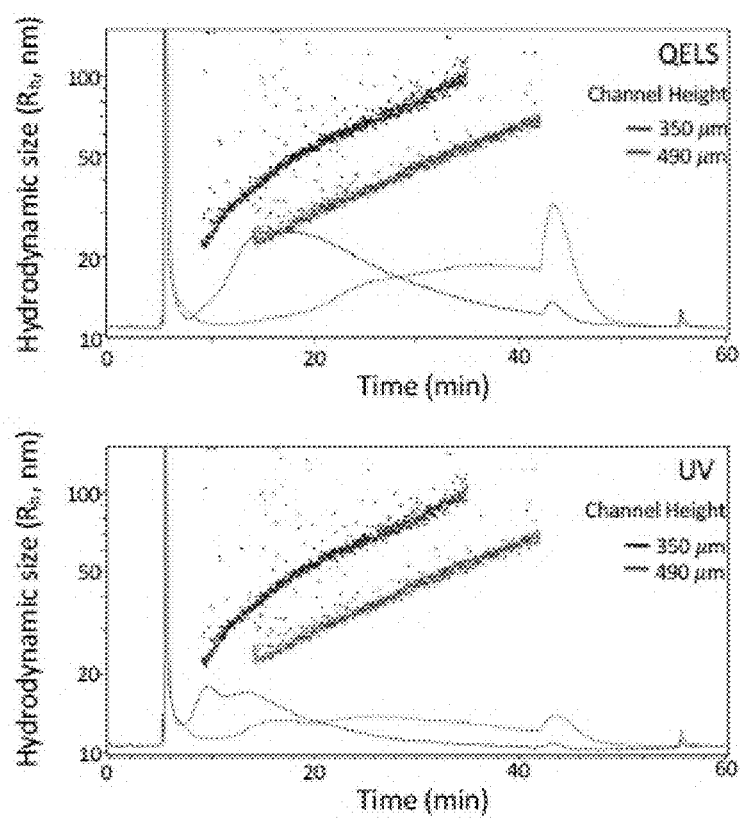
FIG. 17 shows the effect of the channel height upon AF4 fractionation. Shown are AF4 fractionation profiles of B16-F10 sEVs collected using a channel with a spacer of 350 μm (blue) and 490 μm (red). Top, QELS at 100°; bottom, UV absorbance at 280 nm. The other AF4 parameters are; channel flow rate, 1.0 mL/min; a linear gradient of cross-flow decreasing from 0.5 mL/min to 0 mL/min over 45 minutes; sample focus time, 2 minutes; membrane, regenerated cellulose (RC), input amount, 40 μg.

Based on the working principle of AF4, the channel's geometry, including its width, height and shape, is critical for fractionation quality. The short channel utilized in this study is a product of Wyatt Technology (Santa Barbara, USA), which has a trapezoidal geometry (Callen & Antonietti, "Field-Flow Fractionation Techniques for Polymer and Colloid Analysis," Adv. Polym. Sci. 150:67-187 (2000); Litzen & Wahlund, "Zone Broadening and Dilution in Rectangular and Trapezoidal Asymmetrical Flow Field-Flow Fractionation Channels," Analytical Chemistry 63:1001-1007 (1991), which are hereby incorporated by reference in their entirety) with a tip-to-tip length of 152 mm and a linear decrease of the channel width from 21.5 mm (close to the injection port and about 12 mm away from the inlet tip) to 3 mm. With the shape and width already optimized and fixed, the height (i.e., the thickness of the channel, determined by the spacer used between the upper wall and the bottom accumulation membrane) was the only parameter available for further optimization. A series of spacers with different thicknesses (190, 250, 350 and 490 µm) were provided by the manufacturer. The channel height affects the parabolic laminar flow rate profile and thus the separation resolution. It also affects the channel capacity, with a thicker channel allowing for analysis of larger sample amounts. Since enough sample needed to be recovered for downstream analysis, the loading capacity is an important factor for the fractionation and so employing only spacers with a thickness of 350 µm and 490 µm were considered. As shown in FIG. 17, the channel with the 350-µm spacer eluted samples earlier but with narrower peaks and a reduced separation resolution compared to the channel with the 490-µm spacer. Therefore, the 490-µm spacer was chosen for the work.

Example 10—Focusing

Figure 18:
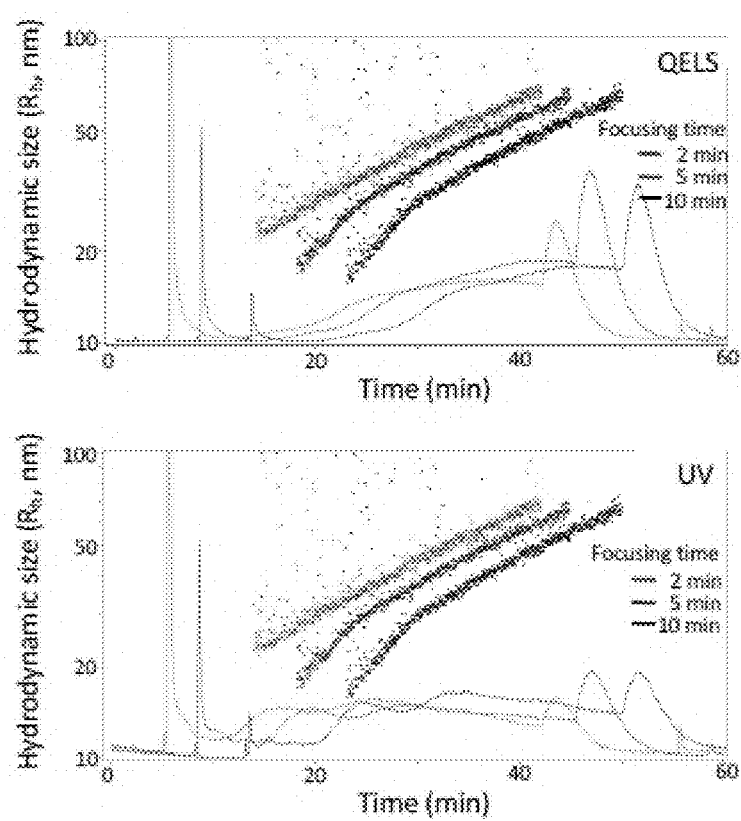
FIG. 18 shows the effect of the focus time upon AF4 fractionation. Shown are AF4 fractionation profiles of B16-F10 sEVs collected using a sample focus time of 2 minutes (red), 5 minutes (blue) or 10 minutes (black). Top, QELS at 100°; bottom, UV absorbance at 280 nm. The other AF4 parameters are: channel flow rate, 1.0 mL/min: a linear gradient of cross-flow decreasing from 0.5 mL/min to 0 mL/min over 45 minutes; channel height, 490 μm; membrane, regenerated cellulose (RC), input amount, 40 μg.

A 100-µL sample loop was used in the instrument for sample loading. It is a significant portion of the total channel capacity, which usually ranges from 200 µL to 1000 µL. Once injected into the channel, the sample would spread throughout the channel and lead to insufficient fractionation. To avoid this, a flow opposing the channel forward flow was introduced from the outlet and, together with the channel flow, focused the sample into a narrow band close to the injection port (i.e., focus mode). First, the focus flow was established and then the samples were injected in the focus mode and given enough time to reach steady-state equilibrium before elution. The focusing flow rate and focusing time determine focusing efficiency. Here, the focusing flow rate was fixed at 0.5 mL/min, the same as the initial cross-flow rate for elution, and then tested different time periods (2, 5, and 10 minutes) for focusing efficiency. As shown in FIG. 18, different focusing times did not significantly affect peak shape or resolution power. Moreover, before exomere elution occurred, the fractograms of both UV and DLS reached similar baselines. Notably, it was observed that the P5 signal intensity increased as focusing time increased, suggesting potential particle aggregation caused by extensive focusing. Therefore, a focusing time of 2 minutes was chosen for the study.

Example 11—Membrane Choice

Figure 19:
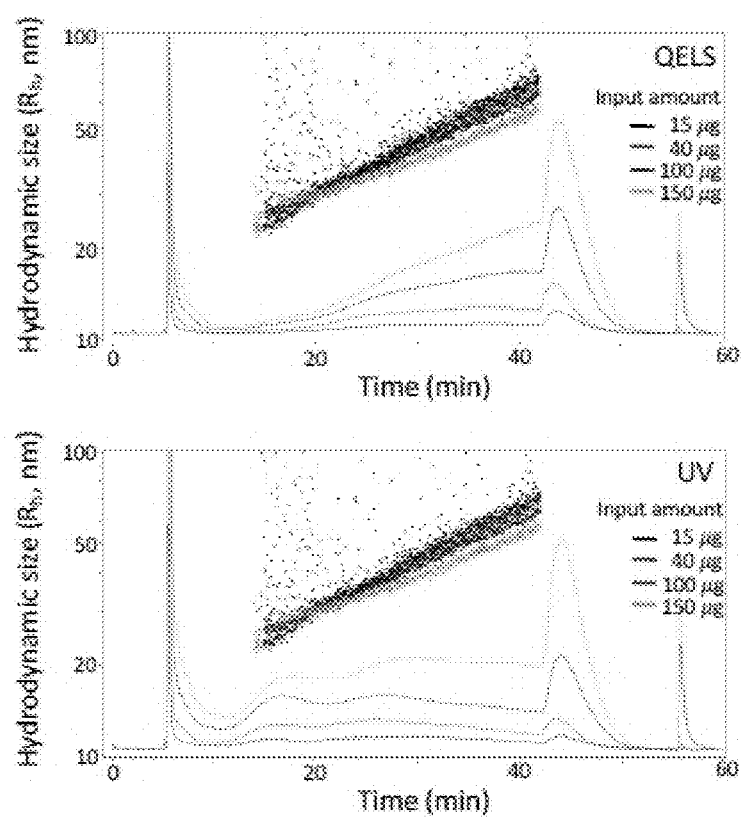
FIG. 19 shows examination of the sample (B16-F10 sEVs) loading capacity for AF4 analysis. Shown are AF4 fractionation profiles of B16-F10 sEVs with an input of 15 μg (black), 40 μg (red); 100 μg (blue), or 150 μg (green).

Since the sample fractionation is performed close to the membrane, in addition to the pore size of the membrane, the compatibility of the membrane material with the samples also needs to be considered. For example, the sample may bind to the membrane non-specifically. Two different types of membranes that are commonly used for biological material concentration or filtration, regenerated cellulose (RC) and polyethersulfone (PES), were tested for exosome fractionation. While keeping other AF4 parameters exactly the same, a delay of sample elution and broader peaks was observed in the channel with PES compared with RC, suggesting potential non-specific interactions between samples and the membrane (FIG. 19). Therefore, the RC membrane was selected for the studies.

Example 12—Amount of Input Sample

Once the key fractionation parameters were determined, the loading capacity of AF4 was then examined. The minimal amount of material required for AF4 is determined primarily by the sensitivity limit of the online detectors, such as DLS and UV monitors. The signal/noise ratio must be adequate for accurate data collection and interpretation. The maximal amount of material is determined by the required resolution of fractionation, which depends on the purpose of the experiment and the complexity of the sample to be analyzed. To efficiently separate exomeres and the two exosome subsets that are reported herein from small (s)EVs prepared using UC, different amounts of B16-F10-derived sEV input samples ranging from 15 μg to 165 μg were tested. As shown in FIG. 20, 15 μg was the lower limit of material for this analysis, as a high level of noise began to be detected, especially at the low end of hydrodynamic size. Inputs of 40 μg and 100 μg yielded almost identical fractionation profiles and hydrodynamic size determinations, indicating comparable fractionation resolution and robust signal detection. However, when the amount of input increased to 165 μg, the elution of all peaks was delayed significantly, resulting in incomplete elution of Exo-L. Bleed-through of each particle population to the adjacent populations increased (and thus poorer separation occurred), as indicated by the increased signal intensity at the valleys between peaks. Therefore, an input ranging from 40 μg to 100 μg was used for this study.

Discussion of Examples 8-12

As illustrated in the above assessments, AF4 technology provides unique capabilities to separate nanoparticles with high resolution within a large size range. Through the highly robust and straightforward means of AF4, distinct exosome subpopulations and exomeres were able to be efficiently separated. These findings exhibit AF4's potential usefulness in identifying other distinct EV subpopulations. Coupled with online monitoring (e.g., multi-angle light scattering (MALS), DLS, UV absorbance and fluorescent detection) and offline analyses (e.g., microscopy, mass spectrometry of proteins, lipids, glycans and metabolites, and DNA and RNA sequencing), AF4 can yield valuable data on ENP analyzes, including particle morphology and size, relative abundance, molecular composition, and other biophysical and biochemical properties. A powerful tool, AF4 can help researchers decipher the complexities and heterogeneity of ENPs that cannot be well addressed with other existing techniques.

The AF4 protocol describes the fractionation of exomeres and exosome subsets from sEVs isolated from the conditioned media of B16-F10 cells and a panel of more than 20 different cancer cell lines and S normal cell lines. This AF4 method can be used to fractionate and characterize sEVs isolated from an array of bodily fluids (including blood plasma or serum, lymphatic fluid, bone marrow plasma, cerebrospinal fluid, urine, saliva, bronchoalveolar lavage, milk and amniotic fluid), given their similar particle compositional complexity. Since all cells are capable of shedding EVs, this protocol can be employed to study the EV biology of any organism.

Not only for biological discovery, this protocol can also be modified for use in the field of quality control in exosome-based pharmaceutical production. Exosomes have become attractive therapeutic delivery vehicles for treating cancer and other types of diseases (Batrakova & Kim, "Using Exosomes, Naturally-Equipped Nanocarriers, for Drug Delivery," *J Contra Release* 219:396-405 (2015), which is hereby incorporated by reference in its entirety). AF4 coupled with sensitive molecular assays can serve as an improved analytic tool to evaluate purity, drug loading efficiency, and the integrity of the exosome product by detecting debris or aggregates.

Last but not least, this protocol can serve as a reference to further develop and optimize methods for fractionating and characterizing other types of ENPs. Some unique advantages of AF4 are its high resolution and large size range of fractionation and that different conditions, such as cross-flow setting and focus time, can be easily tested by simply programing the settings into the software, with minimal handling of the channel. Besides their use in analyzing exosomes and other sEVs, fractionation protocols for large EVs, such as larger microparticles and oncosomes, can be further developed. Specific caution should be taken when fractionating large particles since they may be too large to elute in the normal mode (when the particle is small and considered as point-mass compared to the channel height) but in the steric model instead (FIG. 15). Moreover, other fields, such as electric field, can also be applied to AF4 to stratify particles based on additional biophysical properties other than size, allowing even broader application of AF4 technology.

Taken together, the separation and characterization of distinct EV subpopulations by AF4 are critical to advancing knowledge of the biology of EVs and their functional roles in physiological and pathological conditions. By profiling the molecular cargo of EVs, signature proteins, lipids, glycans and genes as well as specific signaling pathways associated with disease progression can be identified, facilitating the identification of potential diagnostic/prognostic biomarkers, including those related to cancers. Such knowledge will also provide a rationale for developing ENP-based therapies in clinical trials.

Comparison with Other Methods

A multitude of technologies, in addition to AF4, have been developed to isolate pure exosomes and other EV subpopulations. The most commonly used technique makes use of dUC and separates the particles based on their hydrodynamic size and density. Successive centrifugation at different centrifugal forces eliminates dead cells and cellular debris (500×g, 10 min), large oncosomes and apoptotic bodies (2000~3000×g, 20 minutes) and larger microparticles (10,000~12,000×g, 20 minutes), and subsequently pellets sEVs (100,000×g, 70 minutes) (Théry et al, "Isolation and Characterization of Exosomes from Cell Culture Supernatants and Biological fluids," Curr Protoc Cell Biol Chapter 3, Unit 3.22 (2006); Jeppesen et al., "Comparative Analysis of Discrete Exosome Fractions Obtained by Differential Centrifugation," J Extracell Vesicles 3:25011 (2014); Cvjetkovic et al., "The Influence of Rotor Type and Centrifugation Time on the Yield and Purity of Extracellular Vesicles," J Extracell Vesicles 3 (2014), which are hereby incorporated by reference in their entirety). Centrifuge rotor type, centrifugal force and centrifugation time are key factors influencing the product yield and purity of this method. Its performance also varies depending on the cell types studied (Willms et al., "Cells Release Subpopulations of Exosomes with Distinct Molecular and Biological Properties," Sci Rep 6:22519 (2016), which is hereby incorporated by reference in its entirety). dUC can process large volumes and high amounts of sample, but the purity of the material recovered is poor. It can only roughly partition particles into groups, such as large vesicles, microparticles, and sEVs (enriched for exomeres and exosomes), with expected heterogeneity within each group and contamination for other groups. The high centrifugal force may also cause sample aggregation. With the present protocol, the advantage of dUC was used by first stratifying and concentrating the sEV population and then analyzing particles at much higher resolution to further fractionate exomeres and exosome subsets.

Density gradient floatation (DGF) is often used to further purify sEVs first isolated using dUC. In DGF, EVs are overlaid upon a gradient of increasing dilutions of a viscous solution (sucrose or iodixanol are commonly used) and, upon centrifugation, they migrate to the equilibrium density determined by the EV's size, shape and density. DGF is often used to remove non-membranous particles from EVs and has also been employed in several studies to address exosome heterogeneity (Aalberts et al., "Identification of Distinct Populations of Prostasomes that Differentially Express Prostate Stem Cell Antigen, Annexin A1, and GLIPR2 in Humans," Biol Reprod 86:82 (2012); Bobrie et al., "Diverse Subpopulations of Vesicles Secreted by Different Intracellular Mechanisms are Present in Exosome Preparations Obtained by Differential Ultracentrifugation,"J Extracell Vesicles 1 (2012); Willms et al., "Cells Release Subpopulations of Exosomes with Distinct Molecular and Biological Properties," Sci Rep 6:22519 (2016), which are hereby incorporated by reference in their entirety). The major drawbacks of DGF, when compared to the performance of AF4, include its time-consuming preparations, lack of automation, operator-dependent reproducibility and low yield. Long periods of incubation with high sucrose concentrations can also damage EV integrity, necessitating additional washing steps for its removal. In contrast, AF4 is rapid, fully automated, highly reproducible, robust, and compatible with many buffer choices that mimic physiological conditions. Resolution and size range in EV fractionation is far superior with AF4 than with DGF (Tauro et al., "Comparison of Ultracentrifugation, Density Gradient Separation, and Immunoaffinity Capture Methods for Isolating Human Colon Cancer Cell Line LIM1863 Derived Exosomes," Methods 56:293-304 (2012), which is hereby incorporated by reference in its entirety).

SEC, a gentle means of nanoparticle fractionation, has been extensively used for protein and protein complex analysis in biochemical and biophysical studies. Recently, it has been adopted to fractionate EVs (Mol et al., "Higher Functionality of Extracellular Vesicles Isolated Using Size-Exclusion Chromatography Compared to Ultracentrifugation," Nanomedicine 13:2061-2065 (2017); Nordin et al, "Ultrafiltration with Size-Exclusion Liquid Chromatography for High Yield Isolation of Extracellular Vesicles Preserving Intact Biophysical and Functional Properties," Nanomedicine 11:879-883 (2015); Böing et al., "Single-Step Isolation of Extracellular Vesicles by Size-Exclusion Chromatography,"J Extracell Vesicles 3 (2014); Willis et al., "Toward Exosome-Based Therapeutics: Isolation, Heterogeneity, and Fit-for-Purpose Potency," Front Cardiovasc Med 4:63 (2017), which are hereby incorporated by reference in their entirety). In SEC, particles are separated in a column filled with porous polymer beads (stationary phase) based on their size and shape. Smaller-sized particles with a globular shape can penetrate the porous beads more readily, taking a longer route and more time to elute, whereas the larger particles are excluded from penetrating the pores and subsequently elute more rapidly. The elution of particles with abnormal shapes is more complicated due to its potential steric interference with particle traveling through the pores. Compared to other technologies, SEC has a resolution most similar to that of AF4. Still, AF4 demonstrates superior resolution over a much wider size range (Fraunhofer et al., "The Use of Asymmetrical Flow Field-Flow Fractionation in Pharmaceutics and Biopharmaceutics," Eur J Pharm Biopharm 58:369-383 (2004), which is hereby incorporated by reference in its entirety). SEC resolution drops when particles are close to or larger than the upper limits of pore size. Furthermore, SEC is not as flexible as AF4 in changing separation parameters and its size range of separation is fixed for a given column with a specific solitary phase. Moreover, AF4 contains a hollow channel with only a membrane at the accumulation wall but, unlike SEC, requires no stationary phase. This stationary phase in SEC generates shear stress and renders a much larger surface area than AF4 for nonspecific binding of analytes. Similar to AF4 methods, the input sample loading volume for SEC must be restricted and there is an upper limit for the sample capacity to compromise a balance between sufficient yield and exemplary fractionation quality. Sample stratification by dUC and concentration methodologies prior to separation greatly facilitates the separation power of SEC.

UF allows for straightforward isolation of EV populations based on their size by filtering the sample through a series of semipermeable membranes with defined pore sizes (i.e., as reflected by molecular weight cutoffs) (Xu et al., "Highly-Purified Exosomes and Shed Microvesicles Isolated from the Human Colon Cancer Cell Line LIM1863 by Sequential Centrifugal Ultrafiltration are Biochemically and Functionally Distinct," Methods 87:11-25 (2015); Xu et al., "A Protocol for Isolation and Proteomic Characterization of Distinct Extracellular Vesicle Subtypes by Sequential Centrifugal Ultrafiltration," Methods Mol Biol 1545:91-116 (2017), which are hereby incorporated by reference in their entirety). Smaller particles below the cutoff size can penetrate through the pores while larger ones are retained. UF provides a crude separation of EVs due to limitations of membrane pore size availability. Most EVs are not rigid spheres but rather flexible particles and can transfigure to pass through the pores, especially when pressure is applied. Another concern is the uniformity of membrane pore size, which is critical for separation purity. Though the separation power of UF is inferior to AF4, UF can serve as a means to pre-stratify and concentrate input samples for further analysis by AF4.

Distinguishable from methods which separate EVs mainly by their size, IAC relies on the antigenic recognition of EV surface molecules (primarily proteins). IAC is highly selective, fast and flexible to scale for either preparation or analytic purpose. This separation principle has been adapted for different formats of analysis and preparation, including precipitation using immunomagnetic beads, flow analysis, detection by microarray, microscopy, western or ELISA assay, and microfluidic separation (Théry et al., "Isolation and Characterization of Exosomes from Cell Culture Supernatants and Biological Fluids," *Curr Protoc Cell Biol* Chapter 3, Unit 3.22 (2006); Chen et al, "Microfluidic Isolation and Transcriptome Analysis of Serum Microvesicles," *Lab Chip* 10:505-511 (2010); Jorgensen et al., "Extracellular Vesicle (EV) Array: Microarray Capturing of Exosomes and Other Extracellular Vesicles for Multiplexed Phenotyping," *J Extracell Vesicles* 2 (2013); Ko et al., "miRNA Profiling of Magnetic Nanopore-Isolated Extracellular Vesicles for the Diagnosis of Pancreatic Cancer," *Cancer Res.* 78:3688-3697 (2018), which are hereby incorporated by reference in their entirety). The inherent limitation of IAC is that knowledge about the surface antigen is a prerequisite. The other concern is that the IAC antigen may be represented in multiple subpopulations of EVs with divergent sizes and/or origins. Thus, the application of AF4 may further necessitate EV separation based on size. EVs captured by IAC are ideal for molecular content characterization but not for further functional studies due to inefficient removal of the capturing antibody, which may interfere with the functional assay or targeting and uptake by recipient cells. In contrast, AF4 is label-free and enables these functional analyses feasible.

Level of Expertise Needed to Implement the Protocol

The AF4 instrument is commercially available (e.g., Wyatt Technology) and the manufacturer can perform the initial set-up. The method development for specific sample analysis, routine maintenance of instruments, and troubleshooting require a good understanding of the working principles of AF4 and installed detectors, training for handing the AF4 channel and detectors, and being familiar with software used for AF4 operation and data collection. Previous experience with chromatography and/or microfluidics is helpful in mastering the AF4 application. However, once the AF4 fractionation method training has been achieved, only minimal skills, such as familiarity with software interface and proper instructions, are necessary to complete the fractionation process since nearly all the steps are automatic and programmed.

Limitations

One inherent limitation of AF4 is that it fractionates samples based on their size. As a consequence, particles with the same hydrodynamic size but with different morphologies, surface molecules and other biophysical properties cannot be separated from each other via AF4 alone. However, other fields, such as electric field, can also be applied in conjunction with AF4 to provide further separation according to additional characteristics such as particle surface charge. Special consideration is also required when developing a protocol for large particles whose sizes are too large to be considered as point-mass compared to the channel height. These large particles will elute in the steric mode rather than the normal mode, as illustrated in FIG. 1.

A second inherent drawback is that AF4 can accommodate only small amounts of sample (e.g., 40 μg to 100 μg in the present case), which is often not efficient for large-scale preparations in more detailed assessments of nanoparticle properties. The sample instead can be divided into multiple fractionation analyses for improved characterization of specific nanoparticle subsets. A third limitation of AF4 is that due to the loading capacity limitation, the input sample requires UC preparation or other means to first stratify and concentrate the analyzes (i.e. sEVs in the present study) prior to fractionation.

Furthermore, it has to be pointed out that no single formula can be universally applied for analysis of different types of samples. The fractionation method and key parameters discussed above in the protocol development section have to be developed and optimized based on the complexity (i.e. size and abundance of each component) of the sample of interest. In certain cases, different running methods and instrument settings may have to be combined sequentially to efficiently separate different components within a complex sample.

A detailed protocol has been described herein for optimal sEV preparation and fractionation via AF4. The key steps for successful of AF4 separation are: (i) the preparation of sEVs from conditioned media of cell culture; (ii) development and optimization of the AF4 running methods; (iii) online data analysis and fraction collection for offline characterization.

Pre-stratification of the sEVs using methods such as UC is critical to reduce the complexity of the samples to be analyzed in their particle composition. This allows enough material for each subpopulation of sEVs present in the samples to be analyzed by a single run of AF4. Otherwise, a series of AF4 methods for best separation of particles within different size ranges have to be adapted. Another key factor for successful AF4 analysis and fractionation is the amount of input samples loaded onto the AF4 system. Overloading the system will result in poor resolution and inefficient separation of nanoparticles; whereas loading too little a sample will lead to poor signal detection and inaccurate data deduction, as shown in FIG. 19.

Five major parameters for AF4 running method optimization have been discussed, including cross flow, channel height, focus time, loading amount, and membrane type (see FIGS. 16-19). A representative AF4 fractionation profile of B16-F10 derived sEVs is shown in FIG. 22. Based on the method described here, three major subpopulations of sEVs are identified (FIG. 22A, i.e. exomeres, Exo-S and Exo-L, corresponding to peaks P2, P3 and P4, respectively). The autocorrelation function is a key factor to determine the purity of each fraction (FIG. 22B). The separated particles can be further recovered and usually need further concentration fora variety of offline analyses, such as TEM, NTA, BCA assay, biophysical/biochemical property characterization, molecular composition determination, and functional studies. Shown in FIG. 22C is TEM imaging analysis of combined fractions for B16-F10 exomeres, Exo-S and Exo-L, revealing the distinct morphology of each sEV subset.

Example 13—Examination of Systemic Functions of Exomeres, Exo-S, and Exo-L

To investigate their systemic functions, especially in liver, B16-F10 murine melanoma-derived exomeres, Exo-S and Exo-L were intravenously injected into naïve, syngeneic C57BL/6 mice. An equal volume of PBS was injected as the control. 24 hours later, livers were harvested from each group of treated mice and subjected to total RNA extraction and RNA sequencing analysis. As shown in FIG. 23A, a total of 5700, 5320, and 6291 genes were identified to be significantly ($p<0.05$) changed in their expression levels in the liver of mice treated with exomeres, Exo-S and Exo-L when compared with the PBS control group, respectively. Specifically, a list of 140 and 810 genes ore uniquely changed in exomeres when compared with ExoS and Exo-L, respectively.

To further compare the changes in gene expression among each group, one-way ANOVA analysis was performed and the result was illustrated in FIG. 23B for the top 2000 genes that are significantly changed. A large similarity was identified in all three groups of exomeres, Exo-S, and Exo-L treated mice when compared to the PBS control group. Specifically, shown in FIG. 24 are the top 50 gene lists that are up-regulated (FIG. 24A) or down-regulated (FIG. 24B) in all three groups when compared to the PBS control group, respectively. These genes can therefore serve as potential biomarkers for detection of disease, monitoring liver dysfunction, and therapeutic targets to intervene with tumor progression in cancer patients. For example, the Serum Amyloid A family genes (Saa1, Saa2 and Saa3), S100 calcium-binding protein A4 (S100A4), and a subset of ribosomal protein subunits (Rpl41, Rps24, Rpl36, Rpl35, Rpl21, Rps12, Rps18, Rps14, Rpl12, Rpl34, Rps10, and Rpl17) are specifically upregulated in the liver of mice treated with exomeres, Exo-S and Exo-L when compared to the PBS control. On the other hand, transcription factors such as Forkhead box protein N3 (Foxn3), TEA domain family member 1 (Tend1), Nuclear Factor Of Activated T Cells 5 (Nfat5), Forkhead box Q1 (Foxq1), Forkhead box K1 (Foxk1), Kruppel Like Factor 12 (Klf12), and ETS domain-containing protein (Elk4) are among the top 50 genes that are significantly down-regulated genes in all three groups.

To further investigate the functional pathways that are remarkably influenced by exomeres, Exo-S, and Exo-L, Ingenuity Pathway Analysis was conducted upon each dataset. Shown in FIG. 25 are the top five canonical pathways that were identified in each dataset: exomere versus PBS (FIG. 25A); Exo-S versus PBS (FIG. 25B); Exo-L versus PBS (FIG. 25C); exomere versus Exo-S(FIG. 25D), and exomere versus Exo-L (FIG. 25E). Importantly, pathways including E2F signaling, mTOR signaling, and regulation of eIF4 and p70S6K signaling are identified to be remarkably changed in all three groups of exomeres, exo-S, and Exo-L when compared to the PBS control, indicating their fundamental influence on the proliferation and metabolism of the liver. Beyond these findings, pathways of Molecular Mechanisms of Cancer and Glucocorticoid Receptor Signaling are specifically recognized among the top five canonical pathways in the exomere versus PBS group; pathways of Mitochondrial Dysfunction and Oxidative Phosphorylation in the Exo-S versus PBS group; and pathways of Nerve Growth Factor Signaling and Insulin Receptor Signaling in the Exo-L versus PBS group. Furthermore, when the exomere-treated group was compared to the Exo-S or Exo-L-treated groups, the following pathways are specifically recognized: Acute Phase Response Signaling, FXR/RXR Activation. Toll-like Receptor Signaling, LPS/IL-1 Mediated inhibition of RXR Function, and Aryl Hydrocarbon Receptor Signaling in the comparison of exomeres versus Exo-S; Superpathway of Cholesterol Biosynthesis, Cholesterol Biosynthesis I, Cholesterol Biosynthesis II (via 24,25-dihydrolanosterol), Cholesterol Biosynthesis III (via Desmosterol), and IGF-1 Signaling in exomere versus Exo-L. Collectively, detection of the alteration in these signaling pathways may assist in detecting and monitoring tumor progression in cancer patient. They also represent potential therapeutic targets.

Proteomic analysis of exomeres has indicated its potential role in the metabolism of the target cells. To specifically follow up on this hypothesis, the livers harvested from mice 24 hours post injection of B16-F10 derived exomeres, Exo-S and Exo-L in comparison with the PBS control were subjected for metabolite extraction and mass spectrometry analysis. FIG. 26A listed the number of metabolites whose abundance are significantly affected in each comparison group using unpaired t test. One-way ANOVA analysis was utilized to further identify metabolites that are changed in all three experimental groups and those are uniquely affected in each group. FIG. 26B illustrated all the metabolites identified with significant changes and FIG. 26C showed the clustering analysis of the metabolites that are uniquely affected in each group. In particular, the abundance of metabolites including thymine, taurine, and adenylosuccinate are found increased in all three groups of exomeres, Exo-S and Exo-L-treated mouse livers (FIG. 27A); whereas the abundance of the following metabolites including glucose-6-phosphate, L-arginino-succinate, methylcysteine, sn-glycerol-3-phosphate, and tyrosine decreased in all three groups when compared to the PBS control (FIG. 27B). Furthermore, representative metabolites that are uniquely affected in each group (FIG. 26C) are illustrated in FIGS. 28A-28C. Besides the altered gene expression, the aberrant regulation of these metabolites can be utilized as biomarkers to detect and monitor tumor progression and serve as potential therapeutic targets as well for cancer patients.

To further dissect the functional roles of exomeres in liver, immunofluorescent colocalization analysis was conducted and Kupffer cells, the resident macrophages in liver, were identified as the primary cell type that uptakes B16-F10 melanoma derived exomeres. When intravenously administrated into the naïve and syngeneic C57BL/6 mice, more than 95% of exomeres previously labeled with the PKH67 fluorescent dye were observed colocalized with the F4/80 positive Kupffer cells in the liver (FIG. 29). This finding implicates that Kupffer cell function can potentially be manipulated by tumor-derived exomeres and initiate a cascade of systemic effect to favor the tumor growth in vivo, therefore representing a potential target to develop therapeutic strategy for blocking cancer development.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:
1. A method comprising:
selecting a subject having melanoma, breast cancer, or pancreatic cancer;
obtaining, from the selected subject, a sample containing a population of exosomes having a diameter of less than 50 nm;
recovering exomeres from the sample, wherein the recovered exomeres have a diameter of less than 50 nm, a weak negative charge of −2.7 mV to −9.7 mV, a particle stiffness of 145 to 816 mPa, and a lack of an external lipid-bilayer membrane structure; and
contacting the recovered exomeres with one or more reagents suitable to detect higher or lower levels, relative to a standard for subjects not having melanoma, breast cancer, or pancreatic cancer, or the presence or absence, of AARS contained in said exomeres.

2. The method of claim 1, wherein said sample is blood, serum, plasma, ascites, cyst fluid, pleural fluid, peritoneal fluid, cerebrospinal fluid, tears, urine, saliva, sputum, nipple aspirates, lymph fluid, fluid of the respiratory, intestinal, and genitourinary trances, breast milk, intra-organ system fluid, conditioned media from tissue explant culture, or combinations thereof.

3. The method of claim 1, wherein said one or more reagents suitable to detect higher or lower levels, relative to a standard for subjects not having melanoma, breast cancer, or pancreatic cancer, or the presence or absence, of AARS contained in said exomeres measure protein expression level.

* * * * *